US007576094B2

(12) United States Patent
Chu et al.

(10) Patent No.: US 7,576,094 B2
(45) Date of Patent: Aug. 18, 2009

(54) SPIRO DERIVATIVES AS LIPOXYGENASE INHIBITORS

(75) Inventors: Daniel T. W. Chu, Santa Clara, CA (US); Jian Chen, San Jose, CA (US); Wei Zhang, Santa Clara, CA (US); Xianfeng Li, Cupertino, CA (US); Jiangao Song, Sunnyvale, CA (US); Bing Wang, Cupertino, CA (US); Qiang Cong, Sunnyvale, CA (US); Donald R. James, El Sobrante, CA (US)

(73) Assignee: Eli Lilly and Company, Indianapolis, IN (US)

( * ) Notice: Subject to any disclaimer, the term of this patent is extended or adjusted under 35 U.S.C. 154(b) by 195 days.

(21) Appl. No.: 11/298,137

(22) Filed: Dec. 9, 2005

(65) Prior Publication Data

US 2006/0128790 A1 Jun. 15, 2006

Related U.S. Application Data

(60) Provisional application No. 60/702,580, filed on Jul. 26, 2005, provisional application No. 60/675,386, filed on Apr. 27, 2005, provisional application No. 60/656,709, filed on Feb. 25, 2005, provisional application No. 60/656,710, filed on Feb. 25, 2005, provisional application No. 60/635,581, filed on Dec. 13, 2004.

(51) Int. Cl.
*A61K 31/353* (2006.01)
*A61K 31/382* (2006.01)
*A61K 31/4353* (2006.01)
*C07D 221/20* (2006.01)
*C07D 311/96* (2006.01)
*C07D 335/04* (2006.01)

(52) U.S. Cl. .................... 514/278; 514/437; 514/454; 546/18; 549/27; 549/331

(58) Field of Classification Search .................. 514/315, 514/465, 432, 278, 437, 454; 546/204, 18; 549/27, 331
See application file for complete search history.

(56) References Cited

U.S. PATENT DOCUMENTS

| 3,331,846 | A | 7/1967 | Easton et al. |
|---|---|---|---|
| 3,574,627 | A | 4/1971 | Stern et al. |
| 4,105,670 | A | 8/1978 | Noguchi et al. |
| 4,284,644 | A | 8/1981 | Sugihara et al. |
| 4,330,554 | A | 5/1982 | Sugihara et al. |
| 4,342,779 | A | 8/1982 | Sugihara et al. |
| 4,362,740 | A | 12/1982 | Imada et al. |
| 4,497,820 | A | 2/1985 | Merlini et al. |
| 4,568,692 | A | 2/1986 | Evans |
| 4,571,406 | A | 2/1986 | Evans et al. |
| 4,761,403 | A | 8/1988 | Gunn et al. |
| 4,780,469 | A | 10/1988 | Toda et al. |
| 4,814,346 | A | 3/1989 | Albert et al. |
| 4,831,050 | A | 5/1989 | Cassidy et al. |
| 4,845,092 | A | 7/1989 | Sanger et al. |
| 4,857,516 | A | 8/1989 | Terao et al. |
| 4,918,079 | A | 4/1990 | King |
| 4,950,684 | A | 8/1990 | Koszyk et al. |
| 5,013,853 | A | 5/1991 | Gericke et al. |
| 5,015,661 | A | 5/1991 | Walser |
| 5,021,432 | A | 6/1991 | Yamanaka et al. |
| 5,032,591 | A | 7/1991 | Evans et al. |
| 5,059,609 | A | 10/1991 | Eggler et al. |
| 5,076,835 | A | 12/1991 | Condon et al. |
| 5,112,972 | A | 5/1992 | Gericke et al. |
| 5,126,460 | A | 6/1992 | Faruk |
| 5,143,936 | A | 9/1992 | Yamanaka et al. |
| 5,147,866 | A | 9/1992 | Stemp et al. |
| 5,232,938 | A | 8/1993 | Stemp et al. |
| 5,250,547 | A | 10/1993 | Lochead et al. |
| 5,268,386 | A | 12/1993 | Harada et al. |
| 5,318,969 | A | 6/1994 | Yamanaka et al. |
| 5,350,747 | A | 9/1994 | Howard |
| 5,354,729 | A | 10/1994 | Uekawa et al. |
| 5,387,587 | A | 2/1995 | Häusler et al. |
| 5,393,775 | A | 2/1995 | Le Baut et al. |
| 5,399,562 | A | 3/1995 | Becker et al. |
| 5,591,772 | A | 1/1997 | Lane et al. |
| 5,606,006 | A | 2/1997 | Wang |
| 5,618,833 | A | 4/1997 | Foulon et al. |
| 5,624,954 | A | 4/1997 | Evans et al. |
| 5,643,942 | A | 7/1997 | Hester, Jr. et al. |
| 5,665,799 | A | 9/1997 | Inui et al. |
| 5,674,876 | A | 10/1997 | Gilbert et al. |
| 5,686,624 | A | 11/1997 | Di Malta et al. |
| 5,688,810 | A | 11/1997 | Jones et al. |
| 5,688,871 | A | 11/1997 | Inui et al. |

(Continued)

FOREIGN PATENT DOCUMENTS

BE 1004295 10/1992

(Continued)

OTHER PUBLICATIONS

King; Med Chem: Principle and Practice (1994), p. 206-208.*

(Continued)

*Primary Examiner*—Taofiq A Solola
(74) *Attorney, Agent, or Firm*—James B. Myers

(57) ABSTRACT

The present invention is concerned with certain novel spiro substituted heterocylic ring derivatives. These compounds may be useful in the manufacture of pharmaceutical compositions for treating disorders mediated by lipoxygenases. They may also be useful in the manufacture of pharmaceutical formulations for the treatment of lipoxygenase-mediated disorders.

37 Claims, No Drawings

U.S. PATENT DOCUMENTS

| | | | |
|---|---|---|---|
| 5,696,145 | A | 12/1997 | Foulon et al. |
| 5,698,717 | A | 12/1997 | Iyama et al. |
| 5,728,704 | A | 3/1998 | Mylari et al. |
| 5,798,365 | A | 8/1998 | Kirsch et al. |
| 5,849,780 | A | 12/1998 | Di Malta et al. |
| 5,908,860 | A | 6/1999 | Thompson et al. |
| 5,925,673 | A | 7/1999 | Hellberg et al. |
| 5,939,346 | A | 8/1999 | Marks et al. |
| 5,939,452 | A | 8/1999 | Dombroski et al. |
| 5,948,811 | A | 9/1999 | Chan et al. |
| 5,994,350 | A | 11/1999 | Foulon et al. |
| 6,005,007 | A | 12/1999 | Farmer et al. |
| 6,040,308 | A | 3/2000 | Häusler et al. |
| 6,046,341 | A | 4/2000 | Foulon et al. |
| 6,051,601 | A | 4/2000 | Dombroski et al. |
| 6,090,818 | A | 7/2000 | Foulon et al. |
| 6,117,874 | A | 9/2000 | Dombroski et al. |
| 6,127,396 | A | 10/2000 | Cordi et al. |
| 6,133,286 | A | 10/2000 | Dombroski et al. |
| 6,153,627 | A | 11/2000 | Häusler et al. |
| 6,252,090 | B1 | 6/2001 | Vasudevan et al. |
| 6,291,677 | B1 | 9/2001 | Vasudevan et al. |
| 6,313,107 | B1 | 11/2001 | Vasudevan et al. |
| 6,350,759 | B1 | 2/2002 | Casara et al. |
| 6,369,225 | B1 | 4/2002 | Vasudevan et al. |
| 6,596,758 | B1 | 7/2003 | Brunet et al. |
| 6,652,601 | B2 | 11/2003 | Sauter et al. |
| 6,956,033 | B2 | 10/2005 | Ogawa et al. |
| 2003/0212109 | A1 | 11/2003 | Mitchell et al. |
| 2003/0225057 | A1 | 12/2003 | Smith et al. |
| 2004/0152755 | A1 | 8/2004 | He et al. |
| 2005/0020573 | A1 | 1/2005 | Smith et al. |
| 2005/0020617 | A1 | 1/2005 | Bastian et al. |
| 2005/0065099 | A1 | 3/2005 | Walkinshaw et al. |
| 2005/0065149 | A1 | 3/2005 | Wang et al. |
| 2005/0065150 | A1 | 3/2005 | Wang et al. |
| 2005/0165001 | A1 | 7/2005 | Krauss et al. |
| 2006/0106014 | A1 | 5/2006 | Boddupalli et al. |
| 2006/0193797 | A1 | 8/2006 | Zhang et al. |

FOREIGN PATENT DOCUMENTS

| | | |
|---|---|---|
| CA | 2053962 | 10/1991 |
| DE | 4020133 | 1/1991 |
| DE | 4018552 | 12/1991 |
| DE | 4115521 | 11/1992 |
| DE | 19854147 | 5/2000 |
| EP | 0003084 | 7/1979 |
| EP | 0488301 | 6/1992 |
| EP | 0636608 | 2/1995 |
| GB | 2242628 | 10/1991 |
| JP | 53-73560 | 6/1978 |
| JP | 1-246274 | 10/1989 |
| JP | 4-264080 | 9/1992 |
| JP | 7-188210 | 7/1995 |
| WO | WO 91/09593 | 7/1991 |
| WO | WO 91/16888 | 11/1991 |
| WO | WO 92/20672 | 11/1992 |
| WO | WO 92/22293 | 12/1992 |
| WO | WO 94/12173 | 6/1994 |
| WO | WO 94/13297 | 6/1994 |
| WO | WO 96/11925 | 4/1996 |
| WO | WO 98/09956 | 3/1998 |
| WO | WO 99/43670 | 9/1999 |
| WO | WO 02/18361 | 3/2002 |
| WO | WO 02/26727 | 4/2002 |
| WO | WO 02/42285 | 5/2002 |
| WO | WO 2005/016335 | 2/2005 |
| WO | WO 2005/016881 | 2/2005 |
| WO | WO 2005/063745 | 7/2005 |
| WO | WO 2005/075463 | 8/2005 |
| WO | WO 2006/093548 | 9/2006 |

OTHER PUBLICATIONS

Bernard et al., "The First Synthesis of Some Spiro[2,3-Dihydro-2,2-Dimethylbenzofuran-3,1'-Cyclopropanes] through, $Mo(CO)_6$ Catalyzed, One Pot Claisen Rearrangement-Cyclization Reaction of 2-Cyclopropylidene-Aryloxy Alkanes." Synlett, May 1997, 585-6.

Gilbert et al., "Synthesis, Structure Determination, and Analysis of Spiro[2,3-dihydro-5-hydroxy-4,6,7-trimethylbenzofuran-2,1'-cyclopropane]." Journal of Organic Chemistry, 1992, 5271-6, 57(19).

Kabbe, "A simple synthesis of 4-chromanones." Synthesis, 1978, 886-7, 12.

Kawada et al., "Spirocyclopropane Compounds. I. Synthesis and Reactivity of Spiro[cyclopropane-1,2'-[2H]indol]-3'(1'H)-ones." Chemical & Pharmaceutical Bulletin, 1981, 1900-1, 29(7).

Kawada et al., "Spirocyclopropane Compounds. II. Synthesis and Biological Activities of Spiro[cyclopropane-1,2'-[2H]indol]-3'(1'H)-ones." Chemical & Pharmaceutical Bulletin, 1981, 1912-9, 29(7).

Kawada et al., "Spirocyclopropane Compounds. III. Synthesis of Spiro[benzofuran-2(3H),1'-cyclopropan]-3-ones for Evaluation as Gastric Antisecretory and Antiulcer Agents." Chemical & Pharmaceutical Bulletin, 1984, 3532-50, 32(9).

Kawada et al., "Spirocyclopropane Compounds. VI. Synthesis of Spiro[benzo[b]-thiophene-2(3H),1'-cyclopropan]-3-ones." Chemical & Pharmaceutical Bulletin, 1986, 1939-45, 34(5).

Kitazawa et al., "Studies on the Synthesis of Antiulcer Agents." Yakugaku Zasshi, 1989, 241-9, 109(4)—abstract only.

Manev et al., " 5-Lipoxygenase as a Putative Link Between Cardiovascular and Psychiatric Disorders." Critical Reviews in Neurobiology, 2004, 181-6, 16(1-2).

Remers et al., "The Birch Reduction of Typtamine Quaternary Salts." Tetrahedron Letters, 1968, 81-4, 1.

Rola-Pleszczynski et al., "Cytokine Gene Regulation by PGE2, LTB4 and PAF." Mediators of Inflammation, 1992, 5-8, vol. 1.

Uz et al., "5-lipoxygenase (5LOX)-deficient Mice Express Reduced Anxiety-like Behavior." Restorative Neurology and Neuroscience, 2002, 15-20, 20(1-2).

\* cited by examiner

SPIRO DERIVATIVES AS LIPOXYGENASE INHIBITORS

CROSS-REFERENCE TO RELATED APPLICATIONS

This application claims the benefit under 35 U.S.C. 119(e) to provisional applications U.S. Ser. No. 60/635,581 filed on Dec. 13, 2004, U.S. Ser. No. 60/656,709 filed on Feb. 25, 2005, U.S. Ser. No. 60/656,710 filed on Feb. 25, 2005, U.S. Ser. No. 60/675,386 filed on Apr. 27, 2005, and U.S. Ser. No. 60/702,580 filed on Jul. 26, 2005, each of which is incorporated herein by reference in their entirety.

BACKGROUND INFORMATION

The present invention relates to certain novel spiro derivatives of Formula I, IA, IB, II, IIA, III, or IIIA as depicted below, pharmaceutical formulations containing them, and their uses as therapeutic agents, and syntheses therefore. Their uses as therapeutic agents that may act as lipoxygenase inhibitors include, but are not limited to, prevention or treatment of diseases involving apoptosis in cancer cells; diseases involving hypoxia or anoxia; diseases involving inflammation; disorders of the airways; diseases involving central nervous system (CNS) disorders, neurodegeneration and neuroinflammation; and diseases involving the autoimmune system.

The use of compounds having a chroman moiety as lipoxygenase inhibitors has been disclosed, for example, in U.S. Pat. No. 5,059,609; U.S. Pat. No. 4,950,684; U.S. Pat. No. 5,015,661; U.S. Pat. No. 4,780,469; U.S. Pat. No. 5,591,772; U.S. Pat. No. 5,925,673; U.S. Pat. No. 5,250,547; U.S. Pat. No. 5,393,775; U.S. Pat. No. 4,814,346; U.S. Pat. No. 5,939,452, U.S. Pat. No. 6,051,601; U.S. Pat. No. 6,117,874; and U.S. Pat. No. 6,133,286.

Arachidonic acid is an essential fatty acid that exists within the cell membrane and can be released from phospholipids by the action of phospholipase. The released arachidonic acid is metabolized through three major enzymatic pathways, i.e. the lipoxygenase pathway, to form substances such as prostaglandins which are associated with inflammatory responses, and thromboxanes which are associated with the formation of thrombus, or leukotrienes which induce allergic reactions.

Lipoxygenases are non-heme iron-containing enzymes that catalyze the oxidation of polyunsaturated fatty acids and esters thereof. They were originally classified based on their substrate specificity for insertion of molecular oxygen into arachidonic acid at carbon positions 5, 12 and 15, but more recently a phylogenetic classification is being used. This separates the mammalian enzymes in four main subtypes, 5-Lipoxygenase, 12/15-Lipoxygenases, platelet 12-Lipoxygenases and epidermis-type lipoxygenases. The 12/15 family of lipoxygenases includes two sub-families with a high degree of sequence homology, the reticulocyte 15-Lipoxygenases (found in rabbit and humans) and the leukocyte 12-Lipoxygenases (found in mouse, pig, rat, and rabbit). This type of lipoxygenase shares more homology to reticulocyte 15-Lipoxygenase and leukocyte 12-Lipoxygenase, than to platelet 12-Lipoxygenases.

It is believed that oxidative metabolites of the 12/15-Lipoxygenase or the 15-Lipoxygenase cascade have been implicated in the potentiation of thrombin induced platelet activation (Setty et al. *Blood*, (1992), 2765-2773); in the progression of various cancers (Kelavkar et al, *Curr. Urol. Rep.* Vol. 3 no. 3 (2002) pp. 207-214) and related pathologies (Tisdale et al., *Science* Vol. 289 no. 5488 (2000) pp. 2293-4). It has also been shown that treatment with a 15-Lipoxygenase inhibitor suppresses atherogenesis in rabbits fed a high-fat diet (Bocan et al., *Atherosclerosis*, Vol. 136 (1998) pp. 203-16). There is increasing evidence that certain lipoxygenase enzymes are involved in the pathogenesis and acceleration of atherosclerosis by inducing oxidation of LDL to its atherogenic form (Sparrow, C. P., et al., *J. Lipid Res.* Vol. 29 (1988) pp. 745-753. and Steinberg, D., *New Eng. J. Med.* Vol. 320 (1989) pp. 915-924). It has also been reported that 12-Lipoxygenase enzyme plays a role in mediating angiotensin II induced vascular and adrenal actions (Natarajan, R., et al., *Endocrinology* Vol. 131 (1992) pp. 1174-1180). Recent studies (Klein, R. et al., *Science* Vol. 303 no. 5655 (2004) 329-332) have also shown the role of 15-Lipoxygenase enzyme in the regulation of bone density.

The enzyme 5-Lipoxygenase converts arachidonic acid to 5-hydroperoxyeicosatetraenoic acid (5-HPETE). This is the first step in the metabolic pathway yielding 5-hydroxyeicosatetraenoic acid (5-HETE) and the important class of mediators, the leukotrienes. Evidence of the role of leukotrienes in the pathology of certain diseases has been described, for example in Cloud et al., *J. Allergy Clin. Immunol.*, Vol. 79 (1987) pp. 256 (asthma); Turnbull et al., *Lancet II*, (1977) pp. 526-9 (chronic bronchitis); Cromwell et al., *Lancet II*, (1981) pp. 164-5 (cystic fibrosis); Davidson et al., *J. Pharm. Pharmacol.* Vol. 34 no. 61 (982) pp. 410 (rheumatoid arthritis); Rae et al., *Lancet*. Vol. 2 no. 8308 (1982) pp. 1122-4. Cook et al., *J. Pharmacol. Exp. Ther.*, 235, (1985) pp. 470-474 (cardiovascular conditions); Tsuji et al., *Biochem. Pharmacol.* Vol. 55 no. 3: (1998); pp. 297-304 (dermatitis such as psoriasis).

It has also been shown in co-owned U.S. application Ser. No. 11/251,423 filed Oct. 13, 2005, titled Methods for Treating Diabetes, herein incorporated by reference in its entirety, that dual 5-Lipoxygenase and 12/15-Lipoxygenase inhibitors or 5-Lipoxygenase and 15-Lipoxygenase inhibitors are superior in the prevention of treatment of subjects susceptible to diabetes, are able to improve glucose control in animal models of diabetes, and have demonstrated a significant lowering of the baseline serum glucose levels compared to selective 5-Lipoxygenase, 15-Lipoxygenase and 12/15-Lipoxygenase inhibitors.

The compositions, formulations and methods of this invention are particularly applicable in preventing and/or treating diseases or disorders mediated, at least in part, by one or more lipoxygenase enzymes, such as 5-Lipoxygenase enzyme and/or 12/15-Lipoxygenase enzyme.

SUMMARY OF THE INVENTION

The present invention is concerned with certain novel spiro derivatives of Formula I, IA, IB, II, IIA, III, or IIIA which may be useful in the manufacture of pharmaceutical compositions for treating disorders mediated, at least in part, by lipoxygenases.

In a first aspect, the present invention concerns the compounds represented by Formula I:

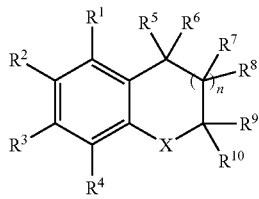

Formula I wherein,

X is O or $S(O)_{0-2}$;

$R^1$, $R^3$, and $R^4$ are independently selected from the group consisting of hydrogen, alkyl, cycloalkyl, halogen, nitro, cyano, amino, aminosulfonyl, sulfonylamino, sulfanyl, aryl, heterocyclyl, hydroxy, acyl, alkoxy, carboxy, alkoxycarbonyl, amido, alkenyl, and alkynyl, with the proviso that said alkenyl and alkynyl are not substituted with aryl or heteroaryl;

or $R^3$ and $R^4$, together with the carbon atoms attached thereto join to form a cycloalkyl, aryl, or heterocyclyl ring;

$R^2$ is selected from the group consisting of hydroxy, amino, carbonylamino, alkoxy, —O—C(O)—O-alkyl, —O-alkenyl, —O-acyl, —O-alkylene-amino, —O—C(O)-alkylene-COOR$^a$, —O—C(O)-amino, —O—C(O)-alkylene-amino, —O—C(O)—O-alkylene-amino, —O—C(O)-heterocyclyl, —O—C(O)-alkylene-heterocyclyl, —O-glucoside, —O-phosphoryl, —O-alkylene-phosphoryl, and —O—C(O)-AA, wherein AA is amino acid or a di-, tri- or tetra-peptide;

$R^5$ and $R^6$ are independently selected from the group consisting of hydrogen, alkyl, cycloalkyl, heterocyclyl, hydroxy, alkoxy, carboxy, alkoxycarbonyl, alkylcarbonyl, amino, aminosulfonyl, sulfonylamino, sulfanyl, nitro, cyano, halogen, —OC(O)NR$^b$R$^c$, —NRC(O)R$^d$, —NROR$^a$, and —NR—NR$^b$R$^c$; or together with the carbon atom to which they are attached, form C=O; C=NOR$^a$, C=N—NR$^b$R$^c$, or an optionally substituted $(C_3-C_4)$cycloalkyl ring;

$R^7$ and $R^8$ are independently selected from the group consisting of hydrogen, alkyl, cycloalkyl, hydroxy, alkoxy, carboxy, alkoxycarbonyl, alkylcarbonyl, amino, aminosulfonyl, sulfonylamino, sulfanyl, nitro, cyano, halogen, aryl, heterocyclyl, —OC(O)NR$^b$R$^c$, —NRC(O)R$^d$, NROR$^a$, and —NR—NR$^b$R$^c$; or together with the carbon atom to which they are attached, form C=O; C=NOR$^a$, C=N—NR$^b$R$^c$, or an optionally substituted $(C_3-C_4)$cycloalkyl ring;

$R^9$ and $R^{10}$ are independently selected from the group consisting of hydrogen, alkyl, cycloalkyl, hydroxy, alkoxy, carboxy, alkoxycarbonyl, alkylcarbonyl, amino, aminosulfonyl, sulfonylamino, sulfanyl, nitro, cyano, halogen, —OC(O)NR$^b$R$^c$, —NRC(O)R$^d$, —NROR$^a$, and —NR—NR$^b$R$^c$; or together with the carbon atom to which they are attached, form C=O; C=NOR$^a$, C=N—NR$^b$R$^c$, or an optionally substituted $(C_3-C_4)$cycloalkyl ring;

R is hydrogen or alkyl;

$R^a$ is selected from the group consisting of hydrogen, alkyl, cycloalkyl, alkenyl, heterocyclyl, and aryl;

$R^b$ and $R^c$ are independently selected from the group consisting of hydrogen, alkyl, cycloalkyl, alkenyl, acyl, aminocarbonyl, heterocyclyl and aryl; or together with the nitrogen atom to which they are attached form an optionally substituted, saturated or unsaturated 3-8 membered ring optionally incorporating 1 to 3 —N—, —O— or —S— atoms;

$R^d$ is selected from the group consisting of hydrogen, alkyl, cycloalkyl, alkenyl, alkoxy, heterocyclyl, and aryl;

and n is 0 or 1;

with the following provisos:
a. at least one of —CR$^5$R$^6$, —CR$^7$R$^8$ or —CR$^9$R$^{10}$ is a $(C_3-C_4)$cycloalkyl ring;
b. no more than one of $R^1$, $R^3$ and $R^4$ is hydrogen; and
c. if n is 0, $R^5$ and $R^6$ independently cannot be hydrogen or together with the carbon atom to which they are attached do not form C=O;

or single stereoisomers, mixtures of stereoisomers, or pharmaceutically acceptable salts thereof.

In one embodiment of Formula I, $R^2$ is hydroxy, and in another embodiment $R^2$ is hydroxy and $R^1$, $R^3$, and $R^4$ are independently of each other hydrogen, halogen, or alkyl. In yet another embodiment, $R^2$ is hydroxy, $R^1$, $R^3$, and $R^4$ are independently of each other hydrogen, halogen, or alkyl, and —CR$^5$R$^6$ is optionally substituted $(C_3-C_4)$cycloalkyl ring. In another embodiment, $R^2$ is hydroxy, $R^1$, $R^3$, and $R^4$ are independently of each other hydrogen, halogen, or alkyl, and n=1, —CR$^7$R$^8$ is optionally substituted $(C_3-C_4)$cycloalkyl ring. In another embodiment, $R^2$ is hydroxy, $R^1$, $R^3$, and $R^4$ are independently of each other hydrogen, halogen, or alkyl, and —CR$^9$R$^{10}$ is optionally substituted cyclopropyl or cyclobutyl. In another embodiment, $R^5$ is —NROR$^a$, $R^6$ is hydrogen, and —CR$^9$R$^{10}$ is an optionally substituted $(C_3-C_4)$cycloalkyl ring, exemplified by —CR$^9$R$^{10}$ forming an optionally substituted cyclobutyl ring. In another embodiment $R^5$ is —NROR$^a$ and —CR$^9$R$^{10}$ is optionally substituted cyclobutyl ring. In yet another embodiment $R^5$ is hydroxy and $R^6$ is hydrogen, and —CR$^9$R$^{10}$ is an optionally substituted $(C_3-C_4)$cycloalkyl ring, exemplified by —CR$^9$R$^{10}$ forming an optionally substituted cyclobutyl ring. One embodiment includes $R^5$ is hydroxy, $R^6$ is hydrogen, and $R^1$, $R^3$, and $R^4$ are independently selected from hydrogen, halogen, and alkyl.

In other embodiments, $R^2$ is hydroxy, $R^1$, $R^3$, and $R^4$ are indepdendently hydrogen, halogen or alkyl and $R^5$ and $R^6$ are hydrogen.

In some embodiments n is 0 and in other embodiments n is 1.

In one embodiment, when any of $R^1$, $R^3$, and $R^4$ are halo, then halo is chloro.

In one embodiment, when any of $R^1$, $R^3$, and $R^4$ are alkyl, then alkyl is optionally substituted and is selected from methyl, ethyl, isopropyl, propyl, t-butyl, 3,7-dimethyloctyl, hydroxymethyl, hydroxyaminomethyl, methoxymethyl, methoxyaminomethyl, ethoxyaminomethyl, 2-quinolin-2-ylethyl, aminomethyl, N-morpholinomethyl, N-methylacetamidomethyl, and acetamidomethyl, In one embodiment, when any of $R^1$, $R^3$ and $R^4$ are alkenyl, then alkenyl is optionally substituted and is selected from vinyl and 3,7-dimethylocta-2,6-dienyl.

In one embodiment, when any of $R^1$, $R^3$, and $R^4$ are heterocyclyl, then heterocyclyl is optionally substituted and is selected from is 5-methoxycarbonyl-4,5-dihydroisoxazol-3-yl, 5-butylisoxazol-3-yl, oxazol-5-yl, 4,5-dimethylimidazol-2-yl, benzofuran-2-yl, and 5,6-dimethylbenzoimidazol-2-yl.

In another embodiment, the invention is directed to compounds of Formula IA:

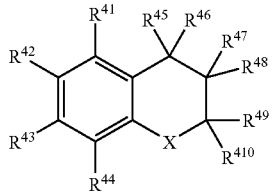

Formula IA wherein

X is O or $S(O)_{0-2}$;

$R^{41}$, $R^{43}$, and $R^{44}$ are independently selected from the group consisting of hydrogen, halo, acyl, alkenyl, heterocyclyl, and alkyl optionally substituted with amino, hydroxy, alkoxy, heterocyclyl, carbonylamino;

$R^{42}$ is selected from the group consisting of hydroxy, alkoxy, —O—C(O)—O-alkyl, —O-acyl, —O-alkylene-amino, —O—C(O)-alkylene-amino, —O—C(O)—O-alkylene-amino, —O—C(O)-heterocyclyl, —O—C(O)-alkylene-heterocyclyl, and —O—C(O)-carbonylamino;

$R^{45}$ and $R^{46}$ are independently selected from the group consisting of hydrogen, alkyl, heterocyclyl, hydroxy, alkoxy, amino, aminosulfonyl, sulfonylamino, sulfanyl, cyano, —OC(O)NR$^b$R$^c$, —NRC(O)R$^d$, —NROR$^a$, or together with the carbon atom to which they are attached, form C=O; C=NOR$^a$; or an optionally substituted ($C_3$-$C_4$)cycloalkyl ring;

$R^{47}$ and $R^{43}$ are independently selected from the group consisting of hydrogen, alkyl, hydroxy, and alkoxy, and heterocyclyl, or together with the carbon atom to which they are attached, form an optionally substituted ($C_3$-$C_4$)cycloalkyl ring;

$R^{49}$ and $R^{410}$ are independently selected from the group consisting of hydrogen, alkyl, cycloalkyl, hydroxy, and alkoxy, or together with the carbon atom to which they are attached, form an optionally substituted ($C_3$-$C_4$)cycloalkyl ring;

$R^a$ is selected from the group consisting of hydrogen, alkyl, cycloalkyl, alkenyl, heterocyclyl, and aryl;

$R^b$ and $R^c$ are independently selected from the group consisting of hydrogen, alkyl, cycloalkyl, alkenyl, acyl, aminocarbonyl, heterocyclyl and aryl; or together with the nitrogen atom to which they are attached form an optionally substituted, saturated or unsaturated 3-8 membered ring optionally incorporating 1 to 3 —N—, —O— or —S— atoms;

with the following provisos:
a. at least one of —CR$^{45}$R$^{46}$—, —CR$^{47}$R$^{48}$ or —CR$^{49}$R$^{410}$ is a ($C_3$-$C_4$)cycloalkyl ring; and
b. no more than one of $R^{41}$, $R^{43}$ and $R^{44}$ is hydrogen;

or single stereoisomers, mixtures of stereoisomers, or pharmaceutically acceptable salts thereof.

In another embodiment, the invention is directed to compounds of Formula IB:

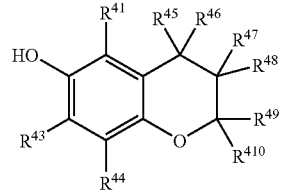

Formula IB wherein $R^{41}$, $R^{43}$, $R^{44}$, $R^{45}$, $R^{46}$, $R^{47}$, $R^{48}$, $R^{49}$ and $R^{410}$ are as defined above.

In another aspect, the invention relates to a pharmaceutical composition containing a therapeutically effective amount of a compound of Formula I, IA, or IB, or a pharmaceutically acceptable salt thereof admixed with at least one pharmaceutically acceptable excipient. In some examples, the pharmaceutical compositions comprise a compound of Formula I, IA, or IB, and a pharmaceutically acceptable excipient; and the compound is selected from the illustrative compounds and stereoisomers, mixture of stereoisomers or pharmaceutically acceptable salts thereof.

In another aspect, the present invention concerns the compounds represented by Formula II:

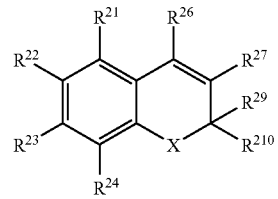

Formula II wherein,

X is O, $S(O)_{0-2}$, or NR$^{200}$;

$R^{21}$, $R^{23}$, and $R^{24}$ are independently selected from the group consisting of hydrogen, alkyl, cycloalkyl, halogen, nitro, cyano, amino, aminosulfonyl, sulfonylamino, sulfanyl, aryl, heterocyclyl, hydroxy, alkoxy, carboxy, alkoxycarbonyl, amido, alkenyl, and alkynyl, with the proviso that said alkenyl and alkynyl are not substituted with aryl or heteroaryl;

or $R^{23}$ and $R^{24}$ together with the carbon atoms attached thereto join to form a cycloalkyl, aryl, or heterocyclyl ring;

$R^{22}$ is selected from the group consisting of hydroxy, amino, carbonylamino, alkoxy, —O-alkenyl, —O-acyl, —O-alkylene-amino, —O—C(O)-alkylene-COOR$^{2a}$, —O—C(O)-amino, —O—C(O)-alkylene-amino, —O—C(O)-heterocyclyl, —O—C(O)-alkylene-heterocyclyl, —O-glucoside, —O-phosphoryl, —O-alkylene-phosphoryl, and —O—C(O)-AA, wherein AA is amino acid or a di-, tri- or tetra-peptide;

$R^{26}$ and $R^{27}$ are independently selected from the group consisting of hydrogen, alkyl, cycloalkyl, hydroxy, alkoxy, carboxy, alkoxycarbonyl, alkylcarbonyl, amino, aminosulfonyl, sulfonylamino, sulfanyl, nitro, cyano, halogen, aryl, heterocyclyl, —C=N—OR$^{20}$, —OC(O)NR$^{2b}$R$^{2c}$, NR$^{2}$C(O)R$^{2d}$, —NR$^{20}$OR$^{2a}$, and —NR$^{20}$—NR$^{2b}$R$^{2c}$;

$R^{29}$ and $R^{210}$ together with the carbon atom to which they are attached form an optionally substituted $(C_3\text{-}C_4)$cycloalkyl ring;

$R^{20}$ is hydrogen or alkyl;

$R^{200}$ is selected from the group consisting of hydrogen, alkyl, aralkyl, cycloalkyl, alkenyl, alkynyl, acyl, aminocarbonyl, heterocyclyl and aryl;

$R^{2a}$ is selected from the group consisting of hydrogen, alkyl, cycloalkyl, alkenyl, heterocyclyl, and aryl;

$R^{2b}$ and $R^{2c}$ are
  independently selected from the group consisting of hydrogen, alkyl, cycloalkyl, alkenyl, acyl, aminocarbonyl, heterocyclyl and aryl; or
  together with the nitrogen atom to which they are attached form an optionally substituted, saturated or unsaturated 3-8 membered ring optionally incorporating 1 to 3 —N—, —O— or —S— atoms; and $R^{2d}$ is selected from the group consisting of hydrogen, alkyl, cycloalkyl, alkenyl, amino, alkoxy, heterocyclyl, and aryl;

with the proviso that when $R^{26}$ or $R^{27}$ is —NR$^{20}$C(O)R$^{2d}$; —NHOR$^{2a}$ or —NH—NR$^{2b}$R$^{2c}$, then no more than one of $R^{21}$, $R^{22}$, $R^{23}$ and $R^{24}$ is hydrogen;

or single stereoisomers, mixtures of stereoisomers, pharmaceutically acceptable salts, tautomers or prodrugs thereof.

In some embodiments, $R^{22}$ is hydroxy, and in another embodiment $R^{22}$ is hydroxy and $R^{21}$, $R^{23}$, and $R^{24}$ are independently of each other hydrogen, halogen, or alkyl.

In one embodiment, when any of $R^{21}$, $R^{23}$, and $R^{24}$ are alkyl, then alkyl is optionally substituted and is selected from methyl, ethyl, and isopropyl.

In still another aspect, the invention relates to compounds of Formula IIA:

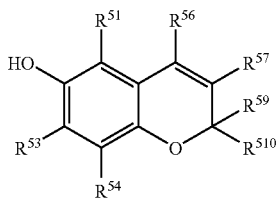

Formula IIA wherein, $R^{51}$, $R^{53}$, and $R^{54}$ are independently selected from the group consisting of hydrogen, alkyl, and hydroxy;

$R^{56}$ and $R^{57}$ are independently selected from the group consisting of hydrogen, alkyl, hydroxy, cyano, and heterocyclyl, $R^{59}$ and $R^{510}$ together with the carbon atom to which they are attached form an optionally substituted $(C_3\text{-}C_4)$cycloalkyl ring;

or single stereoisomers, mixtures of stereoisomers, pharmaceutically acceptable salts, or prodrugs thereof.

In another aspect, the invention relates to a pharmaceutical composition containing a therapeutically effective amount of a compound of Formula II or IIA, or a pharmaceutically acceptable salt thereof admixed with at least one pharmaceutically acceptable excipient. In some examples, the pharmaceutical compositions comprise a compound of Formula II or IIA and a pharmaceutically acceptable excipient; and the compound is selected from the illustrative compounds and stereoisomers, mixture of stereoisomers or pharmaceutically acceptable salts thereof.

In another aspect, the present invention concerns the compounds represented by Formula III:

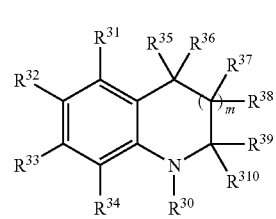

Formula III wherein, $R^{30}$ is selected from the group consisting of hydrogen, alkyl, aralkyl, cycloalkyl, alkenyl, alkynyl, acyl, aminocarbonyl, heterocyclyl and aryl;

$R^{31}$, $R^{33}$, and $R^{34}$ are independently selected from the group consisting of hydrogen, alkyl, cycloalkyl, halogen, nitro, cyano, amino, aminosulfonyl, sulfonylamino, sulfanyl, aryl, heterocyclyl, hydroxy, alkoxy, carboxy, alkoxycarbonyl, amido, alkenyl, and alkynyl, with the proviso that said alkenyl and alkynyl are not substituted with an aryl or heteroaryl group;

or $R^{33}$ and $R^{34}$ together with the carbon atoms attached thereto join to form a cycloalkyl, aryl, or heterocyclyl ring;

$R^{32}$ is selected from the group consisting of hydroxy, alkoxy, —O-alkenyl, —O-acyl, —O-glucoside; —O-phosphoryl, —O—C(O)-AA, wherein AA is amino acid, or a di-, tri- or tetra-peptide;

$R^{35}$ and $R^{36}$ are
  independently selected from the group consisting of hydrogen, alkyl, hydroxy, cycloalkyl, —OC(O)NR$^{3b}$R$^{3c}$, —NR$^{3d}$OR$^{3a}$ and —NR$^{3d}$—NR$^{3b}$R$^{3c}$; or
  together with the carbon atom to which they are attached form C=O, C=NOR$^{3a}$, C=N—NR$^{3b}$R$^{3c}$, optionally substituted $(C_3\text{-}C_4)$cycloalkyl ring;

$R^{37}$ and $R^{38}$ are
  independently selected from the group consisting of hydrogen, hydroxy, alkyl, cycloalkyl, —OC(O)NR$^{3b}$R$^{3c}$, —NR$^{3d}$OR$^{3a}$ and —NR$^{3d}$—NR$^{3b}$R$^{3c}$; or
  together with the carbon atom to which they are attached form C=O, C=NOR$^{3a}$, C=N—NR$^{3b}$R$^{3c}$, optionally substituted $(C_3\text{-}C_4)$cycloalkyl ring;

$R^{39}$ and $R^{310}$ are
  independently selected from the group consisting of hydrogen, alkyl, or cycloalkyl; or
  together with the carbon atom to which they are attached form an optionally substituted $(C_3\text{-}C_4)$cycloalkyl ring;

$R^{3a}$ is selected from the group consisting of hydrogen, alkyl, cycloalkyl, alkenyl, acyl, heterocyclyl, and aryl;

$R^{3b}$ and $R^{3c}$ are
  independently selected from the group consisting of hydrogen, alkyl, cycloalkyl, alkenyl, acyl, aminocarbonyl, heterocyclyl and aryl; or
  together with the nitrogen atom to which they are attached form an optionally substituted, saturated or unsaturated 3-8 membered ring optionally incorporating 1 to 3 N, O, or S atoms;

$R^{3d}$ is hydrogen or alkyl; and m is 0 or 1;

with the followings provisos:
  a. at least one of —CR$^{35}$R$^{36}$, —CR$^{37}$R$^{38}$, and —CR$^{39}$R$^{310}$ is a $(C_3\text{-}C_4)$cycloalkyl ring;
  b. no more than one of $R^{31}$, $R^{33}$ and $R^{34}$ is hydrogen;

c. if m is 0, then —$CR^{35}R^{36}$ is not C=O; and
d. if m is 1 and —$CR^{39}R^{310}$ is a ($C_3$-$C_4$)cycloalkyl ring, then $R^{30}$ is not hydrogen or aminocarbonyl;

or single stereoisomers, mixtures of stereoisomers, or pharmaceutically acceptable salts thereof.

In one embodiment of Formula III, m is 0 and $R^{32}$ is hydroxy, and in another embodiment m is 0; $R^{32}$ is hydroxy; and $R^{31}$, $R^{33}$, and $R^{34}$ are independently of each other hydrogen, halogen, or alkyl. In yet another embodiment, m is 0, $R^{32}$ is hydroxy; $R^{31}$, $R^{33}$, and $R^{34}$ are independently of each other hydrogen, halogen, or alkyl, and —$CR^{35}R^{36}$ is optionally substituted ($C_3$-$C_4$)cycloalkyl ring. In another embodiment, m is 0; $R^{32}$ is hydroxy; $R^{31}$, $R^{33}$, and $R^{34}$ are independently of each other hydrogen, halogen, or alkyl; and —$CR^{39}R^{310}$ is optionally substituted ($C_3$-$C_4$)cycloalkyl ring.

In another embodiment, m is 1 and $R^{32}$ is hydroxy and in another embodiment m is 1; $R^{32}$ is hydroxy and $R^{31}$, $R^{33}$, and $R^{34}$ are independently of each other hydrogen, halogen, or alkyl. In yet another embodiment, m is 1; $R^{32}$ is hydroxy; $R^{31}$, $R^{33}$, and $R^{34}$ are independently of each other hydrogen, halogen, or alkyl; and —$CR^{37}R^{38}$ is optionally substituted ($C_3$-$C_4$)cycloalkyl ring. In another embodiment, m is 1; $R^{32}$ is hydroxy; $R^{31}$, $R^{33}$, and $R^{34}$ are independently of each other hydrogen, halogen, or alkyl; and —$CR^{39}R^{310}$ is optionally substituted ($C_3$-$C_4$)cycloalkyl ring. In another embodiment, m is 1; $R^{32}$ is hydroxy; $R^{31}$, $R^{33}$, and $R^{34}$ are independently of each other hydrogen, halogen, or alkyl; and —$CR^{35}R^{36}$ is optionally substituted ($C_3$-$C_4$)cycloalkyl ring.

In another embodiment, m is 1, $R^{32}$ is hydroxy, $R^{31}$, $R^{33}$, and $R^{34}$ are independently of each other hydrogen, halogen, or alkyl, and $R^{35}$ and $R^{36}$ are both hydrogen.

In another embodiment, —$CR^{35}R^{36}$ is C=O; and in another embodiment, —$CR^{37}R^{38}$ is C=O.

In another embodiment $R^{30}$ is alkyl substituted with an amido, a sulfonylamino or an aminosulfonyl group and in another embodiment $R^{30}$ is —$(CH_2)_{2-6}$—$NHS(O)_2$-aryl, —$(CH_2)_{2-6}$—$S(O)_2NH$-aryl; —$(CH_2)_{2-6}NHC(O)$-aryl or —$(CH_2)_{2-6}$—$C(O)NH$-aryl; illustrated by alkylbenzenesulfonaminoethyl, or alkylbenzenesulfonaminopropyl.

In one embodiment, when any of $R^{31}$, $R^{33}$ or $R^{34}$ are alkyl, then alkyl is selected from methyl and t-butyl.

In one embodiment, when any of $R^{31}$, $R^{33}$ or $R^{34}$ are alkenyl, then alkenyl is 3,7-dimethylocta-2,6-dienyl.

In another embodiment, the invention contemplates compounds of Formula IIIA:

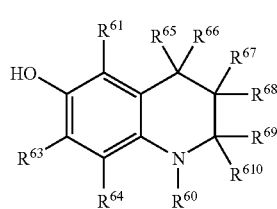

Formula IIIA $R^{60}$ is selected from the group consisting of hydrogen, alkyl, aralkyl, acyl, heterocyclyl and aryl;
$R^{61}$, $R^{63}$, and $R^{64}$ are independently selected from the group consisting of hydrogen, alkyl, halogen, alkenyl, with the proviso that alkenyl is not substituted with an aryl or heteroaryl group;
$R^{65}$ and $R^{66}$ are
    independently selected from the group consisting of hydrogen, alkyl, and hydroxy, or
    together with the carbon atom to which they are attached form C=O or optionally substituted ($C_3$-$C_4$)cycloalkyl ring;
$R^{67}$ and $R^{68}$ are
    independently selected from the group consisting of hydrogen, hydroxy, and alkyl, or
    together with the carbon atom to which they are attached form an optionally substituted ($C_3$-$C_4$)cycloalkyl ring;
$R^{69}$ and $R^{610}$ are
    independently selected from the group consisting of hydrogen, alkyl, or cycloalkyl; or
    together with the carbon atom to which they are attached form an optionally substituted ($C_3$-$C_4$)cycloalkyl ring;

with the followings provisos:
a. at least one of —$CR^{65}R^{66}$, —$CR^{67}R^{68}$ and —$CR^{69}R^{610}$ is a ($C_3$-$C_4$)cycloalkyl ring;
b. no more than one of $R^{61}$, $R^{63}$ and $R^{64}$ is hydrogen;
c. if —$CR^{69}R^{610}$ is a ($C_3$-$C_4$)cycloalkyl ring, then $R^{60}$ is not hydrogen or aminocarbonyl;

or single stereoisomers, mixtures of stereoisomers, or pharmaceutically acceptable salts thereof.

In another aspect, the invention relates to a pharmaceutical composition containing a therapeutically effective amount of a compound of Formula III or IIIA, or a pharmaceutically acceptable salt thereof admixed with at least one pharmaceutically acceptable excipient. In some examples, the pharmaceutical compositions comprise a compound of Formula III or IIIA and a pharmaceutically acceptable excipient; and the compound is selected from the illustrative compounds and stereoisomers, mixture of stereoisomers or pharmaceutically acceptable salts thereof.

It is contemplated that in embodiments where $R^2$, $R^{22}$, and $R^{32}$ are not hydroxy, alkoxy, O-alkenyl, amino or carbonylamino, then the substituent will hydrolyze in vivo to form the active hydroxy substituent. It is further contemplated that in embodiments where $R^{42}$ is not hydroxy, then $R^{42}$ will hydrolyze in vivo to form hydroxy.

In another aspect, the invention relates to a method of inhibiting a lipoxygenase, comprising contacting a cell with an effective amount of one or more compounds of Formula I:

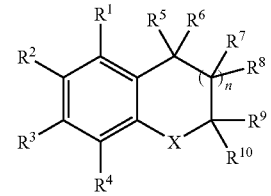

Formula I wherein,
X is O or $S(O)_{0-2}$;
$R^1$, $R^3$, and $R^4$ are independently selected from the group consisting of hydrogen, alkyl, cycloalkyl, halogen, nitro, cyano, amino, aminosulfonyl, sulfonylamino, sulfanyl, aryl, heterocyclyl, hydroxy, alkoxy, acyl, carboxy, alkoxycarbonyl, amido, alkenyl, and alkynyl, with the proviso that said alkenyl and alkynyl are not substituted with aryl or heteroaryl;
or $R^3$ and $R^4$ together with the carbon atoms attached thereto join to form a cycloalkyl, aryl, or heterocyclyl ring;
$R^2$ is selected from the group consisting of hydroxy, amino, carbonylamino, alkoxy, —O—C(O)—O-alkyl, —O-alkenyl, —O-acyl, —O-alkylene-amino, —O—C(O)-alkylene-COOR$^a$, —O—C(O)-amino, —O—C(O)-alkylene-amino, —O—C(O)—O-alkylene-amino, —O—C(O)-heterocyclyl, —O—C(O)-alkylene-heterocyclyl, —O-glucoside, —O-phosphoryl, —O-alkylene-phosphoryl, or —O—C(O)-AA, wherein AA is an amino acid or a di-, tri- or tetra-peptide;

$R^5$ and $R^6$ are independently selected from the group consisting of hydrogen, alkyl, cycloalkyl, heterocyclyl, hydroxy, alkoxy, carboxy, alkoxycarbonyl, alkylcarbonyl, amino, aminosulfonyl, sulfonylamino, sulfanyl, nitro, cyano, halogen, —OC(O)NR$^b$R$^c$, —NRC(O)R$^d$, —NROR$^a$, and —NR—NR$^b$R$^c$; or together with the carbon atom to which they are attached, form C=O; C=NOR$^a$, C=N—NR$^b$R$^c$, or an optionally substituted ($C_3$-$C_4$)cycloalkyl ring;

$R^7$ and $R^8$ are independently selected from the group consisting of hydrogen, alkyl, cycloalkyl, hydroxy, alkoxy, carboxy, alkoxycarbonyl, alkylcarbonyl, amino, aminosulfonyl, sulfonylamino, sulfanyl, nitro, cyano, halogen, aryl, heterocyclyl, —OC(O)NR$^b$R$^c$, —NRC(O)R$^d$, —NROR$^a$, and —NR—NR$^b$R$^c$; or together with the carbon atom to which they are attached, form C=O; C=NOR$^a$, C=N—NR$^b$R$^c$, or an optionally substituted ($C_3$-$C_4$)cycloalkyl ring;

$R^9$ and $R^{10}$ are independently selected from the group consisting of hydrogen, alkyl, cycloalkyl, hydroxy, alkoxy, carboxy, alkoxycarbonyl, alkylcarbonyl, amino, aminosulfonyl, sulfonylamino, sulfanyl, nitro, cyano, halogen, —OC(O)NR$^b$R$^c$, —NRC(O)R$^d$, —NROR$^a$, and —NR—NR$^b$R$^c$; or together with the carbon atom to which they are attached, form C=O; C=NOR$^a$, C=N—NR$^b$R$^c$, or an optionally substituted ($C_3$-$C_4$)cycloalkyl ring;

R is hydrogen or alkyl;

$R^a$ is selected from the group consisting of hydrogen, alkyl, cycloalkyl, alkenyl, heterocyclyl, or aryl;

$R^b$ and $R^c$ are independently selected from the group consisting of hydrogen, alkyl, cycloalkyl, alkenyl, acyl, aminocarbonyl, heterocyclyl and aryl; or together with the nitrogen atom to which they are attached form an optionally substituted, saturated or unsaturated 3-8 membered ring optionally incorporating 1 to 3 —N—, —O— or —S— atoms;

$R^d$ is selected from the group consisting of hydrogen, alkyl, cycloalkyl, alkenyl, alkoxy, heterocyclyl, and aryl;

and n is 0 or 1;

with the following provisos:

a. at least one of —CR$^5$R$^6$, —CR$^7$R$^8$, and —CR$^9$R$^{10}$ is a ($C_3$-$C_4$)cycloalkyl ring; and b. no more than one of R$^1$, R$^3$ and R$^4$ is hydrogen; or single stereoisomers, mixtures of stereoisomers, pharmaceutically acceptable salts or thereof.

In another aspect, the invention relates to a method of inhibiting a lipoxygenase, comprising contacting a cell with an effective amount of one or more compounds of Formula II:

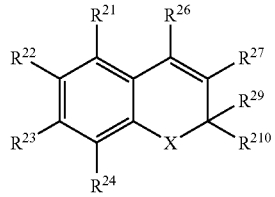

Formula II wherein,

X is O, $S(O)_{0-2}$ or $NR^{200}$;

$R^{21}$, $R^{23}$, and $R^{24}$ are independently selected from the group consisting of hydrogen, alkyl, cycloalkyl, halogen, nitro, cyano, amino, aminosulfonyl, sulfonylamino, sulfanyl, aryl, heterocyclyl, hydroxy, alkoxy, carboxy, alkoxycarbonyl, amido, alkenyl, and alkynyl, with the proviso that said alkenyl and alkynyl are not substituted with aryl or heteroaryl;

or $R^{23}$ and $R^{24}$ together with the carbon atoms attached thereto join to form a cycloalkyl, aryl, or heterocyclyl ring;

$R^{22}$ is selected from the group consisting of hydroxy, amino, carbonylamino, alkoxy, —O-alkenyl, —O-acyl, —O-alkylene-amino, —O—C(O)-alkylene-COOR$^{2a}$, —O—C(O)-amino, —O—C(O)-alkylene-amino, —O—C(O)-heterocyclyl, —O—C(O)-alkylene-heterocyclyl, —O-glucoside, —O-phosphoryl, —O-alkylene-phosphoryl and —O—C(O)-AA, wherein AA is amino acid or a di-, tri- or tetra-peptide;

$R^{26}$ and $R^{27}$ are independently selected from the group consisting of hydrogen, alkyl, cycloalkyl, hydroxy, alkoxy, carboxy, alkoxycarbonyl, alkylcarbonyl, amino, aminosulfonyl, sulfonylamino, sulfanyl, nitro, cyano, halogen, aryl, heterocyclyl, —C=N—OR$^{20}$, —OC(O)NR$^{2b}$R$^{2c}$, —OC(O)NR$^{2b}$R$^{2c}$, —NR$^2$OC(O)R$^{2d}$, —NR$^{20}$S(O)$_2$R$^{2d}$, —NR$^{20}$OR$^{2a}$, and —NR$^{20}$—NR$^{2b}$R$^{2c}$;

$R^{29}$ and $R^{210}$ together with the carbon atom to which they are attached form an optionally substituted ($C_3$-$C_4$)cycloalkyl ring;

$R^{20}$ is hydrogen or alkyl;

$R^{200}$ is selected from the group consisting of hydrogen, alkyl, aralkyl, cycloalkyl, alkenyl, alkynyl, acyl, aminocarbonyl, heterocyclyl and aryl;

$R^{2a}$ is selected from the group consisting of hydrogen, alkyl, cycloalkyl, alkenyl, heterocyclyl, and aryl;

$R^{2b}$ and $R^{2c}$ are independently selected from the group consisting of hydrogen, alkyl, cycloalkyl, alkenyl, acyl, aminocarbonyl, heterocyclyl and aryl; or together with the nitrogen atom to which they are attached form an optionally substituted, saturated or unsaturated 3-8 membered ring optionally incorporating 1 to 3 —N—, —O— or —S— atoms; and $R^{2d}$ is selected from the group consisting of hydrogen, alkyl, cycloalkyl, alkenyl, amino, alkoxy, heterocyclyl, and aryl;

or single stereoisomers, mixtures of stereoisomers, pharmaceutically acceptable salts, tautomers or prodrugs thereof.

In another aspect, the invention relates to a method of inhibiting a lipoxygenase, comprising contacting a cell with an effective amount of one or more compounds of Formula III:

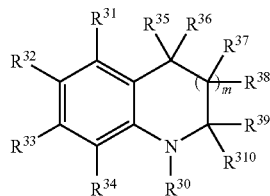

Formula III wherein, $R^{30}$ is selected from the group consisting of hydrogen, alkyl, aralkyl, cycloalkyl, alkenyl, alkynyl, acyl, aminocarbonyl, heterocyclyl and aryl;

$R^{31}$, $R^{33}$, and $R^{34}$ are independently selected from the group consisting of hydrogen, alkyl, cycloalkyl, halogen, nitro, cyano, amino, aminosulfonyl, sulfonylamino, sulfanyl, aryl, heterocyclyl, hydroxy, alkoxy, carboxy, alkoxycarbonyl, amido, alkenyl, and alkynyl, with the proviso that said alkenyl and alkynyl are not substituted with an aryl or heteroaryl group;

or $R^{33}$ and $R^{34}$ together with the carbon atoms attached thereto join to form a cycloalkyl, aryl, or heterocyclyl ring;

$R^{32}$ is selected from the group consisting of hydroxy, alkoxy, —O-alkenyl, —O-acyl, —O-glucoside; —O-phosphoryl, —O—C(O)-AA, wherein AA is amino acid, or a di-, tri- or tetra-peptide;

$R^{35}$ and $R^{36}$ are
  independently selected from the group consisting of hydrogen, alkyl, hydroxy, cycloalkyl, —OC(O)$NR^{3b}R^{3c}$, —$NR^{3d}OR^{3a}$ and —$NR^{3d}$—$NR^{3b}R^{3c}$; or
  together with the carbon atom to which they are attached form C=O, C=$NOR^{3a}$, C=N—$NR^{3b}R^{3c}$, optionally substituted ($C_3$-$C_4$)cycloalkyl ring;

$R^{37}$ and $R^{38}$ are
  independently selected from the group consisting of hydrogen, hydroxy, alkyl, cycloalkyl, —OC(O)$NR^{3b}R^{3c}$, —$NR^{3d}OR^{3a}$ and —$NR^{3d}$—$NR^{3b}R^{3c}$; or
  together with the carbon atom to which they are attached form C=O, C=$NOR^{3a}$, C=N—$NR^{3b}R^{3c}$, optionally substituted ($C_3$-$C_4$)cycloalkyl ring;

$R^{39}$ and $R^{310}$ are
  independently selected from the group consisting of hydrogen, alkyl, and cycloalkyl; or
  together with the carbon atom to which they are attached form an optionally substituted ($C_3$-$C_4$)cycloalkyl ring;

$R^{3a}$ is selected from the group consisting of hydrogen, alkyl, cycloalkyl, alkenyl, acyl, heterocyclyl, and aryl;

$R^{3b}$ and $R^{3c}$ are
  independently selected from the group consisting of hydrogen, alkyl, cycloalkyl, alkenyl, acyl, aminocarbonyl, heterocyclyl and aryl; or
  together with the nitrogen atom to which they are attached form an optionally substituted, saturated or unsaturated 3-8 membered ring optionally incorporating 1 to 3 N, O, or S atoms;

$R^{3d}$ is hydrogen or alkyl; and m is 0 or 1;

with the following provisos:
  a. at least tone of $CR^{35}R^{36}$, —$CR^{37}R^{38}$, and —$CR^{39}R^{310}$ is a ($C_3$-$C_4$)cycloalkyl ring;
  b. no more than one of $R^{31}$, $R^{33}$ and $R^{34}$ is hydrogen;
  c. if m is 0, then —$CR^{35}R^{36}$ is not C=O; and
  d. if m is 1 and —$CR^{39}R^{310}$ is a ($C_3$-$C_4$)cycloalkyl ring, then $R^{30}$ is not hydrogen or aminocarbonyl;

or single stereoisomers, mixtures of stereoisomers, or pharmaceutically acceptable salts thereof.

In another aspect, the invention relates to a method of inhibiting a lipoxygenase, comprising contacting a cell with an effective amount of one or more compounds of Formula IA, IB, IIA and/or IIIA.

In some embodiments, the compound inhibits one or more lipoxygenase enzymes selected from 5-Lipoxygenase, 15-Lipoxygenase, 12/15-Lipoxygenase enzymes and combinations thereof. In other embodiments, the compound inhibits 5-Lipoxygenase enzyme. In other embodiments, the compound inhibits both a 5-Lipoxygenase enzyme and a 15-Lipoxygenase enzyme.

In another aspect the invention relates to treating a subject with a lipoxygenase mediated condition with one or more compounds of Formula I:

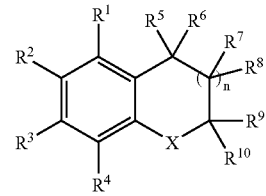

Formula I wherein,

X is O or S(O)$_{0-2}$;

$R^1$, $R^3$, and $R^4$ are independently selected from the group consisting of hydrogen, alkyl, cycloalkyl, halogen, nitro, cyano, amino, aminosulfonyl, sulfonylamino, sulfanyl, aryl, heterocyclyl, hydroxy, alkoxy, acyl, carboxy, alkoxycarbonyl, amido, alkenyl, and alkynyl, with the proviso that said alkenyl and alkynyl are not substituted with aryl or heteroaryl;

or $R^3$ and $R^4$ together with the carbon atoms attached thereto join to form a cycloalkyl, aryl, or heterocyclyl ring;

$R^2$ is selected from the group consisting of hydroxy, amino, carbonylamino, alkoxy, —O—C(O)—O-alkyl, —O-alkenyl, —O-acyl, —O-alkylene-amino, —O—C(O)-alkylene-COOR$^a$, —O—C(O)-amino, —O—C(O)-alkylene-amino, —O—C(O)—O-alkylene-amino, —O—C(O)-heterocyclyl, —O—C(O)-alkylene-heterocyclyl, —O-glucoside, —O-phosphoryl, —O-alkylene-phosphoryl, or —O—C(O)-AA, wherein AA is amino acid or a di-, tri- or tetra-peptide;

$R^5$ and $R^6$ are
  independently selected from the group consisting of hydrogen, alkyl, cycloalkyl, heterocyclyl, hydroxy, alkoxy, carboxy, alkoxycarbonyl, alkylcarbonyl, amino, aminosulfonyl, sulfonylamino, sulfanyl, nitro, cyano, halogen, —OC(O)NR$^b$R$^c$, —NRC(O)R$^d$, —NROR$^a$, and —NR—R$^b$R$^c$; or
  together with the carbon atom to which they are attached, form C=O; C=NOR$^a$, C=N—NR$^b$R$^c$, or an optionally substituted ($C_3$-$C_4$)cycloalkyl ring;

$R^7$ and $R^8$ are
  independently selected from the group consisting of hydrogen, alkyl, cycloalkyl, hydroxy, alkoxy, carboxy, alkoxycarbonyl, alkylcarbonyl, amino, aminosulfonyl, sulfonylamino, sulfanyl, nitro, cyano, halogen, aryl, heterocyclyl, —OC(O)NR$^b$R$^c$, —NRC(O)R$^d$, —NROR$^a$, and —NR—NR$^b$R$^c$; or together with the carbon atom to which they are attached, form C═O; C═NOR$^a$, C═N—NR$^b$R$^c$, or an optionally substituted (C$_3$-C$_4$)cycloalkyl ring;

R$^9$ and R$^{10}$ are independently selected from the group consisting of hydrogen, alkyl, cycloalkyl, hydroxy, alkoxy, carboxy, alkoxycarbonyl, alkylcarbonyl, amino, aminosulfonyl, sulfonylamino, sulfanyl, nitro, cyano, halogen, —OC(O)NR$^b$R$^c$, —NRC(O)Rd, —NROR$^a$, and —NR—NR$^b$R$^c$; or together with the carbon atom to which they are attached, form C═O; C═NOR$^a$, C═N—NR$^b$R$^c$, or an optionally substituted (C$_3$-C$_4$)cycloalkyl ring;

R is hydrogen or alkyl;

R$^a$ is selected from the group consisting of hydrogen, alkyl, cycloalkyl, alkenyl, heterocyclyl, or aryl;

R$^b$ and R$^c$ are independently selected from the group consisting of hydrogen, alkyl, cycloalkyl, alkenyl, acyl, aminocarbonyl, heterocyclyl and aryl; or together with the nitrogen atom to which they are attached form an optionally substituted, saturated or unsaturated 3-8 membered ring optionally incorporating 1 to 3 —N—, —O— or —S— atoms;

R$^d$ is selected from the group consisting of hydrogen, alkyl, cycloalkyl, alkenyl, alkoxy, heterocyclyl, and aryl;

and n is 0 or 1;

with the following provisos:
  a. at least one of —CR$^5$R$^6$, —CR$^7$R$^8$, and -CR$^9$R1$^0$ is a (C$_3$-C$_4$)cycloalkyl ring; and
  b. no more than one of R$^1$, R$^3$ and R$^4$ is hydrogen; or single stereoisomers, mixtures of stereoisomers, pharmaceutically acceptable salts or thereof.

In another aspect the invention relates to treating a subject with a lipoxygenase mediated condition with one or more compounds of Formula II:

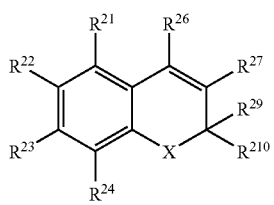

Formula II wherein,

X is O, S(O)$_{0-2}$, or NR$^{200}$;

R$^{21}$, R$^{23}$, and R$^{24}$ are independently selected from the group consisting of hydrogen, alkyl, cycloalkyl, halogen, nitro, cyano, amino, aminosulfonyl, sulfonylamino, sulfanyl, aryl, heterocyclyl, hydroxy, alkoxy, carboxy, alkoxycarbonyl, amido, alkenyl, and alkynyl, with the proviso that said alkenyl and alkynyl are not substituted with aryl or heteroaryl;

or R$^{23}$ and R$^{24}$ together with the carbon atoms attached thereto join to form a cycloalkyl, aryl, or heterocyclyl ring;

R$^{22}$ is selected from the group consisting of hydroxy, amino, carbonylamino, alkoxy, —O-alkenyl, —O-acyl, —O-alkylene-amino, —O—C(O)-alkylene-COOR$^{2a}$, —O—C(O)-amino, —O—C(O)-alkylene-amino, —O—C(O)-heterocyclyl, —O—C(O)-alkylene-heterocyclyl, —O-glucoside, —O-phosphoryl, —O-alkylene-phosphoryl and —O—C(O)-AA, wherein AA is an amino acid or a di-, tri- or tetra-peptide;

R$^{26}$ and R$^{27}$ are independently selected from the group consisting of hydrogen, alkyl, cycloalkyl, hydroxy, alkoxy, carboxy, alkoxycarbonyl, alkylcarbonyl, amino, aminosulfonyl, sulfonylamino, sulfanyl, nitro, cyano, halogen, aryl, heterocyclyl, —C═N—OR$^{20}$, —OC(O)NR$^{2b}$R$^{2c}$, —NR$^{20}$C(O)R$^{2d}$, —NR$^{20}$S(O)$_2$R$^{2d}$, —NR$^{20}$OR$^{2a}$, and —NR$^{20}$—NR$^{2b}$R$^{2c}$;

R$^{29}$ and R$^{210}$ together with the carbon atom to which they are attached form an optionally substituted (C$_3$-C$_4$)cycloalkyl ring;

R$^{20}$ is hydrogen or alkyl;

R$^{200}$ is selected from the group consisting of hydrogen, alkyl, aralkyl, cycloalkyl, alkenyl, alkynyl, acyl, aminocarbonyl, heterocyclyl and aryl;

R$^{2a}$ is selected from the group consisting of hydrogen, alkyl, cycloalkyl, alkenyl, heterocyclyl, and aryl;

R$^{2b}$ and R$^{2c}$ are independently selected from the group consisting of hydrogen, alkyl, cycloalkyl, alkenyl, acyl, aminocarbonyl, heterocyclyl and aryl; or together with the nitrogen atom to which they are attached form an optionally substituted, saturated or unsaturated 3-8 membered ring optionally incorporating 1 to 3 —N—, —O— or —S— atoms; and R$^{2d}$ is selected from the group consisting of hydrogen, alkyl, cycloalkyl, alkenyl, amino, alkoxy, heterocyclyl, and aryl;

or single stereoisomers, mixtures of stereoisomers, pharmaceutically acceptable salts, or prodrugs thereof.

In another aspect the invention relates to treating a subject with a lipoxygenase mediated condition with one or more compounds of Formula III:

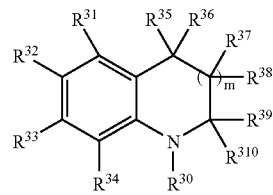

Formula III wherein,

R$^{30}$ is selected from the group consisting of hydrogen, alkyl, aralkyl, cycloalkyl, alkenyl, alkynyl, acyl, aminocarbonyl, heterocyclyl and aryl;

R$^{31}$, R$^{33}$, and R$^{34}$ are independently selected from the group consisting of hydrogen, alkyl, cycloalkyl, halogen, nitro, cyano, amino, aminosulfonyl, sulfonylamino, sulfanyl, aryl, heterocyclyl, hydroxy, alkoxy, carboxy, alkoxycarbonyl, amido, alkenyl, and alkynyl, with the proviso that said alkenyl and alkynyl are not substituted with an aryl or heteroaryl group;

or R$^{33}$ and R$^{34}$ together with the carbon atoms attached thereto join to form a cycloalkyl, aryl, or heterocyclyl ring;

R$^{32}$ is selected from the group consisting of hydroxy, alkoxy, —O-alkenyl, —O-acyl, —O-glucoside; —O-phosphoryl, —O—C(O)-AA, wherein AA is amino acid, or a di-, tri- or tetra-peptide;

$R^{35}$ and $R^{36}$ are
- independently selected from the group consisting of hydrogen, alkyl, hydroxy, cycloalkyl, —OC(O)NR$^{3b}$R$^{3c}$, —NR$^{3d}$OR$^{3a}$ and —NR$^{3d}$—NR$^{3b}$R$^{3c}$; or
- together with the carbon atom to which they are attached form C=O, C=NOR$^{3a}$, C=N—NR$^{3b}$R$^{3c}$, optionally substituted (C$_3$-C$_4$)cycloalkyl ring;

$R^{37}$ and $R^{38}$ are
- independently selected from the group consisting of hydrogen, hydroxy, alkyl, cycloalkyl, —OC(O)NR$^{3b}$R$^{3c}$, —NR$^{3d}$OR$^{3a}$ and —NR$^{3d}$—NR$^{3b}$R$^{3c}$; or
- together with the carbon atom to which they are attached form C=O, C=NOR$^{3a}$, C=N—NR$^{3b}$R$^{3c}$, optionally substituted (C$_3$-C$_4$)cycloalkyl ring;

$R^{39}$ and $R^{310}$ are
- independently selected from the group consisting of hydrogen, alkyl, and cycloalkyl; or
- together with the carbon atom to which they are attached form an optionally substituted (C$_3$-C$_4$)cycloalkyl ring;

$R^{3a}$ is selected from the group consisting of hydrogen, alkyl, cycloalkyl, alkenyl, acyl, heterocyclyl, and aryl;

$R^{3b}$ and $R^{3c}$ are
- independently selected from the group consisting of hydrogen, alkyl, cycloalkyl, alkenyl, acyl, aminocarbonyl, heterocyclyl and aryl; or
- together with the nitrogen atom to which they are attached form an optionally substituted, saturated or unsaturated 3-8 membered ring optionally incorporating 1 to 3 N, O, or S atoms;

$R^{3d}$ is hydrogen or alkyl; and m is 0 or 1;

with the following provisos:
a. at least one of —CR$^{35}$R$^{36}$, —CR$^{37}$R$^{38}$, and —CR$^{39}$R$^{310}$ is a (C$_3$-C$_4$)cycloalkyl ring;
b. no more than one of R$^{31}$, R$^{33}$ and R$^{34}$ is hydrogen;
c. if m is 0, then —CR$^{35}$R$^{36}$ is not C=O; and
d. if m is 1 and —CR$^{39}$R$^{310}$ is a (C$_3$-C$_4$)cycloalkyl ring, then R$^{30}$ is not hydrogen or aminocarbonyl;

or single stereoisomers, mixtures of stereoisomers, or pharmaceutically acceptable salts thereof.

In another aspect the invention relates to treating a subject with a lipoxygenase mediated condition with one or more compounds of Formula IA, IB, IIA and/or IIIA.

In some embodiments, the invention relates to a method of treating a subject with a lipoxygenase mediated disorder such as but not limited to apoptosis in cancer cells including prostatic cancer, gastric cancer, breast cancer, pancreatic cancer, colorectal or esophageal cancer and airways carcinoma; diseases involving hypoxia or anoxia including atherosclerosis, myocardial infarction, cardiovascular disease, heart failure (including chronic and congestive heart failure), cerebral ischemia, retinal ischemia, myocardial ischemia, post surgical cognitive dysfunction and other ischemias; diseases involving inflammation, including diabetes, arterial inflammation, inflammatory bowel disease, Crohn's disease, renal disease, pre-menstrual syndrome, asthma, allergic rhinitis, gout, cardiopulmonary inflammation, rheumatoid arthritis, osteoarthritis, muscle fatigue and inflammatory disorders of the skin including acne, dermatitis and psoriasis; disorders of the airways including asthma, chronic bronchitis, human airway carcinomas, mucus hypersecretion, chronic obstructive pulmonary disease (COPD) pulmonary fibrosis caused by chemotherapy or other drugs, idiopathic pulmonary fibrosis, cystic fibrosis and adult respiratory distress syndrome; diseases involving central nervous system (CNS) disorders including psychiatric disorders including anxiety and depression; neurodegeneration and neuroinflammation including Alzheimer's, dementia and Parkinson's disease; peripheral neuropathy including spinal chord injury, head injury and surgical trauma, and allograft tissue and organ transplant rejection; diseases involving the autoimmune system including psoriasis, eczema, rheumatoid arthritis, and diabetes; and disorders involving bone loss or bone formation. In an illustrative example, the invention relates to a method of treating a subject with a lipoxygenase mediated disorder, such as but not limited to diabetes, arthritis, rheumatoid arthritis, chronic obstructive pulmonary disease (COPD), asthma, allergic rhinitis, Crohn's disease, and/or atherosclerosis.

In some of the embodiments, the compositions, methods of treatment and uses in the manufacture of pharmaceutical compositions therefor, relate to compounds selected from:

5,7,8-trimethyl-3,4-dihydrospiro[chromene-2,1'-cyclobutan]-6-ol;

5-chloro-7,8-dimethyl-3,4-dihydrospiro[chromene-2,1'-cyclobutan]-6-ol;

5',7',8'-trimethyl-2',3'-dihydrospiro[cyclobutane, 1,4'-thiochromen]-6'-ol;

7-chloro-5,8-dimethyl-3,4-dihydrospiro[chromene-2,1'-cyclobutan]-6-ol;

5,7,8-trimethyl-3,4-dihydrospiro[chromene-2,1'-cyclopropan]-6-ol;

5',7',8'-trimethyl-2',3'-dihydrospiro[cyclobutane-1,4'-thiochromen]-6'-ol 1'-oxide;

5',7',8'-trimethyl-2',3'-dihydrospiro[cyclobutane-1,4'-thiochromen]-6'-ol 1',1'-dioxide;

5-chloro-8-methyl-3,4-dihydrospiro[chromene-2,1'-cyclobutan]-6-ol;

5,8-dimethyl-7-(3-methylbutyl)-3,4-dihydrospiro[chromene-2,1'-cyclobutan]-6-ol;

5',7',8'-trimethyl-2',3'-dihydrospiro[cyclobutane-1,4'-thiochromen]-6'-yl (dimethylamino)acetate;

2',2',5',7',8'-pentamethyl-2',3'-dihydrospiro[cyclobutane-1,4'-thiochromen]-6'-ol;

5,7-dimethyl-3,4-dihydrospiro[chromene-2,1'-cyclobutan]-6-ol;

8-chloro-5,7-dimethyl-3,4-dihydrospiro[chromene-2,1'-cyclobutan]-6-ol;

8-chloro-5-methyl-3,4-dihydrospiro[chromene-2,1'-cyclobutan]-6-ol;

8-isopropyl-5-methyl-3,4-dihydrospiro[chromene-2,1'-cyclobutan]-6-ol;

6-hydroxy-7,8-dimethylspiro[chroman-2,1'-cyclopropan]-4(3H)one;

7,8-dimethyl-3,4-dihydrospiro[chromene-2,1'-cyclopropane]-4,6-diol;

7-chloro-5,8-dimethyl-3,4-dihydrospiro[chromene-2,1'-cyclobutan]-6-yl (dimethylamino)acetate;

5-isopropyl-8-methyl-3,4-dihydrospiro[chromene-2,1'-cyclobutan]-6-ol;

7,8-dimethylspiro[chroman-3,1'-cyclopropan]-6-ol;

6-hydroxy-7,8-dimethylspiro[chroman-3,1'-cyclopropan]-4-one O-methyl oxime;

6'-hydroxy-5',7',8'-trimethylspiro[cyclobutane-1,2'-thiochromen]-4'(3'H)-one;

5',7',8'-trimethyl-3',4'-dihydrospiro[cyclobutane-1,2'-thiochromen]'-ol;

6-hydroxy-5,7,8-trimethylspiro[chroman-3,1'-cyclobutan]-4-one;

5,7,8-trimethylspiro[chroman-3,1'-cyclobutane]-4,6-diol;

6'-hydroxy-5',7',8'-trimethylspiro[cyclobutane-1,2'-thiochroman]-4'(3'H)-one O-methyloxime;

4'(methoxyamino)-5',7',8'-trimethyl-3',4'-dihydrospiro[cyclobutane-1,2'-thiochromen]-6'-ol;
7-chloro-5,8-dimethyl-3,4-dihydrospiro[chromene-2,1'-cyclobutan]-6-yl nicotinate;
5,7,8-trimethylspiro[chroman-3,1'-cyclobutan]-6-ol;
4-methoxy-5,7,8-trimethylspiro[chroman-3,1'-cyclobutan]-6-ol;
5',7',8'-trimethyl-3',4'-dihydrospiro[cyclobutane-1,2'-thiochromen]-6'-yl (dimethylamino)acetate;
5,7,8-trimethyl-3,4-dihydrospiro[chromene-2,1'-cyclobutan]-6-yl (dimethylamino)acetate;
6-hydroxy-5,7,8-trimethylthiochroman-4-yl phenylcarbamate;
5,7,8-trimethyl-3,4-dihydrospiro[chromene-2,1'-cyclobutan]-6-yl-2-(4-methylpiperazin-1-yl)acetate;
7,8-dimethyl-3,4-dihydrospiro[chromene-2,1'-cyclobutan]-6-yl phenylcarbamate;
5,7,8-trimethyl-3,4-dihydrospiro[chromene-2,1'-cyclobutan]-6-yl phenyl(phenylcarbamoyl)carbamate;
4-ethoxy-5,7,8-trimethylspiro[chroman-3,1'-cyclobutan]-6-ol;
2-(7-chloro-5,8-dimethylspiro[chroman-2,1'-cyclobutane]-6-yloxy)-N,N-dimethylethanamine;
4-(methoxyamino)-5,7,8-trimethyl-3,4-dihydrospiro[chromene-2,1'-cyclobutan]-6-yl acetate;
4-(methoxyamino)-5,7,8-trimethyl-3,4-dihydrospiro[chromene-2,1'-cyclobutan]-6-ol;
2-(dimethylamino)ethyl 5,7,8-trimethylspiro[chroman-2,1'-cyclobutane]-6-yl carbonate;
5,7,8-trimethyl-3,4-dihydrospiro[chromene-2,1'-cyclobutan]-6-yl 1H-imidazole-1-carboxylate;
2-(7-chloro-5,8-dimethylspiro[chroman-2,1'-cyclobutane]-6-yloxy)-N,N-dimethylpropan-1-amine;
4-amino-5,7,8-trimethyl-3,4-dihydrospiro[chromene-2,1'-cyclobutan]-6-yl acetate;
4-(hexylamino)-5,7,8-trimethylspiro[chroman-3,1'-cyclobutan]-6-ol;
1-(dimethylamino)-3-[(5,7,8-trimethyl-3,4-dihydro-2H-spiro-[chromen-2,1'-cyclobutan]-6-yl)oxy]propan-2-ol;
1-(pyrrolindinyl)-3-[(5,7,8-trimethyl-3,4-dihydro-2H-spiro-[chromen-2,1'-cyclobutan]-6-yl)oxy]propan-2-ol;
5,7,8-trimethyl-4-pyrrolidin-1-yl-3,4-dihydrospiro[chromene-2,1'-cyclobutan]-6-ol;
4-(aminomethyl)-5,7,8-trimethyl-3,4-dihydrospiro[chromene-2,1'-cyclobutane]-4,6-diol;
5,7,8-trimethyl-4-morpholin-4-yl-3,4-dihydrospiro[chromene-2,1'-cyclobutan]-6-ol;
4-(1H-imidazol-1-yl)-5,7,8-trimethyl-3,4-dihydrospiro[chromene-2,1'-cyclobutan]-6-ol;
5,7,8-trimethyl-3,4-dihydrospiro[chromene-2,1'-cyclobutane]-3,6-diol;
4-(cyclopropylamino)-5,7,8-trimethylspiro[chroman-3,1'-cyclobutan]-6-ol;
5,7,8-trimethylspiro[chroman-3,1'-cyclobutane]-6-yl 2-(dimethylamino)acetate;
3-methoxy-5,7,8-trimethyl-3,4-dihydrospiro[chromene-2,1'-cyclobutan]-6-ol;
4-(aminomethyl)-5,7,8-trimethyl-3,4-dihydrospiro[chromene-2,1'-cyclobutan]-6-ol;
N-[(6-hydroxy-5,7,8-trimethyl-3,4-dihydrospiro[chromene-2,1'-cyclobutan]-4-yl)methyl]acetamide;
4-[(ethylamino)methyl]-5,7,8-trimethyl-3,4-dihydrospiro[chromene-2,1'-cyclobutan]-6-ol;
3-(hydroxymethyl)-5,7,8-trimethyl-3,4-dihydrospiro[chromene-2,1'-cyclobutan]-6-ol;
2{[(5,7,8-trimethyl-3,4-dihydrospiro[chromene-2,1'-cyclobutan]-6-yl)oxy]methyl}pyridine;
2{[(5,7,8-trimethyl-3,4-dihydrospiro[chromene-2,1'-cyclobutan]-6-yl)oxy]methyl}quinoline;
6-hydroxy-3,5,7,8-tetramethylspiro[chroman-2,1'-cyclobutan]-4(3H)-one;
3-(morpholinomethyl)-5,7,8-trimethyl-4-oxo-3,4-dihydrospiro[chromene-2,1'-cyclobutan]-6-yl acetate;
3-(morpholinomethyl)-5,7,8-trimethyl-3,4-dihydrospiro[chromene-2,1'-cyclobutane]-4,6-diol;
4-[(diethylamino)methyl]-5,7,8-trimethyl-3,4-dihydrospiro[chromene-2,1'-cyclobutan]-6-ol;
4-methoxy-3,5,7,8-tetramethyl-3,4-dihydrospiro[chromene-2,1'-cyclobutan]-6-ol;
3,5,7,8-tetramethyl-3,4-dihydrospiro[chromene-2,1'-cyclobutane]-4,6-diol;
4-methoxy-3,5,7,8-tetramethyl-3,4-dihydrospiro[chromene-2,1'-cyclobutan]-6-ol;
6-hydroxy-5,7,8-trimethyl-3,4-dihydrospiro[chromene-2,1'-cyclobutane]-4-carbonitrile;
methyl {[(6-hydroxy-5,7,8-trimethyl-3,4-dihydrospiro[chromene-2,1'-cyclobutan]-3-yl)methyl]thio}acetate;
4-ethoxy-5,7,8-trimethyl-3,4-dihydrospiro[chromene-2,1'-cyclobutan]-6-ol;
7,8-dimethyl-3,4-dihydrospiro[chromene-2,1'-cyclobutan]-6-ol;
7,8-dimethylspiro[chroman-3,1'-cyclobutan]-6-ol;
4-methoxy-5,7-dimethyl-3,4-dihydrospiro[chromene-2,1'-cyclobutan]-6-ol;
4-ethoxy-5,7-dimethyl-3,4-dihydrospiro[chromene-2,1'-cyclobutan]-6-ol;
4-(methoxyamino)-5,7-dimethyl-3,4-dihydrospiro[chromene-2,1'-cyclobutan]-6-ol;
4-isopropoxy-5,7-dimethyl-3,4-dihydrospiro[chromene-2,1'-cyclobutan]-6-ol;
5,7-dimethylspiro[chroman-3,1'-cyclobutan]-6-ol;
5,7-dimethyl-4H-spiro[chromene-3,1'-cyclobutane]-4,6-diol;
5,7,8-trimethyl-3,4-dihydrospiro[chromene-2,1'-cyclobutane]-4,6-diol;
5,7-dimethyl-3,4-dihydrospiro[chromene-2,1'-cyclobutane]-4,6-diol;
7,8-dimethyl-4H-spiro[chromene-3,1'-cyclobutane]-4,6-diol;
4-(methoxyamino)-7,8-dimethyl-4H-spiro[chromene-3,1'-cyclobutan]-6-ol;
4-(ethoxyamino)-7,8-dimethyl-4H-spiro[chroman-3,1'-cyclobutan]-6-ol;
8-(hydroxymethyl)-5,7-dimethyl-3,4-dihydrospiro[chromene-2,1'-cyclobutan]-6-ol;
8-(methoxymethyl)-5,7-dimethyl-3,4-dihydrospiro[chromene-2,1'-cyclobutan]-6-ol;
4-(cyclopentyloxy)-5,7,8-trimethyl-3,4-dihydrospiro[chromene-2,1'-cyclobutane]-6-diol;
4-(ethoxyamino)-5,7,8-trimethyl-3,4-dihydrospiro[chromene-2,1'-cyclobutan]-6-ol;
4-(isopropylthio)-5,7,8-trimethyl-3,4-dihydrospiro[chromene-2,1'-cyclobutan]-6-ol;
7,8-dimethyl-3,4-dihydrospiro[chromene-2,1'-cyclobutane]-4,6-diol;
7,8-dimethyl-3,4-dihydrospiro[chromene-2,1'-cyclobutan]-6-yl (dimethylamino)acetate;
4-(methoxyamino)-7,8-dimethyl-3,4-dihydrospiro[chromene-2,1'-cyclobutan]-6-ol;
4'-(ethoxyamino)-5',7',8'-trimethyl-3',4'-dihydrospiro[cyclobutane-1,2'-thiochromen]-6'-ol;

4'-(ethoxyamino)-5',7'-dimethyl-3',4'-dihydrospiro[cyclobutane-1,2'-thiochromen]'-ol;
4-(ethoxyamino)-5,7-dimethyl-3,4-d ihydrospiro[chromene-2,1'-cyclobutan]-6-ol;
5-[1-(ethoxyamino)ethyl]-7,8-dimethyl-3,4-dihydrospiro[chromene-2,1'-cyclobutan]-6-ol;
4-(methoxyamino)-5,7-dimethyl-3,4-dihydrospiro[chromene-2,1'-cyclobutan]-6-yl acetate;
4'-(methoxyamino)-5',7'-dimethyl-3',4'-dihydrospiro[cyclobutane-1,2'-thiochromen]-6'-ol;
4-(ethoxyamino)-7,8-dimethyl-3,4-dihydrospiro[chromene-2,1'-cyclobutan]-6-ol;
4-[methoxy(methyl)amino]-5,7,8-trimethyl-3,4-dihydrospiro[chromene-2,1'-cyclobutan]-6-ol;
6-hydroxy-5,7,8-trimethylspiro[chromene-2,1'-cyclobutan]-4(3H)-one oxime;
4-(hydroxyamino)-5,7,8-trimethyl-3,4-dihydrospiro[chromene-2,1'-cyclobutan]-6-ol;
8-[(methoxyamino)methyl]-5,7-dimethyl-3,4-dihydrospiro[chromene-2,1'-cyclobutan]-6-ol;
5,7-dimethyl-8-vinyl-3,4-dihydrospiro[chromene-2,1'-cyclobutan]-6-ol;
4-[hydroxy(methyl)amino]-5,7,8-trimethyl-3,4-dihydrospiro[chromene-2,1'-cyclobutan]-6-ol;
6-hydroxy-5,7-dimethylspiro[chromene-2,1'-cyclobutan]-4(3H)-one oxime;
4-( hydroxyamino)-5,7-dimethyl-3,4-dihydrospiro[chromene-2,1'-cyclobutan]-6-ol;
4-[hydroxy(methyl)amino]-5,7-dimethyl-3,4-dihydrospiro[chromene-2,1 '-cyclobutan]-6-ol;
8-[(ethoxyamino)methyl]-5,7-dimethyl-3,4-dihydrospiro[chromene-2,1'-cyclobutan]-6-ol;
4-[methoxy(methyl)amino]-5,7-dimethyl-3,4-dihydrospiro[chromene-2,1'-cyclobutan]-6-ol;
4-[ethyl(methoxy)amino]-5,7-dimethyl-3,4-dihydrospiro[chromene-2,1'-cyclobutan]-6-ol;
5,7-dimethyl-4-methoxyamino-3,4-dihydrospiro[chromene-2,1'-cyclobutan]-6-yl (dimethylamino)acetate;
ethyl 4-(methoxyamino)-5,7-dimethyl-3,4-dihydrospiro[chromene-2,1'-cyclobutan]-6-yl carbonate;
6-hydroxy-5,7-dimethylspiro[chromene-2,1'-cyclobutan]-4(3H)-one O-methyloxime
(4E)-6-hydroxy-5,7-dimethylspiro[chromene-2,1'-cyclobutan]-4(3H)-one O-ethyloxime;
(4Z)-6-hydroxy-5,7-dimethylspiro[chromene-2,1'-cyclobutan]-4(3H)-one O-ethyloxime;
5-ethyl-4-(methoxyamino)-7,8-dimethyl-3,4-dihydrospiro[chromene-2,1'-cyclobutan]-6-ol;
4-(ethoxyamino)-5-ethyl-7,8-dimethyl-3,4-dihydrospiro[chromene-2,1'-cyclobutan]-6-ol;
5-ethyl-6-hydroxy-7,8-dimethylspiro[chromene-2,1'-cyclobutan]-4(3H)-one O-methyloxime;
5-ethyl-6-hydroxy-7,8-dimethylspiro[chromene-2,1'-cyclobutan]-4(3H)-one O-ethyloxime;
6'-hydroxy-5',7',8'-trimethylspiro[cyclobutane-1,2'-thiochromen]-4'(3'H)-one O-methyloxime;
6'-hydroxy-5',7',8'-trimethylspiro[cyclobutane-1,2'-thiochromen]-4'(3'H)-one O-ethyloxime;
6'-hydroxy-5',7'-dimethylspiro[cyclobutane-1,2'-thiochromen]-4'(3'H)-one O-methyloxime;
3-[(methoxyamino)methyl]-5,7-dimethylspiro[chromene-2,1'-cyclobutan]-6-yl pivalate;
methyl 3-(6-hydroxy-5,7-dimethyl-3,4-dihydrospiro[chromene-2,1'-cyclobutan]-8-yl)4,5-dihydroisoxazole-5-carboxylate;
6'-hydroxy-5',7'-dimethylspiro[cyclobutane-1,2'-thiochromen]-4'(3'H)-one O-ethyloxime;
5,7-diethyl-6-hydroxyspiro[chromnene-2,1'-cyclobutan]-4(3H)-one O-methyloxime;
5,7-diethyl-6-hydroxyspiro[chromene-2,1'-cyclobutan]-4(3H)-one O-ethyloxime;
5,7-diethyl-6-hydroxyspiro[chromene-2,1'-cyclobutan]-4(3H)-one oxime;
(4S)-4-(methoxyamino)-5,7-dimethyl-3,4-dihydrospiro[chromene-2,1'-cyclobutan]-6-ol;
(4R)-4-(methoxyamino)-5,7-dimethyl-3,4-dihydrospiro[chromene-2,1'-cyclobutan]-6-ol;
5,7-dimethyl-8-(5-butyl-isoxazol-3-yl)-3,4-dihydrospiro[chromene-2,1'-cyclobutan]-6-ol;
4-(ethoxyamino)-5,7-diethyl-3,4-dihydrospiro[chromene-2,1'-cyclobutan]-6-ol;
4-(methoxyamino)-5,7-diethyl-3,4-dihydrospiro[chromene-2,1'-cyclobutan]-6-ol;
N-(6-hydroxy-5,7-dimethyl-3,4-dihydrospiro[chromene-2,1'-cyclobutan]-4-yl)methanesulfonamide;
7-tert-butyl-5-methyl-3,4-dihydrospiro[chromene-2,1'-cyclobutan]-6-ol;
5,7-dimethyl-8-(1,3-oxazol-5-yl)-3,4-dihydrospiro[chromene-2,1'-cyclobutan]-6-ol;
N-(6-hydroxy-5,7-dimethyl-3,4-dihydrospiro[chromene-2,1'-cyclobutan]-4-yl)benzenesulfonamide;
5,7-diisopropyl-3,4-dihydrospiro[chromene-2,1'-cyclobutan]-6-ol;
6-hydroxy-5,7-diisopropyl-3,4-dihydrospiro[chromene-2,1'-cyclobutane]-8-carbaldehyde;
4-(methoxyamino)-5,7-dimethyl-3,4-dihydrospiro[chromene-2,1'-cyclobutan]-6-yl isobutyrate;
3-[(ethoxyamino)methyl]-5,7-dimethyl-3,4-dihydrospiro-[chromene-2,1'-cyclobutan]-6-ol;
3-[(methoxyamino)methyl]-5,7-dimethyl-3,4-dihydrospiro-[chromene-2,1'-cyclobutan]-6-ol;
7,8-dimethyl-5-(2-quinolin-2-ylethyl)) 3,4-dihydrospiro-[chromene-2,1'-cyclobutan]-6-ol;
5,7-diisopropyl-8-[(methoxyamino)methyl] 3,4-dihydrospiro[chromene-2,1'-cyclobutan]-6-ol;
5-(3,7-dimethylocta-2,6-dienyl)-7,8-dimethylspiro[chroman-2,1'-cyclobutan]-6-ol;
5,7-diethyl-3,4-dihydrospiro[chromene-2,1'-cyclobutan]-6-ol;
7-isopropyl-4-(methoxyamino)-5-methyl-3,4-dihydrospiro[chromene-2,1'-cyclobutan]-6-ol;
7-(3,7-dimethylocta-2,6-dienyl)-5,8-dimethylspiro[chroman-2,1'-cyclobutan]-6-ol;
8-(4,5-dimethyl-1H-imidazol-2-yl)-5,7-diethyl-3,4-dihydrospiro[chromene-2,1'-cyclobutan]-6-ol;
7-(4,5-dimethyl-1H-imidazol-2-yl)-5,8-dimethyl-3,4-dihydrospiro[chromene-2,1'-cyclobutan]-6-ol;
7-ethyl-4-(methoxyamino)-5-methyl-3,4-dihydrospiro[chromene-2,1'-cyclobutan]-6-ol;
5-ethyl-4-(methoxyamino)-7-methyl-3,4-dihydrospiro[chromene-2,1'-cyclobutan]-6-ol;
(Z)-5,7-diethyl-8-(hydroxymethyl)-3,4-dihydrospiro[chromene-2,1'-cyclobutan]-6-ol;
5,7-diethyl-8-(hydroxymethyl)-3,4-dihydrospiro[chromene-2,1'-cyclobutan]-6-ol;
7-isopropyl-5-methyl-3,4-dihydrospiro[chromene-2,1'-cyclobutan]-6-ol;
7-(1-benzofuran-2-yl)-2,2,5,8-tetramethylchroman-6-ol;
7-(3,7-dimethyloctyl)-5,8-dimethylspiro[chroman-2,1'-cyclobutan]-6-ol;
8-(hydroxymethyl)-7-isopropyl-5-methylspiro[chroman-2,1'-cyclobutan]-6-ol;

5,7-dimethyl-3-(oxazol-5-yl)spiro[chroman-2,1'-cyclobutan]-6-ol;
7-isopropyl-5-methylspiro[chroman-2,1'-cyclobutane]-4,6-diol;
7-isopropyl-4-methoxy-5-methylspiro[chroman-2,1'-cyclobutan]-6-ol;
7-(5,6-dimethyl-1H-benzo[d]imidazol-2-yl)-5,8-dimethylspiro[chroman-2,1'-cyclobutan]-6-ol;
7-tert-butyl-5-(morpholinomethyl)spiro[chroman-2,1'-cyclobutan]-6-ol;
8-(hydroxymethyl)-5,7-diisopropylspiro[chroman-2,1'-cyclobutan]-6-ol;
8-((hydroxyamino)methyl)-5,7-diisopropylspiro[chroman-2,1'-cyclobutan]-ol;
5,8-dimethyl-7-(2-(quinolin-2-yl)ethyl)spiro[chroman-2,1'-cyclobutan]-4-ol;
N-((6-hydroxy-5,7-diisopropylspiro[chroman-2,1'-cyclobutane]-8-yl)methyl)-N-methylacetamide;
5,7-diisopropyl-8-(methoxymethyl)spiro[chroman-2,1'-cyclobutan]-6-ol;
5,7-diethyl-3-(hydroxymethyl)spiro[chroman-2,1'-cyclobutan]-6-ol;
8-(acetamidomethyl)-5,7-diisopropylspiro[chroman-2,1'-cyclobutan]-6-ol;
methyl 2-((5,7-diethyl-6-hydroxyspiro[chroman-2,1'-cyclobutane]-3-yl)methylthio)acetate;
(5,7-diethyl-6-hydroxyspiro[chroman-2,1'-cyclobutane]-3-yl)methyl carbamate;
7-tert-butyl-5-methylspiro[chroman-2,1'-cyclobutane]-4,6-diol;
7-tert-butyl-4-hydroxy-5-methylspiro[chroman-2,1'-cyclobutane]-6-yl acetate;
5,7-diisopropylspiro[chroman-2,1'-cyclobutane]-6-yl 2-amino-2-oxoacetate;
2-hydroxy-2-(6-hydroxy-5,7-diisopropylspiro[chroman-2,1'-cyclobutane]-8-yl)acetonitrile;
7-isopropyl-5-methylspiro[chroman-3,1'-cyclobutane]-4,6-diol;
5-ethyl-7-isopropylspiro[chroman-2,1'-cyclobutane]-4,6-diol;
(S)-5,7-diethylspiro[chroman-2,1'-cyclobutane]-4,6-diol;
(R)-5,7-diethylspiro[chroman-2,1'-cyclobutane]-4,6-diol;
(S)-7-isopropyl-5-methylspiro[chroman-2,1'-cyclobutane]-4,6-diol;
(R)-7-isopropyl-5-methylspiro[chroman-2,1'-cyclobutane]-4,6-diol;
5,7-diethylspiro[chroman-3,1'-cyclobutane]-4,6-diol;

and single stereoisomers, mixtures of stereoisomers, or pharmaceutically acceptable salts thereof.

In some particular embodiments, the compositions, methods of treatment and uses in the manufacture of pharmaceutical compositions therefor, relate to compounds of Formula I, IA, and IB selected from:
5,7,8-trimethylspiro[chroman-3,1'-cyclobutane]-4,6-diol;
5,7-dimethyl-4H-spiro[chromene-3,1'-cyclobutane]-4,6-diol;
5,7,8-trimethyl-3,4-dihydrospiro[chromene-2,1'-cyclobutane]-4,6-diol;
5,7-dimethyl-3,4-dihydrospiro[chromene-2,1'-cyclobutane]-4,6-diol;
7,8-dimethylspiro[chroman-3,1'-cyclobutane]-4,6-diol;
5,7-diethyl-8-(hydroxymethyl)-3,4-dihydrospiro[chromene-2,1'-cyclobutan]-6-ol;
7-isopropyl-5-methylspiro[chroman-2,1'-cyclobutane]-4,6-diol;
7-tert-butyl-5-methylspiro[chroman-2,1'-cyclobutane]-4,6-diol;
7-isopropyl-5-methylspiro[chroman-3,1'-cyclobutane]-4,6-diol; and
5-ethyl-7-isopropylspiro[chroman-2,1'-cyclobutane]-4,6-diol;
(S)-5,7-diethylspiro[chroman-2,1'-cyclobutane]-4,6-diol;
(R)-5,7-diethylspiro[chroman-2,1'-cyclobutane]-4,6-diol;
(S)-7-isopropyl-5-methylspiro[chroman-2,1'-cyclobutane]-4,6-diol;
(R)-7-isopropyl-5-methylspiro[chroman-2,1'-cyclobutane]-4,6-diol;
5,7-diethylspiro[chroman-3,1'-cyclobutane]-4,6-diol;

and single stereoisomers, mixtures of stereoisomers, or pharmaceutically acceptable salts thereof.

In another embodiment, the compositions, methods of treatment and uses in the manufacture of a pharmaceutical composition relate to compounds selected from the group consisting of:
4'(methoxyamino)-5',7',8'-trimethyl-3',4'-dihydrospiro[cyclobutane-1,2'-thiochromen]-6'-ol;
4-(methoxyamino)-5,7-dimethyl-3,4-dihydrospiro[chromene-2,1'-cyclobutan]-6-ol;
4-(methoxyamino)-7,8-dimethyl-4H-spiro[chromene-3,1'-cyclobutan]-6-ol;
4-(ethoxyamino)-7,8-dimethyl-4H-spiro[chromene-3,1'-cyclobutan]-6-ol;
4-(ethoxyamino)-5,7,8-trimethyl-3,4-dihydrospiro[chromene-2,1'-cyclobutan]-6-ol;
4'-(ethoxyamino)-5',7',8'-trimethyl-3',4'-dihydrospiro[cyclobutane-1,2'-thiochromen]-6'-ol;
4'-(ethoxyamino)-5',7'-dimethyl-3',4'-dihydrospiro[cyclobutane-1,2'-thiochromen]-6'-ol;
4-(ethoxyamino)-5,7-dimethyl-3,4-dihydrospiro[chromene-2,1'-cyclobutan]-6-ol;
4'-(methoxyamino)-5',7'-dimethyl-3',4'-dihydrospiro[cyclobutane-1,2'-thiochromen]-6'-ol;
4-[ethyl(methoxy)amino]-5,7-dimethyl-3,4-dihydrospiro[chromene-2,1'-cyclobutan]-6-ol;
5-ethyl-4-(methoxyamino)-7,8-dimethyl-3,4-dihydrospiro[chromene-2,1'-cyclobutan]-6-ol;
4-(ethoxyamino)-5-ethyl-7,8-dimethyl-3,4-dihydrospiro[chromene-2,1'-cyclobutan]-6-ol;
(4S)-4-(methoxyamino)-5,7-dimethyl-3,4-dihydrospiro[chromene-2,1'-cyclobutan]-6-ol;
(4R)-4-(methoxyamino)-5,7-dimethyl-3,4-dihydrospiro[chromene-2,1'-cyclobutan]-6-ol;
4-(methoxyamino)-5,7-diethyl-3,4-dihydrospiro[chromene-2,1'-cyclobutan]-6-ol;
3-[(methoxyamino)methyl]-5,7-dimethyl-3,4-dihydrospiro-[chromene-2,1'-cyclobutan]-6-ol;
7-isopropyl-4-(methoxyamino)-5-methyl-3,4-dihydrospiro[chromene-2,1'-cyclobutan]-6-ol;
7-ethyl-4-(methoxyamino)-5-methyl-3,4-dihydrospiro[chromene-2,1'-cyclobutan]-6-ol;
5-ethyl-4-(methoxyamino)-7-methyl-3,4-dihydrospiro[chromene-2,1'-cyclobutan]-6-ol;

and single stereoisomers, mixtures of stereoisomers, or pharmaceutically acceptable salts thereof.

In another embodiment, the compositions, methods of treatment and uses in the manufacture of a pharmaceutical composition relate to compounds selected from the group consisting of:
7-isopropyl-5-methyl-3,4-dihydrospiro[chromene-2,1'-cyclobutan]-6-ol;

5,7-diethyl-3,4-dihydrospiro[chromene-2,1'-cyclobutan]-6-ol;
7-tert-butyl-5-methyl-3,4-dihydrospiro[chromene-2,1'-cyclobutan]-6-ol;
5,7-dimethyl-8-vinyl-3,4-dihydrospiro[chromene-2,1'-cyclobutan]-6-ol;
5,7-dimethylspiro[chroman-3,1'-cyclobutan]-6-ol;
7,8-dimethylspiro[chroman-3,1'-cyclobutan]-6-ol;
7,8-dimethyl-3,4-dihydrospiro[chromene-2,1'-cyclobutan]-6-ol;
5,7,8-trimethylspiro[chroman-3,1'-cyclobutan]-6-ol;
7,8-dimethylspiro[chroman-3,1'-cyclopropan]-6-ol;
8-chloro-5,7-dimethyl-3,4-dihydrospiro[chromene-2,1'-cyclobutan]-6-ol;
5,7-dimethyl-3,4-dihydrospiro[chromene-2,1'-cyclobutan]-6-ol;
5,7,8-trimethyl-3,4-dihydrospiro[chromene-2,1'-cyclopropan]-6-ol;

and single stereoisomers, mixtures of stereoisomers, or pharmaceutically acceptable salts thereof.

In other embodiment, the compositions, methods of treatment and uses in the manufacture of a pharmaceutical composition relate to compounds of Formula I selected from:
N-(6-hydroxy-5,7,8-trimethyl-3,4-dihydrospiro[chromene-2,1'-cyclobutan]-4-yl)acetamide;
N-(6-hydroxy-5,7-dimethyl-3,4-dihydrospiro[chromene-2,1'-cyclobutan]-4-yl)acetamide;
N-(6-hydroxy-5,7,8-trimethyl-3,4-dihydrospiro[chromene-2,1'-cyclobutan]-4-yl)butanamide;
N-(5,7-diethyl-6-hydroxyspiro[chroman-2,1'-cyclobutane]-4-yl)acetamide;

and single stereoisomers, mixtures of stereoisomers, or pharmaceutically acceptable salts thereof.

In some of the embodiments, the compositions, methods of treatment and uses in the manufacture of pharmaceutical compositions therefor, relate to compounds of Formula II and IIA selected from:
5',7',8'-trimethylspiro[cyclobutane-1,2'-thiochromen]-6'-ol;
3-(hydroxymethyl)-5,7,8-trimethylspiro[chromene-2,1'-cyclobutan]-6-ol;
4-(aminomethyl)-5,7,8-trimethylspiro[chromene-2,1'-cyclobutan]-6-ol;
N-[(6-hydroxy-5,7,8-trimethylspiro[chromene-2,1'-cyclobutan]-4-yl)methyl]acetamide;
3-(methoxymethyl)-5,7,8-trimethylspiro[chromene-2,1'-cyclobutan]-6-ol;
3,5,7,8-tetramethylspiro[chromene-2,1'-cyclobutan]-6-ol;
6-hydroxy-5,7,8-trimethylspiro[chromene-2,1'-cyclobutane]-4-carbonitrile;
6-hydroxy-5,7-dimethylspiro[chromene-2,1'-cyclobutane]-3-carbaldehyde O-methyloxime;
3-[(methoxyamino)methyl]-5,7-dimethylspiro[chromene-2,1'-cyclobutan]-6-ol;
3-(1-methoxyethyl)-5,7,8-trimethylspiro[chromene-2,1'-cyclobutan]-6-ol;
3-(1-hydroxyethyl)-5,7,8-trimethylspiro[chromene-2,1'-cyclobutan]-6-ol;
5,7-dimethylspiro[chromene-2,1'-cyclobutan]-6-ol;
6-hydroxy-5,7-dimethylspiro[chromene-2,1'-cyclobutane]-3-carbaldehyde O-ethyloxime;
3-[(ethoxyamino)methyl]-5,7-dimethylspiro[chromene-2,1'-cyclobutan]-6-ol;
5,7-dimethyl-3-(1,3-oxazol-5-yl)spiro[chromene-2,1'-cyclobutan]-6-ol;
5,7-dimethyl-3-(-(4,5-dimethyl-1H-imidazol-2-yl)spiro[chromene-2,1'-cyclobutan]-6-ol;
7-isopropyl-5-methylspiro[chromene-2,1'-cyclobutan]-6-ol;
5,7-diethylspiro[chromene-2,1'-cyclobutan]-6-ol;
5,7-diisopropylspiro[chromene-2,1'-cyclobutan]-6-ol;

and single stereoisomers, mixtures of stereoisomers, or pharmaceutically acceptable salts thereof.

In some of the embodiments, the compositions, methods of treatment and uses in the manufacture of pharmaceutical compositions therefor, relate to compounds of Formula III and IIIA selected from:
1'-(4-chlorophenyl)-5',7',8'-trimethyl-2',4'-dihydro-1'H-spiro[cyclobutane-1,3'-quinolin]-6'-ol;
1'-(4-chlorophenyl)-5',7',8'-trimethyl-2',4'-dihydro-1'H-spiro[cyclobutane-1,3'-quinoline]-4',6'-diol;
1'-(4-chlorophenyl)-6'-hydroxy-5',7',8'-trimethyl-1'H-spiro[cyclobutane-1,3'-quinolin]-4'(2'H)-one;
1'-(4-chlorophenyl)-7',8'-dimethyl-2',4'-dihydro-1'H-spiro[cyclobutane-1,3'-quinolin]-6'-ol;
1'-ethyl-7',8'-dimethyl-2',4'-dihydro-1'H-spiro[cyclobutane-1,3'-quinolin]-6'-ol;
1'-(4-chlorophenyl)-6'-hydroxy-7',8'-dimethyl-1'H-spiro[cyclobutane-1,3'-quinolin]-4'(2'H)-one;
7',8'-dimethyl-1'-(pyridin-2-yl)-2',4'-dihydro-1'H-spiro[cyclobutane-1,3'-quinolin]-6'-ol;
1'-(4-hydroxyphenyl)-7',8'-dimethyl-2',4'-dihydro-1'H-spiro[cyclobutane-1,3'-quinolin]-6'-ol;
1'-(4-chlorophenyl)-7',8'-dimethyl-2',4'-dihydro-1'H-spiro[cyclobutane-1,3'-quinoline]-4',6'-diol;
1'-(4-fluorophenyl)-7',8'-dimethyl-2',4'-dihydro-1'H-spiro[cyclobutane-1,3'-quinolin]-6'-ol;
1'-(4-methoxyphenyl)-7',8'-dimethyl-2',4'-dihydro-1'H-spiro[cyclobutane-1,3'-quinolin]-6'-ol;
6'-hydroxy-7',8'-dimethyl-2',4'-dihydro-1'H-spiro[cyclobutane-1,3'-quinoline]-1'-carbaldehyde;
4-(6'-methoxy-7',8'-dimethyl-2',4'-dihydro-1'H-spiro[cyclobutane-1,3'-quinoline]-1'-yl)phenol;
7',8'-dimethyl-1'-p-tolyl-2',4'-dihydro-1'H-spiro[cyclobutane-1,3'-quinolin]-6'-ol;
1'-(3-hydroxyphenyl)-7',8'-dimethyl-2',4'-dihydro-1'H-spiro[cyclobutane-1,3'-quinolin]-6'-ol;
7',8'-dimethyl-1'-(4-(methylsulfonyl)phenyl)-2',4'-dihydro-1'H-spiro[cyclobutane-1,3'-quinolin]-6'-ol;
methyl 4-(6'-hydroxy-7',8'-dimethyl-2',4'-dihydro-1'H-spiro[cyclobutane-1,3'-quinoline]-1'-yl)benzoate;
7',8'-dimethyl-2',4'-dihydro-1'H-spiro[cyclopropane-1,3'-quinolin]-6'-ol;
1',7',8'-trimethyl-2',4'-dihydro-1'H-spiro[cyclopropane-1,3'-quinolin]-6'-ol;
3-(6'-methoxy-7',8'-dimethyl-2',4'-dihydro-1'H-spiro[cyclobutane-1,3'-quinoline]-1'-yl)benzoic acid;
4-(6'-hydroxy-7',8'-dimethyl-2',4'-dihydro-1'H-spiro[cyclobutane-1,3'-quinoline]-1'-yl)benzoic acid;
7',8'-dimethyl-1'-(6-(piperazin-1-yl)pyridin-3-yl)-2',4'-dihydro-1'H-spiro[cyclobutane-1,3'-quinolin]-6'-ol;
1'-(4-chlorobenzyl)-5',7'-dimethyl-3',4'-dihydro-1'H-spiro[cyclobutane-1,2'-quinolin]-6'-ol;
1'-(4-hydroxyphenyl)-7',8'-dimethyl-3',4'-dihydro-1'H-spiro[cyclopropane-1,2'-quinolin]-6'-ol;
1',7',8'-trimethyl-3',4'-dihydro-1'H-spiro[cyclopropane-1,2'-quinolin]-6'-ol;
methyl 2-(6'-hydroxy-7',8'-dimethyl-2',4'-dihydro-1'H-spiro[cyclopropane-1,3'-quinoline]-1'-yl)acetate;
3-(6'-hydroxy-7',8'-dimethyl-2',4'-dihydro-1'H-spiro[cyclobutane-1,3'-quinoline]-1'-yl)benzoic acid;

4-((6'-hydroxy-5',7'-dimethyl-3',4'-dihydro-1'H-spiro[cyclobutane-1,2'-quinoline]-1'-yl)methyl)benzoic acid;
methyl 4-((6'-hydroxy-5',7'-dimethyl-3',4'-dihydro-1'H-spiro[cyclobutane-1,2'-quinoline]-1'-yl)methyl)benzoate;
1'-(benzo[d]thiazol-2-yl)-7',8'-dimethyl-2',4'-dihydro-1'H-spiro[cyclobutane-1,3'-quinolin]-6'-ol;
7',8'-dimethyl-1'-(pyridin-3-yl)-2',4'-dihydro-1'H-spiro[cyclobutane-1,3'-quinolin]-6'-ol;
1'-(6-(dimethylamino)pyridin-3-yl)-7',8'-dimethyl-2',4'-dihydro-1'H-spiro[cyclobutane-1,3'-quinolin]-6'-ol;
5',7'-dimethyl-1'-(quinolin-2-ylmethyl)-3',4'-dihydro-1'H-spiro[cyclobutane-1,2'-quinolin]-6'-ol;
7',8'-dimethyl-1'-(4-phenylthiazol-2-yl)-2',4'-dihydro-1'H-spiro[cyclobutane-1,3'-quinolin]-6'-ol;
5'-(3,7-dimethylocta-2,6-dienyl)-1'-(4-methoxyphenyl)-7',8'-dimethyl-2',4'-dihydro-1'H-spiro[cyclobutane-1,3'-quinolin]'-ol;
7',8'-dimethyl-1'-(4-methylthiazol-2-yl)-2',4'-dihydro-1'H-spiro[cyclobutane-1,3'-quinolin]-6'-ol;
7',8'-dimethyl-1'-(thiazol-2-yl)-2',4'-dihydro-1'H-spiro[cyclobutane-1,3'-quinolin]-6'-ol;
1'-(1-(2-bromophenyl)-1H-tetrazol-5-yl)-7',8'-dimethyl-2',4'-dihydro-1'H-spiro[cyclobutane-1,3'-quinolin]-6'-ol;
7',8'-dimethyl-1'-(4-(trifluoromethyl)oxazol-2-yl)-2',4'-dihydro-1'H-spiro[cyclobutane-1,3'-quinolin]-6'-ol;
2-(3-(6'-hydroxy-7',8'-dimethyl-2',4'-dihydro-1'H-spiro[cyclopropane-1,3'-quinoline]-1'-yl)propyl)isoindoline-1,3-dione;
7',8'-dimethyl-1'-(quinolin-2-ylmethyl)-2',3'-dihydro-1'H-spiro[cyclobutane-1,4'-quinolin]-6'-ol;
2-tert-butoxy-6-(6'-methoxy-7',8'-dimethyl-2',4'-dihydro-1'H-spiro[cyclobutane-1,3'-quinoline]-1'-yl)pyridin-3-ol;
N-(2-(6'-hydroxy-7',8'-dimethyl-2',4'-dihydro-1'H-spiro[cyclobutane-1,3'-quinoline]-1'-yl)ethyl)-4-propylbenzenesulfonamide;
N-(2-(6'-hydroxy-7',8'-dimethyl-2',4'-dihydro-1'H-spiro[cyclobutane-1,3'-quinoline]-1'-yl)ethyl)-4-methylbenzenesulfonamide;
1'-(5-hydroxypyridin-2-yl)-7',8'-dimethyl-2',4'-dihydro-1'H-spiro[cyclobutane-1,3'-quinolin]-6'-ol;
N-(3-(6'-hydroxy-7',8'-dimethyl-2',4'-dihydro-1'H-spiro[cyclobutane-1,3'-quinoline]-1'-yl)propyl)-4-propyl-benzenesulfonamide;
N-(3-(6'-hydroxy-7',8'-dimethyl-2',4'-dihydro-1'H-spiro[cyclobutane-1,3'-quinoline]-1'-yl)propyl)-4-methylbenzenesulfonamide;
N-(3-(6'-hydroxy-7',8'-dimethyl-2',4'-dihydro-1'H-spiro[cyclobutane-1,3'-quinoline]-1'-yl)propyl)methanesulfonamide;
N-(3-(6'-hydroxy-7',8'-dimethyl-2',4'-dihydro-1'H-spiro[cyclobutane-1,3'-quinoline]-1'-yl)propyl)benzamide;
N-(2-(6'-methoxy-7',8'-dimethyl-2',4'-dihydro-1'H-spiro[cyclobutane-1,3'-quinoline]-1'-yl)ethyl)-4-propylbenzenesulfonamide;
7'-tert-butyl-1'-(5-hydroxypyridin-2-yl)-6'-methoxy-5'-methyl-1'H-spiro[cyclobutane-1,3'-quinolin]-4'(2'H)-one;
6-(7'-tert-butyl-6'-methoxy-5'-methyl-2',4'-dihydro-1'H-spiro[cyclobutane-1,3'-quinoline]-1'-yl)pyridin-3-ol;
7'-tert-butyl-1'-(5-hydroxypyridin-2-yl)-5'-methyl-2',4'-dihydro-1'H-spiro[cyclobutane-1,3'-quinolin]-6'-ol;

and single stereoisomers, mixtures of stereoisomers, or pharmaceutically acceptable salts thereof.

Compounds also contemplated by this invention are those selected from the following:
4-(N-methoxyacetamido)-5,7-dimethylspiro[chroman-2,1'-cyclobutane]-6-yl acetate;
ethyl 6-(ethoxycarbonyloxy)-5,7-dimethylspiro[chroman-2,1'-cyclobutane]-4-yl(methoxy)carbamate;
benzyl 6-(benzyloxycarbonyloxy)-5,7-dimethylspiro[chroman-2,1'-cyclobutane]-4-yl(methoxy)carbamate;
N-(6-hydroxy-5,7-dimethyl-3,4-dihydrospiro[chromene-2,1'-cyclobutan]-4-yl)-N-methoxyformamide;
N-(6-hydroxy-5,7-dimethyl-3,4-dihydrospiro[chromene-2,1'-cyclobutan]-4-yl)-N-methoxyacetamide;
ethyl (6-hydroxy-5,7-dimethyl-3,4-dihydrospiro[chromene-2,1'-cyclobutan]-4-yl)-N-methoxycarbamate;
benzyl-methoxy(6-hydroxy-5,7-dimethyl-3,4-dihydrospiro[chromene-2,1'-cyclobutan]-4-yl)carbamate;
(Z)-5,8-dimethyl-7-(2-(quinolin-2-yl)vinyl)spiro[chroman-2,1'-cyclobutan]-6-ol;
7-tert-butyl-3,4-dihydrospiro[chromene-2,1'-cyclobutan]-6-ol;
7,8-dimethyl-5-[(Z)-2-quinolin-2-ylvinyl]-3,4-dihydrospiro-[chromene-2,1'-cyclobutan]-6-ol;
(E)-5,8-dimethyl-7-(2-(quinolin-2-yl)vinyl)spiro[chroman-2,1'-cyclobutan]-6-ol;
8-tert-butylspiro[chroman-2,1'-cyclobutan]-6-ol;
3,4-dihydrospiro[chromene-2,1'-cyclobutan]-6-ol;
spiro[chroman-3,1'-cyclobutan]-6-ol;
spiro[chroman-3,1'-cyclobutan]-8-ol;
7-methylspiro[chroman-3,1'-cyclobutan]-8-ol;
7',8'-dimethyl-4'H-spiro[cyclobutane-1,3'-quinolin]-6'-ol;
7'-tert-butyl-6'-hydroxy-1'-(5-hydroxypyridin-2-yl)-5'-methyl-1'H-spiro[cyclobutane-1,3'-quinolin]-4'(2'H)-one;
6-(7'-tert-butyl-6'-methoxy-5'-methyl-2',4'-dihydro-1'H-spiro[cyclobutane-1,3'-quinoline]-1'-yl)pyridin-3-ol;
7'-tert-butyl-1'-(5-hydroxypyridin-2-yl)-5'-methyl-2',4'-dihydro-1'H-spiro[cyclobutane-1,3'-quinolin]-6'-ol;

and single stereoisomers, mixtures of stereoisomers, or pharmaceutically acceptable salts thereof.

Another aspect of this invention is the processes for preparing compounds of the invention and is set forth in "Detailed Description of the Invention."

DETAILED DESCRIPTION OF THE INVENTION

Definitions

As used in the present specification, the following words and phrases are generally intended to have the meanings as set forth below, except to the extent that the context in which they are used indicates otherwise.

The term "optional" or "optionally" means that the subsequently described event or circumstance may or may not occur, and that the description includes instances where said event or circumstance occurs and instances in which it does not.

It will be understood by those skilled in the art with respect to any group containing one or more substituents that such groups are not intended to introduce any substitution or substitution patterns that are sterically impractical and/or physically non-feasible.

The term "acyl" refers to the groups —C(O)—H, —C(O)-(alkyl), —C(O)-(cycloalkyl), —C(O)-(alkenyl), —C(O)-(cycloalkenyl), —C(O)-(aryl), and —C(O)-(heterocyclyl).

The term "acyloxy" refers to the moiety —O-acyl, including, for example, —O—C(O)-alkyl.

The term "alkenyl" refers to a monoradical branched or unbranched, unsaturated or polyunsaturated hydrocarbon chain, having from about 2 to 20 carbon atoms, for example 2 to 10 carbon atoms. This term is exemplified by groups such as ethenyl, but-2-enyl, 3-methyl-but-2-enyl (also referred to as "prenyl", octa-2,6-dienyl, 3,7-dimethyl-octa-2,6-dienyl (also referred to as "geranyl"), and the like. The term also includes substituted alkenyl groups, and refers to an alkenyl group in which 1 or more, for example, 1 to 3 hydrogen atoms is replaced by a substituent independently selected from the group: =O, =S, acyl, acyloxy, alkoxy, amino (wherein the amino group may be a cyclic amine), aryl, heterocyclyl, carboxyl, carbonyl, amido, cyano, cycloalkyl, cycloalkenyl, halogen, hydroxyl, nitro, sulfamoyl (—SO$_2$NH$_2$), sulfanyl, sulfinyl (—S(O)H), sulfonyl (—SO$_2$H), and sulfonic acid (—SO$_2$OH). One of the optional substituents for alkenyl may be heterocyclyl, exemplified by 2-quinolyl-2-vinyl.

The term "alkenylene" refers to a diradical derived from the above defined monoradical, alkenyl.

The term "alkoxy" refers to the groups: —O-alkyl, —O-alkenyl, —O-cycloalkyl, —O-cycloalkenyl, and —O-alkynyl. Alkoxy groups that are —O-alkyl include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like. The term "alkoxy" also includes substituted alkoxy groups and refers to the groups —O-(substituted alkyl), —O-(substituted alkenyl), —O-(substituted cycloalkyl), —O-(substituted cycloalkenyl), —O-(substituted alkynyl) and —O-(optionally substituted alkylene)-alkoxy.

The term "alkyl" refers to a monoradical branched or unbranched saturated hydrocarbon chain having from about 1 to 20 carbon atoms. The term "alkyl" also means a combination of linear or branched and cyclic saturated hydrocarbon radical consisting solely of carbon and hydrogen atoms. This term is exemplified by groups such as methyl, ethyl, n-propyl, iso-propyl, n-butyl, iso-butyl, n-hexyl, n-decyl, tetradecyl, and the like. The term "alkyl" also includes substituted alkyl and refers to an alkyl group in which 1 or more, such as 1 to 5, hydrogen atoms is replaced by a substituent independently selected from the group: =O, =S, acyl, acyloxy, alkoxy, alkoxyamino, hydroxyamino, amino (wherein the amino group may be a cyclic amine), aryl, heterocyclyl, azido, carboxyl, alkoxycarbonyl, amido, cyano, cycloalkyl, cycloalkenyl, halogen, hydroxyl, nitro, sulfonylamino, aminosulfonyl, sulfanyl, sulfinyl, sulfonyl, and sulfonic acid. One of the optional substituents for alkyl may be hydroxy or amino, exemplified by hydroxyalkyl groups, such as 2-hydroxyethyl, 3-hydroxypropyl, 3-hydroxybutyl, 4-hydroxybutyl, and the like; dihydroxyalkyl groups (glycols), such as 2,3-dihydroxypropyl, 3,4-dihydroxybutyl, 2,4-dihydroxybutyl, and those compounds known as polyethylene glycols, polypropylene glycols and polybutylene glycols, and the like; or aminoalkyl groups exemplified by groups such as aminomethyl, dimethylaminomethyl, diethylaminomethyl, ethylaminomethyl, piperidinylmethyl, morpholinylmethyl, and the like. Another substituent for alkyl may be halogen, such as trifluoromethyl. Another substituent may be hydroxyamino or alkoxyamino, exemplified by groups such as hydroxyaminomethyl, methoxyaminomethyl or ethoxyaminomethyl. Another substituent may be sulfanyl, exemplified by groups such as methyl (2-methylthioacetate). Another substituent may be aryl or heterocyclyl exemplified by methylbenzoate, propylisoindoline-1,3-dione, quinoline-methyl or 2-quinolyl-2-ethyl. Another substituent may be amido, aminosulfonyl or sulfonylamino, exemplified by 4-propylbenzensulfonamide-2-ethyl; 4-methylbenzenesulfonamide-2-ethyl, 4-propylbenzensulfonamide-3-propyl; 4-methylbenzenesulfonamide-3-propyl, or methyl-N-methylacetamide. Another substituent may be aminocarbonyloxy (—OC(O)amino), such as —OC(O)NH$_2$ or —OC(O)-substituted amino.

The term "alkylene" refers to a diradical alkyl group, whereby alkyl is as defined above.

The term "alkynyl" refers to a monoradical branched or unbranched, unsaturated or polyunsaturated hydrocarbon chain, having from about 2 to 20 carbon atoms, for example 2 to 10 carbon atoms and comprising at least one triple bond, and preferably 1 to 3. The term also includes substituted alkynyl groups, and refers to an alkynyl group in which 1 or more hydrogen atoms is replaced by a substituent independently selected from the group: acyl, acyloxy, alkoxy, amino (wherein the amino group may be a cyclic amine), aryl, heterocyclyl, carboxyl, carbonyl, amido, cyano, cycloalkyl, cycloalkenyl, halogen, hydroxyl, nitro, sulfamoyl, sulfanyl, sulfinyl, sulfonyl, and sulfonic acid.

The term "amido" refers to the moieties —C(O)—NR$^{100}$R$^{101}$ and —NR$^{100}$C(O)R$^{101}$, wherein R$^{100}$ and R$^{101}$ are independently selected from the group consisting of hydrogen, alkyl, substituted alkyl, alkenyl, alkynyl, cycloalkyl, cycloalkenyl, cycloalkynyl, and heterocyclyl, provided that R$^{100}$ and R$^{101}$ are not aryl or heteroaryl.

The term "amino" refers to the group —NH$_2$ as well as to the substituted amines such as —NHR$^x$ or —NR$^x$R$^x$ where each R$^x$ is independently selected from the group: alkyl, cycloalkyl, alkenyl, cycloalkenyl, alkynyl, aryl, heterocyclyl, acyl, optionally substituted alkoxy, carboxy and alkoxycarbonyl, and where —NR$^x$R$^x$ may also be a cyclic saturated or unsaturated amine, optionally incorporating one or more, for example 1 to 3, additional atoms chosen form N, O or S, and optionally substituted with a substituent selected from the group consisting of =O, =S, alkyl, hydroxy, acyloxy, halo, cyano, nitro, sulfanyl, alkoxy, and phenyl. This term is exemplified by such groups as amino, cyclopropylamino, dimethylamino, diethylamino, hexylamino. The term "cyclic amine" or "cyclic amino" is exemplified by the group morpholinyl. The term "alkoxyamino" refers to embodiments wherein at least one of R$^x$ is alkoxy. The term "hydroxyamino" refers to embodiments wherein at least one of R$^x$ is hydroxy.

"Amino acid" refers to any of the naturally occurring amino acids, as well as synthetic analogs (e.g., D-stereoisomers of the naturally occurring amino acids, such as D-threonine) and derivatives thereof. α-Amino acids comprise a carbon atom to which is bonded an amino group, a carboxyl group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl or aralkyl (e.g., as in phenylalanine and tryptophan), substituted arylalkyl (e.g., as in tyrosine), and heteroarylalkyl (e.g., as in histidine). The term "naturally occurring amino acids" refers to these amino acids.

Unnatural amino acids are also known in the art, as set forth in, for example, Williams (ed.), Synthesis of Optically Active .alpha.-Amino Acids, Pergamon Press (1989); Evans et al., *J. Amer. Chem. Soc.*, 112:4011-4030 (1990); Pu et al., *J. Org Chem.*, 56:1280-1283 (1991); Williams et al., *J. Amer. Chem. Soc.*, 113:9276-9286 (1991); and all references cited therein.

The term "peptide" refers to any of various. natural or synthetic compounds containing two or more amino acids linked by the carboxyl group of one amino acid to the amino group of another. A "dipeptide" refers to a peptide that contains 2 amino acids. A "tripeptide" refers to a peptide that contains 3 amino acids. A "tetrapeptide" refers to a peptide that contains 4 amino acids.

The term "aromatic" refers to a cyclic or polycyclic moiety having a conjugated unsaturated (4n+2) π electron system (where n is a positive integer), sometimes referred to as a delocalized π electron system.

The term "aryl" refers to an aromatic cyclic hydrocarbon group of from 6 to 20 carbon atoms having a single ring (e.g., phenyl) or multiple condensed (fused) rings (e.g., naphthyl or anthryl). Aryls include phenyl, naphthyl and the like. The term "aryl" also includes substituted aryl rings and refers to an aryl group as defined above, which unless otherwise constrained by the definition for the aryl substituent, is substituted with one or more, such as 1 to 5, substituents, independently selected from the group consisting of: hydroxy, acyl, acyloxy, alkenyl, alkoxy, alkyl, alkynyl, amino, aryl, aryloxy, azido, carboxyl, alkoxycarbonyl, amido, cyano, cycloalkyl, cycloalkenyl, halogen, heterocyclyl, heterocyclyloxy, nitro, sulfonylamino, aminosulfonyl, sulfanyl, sulfinyl, sulfonyl, and sulfonic acid.

The term "aryloxy" refers to the group —O-aryl.

The term "aralkyl" refers to the group -alkylene-aryl, wherein alkylene and aryl are defined herein.

The term "carbonyl" refers to the di-radical "C=O", which is also illustrated as "—C(O)—". This moiety is also referred as "keto."

The term "alkylcarbonyl" refers to the groups: —C(O)-(alkyl), —C(O)-(cycloalkyl), —C(O)-(alkenyl), and —C(O)-(alkynyl).

The term "alkoxycarbonyl" refers to the groups: —C(O) O-(alkyl), —C(O)O-(cycloalkyl), —C(O)O-(alkenyl), and —C(O)O-(alkynyl). These moieties may also be referred to as esters.

The term "aminosulfonyl" refers to the group —S(O)$_2$-(amino). The term "sulfonylamino" refers to the group -(amino) —S(O)$_2$-R$^y$, wherein R$^y$ is alkyl, cycloalkyl, alkenyl, aryl or heterocyclyl.

The term "aminocarbonyl" refers to the group —C(O)-(amino) and the term "cabonylamino" refers to the group -amino-C(O)—R$^y$, wherein R$^y$ is alkyl, cycloalkyl, alkenyl, aryl or heterocyclyl and the term amino is as described herein.

The term "carboxy" or "carboxyl" refers to the moiety "—C(O)OH," which is also illustrated as "—COOH." The salts of —COOH are also included.

The term "cycloalkyl" refers to non-aromatic cyclic hydrocarbon groups having about 3 to 12 carbon atoms having a single ring or multiple condensed or bridged rings. Such cycloalkyl groups include, by way of example, single ring structures such as cyclopropyl, cyclobutyl, cyclopentyl, cyclohexyl, and the like, or multiple ring structures such as adamantyl, and the like. The term "cycloalkyl" additionally encompasses spiro systems wherein the cycloalkyl ring has a carbon ring atom in common with another ring. The term "cycloalkyl" also includes substituted cycloalkyl rings and refers to a cycloalkyl group substituted with one or more, such as 1 to 5, substituents, independently selected from the group consisting of: =O, =S, acyl, acyloxy, alkenyl, alkoxy, alkyl, alkynyl, amino, aryl, aryloxy, azido, carboxyl, alkoxycarbonyl, amido, cyano, cycloalkyl, cycloalkenyl, halogen, heterocyclyl, heterocyclyloxy, hydroxyl, nitro, sulfonylamino, aminosulfonyl, sulfanyl, sulfinyl, sulfonyl, and sulfonic acid. A cycloalkyl ring substituted with an alkyl group is also referred as "alkylcycloalkyl."

The term "cycloalkenyl" refers to cyclic alkenyl groups of from 3 to 10 carbon atoms having single or multiple cyclic rings. This also includes substituted cycloalkenyl which includes substituents as those listed with cycloalkyl.

The term "halo" or "halogen" refers to fluoro, chloro, bromo, and iodo.

The term "heteroaryl" refers to an aromatic carbocyclic radical having one or more, such as 1 to 3, rings incorporating one or more, such as 1 to 4, heteroatoms within the ring (chosen from nitrogen, oxygen, and/or sulfur). This term excludes saturated carbocyclic radical having one or more rings incorporating one or more heteroatoms within the ring (chosen from nitrogen, oxygen, and/or sulfur).

The terms "heterocycle," "heterocyclic," "heterocyclo," and "heterocyclyl" refer to a monovalent, saturated, partially unsaturated or fully unsaturated (aromatic) carbocyclic radical having one or more, such as 1 to 3, rings incorporating one or more, such as 1 to 4, heteroatoms within the ring (chosen from nitrogen, oxygen, and/or sulfur). Heterocycles include morpholine, piperidine, piperazine, thiazole, thiazolidine, isothiazole, oxazole, isoxazole, pyrazole, pyrazolidine, pyrazoline, imidazole, imidazolidine, benzothiazole, pyridine, pyrazine, pyrimidine, pyridazine, pyrrole, pyrrolidine, quinoline, quinazoline, purine, carbazole, benzimidazole, thiophene, benzothiophene, pyran, tetrahydropyran, benzopyran, furan, tetrahydrofuran, indole, indoline, indazole, xanthene, thioxanthene, acridine, quinuclidine, and the like. The terms "heterocycle," "heterocyclic," "heterocyclo," and "heterocyclyl" also include substituted rings and refer to a heterocycle group as defined above, which unless otherwise constrained by the definition for the heterocycle, is substituted with one or more, such as 1 to 5, substituents, independently selected from the group consisting of: hydroxy, acyl, acyloxy, alkenyl, alkoxy, alkyl, alkynyl, amino, aryl, aryloxy, azido, carboxyl, alkoxycarbonyl, amido, cyano, cycloalkyl, cycloalkenyl, halogen, heterocyclyl, heterocyclo-oxy, nitro, sulfonylamino, aminosulfonyl, sulfanyl, sulfinyl, sulfonyl, and sulfonic acid. This term is exemplified by 4,5-dihydroisoxazole-5-methylcarboxylate, 5-butylisoxazol, pyrrolidinyl, morpholinyl, imidazolyl, 5-hydroxypyridin-2-yl, dimethylaminopyridin-3-yl, isoindolinedione, trifluoromethyloxazolyl, 2-bromophenyl-1H-tetrazol-5-yl, methylthiazolyl, phenylthiazolyl, and benzothiazolyl.

The term "heterocyclyloxy" refers to the moiety —O-heterocyclyl.

The term "inflammation," "inflammatory conditions," or "inflammation conditions" includes but is not limited to muscle fatigue, osteoarthritis, rheumatoid arthritis, inflammatory bowel syndrome or disorder, Crohn's disease, skin inflammation, such as atopic dermatitis, contact dermatitis, allergic dermatitis, xerosis, eczema, rosacea, seborrhea, psoriasis, atherosclerosis, thermal and radiation burns, acne, oily skin, wrinkles, excessive cellulite, excessive pore size, intrinsic skin aging, photo aging, photo damage, harmful UV damage, keratinization abnormalities, irritation including retinoid induced irritation, hirsutism, alopecia, dyspigmentation, inflammation due to wounds, scarring or stretch marks, loss of elasticity, skin atrophy, and gingivitis.

The term "ischemia" refers to deficiency of blood to an organ or tissue due to functional constriction or actual obstruction of a blood vessel.

The term "isomers" or "stereoisomers" relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A mixture of equal amounts of stereoisomers of a molecule is termed a "racemate" or a "racemic mixture." A carbon atom bonded to four non-identical substituents is termed a "chiral center." Certain compounds of the present invention have one or more chiral centers and therefore may exist as either individual stereoisomers or as a mixture of stereoisomers. Configurations of stereoisomers that owe their existence to hindered rotation about double bonds are differentiated by their prefixes cis and trans, (or Z and E), which indicate that the groups are on the same side (cis or Z) or on opposite sides (trans or E) of the double bond in the molecule according to the Cahn-Ingold-Prelog rules. This invention includes all possible stereoisomers as individual stereoisomers, racemates, or mixtures of stereoisomers.

A "lipoxygenase-mediated condition" or a "disorder mediated by lipoxygenases" means any condition, disorder or disease mediated, at least in part, by a lipoxygenase enzyme. This includes disorders related to or otherwise associated with a lipoxygenase enzyme or the inhibition thereof, including, by way of example and without limitation, diseases involving apoptosis in cancer cells such as prostatic cancer, gastric cancer, breast cancer, pancreatic cancer, colorectal or esophageal cancer and airways carcinoma; diseases involving hypoxia, or anoxia such as atherosclerosis, myocardial infarction, cardiovascular disease, heart failure (including chronic and congestive heart failure), cerebral ischemia, retinal ischemia, myocardial ischemia, post surgical cognitive dysfunction and other ischemias; diseases involving inflammation, including diabetes, arterial inflammation, inflammatory bowel disease, Crohn's disease, renal disease, pre-menstrual syndrome, asthma, allergic rhinitis, gout; cardiopulmonary inflammation, rheumatoid arthritis, osteoarthritis, muscle fatigue and inflammatory disorders of the skin including acne, dermatitis and psoriasis; disorders of the airways such as asthma, chronic bronchitis, human airway carcinomas, mucus hypersecretion, chronic obstructive pulmonary disease (COPD), pulmonary fibrosis caused by chemotherapy or other drugs, idiopathic pulmonary fibrosis, cystic fibrosis, and adult respiratory distress syndrome; diseases involving central nervous system (CNS) disorders including psychiatric disorders including anxiety and depression; neurodegeneration and neuroinflammation including Alzheimer's, dementia and Parkinson's disease; peripheral neuropathy including spinal chord injury, head injury and surgical trauma, and allograft tissue and organ transplant rejection; diseases involving the autoimmune system such as psoriasis, eczema, rheumatoid arthritis, and diabetes; and disorders involving bone loss or bone formation.

The term "pharmaceutically acceptable carer" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "pharmaceutically acceptable salt" refers to salts which retain the biological effectiveness and properties of the compounds of this invention and which are not biologically or otherwise undesirable. In some cases, the compounds of this invention are capable of forming acid and/or base salts by virtue of the presence of phenolic, amino and/or carboxyl groups or groups similar thereto. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heterocyclic, and the like. Also included are amines where the two or three substituents, together with the amino nitrogen, form a heterocyclic group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

It should be understood that for the purpose of this invention, all references to acceptable salts also include solvent addition forms (solvates) or polymorphs (crystal forms). "Solvate" means solvent addition form that contains either stoichiometric or non-stoichiometric amounts of solvent. Some compounds have a tendency to trap a fixed molar ratio of solvent molecules in the crystalline solid state, thus forming a solvate. If the solvent is water the solvate formed is a "hydrate," when the solvent is alcohol, the solvate formed is an "alcoholate." "Polymorphs" (or "crystal forms") means crystal structures in which a compound can crystallize in different crystal packing arrangements, all of which have the same elemental composition. Different crystal forms usually have different X-ray diffraction patterns, infrared spectra, melting points, density, hardness, crystal shape, optical and electrical properties, stability and solubility. Recrystallization solvent, rate of crystallization, storage temperature, and other factors may cause one crystal form to dominate.

The term "prodrug" refers to an inactive form of a compound which must be metabolized in vivo, e.g., by biological fluids or enzymes, by a subject after administration into an active form of the parent compound in order to produce the desired pharmacological effect. The prodrug can be metabolized before absorption, during absorption, after absorption, or at a specific site. Prodrug forms of compounds may be utilized, for example, to improve bioavailability, improve subject acceptability such as masking or reducing unpleasant characteristics such as a bitter taste, odor, or gastrointestinal irritability, alter solubility, provide for prolonged or sustained release or delivery, improve ease of formulation, or provide site-specific delivery of the compound.

Prodrugs of a compound of this invention are prepared by modifying one or more functional group(s) present in the compound in such a way that the modification(s) may be cleaved in vivo to release the parent compound. Prodrugs include compounds wherein a hydroxyl group in a compound of the invention is bonded to any group that may be cleaved in vivo to regenerate the free hydroxyl, amino. Examples of prodrugs include, but are not limited to, esters (e.g., acetate, formate, and benzoate derivatives), carbamates (e.g., N,N-dimethylaminocarbonyl) of hydroxy functional groups in compounds of the invention, see Bundegaard, H. *Design of Prodrugs*. New York-Oxford: Elsevier, 1985, pp. 1-92, and the like. Reference to a compound herein includes prodrug forms of said compound.

The term "subject" includes, but is not limited to, humans and animals, such as farm animals (cattle, horses, sheep, goats, and swine) and domestic animals (rabbits, dogs, cats, rats, mice and guinea pigs. The term "subject" does not denote a particular age or sex.

The term "sulfanyl" or "thio" refers to the groups: —S—H, —S-(alkyl), —S-(aryl), or —S-(heterocyclyl). The term is exemplified by groups such as isopropylthio and methyl thioacetate.

It will also be apparent to those skilled in the art that the compounds of the invention, including the compounds of Formula II, may be subject to tautomerization and may therefore exist in various tautomeric forms wherein a proton of one atom of a molecule shifts to another atom and the chemical bonds between the atoms of the molecules are consequently rearranged. See, e.g., March, *Advanced Organic Chemistry: Reactions, Mechanisms and Structures*, Fourth Edition, John Wiley & Sons, pages 69-74 (1992). As used herein, the term "tautomer" refers to the compounds produced by the proton shift, and it should be understood that the all tautomeric forms, insofar as they may exist, are included within the invention.

The term "therapeutically effective amount" refers to that amount of a compound of this invention that is sufficient to effect treatment, as defined below, when administered to a subject in need of such treatment. The therapeutically effective amount will vary depending upon the subject and disease condition being treated, the weight and age of the subject, the severity of the disease condition, the particular compound chosen, the dosing regimen to be followed, timing of administration, the manner of administration and the like, all of which can readily be determined by one of ordinary skill in the art.

The term "treatment" or "treating" means any treatment of a disease or disorder in a subject, including:
  preventing or protecting against the disease or disorder, that is, causing the clinical symptoms not to develop;
  inhibiting the disease or disorder, that is, arresting or suppressing the development of clinical symptoms; and/or
  relieving the disease or disorder that is, causing the regression of clinical symptoms.

It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" as defined herein. The term "protection," as used herein, is meant to include "prophylaxis."

Nomenclature

In general, the nomenclature used in this Application was generated using or with the help of version 2.2 of the AUTONOM™ naming package within the ChemOffice® version 7.0.3 suite of programs by CambridgeSoft Corp (Cambridge, Mass.) or by Chemsketch Freeware version 5.12. A compound of Formula I, wherein $R^1$ is chloro, $R^2$ is hydroxy, $R^3$ and $R^4$ are methyl, $R^5$ to $R^8$ are hydrogen, and $R^9$ and $R^{10}$ together with the carbon to which they are attached form a cyclobutane ring, may be named: 5-chloro-7,8-dimethyl-3,4-dihydrospiro[chromene-2,1'-cyclobutan]-6-ol. A compound of Formula I, wherein $R^1$, $R^3$, and $R^4$ are methyl, $R^2$ is hydroxy, $R^7$ to $R^{10}$ are hydrogen, and $R^5$ and $R^6$ together with the carbon to which they are attached form a cyclobutane ring may be named 5',7',8'-trimethyl-2',3'-dihydrospiro[cyclobutane, 1,4'-thiochromen]-6'-ol.

Synthesis of the Compounds of the Invention

Synthetic Reaction Parameters

The terms "solvent," "inert organic solvent," or "inert solvent" mean a solvent inert under the conditions of the reaction being described in conjunction therewith. Solvents employed in synthesis of the compounds of the invention include, for example, methanol ("MeOH"), acetone, water, acetonitrile, 1,4-dioxane, dimethylformamide ("DMF"), benzene, toluene, tetrahydrofuran ("THF"), chloroform, methylene chloride (also named dichloromethane,("DCM")), diethyl ether, ethyl acetate ("EtOAc"), pyridine and the like, as well as mixtures thereof. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Unless specified to the contrary, the reactions described herein take place at atmospheric pressure within a temperature range from −10° C. to 110° C. and in some cases at "room" or "ambient" temperature, e.g., 20° C. Further, unless otherwise specified, the reaction times and conditions are intended to be approximate.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used.

A synthesis of certain spiro-chromanones has been described by H. J. Kabbe. *Synthesis*, Vol. 12 (1978), pp. 886-7. A synthesis of certain spiro-dihydroquinolines has been described in U.S. Pat. No. 3,331,846. Synthesis of certain spiro tetrahydroquinolines has been also described in Dorey, G. et al. *Biorg. & Med. Chem. Lett.*, Vol. 10, no. 9 (2000), pp. 935-939.

Unless otherwise indicated, the variables used in the reactions schemes below have the same meanings as described in the Summary of the Invention.

Reaction Scheme 1

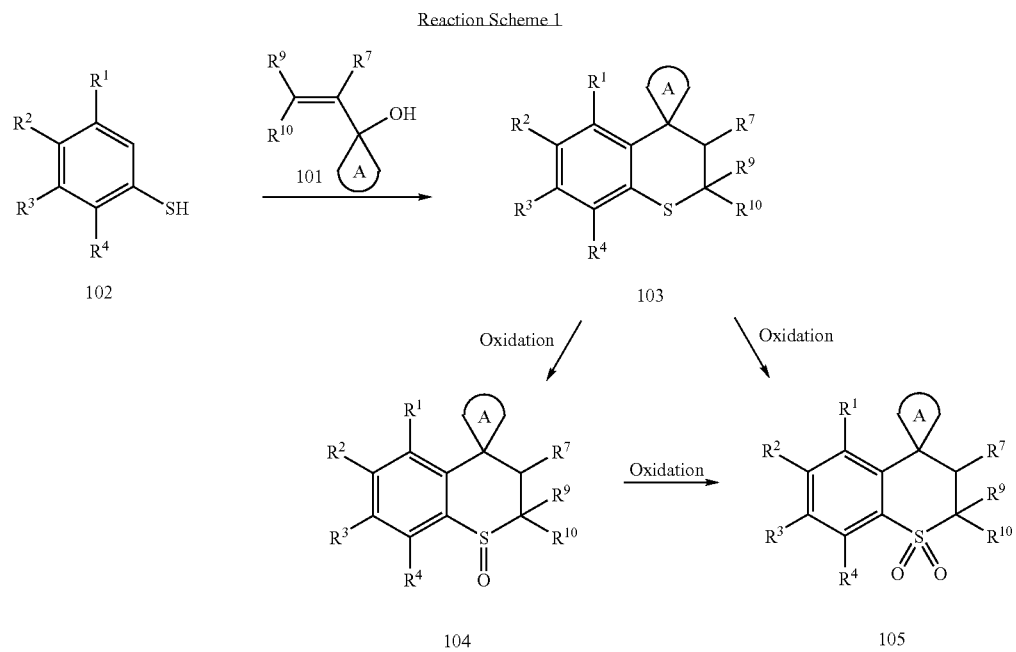

Compounds of Formula I of the present invention wherein X is $S(O)_{0-2}$, $R^2$ is hydroxy or alkoxy, n is 1, $-CR^5R^6$ form a cyclobutyl ring, $R^7$ to $R^{10}$ are independently of each other hydrogen or alkyl, and $R^1$, $R^3$ and $R^4$ are as described above, can be prepared following Scheme 1.

The vinyl alcohol of formula 101, wherein A is a cyclobutyl ring can be prepared by Grignard reaction of a vinyl magnesium bromide of formula $-CR^9R^{10}=CR^7MgBr$ with a cyclobutyl ketone of Formula A(O), wherein A is a cyclobutyl ring, under inert conditions in a solvent such as tetrahydrofuran. Certain vinyl alcohols of formula 101 such as 1-vinylcyclohexanol may be available from Sigma-Aldrich, at www.sigma-aldrich.com. Reaction of the vinyl alcohol of formula 101 with the mercaptophenol of formula 102 in the presence of a Lewis acid such as $BF_3$-ether, methane sulfonic acid, p-toluene sulfonic acid, or aluminum chloride, can give the desired thiochroman of formula 103, wherein A is a cyclobutyl ring. Oxidation with one equivalent of a mild oxidant such as m-chloro-perbenzoic acid (MCPBA) may give the thio-chroman1-oxide derivative of formula 104, which can be further oxidized with another equivalent of oxidant to the disulfoxide of formula 105. Alternatively the disulfoxide can be synthesized from the thiochroman of formula 103 with an excess of mild oxidant.

Reaction Scheme 2

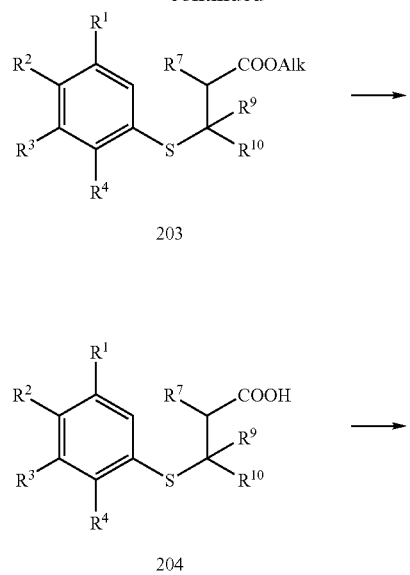

-continued

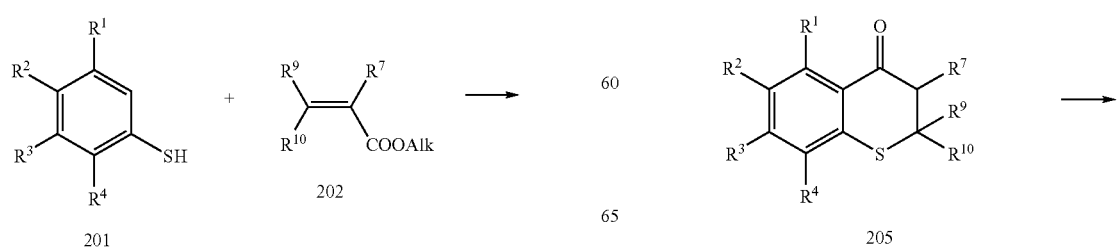

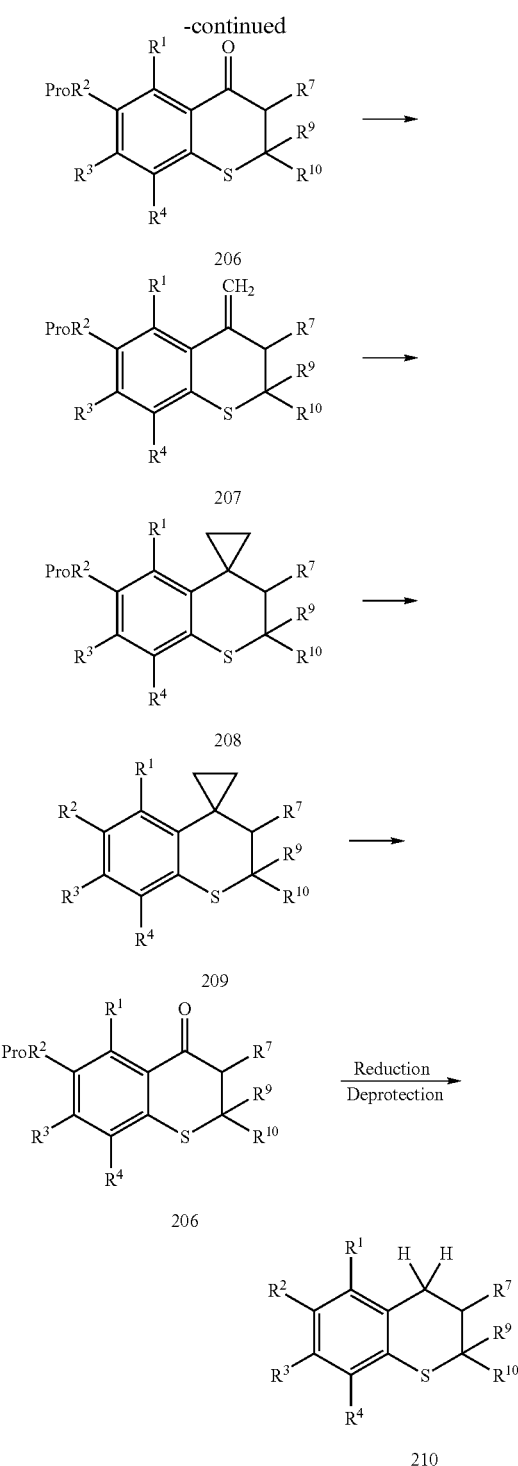

methanol, to give the ester of formula 203, which can further, in the presence of a base such as sodium hydroxide, undergo hydrolysis of the ester group to give the acid of formula 204. Cyclization under acidic condition can give the thio-chromanone of formula 205, which may undergo protection of its substituent $R^2$ under conditions well known in the art to give the compound of formula 206, wherein Pro is a protective group. If the substituent $R^2$ of formula 205 is hydroxy, said substituent may be protected with, for example, triisopropylsilyl chloride or t-butyldimethylsilyl chloride. Methylenation of the ketone of formula 206, may be achieved with the titanium carbene complex (Tebbe) reagent (available from Sigma-Aldrich) or with methyl phosphonium (Wittig reaction) under basic conditions, see i.e. Pine, S. H. & Shen, G. S. & Hoang, H. "Ketone Methylenation using the Tebbe and Wittig Reagents." *Synthesis* (1991), p. 165; followed by cyclopropylation with diiodomethane/diethyl zinc, to yield a compound of Formula 208, wherein Pro is a protective group. Deprotection with, for example, tetrabutylammonium fluoride may yield the thiochroman of formula 209, which can further be oxidized as in Scheme 1 into the sulfoxide or the disulfoxide derivatives thereof.

Alternatively, compound of formula 206 can undergo reduction of the carbonyl group as is well known in the art, for example using the method of the Clemmensen reduction with zinc/mercury amalgam in aqueous hydrochloric acid or any other modifications to give a compound of formula 210.

Reaction Scheme 3

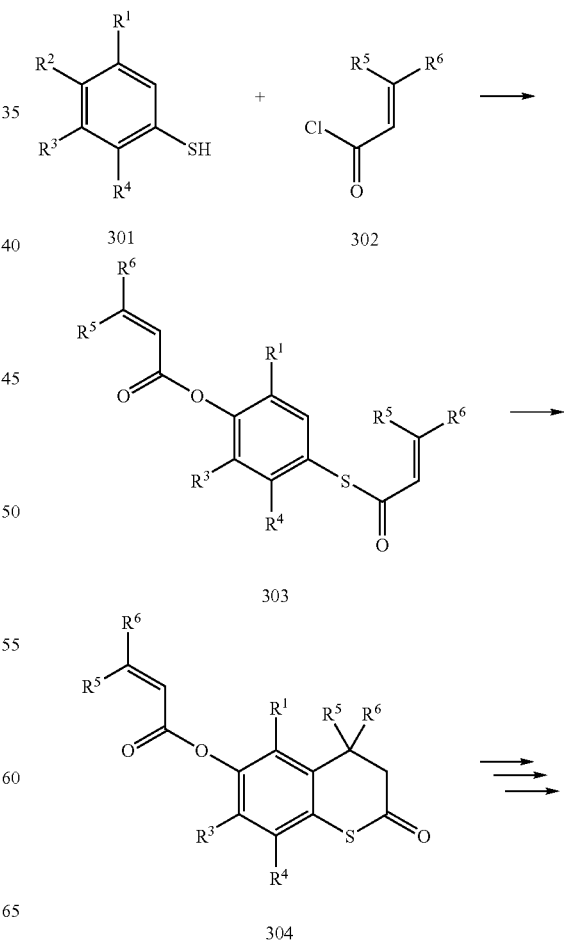

Scheme 2 describes an alternate synthesis for compounds of formula I of the present invention, wherein X is $S(O)_{0-2}$, $R^5$ and $R^6$ form a cyclopropyl ring, $R^9$ and $R^{10}$ are independently of each other hydrogen or alkyl or together with the carbon atom to which they are attached form a cycloalkyl ring, n is 1, $R^7$ is hydrogen, and $R^1$ to $R^4$ and $R^8$ are as defined above. Under Michael addition conditions, the mercaptophenol of formula 201 is alkylated with an acrylate of formula 202, wherein Alk is an alkyl group, in an anhydrous solvent such as -continued

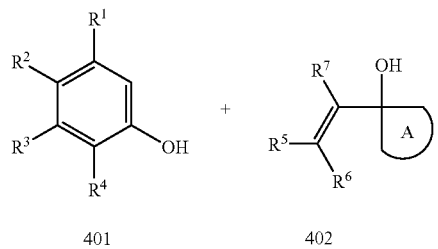

305

Scheme 3 describes a synthesis for compounds of Formula I, wherein X is $S(O)_{0-2}$, $R^2$ is hydroxy, $R^9$ and $R^{10}$ form a cyclopropyl ring, $R^7$ and $R^8$ are hydrogen, n is 1 and $R^1$, $R^3$ to $R^6$ are as defined above. Treatment of a 4-mercaptophenol of formula 301 with acryloyl chloride of formula 302 in a solvent such as toluene or benzene may give a compound of Formula 303, which may undergo cyclization to give compound of formula 304. Following the methylenation of the carbonyl group as described in Scheme 2 and deprotection may give compound of formula 305, which may be further oxidized as described in Scheme 1 to give the sulfoxide or the disulfoxide derivative thereof. Compounds of Formula I, wherein $R^2$ is amino or alkoxy may also be synthesized following this scheme.

Reaction Scheme 4

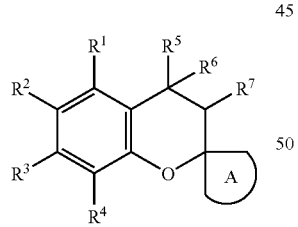

403

Scheme 4 describes a synthesis for compounds of Formula I, wherein X is O, $R^9$ and $R^{10}$ form a cyclobutyl ring, $R^8$ is hydrogen, n is 1 and $R^1$ to $R^4$, and $R^5$ to $R^7$ are as defined above. The vinyl-cycloalcohol of formula 402, which may be prepared as described in Scheme 1 or which may be available commercially, may react with the phenol of formula 401 in the presence of a Lewis acid, such as $BF_3$-ether, methane sulfonic acid, p-toluene sulfonic acid, or aluminum chloride, to give the compound of formula 403, wherein A is a cyclobutyl ring.

Reaction Scheme 4A

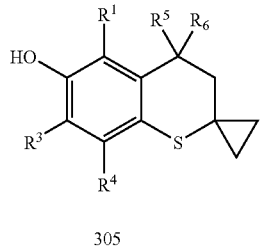

404

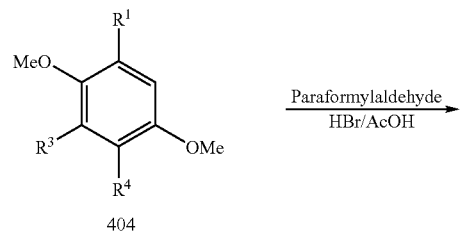

405

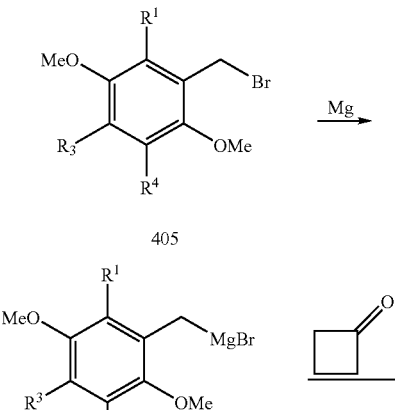

406

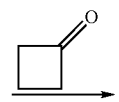

407

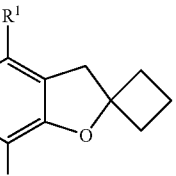

408

Scheme 4A describes a synthesis for compounds of Formula I, wherein X is O, $R^9$ and $R^{10}$ form a cyclobutyl ring, $R^5$ and $R^6$ are hydrogen, n is 0, $R^2$ is OH, and $R^1$, $R^3$, $R^4$, are as defined above. The dimethoxy compound of formula 404 is treated with paraformaldehyde, followed with acid bromide in the presence of acetic acid to give the bromide of Formula 405. Treatment with magnesium will give the Grignard reagent of formula 406 which may be reacted with cyclobutanone in a solvent such as THF, to give the compound of formula 407. Internal cyclization in the presence of a Lewis Acid such as boron trifluoride may give compound of formula 408.

Reaction Scheme 4B

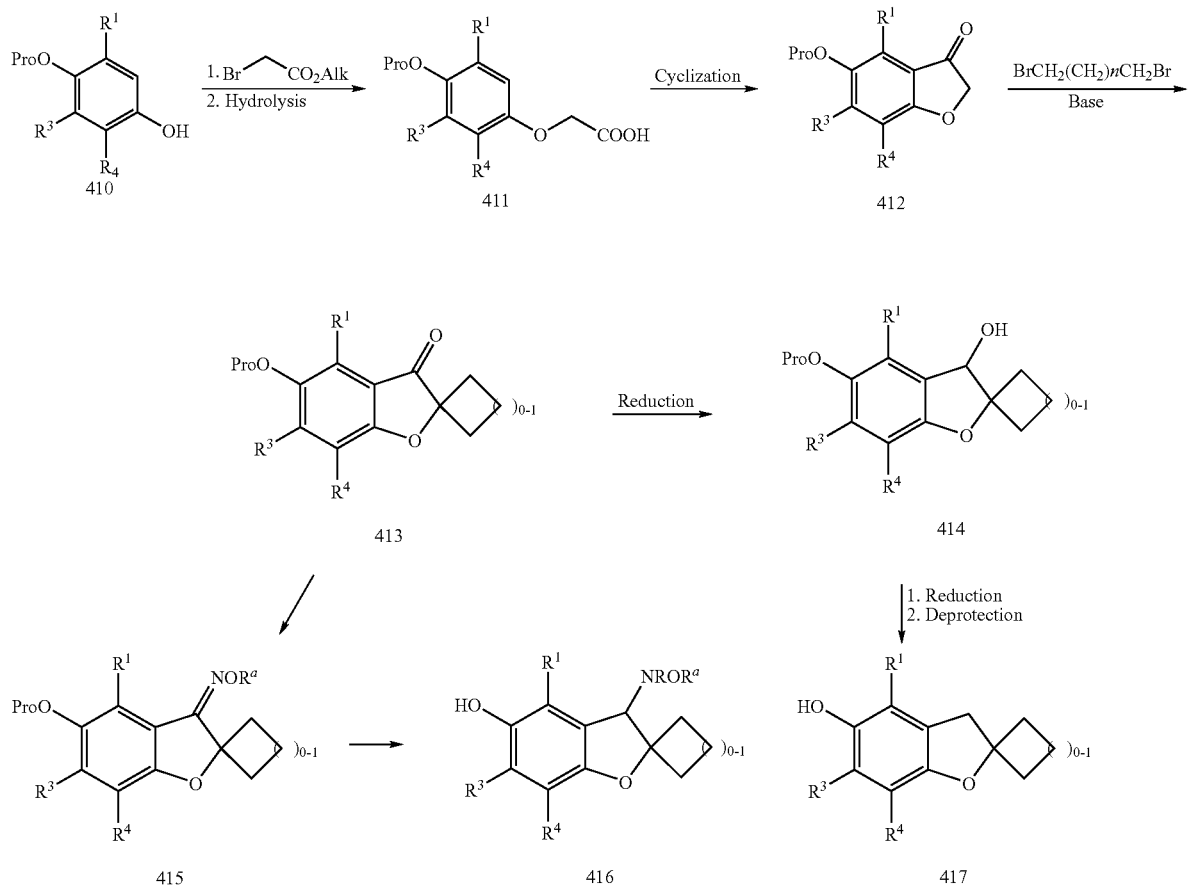

Scheme 4B describes a synthesis for compounds of Formula I, wherein X is O, $R^9$ and $R^{10}$ form a $C_{(3-4)}$ cycloalkyl ring, n is 0, $R^2$ is OH, and $R^1$, $R^3$, $R^4$, are as defined above, and $R^5$ and $R^6$ are hydrogen, hydroxy, oxime or alkoxyamine.

The protected hydroquinone of formula 410, wherein Pro is a protective group, is treated with sodium hydride and alkylated with alkylbromoacetate to give, after hydrolysis of the ester group, a compound of formula 411. Internal cyclization with a Lewis acid such as methanesulfonic acid in an inert solvent such as benzene or toluene, may give compound of formula 412. Alkylation with dihalo alkyl such as dibromoalkyl in the presence of a base may give the spiro compound 413, which can be reduced with for example sodium borohydride in a solvent such as methanol, to give the hydroxy spiro compound of formula 414. Further reduction of compound 414 under acidic conditions, followed by deprotection may give compound of formula 417.

Alternatively, the compound of formula 413 may be treated with hydroxyamine or alkoxyamine to give an oxime of formula 415, which may be reduced to give the hydroxyamine or alkoxyamine compound of formula 416. Alkylation of the compound of formula 416 wherein R is hydrogen may give compounds of formula 416 wherein R is different than hydrogen, for example wherein R is alkyl. Deprotection of these compounds can be done by ways well known in the art.

Reaction Scheme 4C

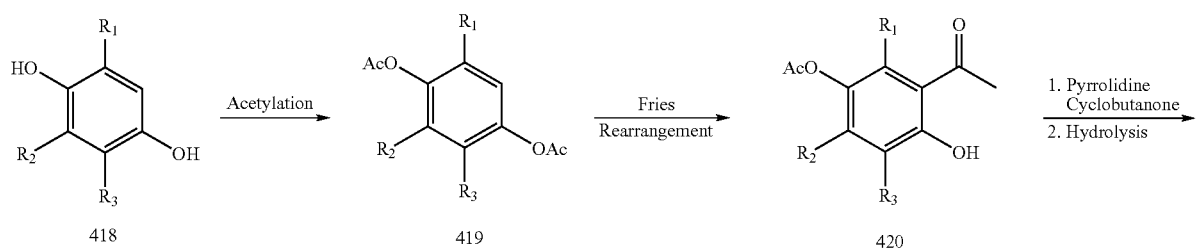

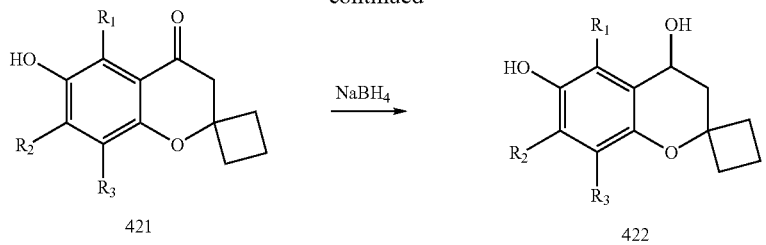

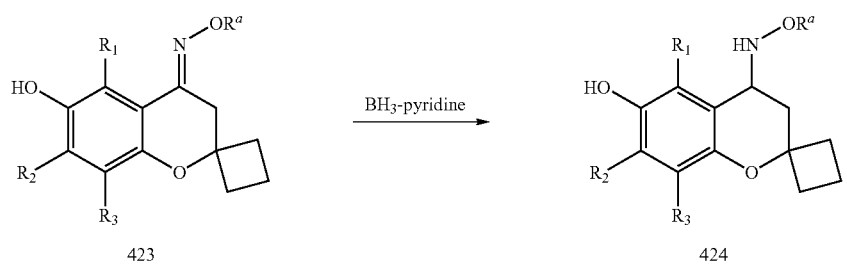

Scheme 4C describes a synthesis for compounds of Formula I, wherein X is O, $R^9$ and $R^{10}$ with the atom to which they are attached form a cyclobutyl ring, $R^7$ and $R^8$ are hydrogen, n is 1, $R^2$ is OH, $R^5$ is hydrogen, $R^6$ is either OH or alkoxyamine, and $R^1$, $R^3$, $R^4$, and $R^8$ are defined as above. Acetylation of a hydroquinone of formula 418, followed by a Fries rearrangement reaction catalyzed by $BF_3$ gives an intermediate of formula 420. This intermediate may be furtherreacted with cyclobutanone in the presence of pyrrolidine and subsequently hydrolyzed with an aqueous base, to yield a chromanone of formula 421. Reduction of this chromanone with sodium borohydride may lead to a hydroxy derivative compound of formula 422. Alternatively, a condensation reaction of the chromanone of formula 421 with an alkoxyamine may give an O-alkyl oxime of formula 423, which after treatment with reducing reagent $BH_3$-pyrindine complex may give a compound of formula 424.

Reaction Scheme 5

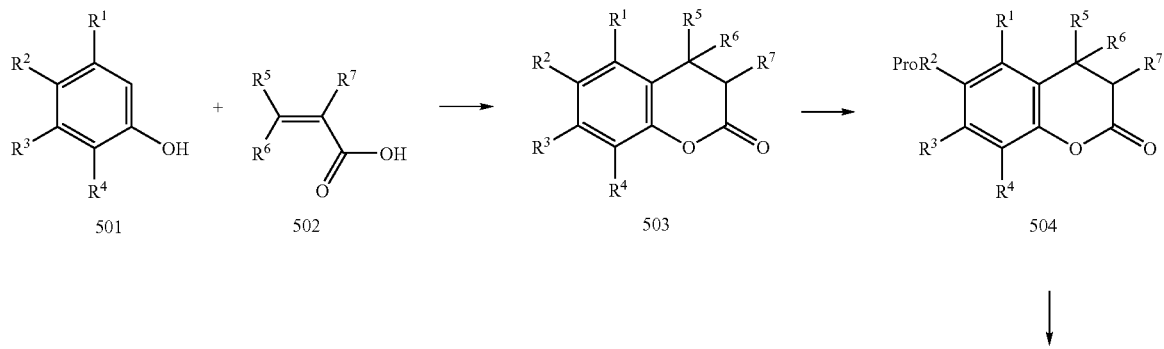

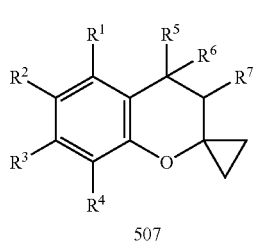
507

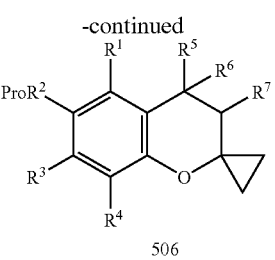
506

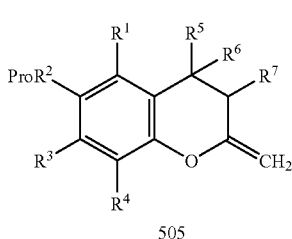
505

Scheme 5 describes an alternate synthesis for compounds of Formula I, wherein X is O, n is 1, $R^9$ and $R^{10}$ form a cyclopropyl ring, $R^8$ is hydrogen, and $R^1$ to $R^4$, and $R^5$ to $R^7$ are as defined above. The phenol of formula 501 may react with an acrylic acid derivative of formula 502 under acidic conditions to give after ring cyclization a compound of formula 503. The substituent $R^2$ is subsequently protected with, for example, triisopropylsilyl or t-butyldimethylsilyl, and the protected compound of formula 504, wherein Pro is a protective group, is methylenated followed by ring formation as described in Scheme 2, to give compound of formula 506. Deprotection with, for example, t-butyl ammonium fluoride, may give a compound of formula 507.

Reaction Scheme 6

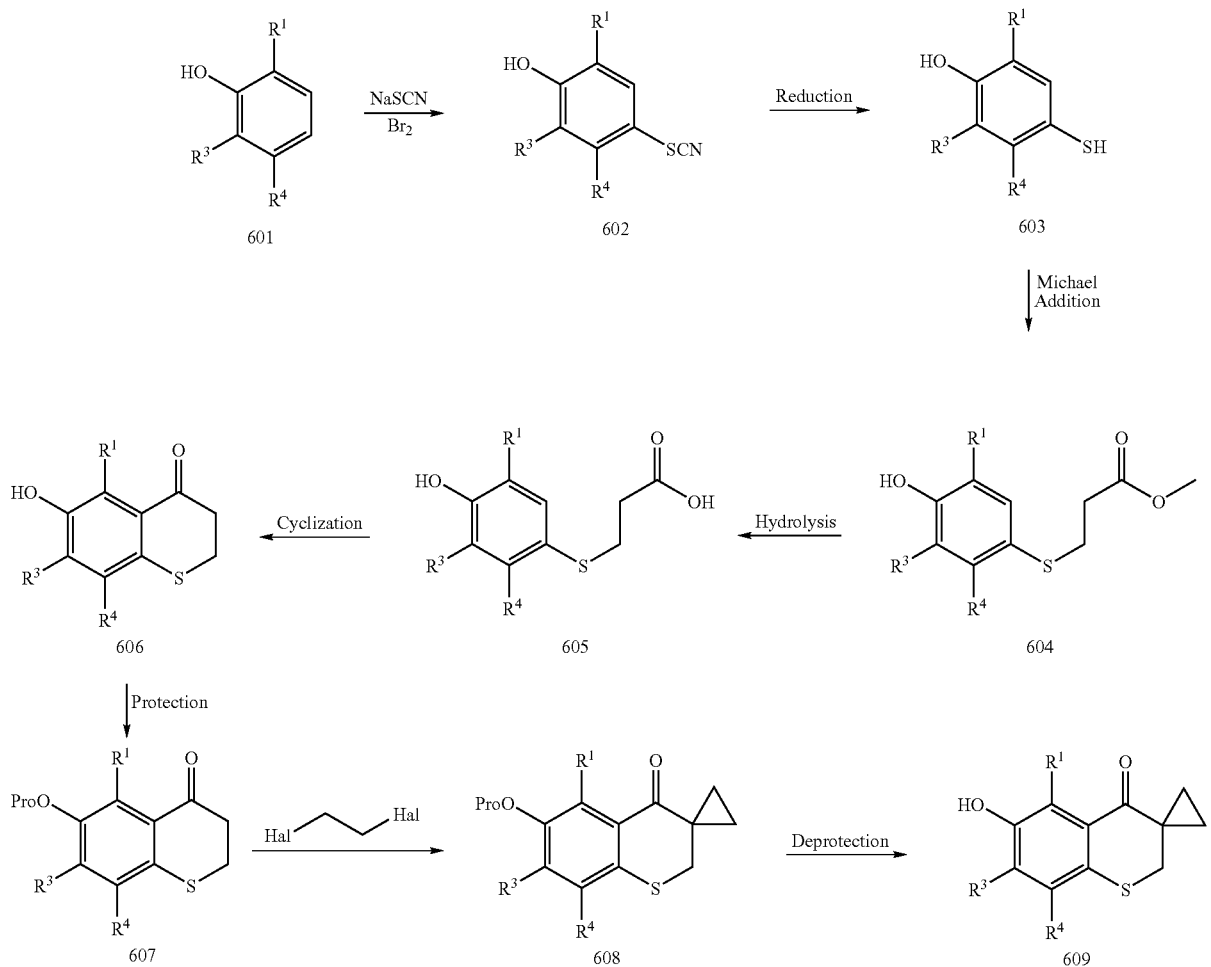

Scheme 6 describes a synthesis for compounds of Formula I, wherein X is S, n is 1, $R^7$ and $R^8$ form a cyclopropyl ring and $R^5$ and $R^6$ form a carbonyl group. The phenol of formula 601 is treated with sodium or potassium thiocyanate and bromine, in the presence of a sodium halide, such as sodium bromide, that may give the para substituted thiocyanate of formula 602, which may undergo reduction in the presence of Lithium Aluminum Hydride to give the thiol of formula 603. Michael addition with methyl acrylate, followed by hydrolysis to the acid and cyclization, as described herein, may yield the chromanone of formula 606. The phenolic hydroxyl group is protected with, for example, methoxymethoxychloride and the resulting compound of formula 607 is reacted with a dihaloethane, such as 1,4-dichloroethane of 1,4-dibromoethane, in the presence of sodium hydride in a solvent such as THF or DMF to yield the protected 3-cyclopropylchroman-4-one of formula 608. Deprotection by means well known in the art may lead to the desired compound of formula 609.

Reaction Scheme 6A

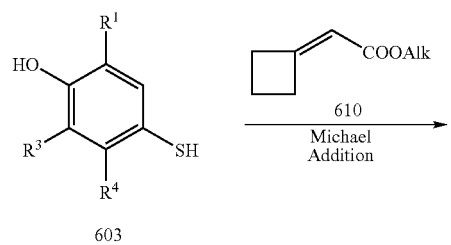

603

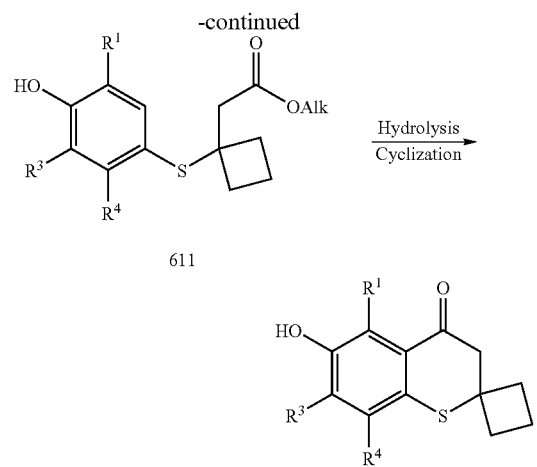

Scheme 6A describes a synthesis for compounds of Formula I, wherein X is S, n is 1, $R^9$ and $R^{10}$ form a cyclobutyl ring and $R^5$ and $R^6$ form a carbonyl group. The thiol of formula 603, prepared as described in Reaction Scheme 6, may undergo a Michael addition with a 2-cyclobutylideneacetate of formula 610 wherein Alk is alkyl, such as methylcyclobutylidene acetate to give a compound of formula 611 which may undergo hydrolysis and cyclization go give compound of formula 612.

Reaction Scheme 7

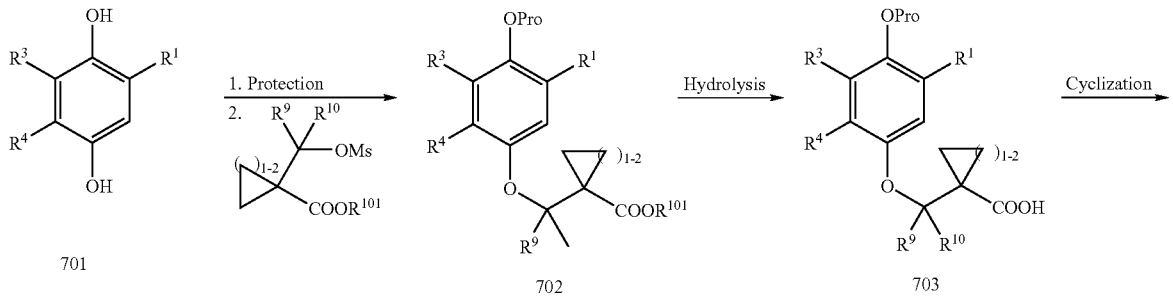

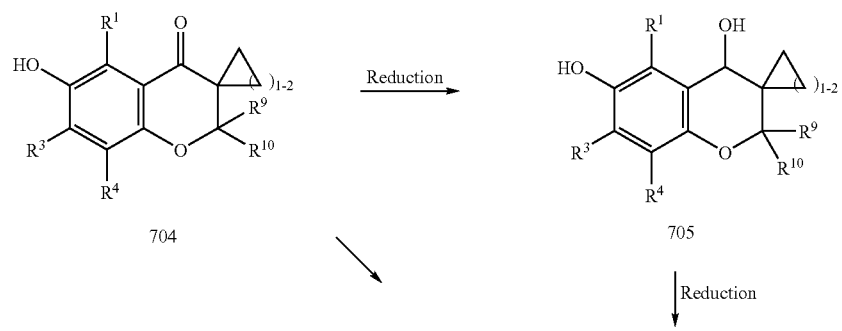

-continued

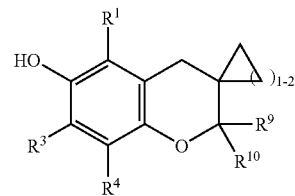

706

Scheme 7 describes a synthesis for compounds of Formula I, wherein X is O, n is 1, $R^7$ and $R^8$ form a ($C_3$-$C_4$)cycloalkyl spiro ring and $R^5$ and $R^6$ together form a carbonyl group, or $R^5$ is hydroxy or hydrogen and $R^6$ is hydrogen, and $R^1$, $R^3$, $R^4$, $R^9$ and $R^{10}$ are as defined above. One of the hydroxyl groups of the hydroquinone of formula 701 is protected with, for example, a benzyl group, by reaction with one equivalent of, for example, benzyl bromide. Addition of 1-methanesulfonyloxymethyl-cyclopropanecarboxylic acid ester to the protected hydroquinone in a solvent such as dimethylformamide in the presence of a base, such as cesium carbonate, may yield a compound of formula 702, wherein $R^{101}$ is alkyl, which after hydrolysis and cyclization may yield the 3-spiro-4-chromanone derivative of formula 704. Reduction of the carbonyl group with a metallic hydride such as, for example, lithium aluminum hydride or sodium borohydride, may yield the 4-hydroxy derivative of formula 705, which can be further reduced to compound of formula 706 with additional reducing agent. This scheme may also be used for the preparation of thiochromans of this invention by substituting the hydroquinone of formula 701 with the correspondent 4-mercaptophenol.

Oxime and hydrazone analogues of compounds of Formula I may be prepared as known in the art by addition of hydroxylamine, alkoxyamine or hydrazine as described in Examples. The oxime and hydrazone analogues may be further reduced with, for example, sodium cyanoborohydride or borane/pyridine to give alkoxyamines or hydrazines. Addition of an alkylhalide or alkylaldehyde to the alkoxyamines or hydrazines may yield compounds of Formula I wherein $R^5$ or $R^7$ may be —$NROR^a$ or —NR—$NR^bR^c$, wherein R is alkyl and $R^a$, $R^b$, $R^c$ are as defined herein.

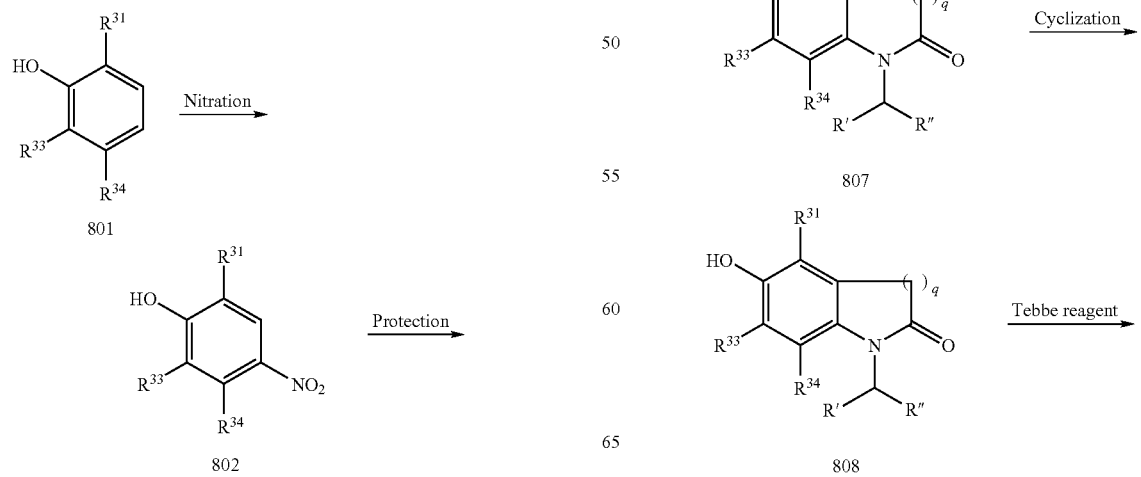

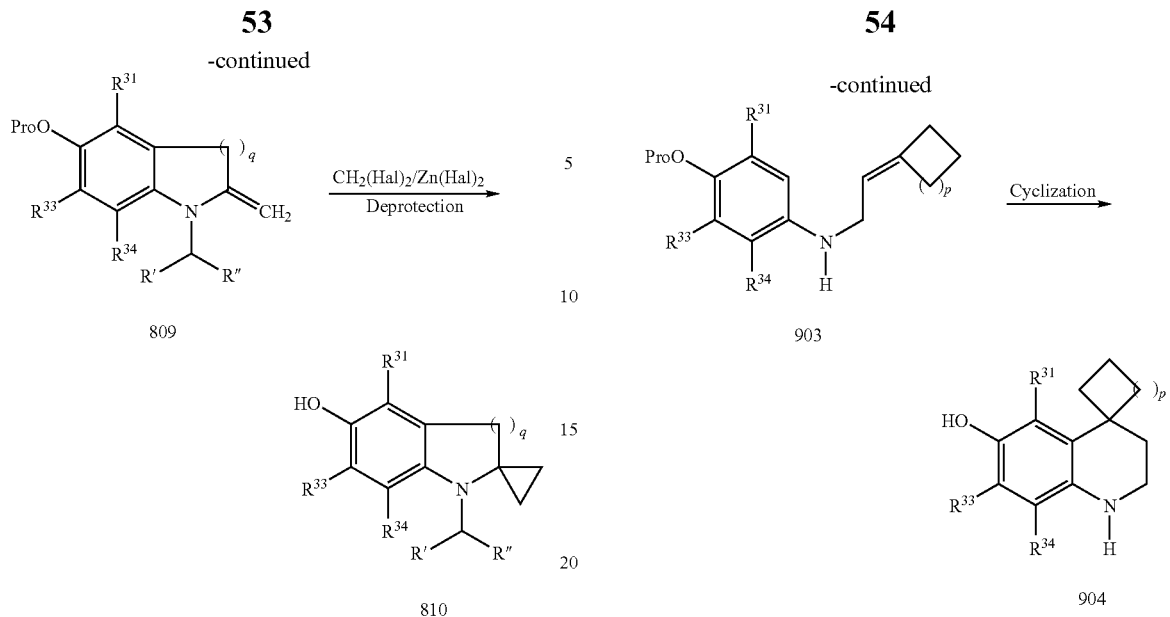

Scheme 8 describes a synthesis for compounds of Formula III of the present invention wherein q is 1 or 2, —$CR^9R^{10}$ form a cyclopropyl ring; $R^5$, $R^6$, are hydrogen; R is —CR'R" wherein R' and R" are alkyl, alkenyl and together may form a ring optionally including an additional heteroatom such as N, O or S; and $R^1$, $R^3$, $R^4$ are as defined above. Nitration of compound of formula 801 can be effected, for example, by nitric acid or with esters of nitric acid such as ethyl nitrate, or other nitration reagents well known in the art. The hydroxy group of compound of formula 802 is protected with a group such as triisopropylsilyl chloride or butyldimethysilyl chloride, and the protected compound of formula 803, wherein Pro is a protective group, is reduced with, for example, iron or hydrogen/palladium to give the amino compound of formula 804. Reductive alkylation may be effected with reducing agents such as sodium cyanoborohydride or sodium borohydride in the presence of an acid such as formic acid or acetic acid, or with Zn and hydrochloric acid to give a compound of formula 805. Acylation of the amino group with an acyl halide of formula 806 wherein q is 1 or 2 and Hal is a halogen group, may give compound of formula 807, which can undergo cyclization and deprotection under Friedel-Crafts conditions with for example $AlCl_3$ to give a compound of formula 808. Methylenation of the carbonyl group may be effected with the titanium carbene complex (Tebbe) reagent available from Sigma-Aldrich or with methyl phosphonium (Wittig reaction) under basic conditions, followed by cyclopropylation with dihalomethane and dihalo zinc or diethyl zinc. Deprotection with, for example, tetrabutyl ammonium fluoride may yield a compound of formula 810.

Scheme 9A describes a synthesis for compounds of Formula III of the present invention wherein —$CR^{35}R^{36}$ form a cyclopropyl or a cyclobutyl ring; $R^{37}$, $R^{38}$, $R^{39}$, $R^{310}$ are hydrogen, $R^{30}$ is hydrogen. Compound 901 that may be synthesized similarly to the compound of formula 105 in scheme 1, can be treated with an allyl halide of formula 902, wherein L is a leaving group such as a halide for example a chloride, a bromide or an iodide, and p is 0 or 1, to give a compound of formula 903 wherein Pro is a protective group. Internal cyclization with a Lewis acid such as boron trifluoride, followed by deprotection may yield a compound of formula 904 wherein p is 0 or 1. Coupling of a compound of formula 904 with a compound $R^{30}L$ wherein $R^{30}$ is as described herein but not hydrogen, and L is a leaving group such as an halide for example a chloride, a bromide or an iodide may yield a derivative of Formula III with $R^{30}$ substitution on the nitrogen atom.

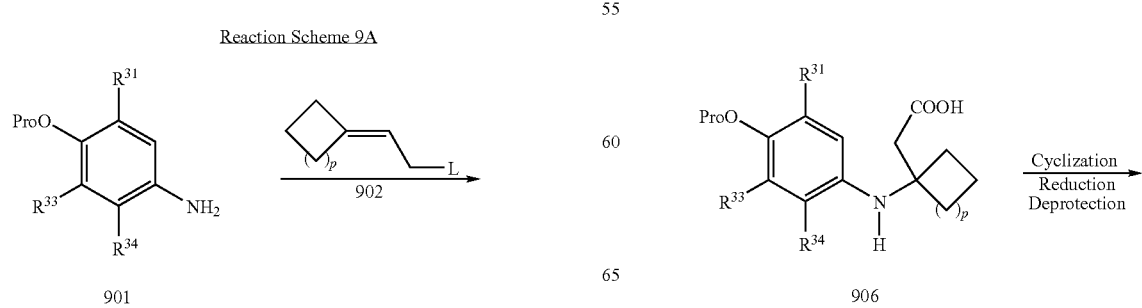

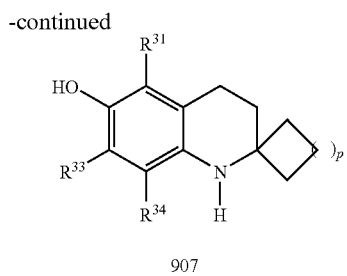

907

Similarly, Scheme 9B describes the synthesis for compounds of Formula III wherein $R^{39}$ and $R^{310}$ form a cyclopropyl or a cyclobutyl ring; $R^{35}$, $R^{36}$, $R^{37}$, $R^{38}$ are hydrogen, and $R^{30}$ is hydrogen, starting from compound of formula 901, wherein Pro is a protective group, and treating it with a cycloalkylidene carboxylate of formula 905, wherein Alk is alkyl to give a compound of formula 906. Internal cyclization with a Lewis acid, followed by reduction and deprotection may yield compound of formula 907. Coupling of compound of formula 907 with a compound $R^{30}L$ wherein $R^{30}$ is as described herein but not hydrogen, and L is a leaving group such as an halide for example a chloride, a bromide or an iodide may yield a derivative of Formula III with $R^{30}$ substitution on the nitrogen atom.

Reaction Scheme 9C

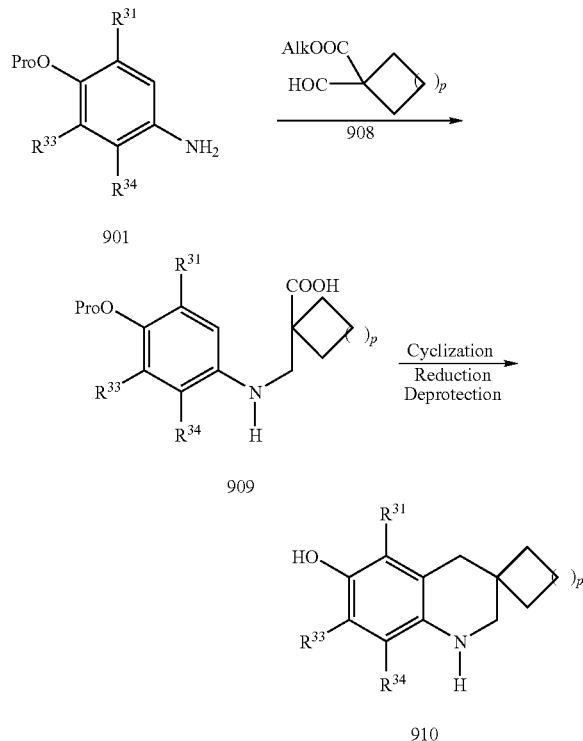

Similarly Scheme 9C describes the synthesis for compounds of Formula III wherein $R^{37}$ and $R^{38}$ form a cyclobutyl or a cyclopropyl ring, $R^{35}$, $R^{36}$, $R^{39}$, $R^{310}$ are hydrogen, and $R^{30}$ is hydrogen, starting from compound of formula 901, wherein Pro is a protective group, and treating it with an aldehyde of formula 908, wherein Alk is alkyl and p is 0-1, to give a compound of formula 909. Internal cyclization with a Lewis acid, followed by reduction and deprotection may yield compound of formula 910. Coupling of compound of formula 910 with an halide of Formula $R^{30}L$ wherein $R^{30}$ is as described herein but not hydrogen, and L is a leaving group such as an halide for example a chloride, a bromide or an iodide, may yield a derivative of Formula III with $R^{30}$ substitution on the nitrogen atom.

The reaction scheme examples given herein should not be considered as limiting the scope of the invention, but merely as being illustrative and representative thereof. The features of the invention will become more fully apparent when the schemes are considered in conjunction with the Examples.

Preferred Compounds

The compounds of Formula I, IA, IB, II, IIA, III, and IIIA encompass the spiro derivatives of the invention as disclosed, and/or the pharmaceutically acceptable salts, solvates, or polymorphs of such compounds. In addition, the compounds of this invention include the individual stereochemical isomers and mixtures thereof, arising from the selection of substituent groups. Certain compounds of this invention may exist in isomeric forms. The invention contemplates all such stereoisomers both in pure form and in admixture, as well as racemic mixtures.

Examples of compounds of the invention include, but are not limited to those shown in the tables below:

| EXEMPLARY COMPOUNDS OF FORMULA I, IA, IB | |
|---|---|
| STRUCTURE | NAME |
| | 5,7,8-Trimethyl-3,4-dihydrospiro-[chromene-2,1'-cyclobutan]-6-ol |
| | 5-Chloro-7,8-dimethyl-3,4-dihydrospiro-[chromene-2,1'-cyclobutan]-6-ol |
| | 5',7',8'-Trimethyl-2',3'-dihydrospiro-[cyclobutane, 1,4'-thiochromen]-6'-ol |
| | 7-Chloro-7,8-dimethyl-3,4-dihydrospiro-[chromene-2,1'-cyclobutan]-6-ol |

-continued

EXEMPLARY COMPOUNDS OF FORMULA I, IA, IB

| STRUCTURE | NAME |
|---|---|
| 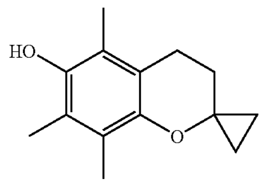 | 5,7,8-Trimethyl-3,4-dihydrospiro-[chromene-2,1'-cyclopropan]-6-ol |
| 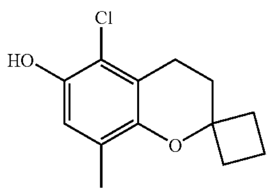 | 5-Chloro-8-methyl-3,4-dihydrospiro-[chromene,2,1'-cyclobutan]-6-ol |
| 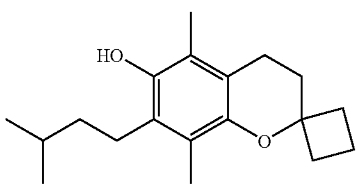 | 5,8-Dimethyl-7-(3-methylbutyl)-3,4-dihydrospiro-[chromene-2,1'-cyclobutan]-6-ol |
| 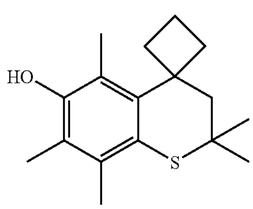 | 2',2',5',7',8'-Pentamethyl-2',3'-dihydrospiro-[cyclobutane-1,4'-thiochromen]-6'-ol |
| 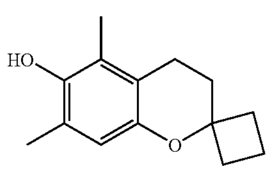 | 5,7-Dimethyl-3,4-dihydrospiro-[chromene,2,1'-cyclobutan]-6-ol |
| 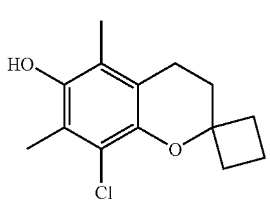 | 8-Chloro-5,7-dimethyl-3,4-dihydrospiro-[chromene-2,1'-cyclobutan]-6-ol |
| 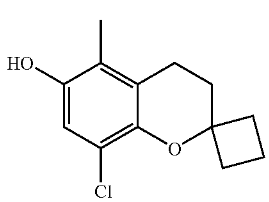 | 8-Chloro-5-methyl-3,4-dihydrospiro-[chromene-2,1'-cyclobutan]-6-ol |

-continued

EXEMPLARY COMPOUNDS OF FORMULA I, IA, IB

| STRUCTURE | NAME |
|---|---|
| 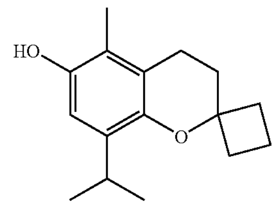 | 8-Isopropyl-5-methyl-3,4-dihydrospiro-[chromene-2,1'-cyclobutan]-6-ol |
| 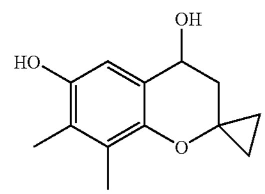 | 7,8-Dimethyl-3,4-dihydrospiro-[chromene-2,1'-cyclopropane]-4,6-diol |
| 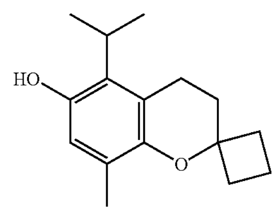 | 5-Isopropyl-8-methyl-3,4-dihydrospiro-[chromene-2,1'-cyclobutan]-6-ol |
| 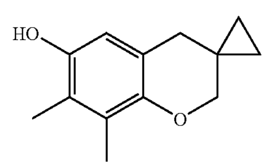 | 7,8-Dimethylspiro[chroman-3,1'-cyclopropan]-6-ol |
| 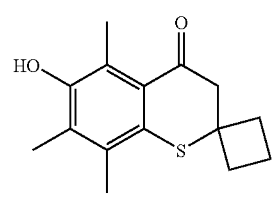 | 6'-Hydroxy-5',7',8'-trimethylspiro-[cyclobutan-1,2'-thiochroman]-4'-one |
| 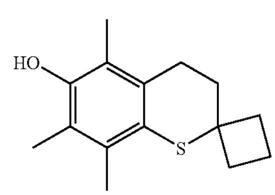 | 5',7',8'-Trimethyl-3',4'-dihydrospiro-[cyclobutane-1,2'-thiochromen]-6'-ol |
| 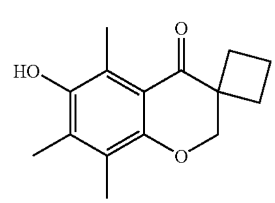 | 6-Hydroxy-5,7,8-trimethylspiro-[chroman-3,1'-cyclobutane]-4-one |

EXEMPLARY COMPOUNDS OF FORMULA I, IA, IB

| STRUCTURE | NAME |
|---|---|
| | 5,7,8-Trimethylspiro[chroman-3,1'-cyclobutan]-4,6-diol |
| | 6'-Hydroxy-5',7',8'-trimethylspiro[cyclobutane-1,2'-thiochromen]-4'(3'H)-one O-methyloxime |
| | 4'-(Methoxyamino)-5',7',8'-trimethyl-3',4'-dihydrospiro[cyclobutane-1,2'-thiochromen]-6'-ol |
| | 5,7,8-Trimethylspiro[chroman-3,1'-cyclobutan]-6-ol |
| | 4-Methoxy-5,7,8-trimethylspiro[chroman-3,1'-cyclobutan]-6-ol |
| | 4-Ethoxy-5,7,8-trimethylspiro[chroman-3,1'-cyclobutan]-6-ol |
| | 4-(Methoxyamino)-5,7,8-trimethyl-3,4-dihydrospiro[chromene-2,1'-cyclobutan]-6-ol |
| | 4-(Hexylamino)-5,7,8-trimethylspiro[chroman-3,1'-cyclobutan]-6-ol |
| | 3-Methoxy-5,7,8-trimethyl-3,4-dihydrospiro[chromene-2,1'-cyclobutan]-6-ol |
| | 6-Hydroxy-3,5,7,8-tetramethylspiro[chroman-2,1'-cyclobutan]-4(3H)-one |
| | 4-Methoxy-5,7,8-trimethyl-3,4-dihydrospiro[chromene-2,1'-cyclobutan]-6-ol |
| | 6-Hydroxy-5,7,8-trimethyl-3,4-dihydrospiro[chromene-2,1'-cyclobutane]-4-carbonitrile |
| | Methyl {[(6-hydroxy-5,7,8-trimethyl-3,4-dihydrospiro[chromene-2,1'-cyclobutan]-3-yl)methyl]thio}acetate |
| | 4-Ethoxy-5,7,8-trimethyl-3,4-dihydrospiro[chromene-2,1'-cyclobutan]-6-ol |

EXEMPLARY COMPOUNDS OF FORMULA I, IA, IB

| STRUCTURE | NAME |
|---|---|
| 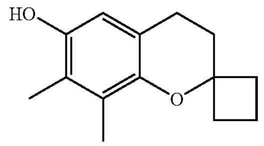 | 7,8-Dimethyl-3,4-dihydrospiro-[chromene-2,1'-cyclobutan]-6-ol |
| 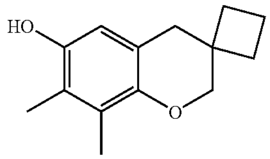 | 7,8-Dimethyl-4H-spiro-[chroman-3,1'-cyclobutan]-6-ol |
| 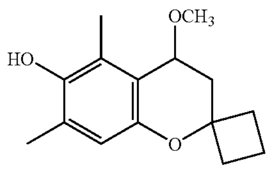 | 4-Methoxy-5,7-dimethyl-3,4-dihydrospiro-[chromene-2,1'-cyclobutan]-6-ol |
| 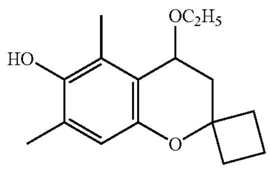 | 4-Ethoxy-5,7-dimethyl-3,4-dihydrospiro-[chromene-2,1'-cyclobutan]-6-ol |
| 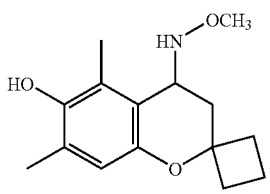 | 4-(Methoxyamino)-5,7-dimethyl-3,4-dihydrospiro-[chromene-2,1'-cyclobutan]-6-ol |
| 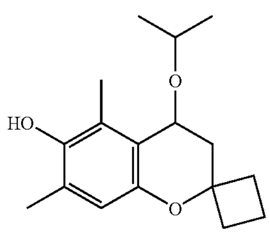 | 4-Isopropoxy-5,7-dimethyl-3,4-dihydrospiro-[chromene-2,1'-cyclobutan]-6-ol |
| 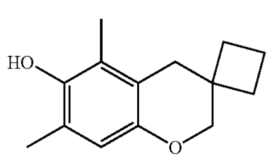 | 5,7-Dimethylspiro-[chroman-3,1'-cyclobutan]-6-ol |
| 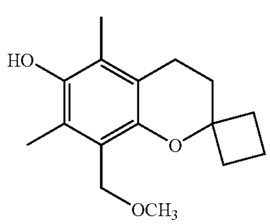 | 8-(Methoxymethyl)-5,7-dimethyl-3,4-dihydrospiro-[chromene-2,1'-cyclobutan]-6-ol |
| | 4-(Cyclopentyloxy)-5,7,8-trimethyl-3,4-dihydrospiro-[chromene-2,1'-cyclobutane]-6-diol |
| | 4-(Ethoxyamino)-5,7,8-trimethyl-3,4-dihydrospiro-[chromene-2,1'-cyclobutan]-6-ol |
| | 4-(Isopropylthio)-5,7,8-trimethyl-3,4-dihydrospiro-[chromene-2,1'-cyclobutan]-6-ol |
| | 7,8-Dimethyl-3,4-dihydrospiro-[chromene-2,1'-cyclobutane]-4,6-diol |
| | 4'-(Ethoxyamino)-5',7',8'-trimethyl-3',4'-dihydrospiro-[cyclobutane-1,2'-thiochromen]-6'-ol |
| | 4'-(Ethoxyamino)-5',7'-dimethyl-3',4'-dihydrospiro-[cyclobutane-1,2'-thiochromen]-6'-ol |

EXEMPLARY COMPOUNDS OF FORMULA I, IA, IB

| STRUCTURE | NAME |
|---|---|
| | 4-(Ethoxyamino)-5,7-dimethyl-3,4-dihydrospiro[chromene-2,1'-cyclobutan]-6-ol |
| | 4'-(Methoxyamino)-5',7'-dimethyl-3',4'-dihydrospiro[cyclobutane-1,2'-thiochromen]-6'-ol |
| | 4-(Ethoxyamino)-7,8-dimethyl-3,4-dihydrospiro[chromene-2,1'-cyclobutan]-6-ol |
| | 4-(Hydroxyamino)-5,7,8-trimethyl-3,4-dihydrospiro[chromene-2,1'-cyclobutan]-6-ol |
| | 8-[(Methoxyamino)methyl]-5,7-dimethyl-3,4-dihydrospiro[chromene-2,1'-cyclobutan]-6-ol |
| | 5,7-Dimethyl-8-vinyl-3,4-dihydrospiro[chromene-2,1'-cyclobutan]-6-ol |
| | 4-(Hydroxy(methyl)amino)-5,7,8-trimethylspiro[chroman-2,1'-cyclobutan]-6-ol |
| | 6-Hydroxy-5,7-dimethylspiro[chromene-2,1'-cyclobutan]-4(3H)-one oxime |
| | 4-(Hydroxy(methyl)amino)-5,7-dimethylspiro[chroman-2,1'-cyclobutan]-6-ol |
| | 8-[(Ethoxyamino)methyl]-5,7-dimethyl-3,4-dihydrospiro[chromene-2,1'-cyclobutan]-6-ol |
| | Benzyl-methoxy(6-hydroxy-5,7-dimethyl-3,4-dihydrospiro[chromene-2,1'-cyclobutan]-4-yl)carbamate |
| | 6-Hydroxy-5,7-dimethylspiro[chromene-2,1'-cyclobutan]-4(3H)-one O-methyloxime |
| | (4E)-6-Hydroxy-5,7-dimethylspiro[chromene-2,1'-cyclobutan]-4(3H)-one O-ethyloxime |
| | (4Z)-6-Hydroxy-5,7-dimethylspiro[chromene-2,1'-cyclobutan]-4(3H)-one O-ethyloxime |

-continued

EXEMPLARY COMPOUNDS OF FORMULA I, IA, IB

| STRUCTURE | NAME |
|---|---|
| 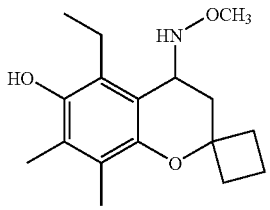 | 5-Ethyl-4-(methoxyamino)-7,8-dimethyl-3,4-dihydrospiro-[chromene-2,1'-cyclobutan]-6-ol |
| 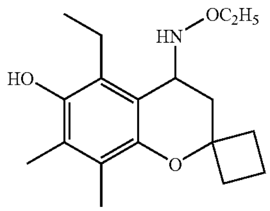 | 4-(Ethoxyamino)-5-ethyl-7,8-dimethyl-3,4-dihydrospiro-[chromene-2,1'-cyclobutan]-6-ol |
| 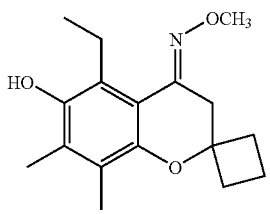 | 5-Ethyl-6-hydroxy-7,8-dimethylspiro-[chromene-2,1'-cyclobutan]-4(3H)-one O-methyloxime |
| 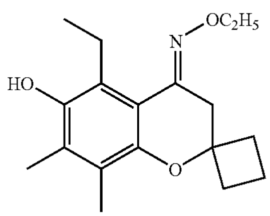 | 5-Ethyl-6-hydroxy,7,8-dimethylspiro-[chromene-2,1'-cyclobutan]-4(3H)-one O-ethyloxime |
| | 6'-Hydroxy-5',7',8'-trimethylspiro-[cyclobutane-1,2'-thiochromen]-4'(3'H)-one O-methyloxime |
| | 6'-Hydroxy-5',7',8'-trimethylspiro-[cyclobutane-1,2'-thiochromen]-4'(3'H)-one O-ethyloxime |
| 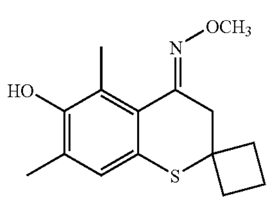 | 6'-Hydroxy-5',7'-dimethylspiro-[cyclobutane-1,2'-thiochromen]-4'(3'H)-one O-methyloxime |

-continued

EXEMPLARY COMPOUNDS OF FORMULA I, IA, IB

| STRUCTURE | NAME |
|---|---|
| 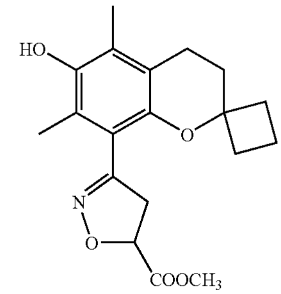 | Methyl 3-(6-hydroxy-5,7-dimethyl-3,4-dihydrospiro-[chromene-2,1'-cyclobutan]-8-yl)-4,5-dihydroisoxazole-5-carboxylate |
| 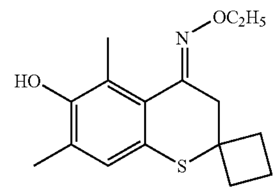 | 6'-Hydroxy-5'-7'-dimethylspiro-[cyclobutane-1,2'-thiochromen]-4'(3'H)-one O-ethyloxime |
| 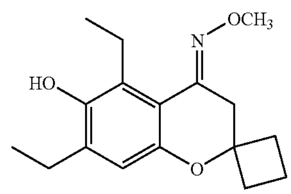 | 5,7-Diethyl-6-hydroxyspiro-[chromene-2,1'-cyclobutan]-4(3H)-one O-methyloxime |
| 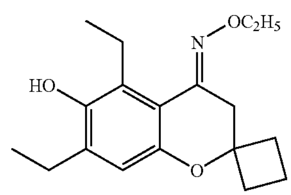 | 5,7-Diethyl-6-hydroxyspiro-[chromene-2,1'-cyclobutan]-4(3H)-one O-ethyloxime |
| 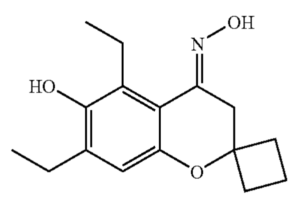 | 5,7-Diethyl-6-hydroxyspiro-[chromene-2,1'-cyclobutan]-4(3H)-one oxime |
| 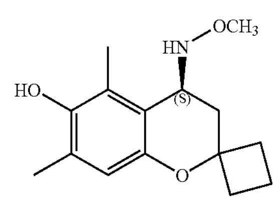 | (4R)-4-(Methoxyamino)-5,7-dimethyl-3,4-dihydrospiro-[chromene-2,1'-cyclobutan]-6-ol |
| 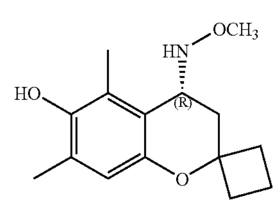 | (4S)-4-(Methoxyamino)-5,7-dimethyl-3,4-dihydrospiro-[chromene-2,1'-cyclobutan]-6-ol |

EXEMPLARY COMPOUNDS OF FORMULA I, IA, IB

| STRUCTURE | NAME |
|---|---|
| 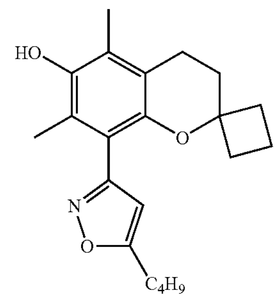 | 5,7-Dimethyl-8-(5-butyl-isoxazol-3-yl)-3,4-dihydrospiro-[chromene-2,1'-cyclobutan]-6-ol |
| 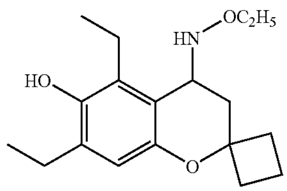 | 4-(Ethoxyamino)-5,7-diethyl-3,4-dihydrospiro-[chromene-2,1'-cyclobutan]-6-ol |
| 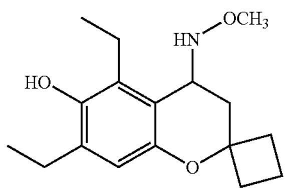 | 4-(Methoxyamino)-5,7-diethyl-3,4-dihydrospiro-[chromene-2,1'-cyclobutan]-6-ol |
| 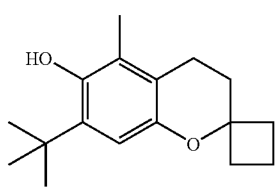 | 7-tert-Butyl-5-methyl-3,4-dihydrospiro-[chromene-2,1'-cyclobutan]-6-ol |
| 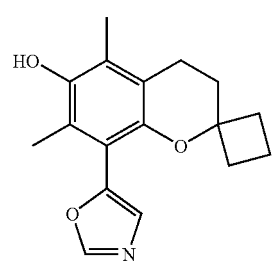 | 5,7-Dimethyl-8-(1,3-oxazol-5-yl)-3,4-dihydrospiro-[chromene-2,1'-cyclobutan]-6-ol |
| 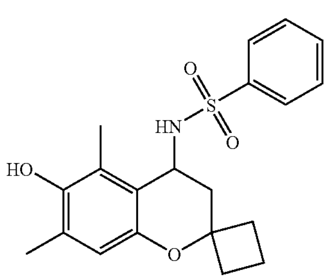 | N-(6-Hydroxy-5,7-dimethyl-3,4-dihydrospiro-[chromene-2,1'-cyclobutan]-4-yl)-benzenesulfonamide |
| | 5,7-Diisopropyl-3,4-dihydrospiro-[chromene-2,1'-cyclobutan]-6-ol |
| | 6-Hydroxy-5,7-diisopropyl-3,4-dihydrospiro-[chromene-2,1'-cyclobutane]-8-carbaldehyde |
| | 3-[(Methoxyamino)-methyl]-5,7-dimethyl-3,4-dihydrospiro-[chromene-2,1'-cyclobutan]-6-ol |
| | 5,7-Dimethyl-3-(1,3-oxazol-5-yl)spiro-[chromene-2,1'-cyclobutan]-6-ol |
| | 5,7-Diisopropyl-8-[(methoxyamino)methyl]-3,4-dihydrospiro-[chromene-2,1'-cyclobutan]-6-ol |
| | 5-(3,7-Dimethylocta-2,6-dienyl)-7,8-dimethylspiro-[chroman-2,1'-cyclobutan]-6-ol |

EXEMPLARY COMPOUNDS OF FORMULA I, IA, IB

| STRUCTURE | NAME |
|---|---|
| 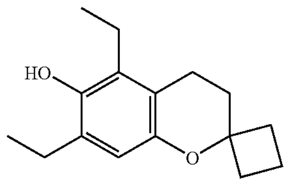 | 5,7-Diethyl-3,4-dihydrospiro-[chromene-2,1'-cyclobutan]-6-ol |
| 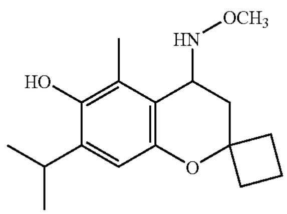 | 7-Isopropyl-4-(methoxyamino)-5-methyl-3,4-dihydrospiro-[chromene-2,1'-cyclobutan]-6-ol |
| 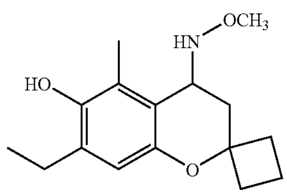 | 7-Ethyl-4-(methoxyamino)-5-methyl-3,4-dihydrospiro-[chromene-2,1'-cyclobutan]-6-ol |
| 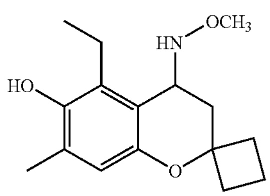 | 5-Ethyl-4-(methoxyamino)-7-methyl-3,4-dihydrospiro-[chromene-2,1'-cyclobutan]-6-ol |
| 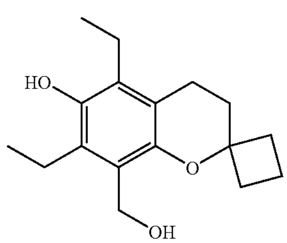 | 5,7-Diethyl-8-(hydroxymethyl)-3,4-dihydrospiro-[chromene-2,1'-cyclobutan]-6-ol |
| 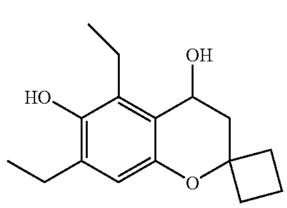 | 5,7-Diethyl-8-(hydroxymethyl)3,4-dihydrospiro-[chromene-2,1'-cyclobutan]-6-ol |
| 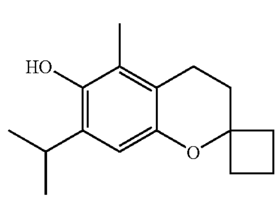 | 7-Isopropyl-5-methyl-3,4-dihydrospiro-[chromene-2,1'-cyclobutan]-6-ol |
| | 8-(Hydroxymethyl)-7-isopropyl-5-methylspiro-[chroman-2,1'-cyclobutan]-6-ol |
| | 5,7-Dimethyl-3-(oxazol-5-yl)spiro-[chroman-2,1'-cyclobutan]-6-ol |
| | 7-Isopropyl-5-methylspiro-[chroman-2,1'-cyclobutane]-4,6-diol |
| | 5,7-Diethyl-6-hydroxyspiro-[chroman-2,1'-cyclobutane]-3-yl)methyl carbamate |
| | 7-Isopropyl-4-methoxy-5-methylspiro-[chroman-2,1'-cyclobutan]-6-ol |
| | 8-(Hydroxymethyl)-5,7-diisopropylspiro-[chroman-2,1'-cyclobutan]-6-ol |
| | 8-((Hydroxyamino)methyl)-5,7-diisopropylspiro-[chroman-2,1'-cyclobutan]-6-ol |

-continued

EXEMPLARY COMPOUNDS OF FORMULA I, IA, IB

| STRUCTURE | NAME |
|---|---|
| 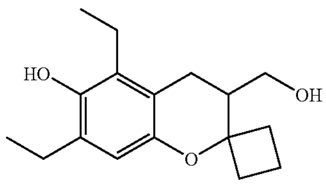 | 5,7-Diethyl-3-(hydroxymethyl)spiro-[chroman-2,1'-cyclobutan]-6-ol |
| 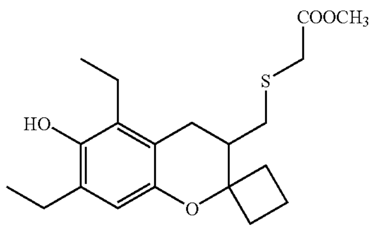 | Methyl 2-((5,7-diethyl-6-hydroxyspiro-[chroman-2,1'-cyclobutane]-3-yl)-methylthio) acetate |
| 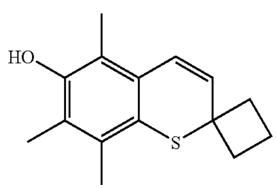 | 5',7',8'-Trimethylspiro-[cyclobutane-1,2'-thiochromen]-6'-ol |
| 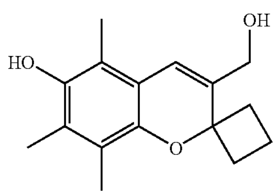 | 3-(Hydroxymethyl)-5,7,8-trimethylspiro-[chromene-2,1'-cyclobutan]-6-ol |
| 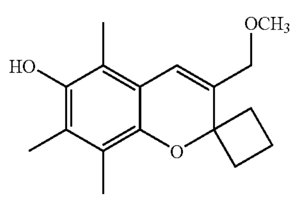 | 3-(Methoxymethyl)-5,7,8-trimethylspiro-[chromene-2,1'-cyclobutan]-6-ol |
| 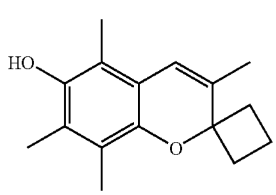 | 3,5,7,8-Tetramethylspiro-[chromene-2,1'-cyclobutan]-6-ol |
| 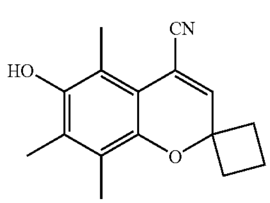 | 6-Hydroxy-5,7,8-trimethylspiro-[chromene-2,1'-cyclobutane]-4-carbonitrile |

-continued

EXEMPLARY COMPOUNDS OF FORMULA I, IA, IB

| STRUCTURE | NAME |
|---|---|
| 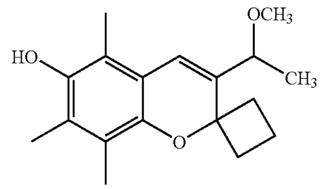 | 3-(1-Methoxyethyl)-5,7,8-trimethylspiro-[chromene-2,1'-cyclobutan]-6-ol |
| 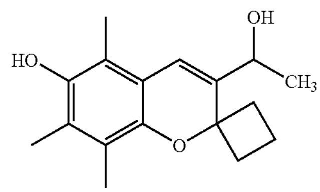 | 3-(1-Hydroxyethyl)-5,7,8-trimethylspiro-[chromene-2,1'-cyclobutan]-6-ol |
| 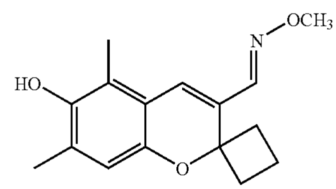 | 6-Hydroxy-5,7-dimethylspiro-[chromene-2,1'-cyclobutane]-3-carbaldehyde O-methyloxime |
| 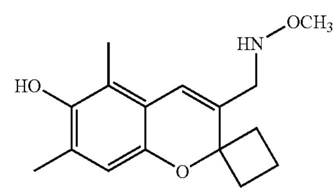 | 3-[(Methoxyamino)-methyl]-5,7-dimethylspiro-[chromene-2,1'-cyclobutan]-6-ol |
| 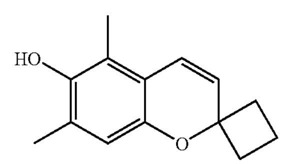 | 5,7-Dimethylspiro-[chromene-2,1'-cyclobutan]-6-ol |
| 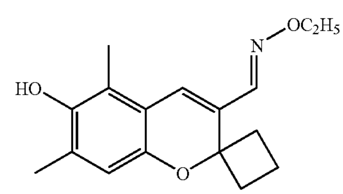 | 6-Hydroxy-5,7-dimethylspiro-[chromene-2,1'-cyclobutane]-3-carbaldehyde O-ethyloxime |
| 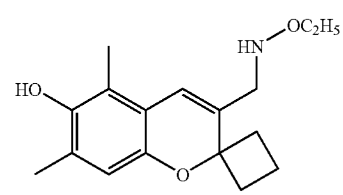 | 3-[(Ethoxyamino)-methyl]-5,7-dimethylspiro-[chromene-2,1'-cyclobutan]-6-ol |
|  | 5,7-Diethylspiro-[chromene-2,1'-cyclobutan]-6-ol |

-continued

| EXEMPLARY COMPOUNDS OF FORMULA I, IA, IB | |
|---|---|
| STRUCTURE | NAME |
| | 5,7-Diisopropylspiro-[chromene-2,1'-cyclobutan]-6-ol |
| | 7-Isopropyl-5-methylspiro-[chromene-2,1'-cyclobutan]-6-ol |

| EXEMPLARY COMPOUNDS OF FORMULA III, IIIA | |
|---|---|
| STRUCTURE | NAME |
| | 1'-(4-Chlorophenyl)-5',7',8'-trimethyl-2',4'-dihydro-1'H-spiro[cyclobutane-1,3'-quinoline]-4',6'-diol |
| | 1'-Ethyl-7',8'-dimethyl-2',4'-dihydro-1'H-spiro[cyclobutane-1,3'-quinoline]-6'-ol |
| | 7',8'-Dimethyl-1'-(pyridin-2-yl)-2',4'-dihydro-1'H-spiro[cyclobutane-1,3'-quinolin]-6'-ol |

-continued

| EXEMPLARY COMPOUNDS OF FORMULA III, IIIA | |
|---|---|
| STRUCTURE | NAME |
| | 1'-(4-Hydroxyphenyl)-7',8'-dimethyl-2',4'-dihydro-1'H-spiro[cyclobutane-1,3'-quinoline]-6'-ol |
| | 4-(6'-Methoxy-7',8'-dimethyl-2',4'-dihydro-1'H-spiro[cyclobutane-1,3'-quinoline]-1'-yl)phenol |
| | 7',8'-Dimethyl-1'-p-tolyl-2',4'-dihydro-1'H-spiro[cyclobutane-1,3'-quinolin]-6'-ol |
| | 1'-(3-Hydroxyphenyl)-7',8'-dimethyl-2',4'-dihydro-1'H-spiro[cyclobutane-1,3'-quinolin]-6'-ol |
| | Methyl 4-(6'-hydroxy-7',8'-dimethyl-2',4'-dihydro-1'H-spiro[cyclobutane-1,3'-quinoline]-1'-yl)benzoate |

-continued

EXEMPLARY COMPOUNDS OF FORMULA III, IIIA

| STRUCTURE | NAME |
|---|---|
| 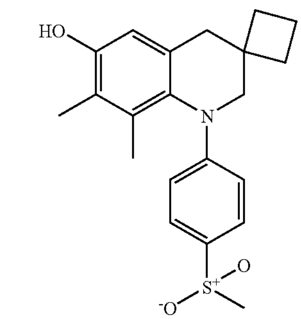 | 7',8'-Dimethyl-1'-(4-(methylsulfonyl)phenyl)-2',4'-dihydro-1'H-spiro[cyclobutane-1,3'-quinolin]-6'-ol |
| 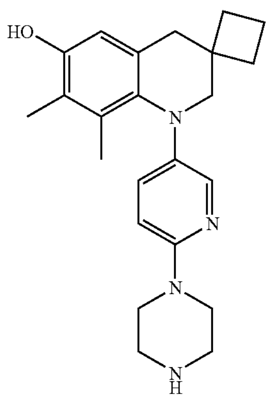 | 7',8'-Dimethyl-1'-(6-(piperazin-1-yl)pyridin-3-yl)-2',4'-dihydro-1'H-spiro[cyclobutane-1,3'-quinolin]-6'-ol |
| 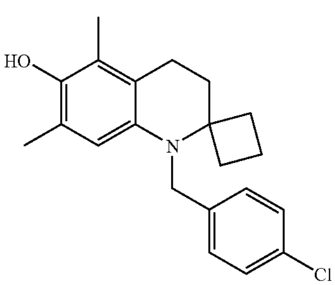 | 1'-(4-Chlorobenzyl)-5',7'-dimethyl-3',4'-dihydro-1'H-spiro[cyclobutane-1,2'-quinolin]-6'-ol |
| 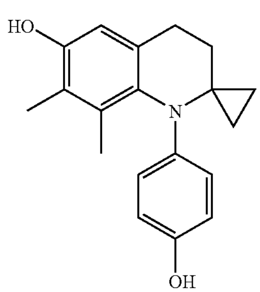 | 1'-(4-Hydroxyphenyl)-7',8'-dimethyl-3',4'-dihydro-1'H-spiro[cyclopropane-1,2'-quinolin]-6'-ol |
| 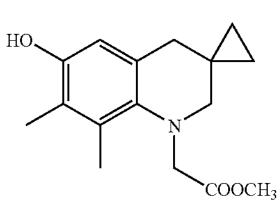 | Methyl 2-(6'-hydroxy-7',8'-dimethyl-2',4'-dihydro-1'H-spiro[cyclopropane-1,3'-quinoline]-1'-yl)acetate |

-continued

EXEMPLARY COMPOUNDS OF FORMULA III, IIIA

| STRUCTURE | NAME |
|---|---|
| 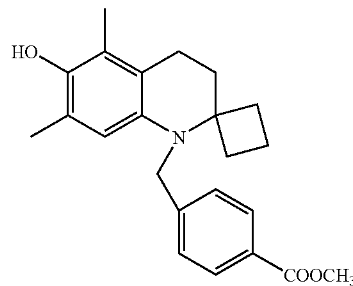 | Methyl 4-((6'-hydroxy-5',7'-dimethyl-3',4'-dihydro-1'H-spiro[cyclobutane-1,2'-quinoline]-1'-yl)methyl)benzoate |
| 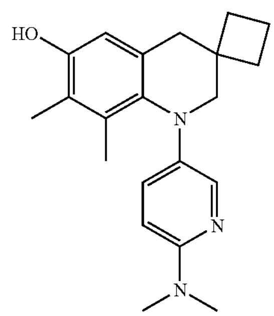 | 1'-(6-(Dimethylamino)-pyridin-3-yl)-7',8'-dimethyl-2',4'-dihydro-1'H-spiro[cyclobutane-1,3'-quinolin]-6'-ol |
| 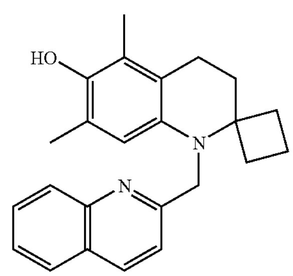 | 5',7'-Dimethyl-1'-(quinolin-2-ylmethyl)-3',4'-dihydro-1'H-spiro[cyclobutane-1,2'-quinolin]-6'-ol |
| 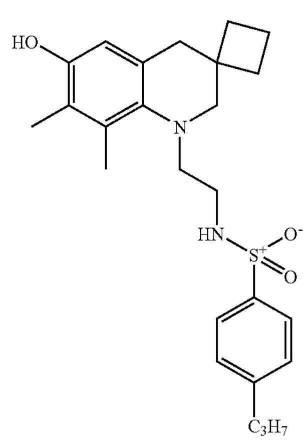 | N-(2-(6'-Hydroxy-7',8'-dimethyl-2',4'-dihydro-1'H-spiro[cyclobutane-1,3'-quinoline]-1'-yl)ethyl)-4-propylbenzenesulfonamide |

-continued

EXEMPLARY COMPOUNDS OF FORMULA III, IIIA

| STRUCTURE | NAME |
|---|---|
| 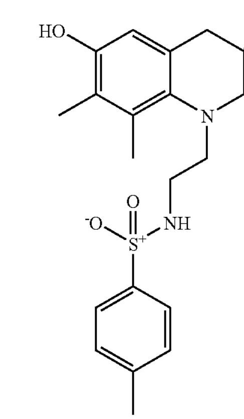 | N-(2-(6'-Hydroxy-7',8'-dimethyl-2',4'-dihydro-1'H-spiro[cyclobutane-1,3'-quinoline]-1'-yl)ethyl)-4-methylbenzenesulfonamide |
| 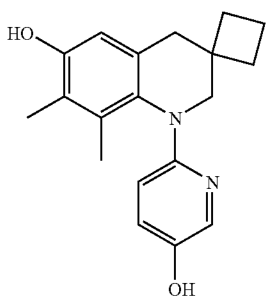 | 1'-(5-Hydroxypyridin-2-yl)-7',8'-dimethyl-2',4'-dihydro-1'H-spiro[cyclobutane-1,3'-quinolin]-6'-ol |
| 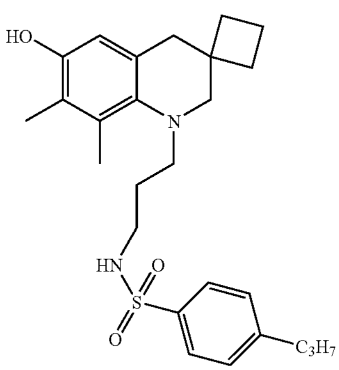 | N-(3-(6'-Hydroxy-7',8'-dimethyl-2',4'-dihydro-1'H-spiro[cyclobutane-1,3'-quinoline]-1'-yl)propyl)-4-propylbenzenesulfonamide |
| 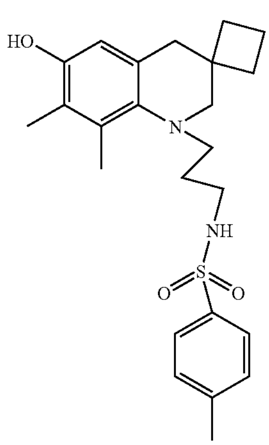 | N-(3-(6'-Hydroxy-7',8'-dimethyl-2',4'-dihydro-1'H-spiro[cyclobutane-1,3'-quinoline]-1'-yl)propyl)-4-methylbenzenesulfonamide |
| | N-(3-(6'-Hydroxy-7',8'-dimethyl-2',4'-dihydro-1'H-spiro[cyclobutane-1,3'-quinoline]-1'-yl)propyl)-methanesulfonamide |
| | N-(3-(6'-Hydroxy-7',8'-dimethyl-2',4'-dihydro-1'H-spiro[cyclobutane-1,3'-quinoline]-1'-yl)propyl)-benzamide |
| | N-(2-(6'-Methoxy-7',8'-dimethyl-2',4'-dihydro-1'H-spiro[cyclobutane-1,3'-quinoline]-1'-yl)ethyl)-4-propyl-benzenesulfonamide |

It will be understood by those skilled in the art with respect to any group containing one or more substituents that such groups are not intended to introduce any substitution or substitution patterns that are sterically impractical and/or synthetically non-feasible.

Utility, Testing and Administration

General Utility

Without subscribing to a particular theory or mechanism of action, compounds of the invention may target certain enzymes known as "oxidoreductases" that function widely across a variety of physiological processes, for example, certain compounds of the present invention may target lipoxygenases such as 5-Lipoxygenase, 12-Lipoxygenase, 15-Lipoxygenase, and/or 12/15-Lipoxygenase. In particular, oxidoreductases catalyze reactions in which two molecules interact so that one molecule is oxidized and the other is reduced. Alterations in oxidoreductases are thought to account for as many as 3% of all known human genetic diseases. Abnormalities in oxidoreductase activity may underlie such disorders as congestive heart failure, respiratory chain defects (e.g., abnormalities associated with enzymes of the respiratory chain, acute respiratory distress syndrome (ARDS)), glycogen storage disease, end-stage renal disease, and rheumatoid arthritis. Inhibitors of lipoxygenases are known to be useful in the prevention or treatment of, for example, disorders selected from apoptosis in cancer cells including prostatic cancer, gastric cancer, breast cancer, pancreatic cancer, colorectal or esophageal cancer and airways carcinoma; diseases involving hypoxia or anoxia, including atherosclerosis, myocardial infarction, cardiovascular disease, heart failure (including chronic and congestive heart failure), cerebral ischemia, retinal ischemia, myocardial ischemia, post surgical cognitive dysfunction and other ischemias; diseases involving inflammation, including diabetes, arterial inflammation, inflammatory bowel disease, Crohn's disease, renal disease, pre-menstrual syndrome, asthma, allergic rhinitis, gout, cardiopulmonary inflammation, rheumatoid arthritis, osteoarthritis, muscle fatigue and inflammatory disorders of the skin including acne, dermatitis and psoriasis; disorders of the airways including asthma, chronic bronchitis, human airway carcinomas, mucus hypersecretion, chronic obstructive pulmonary disease (COPD), pulmonary fibrosis caused by chemotherapy or other drugs, idiopathic pulmonary fibrosis, cystic fibrosis, and adult respiratory distress syndrome; diseases involving central nervous system (CNS) disorders including psychiatric disorders including anxiety and depression; neurodegeneration and neuroinflammation including Alzheimer's, dementia and Parkinson's disease; peripheral neuropathy including spinal chord injury, head injury and surgical trauma, and allograft tissue and organ transplant rejection; diseases involving the autoimmune system including psoriasis, eczema, rheumatoid arthritis, and diabetes; and disorders involving bone loss or bone formation Certain compounds of the present invention are also useful in treating conditions falling with the group of dermatologic conditions, such as prevention and protection of skin tissue against age-related damage or damage resulting from insults such as harmful ultraviolet (UV) radiation, use of retinoids, wearing diapers, stress and fatigue, and in the treatment of contact dermatitis, skin irritation, skin pigmentation, psoriasis, or acne.

Testing

This section describes how compositions incorporating compositions of the present invention are selected, using in vitro and/or in vivo models, and used as therapeutic interventions in the exemplary indications in support of the present invention.

The 5-Lipoxygenase pathway is a major synthetic pathway relevant to human inflammatory disease. The enzyme 5-Lipoxygenase catalyses the two first steps in the oxygenation of arachidonic acid (a polyunsaturated 20-carbon fatty acid) to leukotrienes. Leukotrienes are known to be important mediators of inflammatory and allergic reactions. The first step in the synthesis of leukotrienes, which is catalyzed by 5-Lipoxygenase, is the formation of 5-HPETE. The rearrangement of 5-HPETE to form the unstable $LTA_4$, the rate-limiting step in the synthesis of the leukotrienes, is also catalyzed by 5-Lipoxygenase. $LTA_4$ is then converted to either $LTB_4$ or $LTC_4$. $LTC_4$ is rapidly metabolized to $LTD_4$ and then to $LTE_4$. $LTC_4$, $LTD_4$ and $LTE_4$ are collectively referred to as the cysteinyl (Cys) leukotrienes.

Biosynthesis of $LTB_4$, $LTC_4$, $LTD_4$ and $LTE_4$ occurs predominantly in leukocytes, in response to a variety of immunological stimuli. The primary target of $LTB_4$ is the leukocyte where it elicits enzyme release, chemotaxis, adherence, and aggregation in nM concentrations. $LTB_4$ modulates immune responses and participates in the host-defense against infections. Hence, $LTB_4$ is an important chemical mediator in the development and maintenance of inflammatory reactions and disease states.

Endogenous lipoxygenase metabolites may also be involved in enhanced cytokine tumor necrosis factor a (TNF-$\alpha$) production following certain stimuli such as silica, asbestos and lipopolysaccharides (Rola-Pleszczynski, M et al. *Mediators of Inflammation* 1:5-8 (1992)). Consistent with selective lipoxygenase inhibitory effect, certain compounds of the present invention have also shown to have an inhibitory effect on TNF-$\alpha$ synthesis and/or release. The "TNF-$\alpha$" has a broad spectrum of biological activities, plays an important role in coordinating the body's response to infection, and serves as an important mediator of inflammation. It is known that inflammatory cytokines have been shown to be pathogenic in several diseases including, but not limited to asthma (N. M. Cembrzynska et al., *Am. Rev. Respir. Dis.*, 147, 291 (1993)), Adult Respiratory Distress Syndrome (ARDS). (Miller et al., *Lancet* 2 (8665); 712-714 (1989) and Ferrai-Baliviera et al., *Arch. Surg.* 124 (12): 1400-1405 (1989)), lung fibrosis (Piguet et al., *Nature*, 344:245-247 (1990) and Bissonnette et al., *Inflammation* 13 (3): 329-339 (1989)), bone resorption diseases (Bertolini et al., *Nature* 319: 516-518 (1986) and Johnson et al., *Endocrinology* 124 (3): 1424-1427 (1989)), auto-immune diseases (W. Fiers, *FEBS Lett.*, 1991, 285, p. 199). It will be therefore appreciated that compounds of the present invention showing an inhibitory effect on both 5-Lipoxygenase and TNF-$\alpha$ should be superior in the treatment or amelioration of for example diseases such as respiratory disorders, antiprolilferative disorders or autoimmune disorders.

In vitro evaluation of the ability of a composition to inhibit the enzymes 5-Lipoxygenase, 15-Lipoxygenase, or 12/15-Lipoxygenase as described in Walidge, N. B. et al. *Anal. Biochem.*, Vol. 231 (1995), pp. 354-358 using a high throughput colorimetric method; as well as in vitro evaluation of inhibiting $LTB_4$ is described in Examples.

In vitro cell-based assays for inflammation are well known in the art, for example, e-selectin (also named Endothelial Leukocyte Adhesion Molecule or ELAM) or C-reactive protein (CRP). The ELAM assay measures in vitro activity of the test compounds in reducing expression of ELAM in activated endothelial cells. Briefly, endothelial cells are created by adding known activators such as lipopolysaccharides, TNF or IL-1$\beta$, alone or in some combination. Activated cells produce ELAM, which can be measured using, for example, an E-selectin monoclonal antibody-based ELISA assay.

In vivo evaluation of anti-inflammatory activity can be determined by well characterized assays measuring Carrageenan-Induced Paw Edema, by Mouse Ear Inflammatory Response to Topical Arachidonic Acid (Gabor, M. *Mouse Ear Inflammation Models and their Pharmacological Applications* (2000)), or by the in vivo murine Zymosan peritonitis assay. Carrageenan-Induced Paw Edema is a model of inflammation, which causes time-dependent edema formation following carrageenan administration into the intraplantar surface of a rat paw. The application of arachidonic acid (AA) to the ears of mice produces immediate vasodilation and erythema, followed by the abrupt development of edema, which is maximal at 40 to 60 min. The onset of edema coincides with the extravasations of protein and leukocytes. After one hour the edema wanes rapidly and the inflammatory cells leave the tissue so that at 6 hours the ears have returned to near normal.

Administration of Zymosan-A, a purified polysaccharide fraction of yeast cell wall has been used since the 1980s to induce acute inflammatory response in rodents. The inflammatory response is characterized by marked induction of pro-inflammatory cytokines, influx of inflammatory cells and biosynthesis of arachidonic acid metabolites as early as five minutes after the Zymosan injection. The purpose of this model is to evaluate the ability of compounds to reduce inflammatory response induced by administration of Zymosan-A and assessed by the level of inflammatory cytokines and arachidonic metabolites in the fluid exudates.

These assays, as described in the Examples, measure a test compound's ability to treat these inflammatory processes via systemic and topical routes of administration.

Protection against redox stress can be evaluated in cell culture using high glutamate induced oxidative stress (HGOS) in mouse dopaminergic cell lines. The cytotoxic effect of glutamate is not due to excitotoxicity, as this cell line is devoid of inotropic glutamate receptors. Rather, the glutamate-induced toxicity of dopaminergic cells is associated with an inhibition of cystne transport which subsequently leads to depletion of intracellular glutathione (GSH) levels (Murphy T. H., et al. *Neuron*, Vol. 2 (1989), pp. 1547-1558), activation of neuronal 12-Lipoxygenase (Li, Y. et al. *Neuron*, Vol. 19 (1997), pp. 453-463), increased ROS production (Tan S. et al. *J. Cell Biol.*, Vol. 141 (1998), pp. 1423-1432) and elevated intracellular $Ca^{2+}$ (Li, Y. et al. see supra). Some molecules were measured for their ability to protect cells against glutamate-induced stress and the assay is detailed in Examples.

Further validation of neuroantiinflammatory activity of compounds can be assessed in vitro by the inhibition of IL-1.beta. release from a microglial cell line.

Interleukin-1 (IL-1) is a pro-inflammatory cytokine that exists in two separate forms that share 30% sequence homology (alpha and beta). Constitutive expression of IL-1 is low in the brain but levels of both forms of this cytokine increase dramatically after injury. There is substantial evidence that IL-1 is an important mediator of neurodegeneration induced by cerebral ischemia (Touzani, O. et al. *J. Neuroimmunol.*, Vol. 100 (1999), pp. 203-215). Both IL-1 forms are rapidly induced in experimental models of stroke and administration of recombinant IL-1β enhances ischemic injury (see Hill J. K., et al. *Brain Res.*, Vol. 820 (1999), pp. 45-54); Hillhouse E. W. et al. *Neurosci. Left.* Vol. 249 (1998), pp. 177-179; Loddick S. A. et al. *J. Cereb. Blood Flow Metab.* Vol. 16 (1996), pp. :932-940; Stroemer R. P. et al. *J. Cereb. Blood Flow Metab.* Vol. 18 (1998), pp. 833-839). Conversely, blocking IL-1 actions with a receptor antagonist or a neutralizing antibody markedly reduces neuronal death and inflammation in models of ischemic damage (see Betz, A. L., *J. Cereb. Blood Flow Metab.* Vol. 15 (1995), pp. 547-551; Relton, J. K., *Brain Res. Bull.* Vol. 29 (1992), pp. 243-246; Yamasaki, Y. et al. Stroke, Vol. 26 (1995), pp. 676-680). Furthermore, mice with decreased IL-1β production (caspase-1 knockouts) are significantly protected from ischemic injury (Schielke, G. P. et al. *J. Cereb. Blood Flow Metab.* Vol. 18 (1998), pp. 180-185) and IL-1$^\alpha$ and β double knockouts exhibit dramatically reduced ischemic infarct volumes compared with wild-type mice (87% reduction in cortex) (Boutin, H. et al. *J. Neurosci.* Vol. 21 (2001), pp. 5528-5534).

In addition to a role in ischemic damage, IL-1 elevation has been associated with many neurodegenerative diseases. There is increasing evidence for a role of IL-1 in Alzheimer's disease (AD) (Mrak, R. E. et al. *Neurobiol. Aging*, Vol. 22, no. 6 (2001), pp. 903-908). Elevated levels of IL-1β have been shown to surround amyloid plaques in the disease and recent genetic studies have indicated that a polymorphism in IL-1$^\alpha$ is linked to an increased risk of AD (3-6 fold increase) (Griffin, W. S. et al. *J. Leukoc. Biol.* Vol. 72, no. 2 (2002), pp. 233-238). This polymorphism has also been correlated with rate of cognitive decline in AD patients (Murphy, G. M. et al. *Neurology*, Vol. 56, no. 11 (2001), pp. 1595-1597). The risk of AD is increased even further when the polymorphism in IL-1.alpha. is found in combination with another polymorphism in IL-1β (see Griffin, W. S., supra), providing convincing evidence that these cytokines play an important role in the pathology of the disease.

This assay measures the release of IL-1β from a mouse microglial cell line following an inflammatory challenge with LPS and interferon-gamma. The ability of test articles to inhibit microglial cell activation and IL-1β release is determined by co-incubation of the test article with the inflammatory challenge.

Cerebral ischemic insults are modeled in animals by occluding vessels to, or within, the cranium (Molinari, G. F. in: Barnett, H. J. M. et al. (Eds.), *Stroke: Pathophysiology, Diagnosis and Management*, Vol. 1 (New York, Churchill Livingstone, 1986). The rat middle cerebral artery occlusion (MCAO) model is one of the most widely used techniques to induce transient focal cerebral ischemia approximating cerebral ischemic damage in humans, e.g., those who suffer from a stroke. The middle cerebral artery used as the ischemic trigger in this model is the most affected vessel in human stroke. The model also entails a period of reperfusion, which typically occurs in human stroke victims. MCAO involving a two-hour occlusion has been found to produce the maximum size of cortical infarction obtainable without increased mortality at twenty-four hours.

Administration

The compounds of the invention are administered at a therapeutically effective dosage, e.g., a dosage sufficient to provide treatment for the disease states previously described. Administration of the compounds of the invention or the pharmaceutically acceptable salts thereof can be via any of the accepted modes of administration for agents that serve similar utilities.

While human dosage levels have yet to be optimized for the compounds of the invention, a dose may be from about 1 mg to 1 g, preferably 10 mg to 500 mg and most preferably 10 mg to 100 mg per administration. The amount of active compound administered will, of course, be dependent on the subject and disease state being treated, the severity of the affliction, the manner and schedule of administration, and the judgment of the prescribing physician.

In employing the compounds of this invention for treatment of the above conditions, any pharmaceutically acceptable mode of administration can be used. The compounds of this invention can be administered either alone or in combination with other pharmaceutically acceptable excipients, including solid, semi-solid, liquid or aerosol dosage forms, such as, for example, tablets, capsules, powders, liquids, suspensions, suppositories, aerosols or the like. The compounds of this invention can also be administered in sustained or controlled release dosage forms, including depot injections, osmotic pumps, pills, transdermal (including electrotransport) patches, and the like, for the prolonged administration of the compound at a predetermined rate, for example, in unit dosage forms suitable for single administration of precise dosages. The compositions will typically include a conventional pharmaceutical carrier or excipient and a compound of this invention or a pharmaceutically acceptable salt thereof. In addition, these compositions may include other medicinal agents, pharmaceutical agents, carriers, adjuvants, and the like, including, but not limited to, anticoagulants, blood clot dissolvers, permeability enhancers, and slow release formulations.

Generally, depending on the intended mode of administration, the pharmaceutically acceptable composition will contain about 0.1% to 90%, for example about 0.5% to 50%, by weight of a compound or salt of this invention, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations, and the like.

Certain compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, sodium acetate, sodium citrate, cyclodextrine derivatives, sorbitan monolaurate, triethanolamine acetate, triethanolamine oleate, etc. Actual methods of preparing such dosage forms are known, or will be apparent, to those skilled in this art; for example, see *Remington's Pharmaceutical Sciences*, 15$^{th}$ Edition, Easton, Pa., Mack Publishing Company, 1975. The composition or formulation to be administered will, in any event, contain a quantity of the active compound in an amount effective to alleviate the symptoms of the subject being treated. Dosage forms or compositions containing active ingredient in the range of 0.005% to 95% with the balance made up from non-toxic carrier may be prepared.

For a solid dosage form, the solution or suspension in for example, propylene carbonate, vegetable oils or triglycerides, is encapsulated in a gelatin capsule. Such diester solutions, and the preparation and encapsulation thereof, are disclosed in U.S. Pat. Nos. 4,328,245; 4,409,239; and 4,410,545. For a liquid dosage form, the solution, e.g. in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and the like, and encapsulating these solutions or suspensions in hard or soft gelatin capsule shells.

The formulation can be administered in a single unit dosage form for continuous treatment or in a single unit dosage form ad libitum when relief of symptoms is specifically required. For example, the formulation may be administered as a bolus or as a continuous intravenous infusion after onset of symptoms of stroke, myocardial infarction or chronic heart failure.

Another manner of administration is the topical administration. "Topical administration" refers to application of the present compositions by spreading, spraying, etc. onto the surface of the skin. The typical amount applied may vary from about 0.1 mg of composition per square centimeter of skin to about 25 mg of composition per square centimeter of skin. Certain compounds of the present invention may be formulated for topical administration to the epidermis as ointments, creams or lotions, or as transdermal patch. Formulations suitable for topical administration in the mouth include lozenges, pastilles and mouthwashes.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as, for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid which will be subsequently diluted to the above percentages.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

EXAMPLES

The following preparations and examples are given to enable those skilled in the art to more clearly understand and to practice the present invention. They should not be considered as limiting the scope of the invention, but merely as being illustrative and representative thereof.

General Characterization Methods

As reported in the following examples, Nuclear Magnetic Resonance (NMR) spectra were recorded on a Bruker DTX 300 spectrometer using, in most cases, tetramethyl silane (TMS) as the internal reference. Mass spectra were obtained on an Agilent 1100 LC/MSD instrument using either electrospray ionization (positive or negative mode) (ESI) or atmospheric pressure chemical ionization (positive or negative mode) (APCI).

Further, abbreviations used throughout the specification have the following meanings:

| | |
|---|---|
| μg = | microgram |
| aq. = | aqueous |
| Ar = | aryl |
| br s = | broad singlet |
| cc = | cubic centimeters, milliliters |
| conc. = | concentrated |
| d = | doublet |
| DCM = | dichloromethane |
| dd = | doublet of doublets |
| dil. = | diluted |
| DMEM = | Dulbecco's Modification of Eagle's Medium |
| DMEM-No Glu = | Dulbecco's modified Eagle's medium without glucose |
| DMF = | dimethyl formamide |
| DMSO = | dimethylsufloxide |
| $EC_{50}$ = | The molar concentration of a drug, which produces 50% of the maximum possible effect for that drug. |
| ELISA = | enzyme-linked immunosorbant assay |
| eq. = | equivalents |
| Et = | ethyl |
| $Et_2O$ = | diethyl ether |
| EtOAc = | ethyl acetate |
| FBS = | fetal bovine serum |
| g = | gram |
| h = | hour |
| HBSS = | Hanks' balanced salt solution |
| Hz = | Hertz |
| I.P. = | intraperitoneal |
| I.V. = | intravenous |
| $IC_{50}$ = | The molar concentration of a drug, which produces 50% of the maximum possible inhibition for that drug |
| LPS = | lipopolysaccharide |
| M = | Molar |
| m = | multiplet |
| m/z = | mass to charge ratio |
| Me = | methyl |
| MeOH = | methanol |
| mg = | milligram |
| MHz = | mega Hertz |
| min = | minute |
| mL = | milliliter |
| mM = | millimolar |
| mmol = | millimole |
| MOM = | methoxymethyl |
| N = | normal |
| NaOtBu = | sodium t-butoxide |
| nM = | nanomolar |
| NMR = | nuclear magnetic resonance |
| PBS = | phosphate buffered saline |
| ppm = | parts per million |
| psi = | pounds per square inch |
| q = | quartet |
| s = | singlet |
| sat. = | saturated |
| t = | triplet |
| tBu = | t-butyl |
| TFA = | trifluoroacetic acid |
| THF = | tetrahydrofuran |
| TLC = | thin layer chromatography |
| tt = | triplet of triplets |
| UV = | ultraviolet |
| v/v = | volume/volume |
| μL = | microliter |
| μM = | micromolar |
| μmol = | micromole |

Example 1

1-Vinyl-cyclobutanol

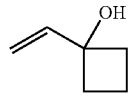

To a solution of cyclobutanone (4.1 g, 58.5 mmol) in anhydrous tetrahydrofuran (40 mL) under nitrogen, was added dropwise vinyl magnesium bromide (82 mL, 1 M solution in tetrahydrofuran) keeping the temperature between −40° C. and −10° C. The solution was then allowed to slowly warm up to room temperature by removal of the cool bath. The solution was cooled down to −20° C., quenched with water (5 mL), and diluted with ethylacetate (100 mL). The clear solution was decanted from the solid material, dried over anhydrous sodium sulfate, and evaporated. Chromatography (silica gel, hexane-ethyl acetate 5% to 15%) gave 2.04 g of 1-vinyl-cyclobutanol as a colorless liquid.

$^1$H-NMR (300 MHz, CDCl$_3$) δ=6.15 (dd, 1H, C=CH), 5.28, 5.10 (d, 2H, C=CH$_2$), 2.20 (m, 4H, CH$_2$), 1.83 (m, 2H, CH$_2$) ppm. $^{13}$C-NMR (75 Hz, CDCl$_3$) δ=142.4, 111.3, 75.2, 35.9, 12.0 ppm.

Similarly following the procedure described herein, but substituting vinyl magnesium bromide for the appropriate alkenyl bromide, the following compound was produced:

1-(2-methyl-propenyl)-cyclobutanol; $^1$H-NMR (300 MHz, CDCl$_3$) δ=5.58 (s, 1H, C=CH), 2.21 (m, 4H, CH$_2$), 1.81 (m, 2H, CH$_2$), 1.76 (s, 3H, CH$_3$), 1.73 (s, 3H, CH$_3$) ppm. $^{13}$C-NMR (75 MHz, CDCl$_3$), δ=138.4, 131.4, 73.7, 38.6, 25.4, 19.0, 13.0 ppm.

Example 2

5',7',8'-Trimethyl-2',3'-dihydrospiro[cyclobutane, 1,4'-thiochromen]-6'-ol

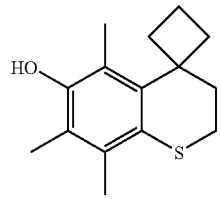

To a stirred mixture of 4-mercapto-2,3,6-trimethyl-phenol (464 mg) in 6 mL of dioxane, and 1.2 mL of BF$_3$-ether, was added dropwise at 120° C., a solution of 1-vinyl-cyclobutanol (300 mg, 3.1 mmol) in 1 mL of dioxane. Subsequently, the reaction was allowed to stir for 30 min at 120° C. After the reaction was complete, the mixture was extracted 3 times with ethyl acetate. The organic layer was washed with water and dried over anhydrous sodium sulfate, and concentrated in vacuo. The residue was purified by flash chromatography eluted with 10% ethyl acetate in hexane to give 41 mg of 5',7',8'-trimethyl-2',3'-dihydrospiro[cyclobutane, 1,4'-thiochromen]-6'-ol as a light-yellow paste.

$^1$H-NMR (300 MHz, CDCl$_3$) δ=4.70 (s, 1H, ArOH), 2.87 (m, 2H, CH$_2$), 2.7-2.0 (m, 6H, CH$_2$), 2.49 (s, 3H, ArCH$_3$), 2.39 (m, 2H, CH$_2$), 2.27 (s, 3H, ArCH$_3$), 2.20 (s, 3H, ArCH$_3$)

ppm. $^{13}$C-NMR (75 MHz, CDCl$_3$) δ=150.25, 139.10, 131.98, 125.54, 120.40, 120.34, 42.96, 39.46, 34.74, 24.20, 16.61, 14.97, 14.52, 12.49 ppm. MS: (m/z)=249.1 (M+H$^+$).

Preparation of the sulfoxide and sulfodioxide derivatives

5',7',8'-Trimethyl-2',3'-dihydrospiro[cyclobutane-1,4'-thiochromen]-6'-ol 1'-oxide 5',78'-Trimethyl-2 3'-dihydrospiro[cyclobutane-1,4'-thiochromen]-6'-ol 1',1'-dioxide To a solution of 5',7',8'-trimethyl-2',3'-dihydrospiro[cyclobutane, 1,4'-thiochromen]-6'-ol (127 mg), prepared as described above, in 4 mL of chloromethane was added m-chloroperbenzoic acid (MCPBA) (133 mg). The reaction was allowed to stir at room temperature for 0.5 hour. The mixture was diluted with more CH$_2$Cl$_2$ and washed with NaHCO$_3$. The organic layer was dried over anhydrous Na$_2$SO$_4$, and concentrated in vacuo. The residue was purified by flash chromatography eluted with 50% ethyl acetate in hexane and then 10% methanol in dichloromethane to give 29 mg of the sulfoxide and 68.4 mg of the sulfodioxide.

5',7',8'-Trimethyl-2',3'-dihydrospiro[cyclobutane-1 ,4'-thiochromen]-6'-ol 1'-dioxide $^1$H-NMR (300 MHz, CDCl$_3$) δ=5.51 (s, 1H, ArOH), 3.26 (m, 2H, ArCH$_2$), 2.63 (s, 3H, ArCH$_3$), 2.54 (s, 3H, ArCH$_3$), 2.15 (s, 3H, ArCH$_3$), 2.76-1.91 (m, 8H, CH$_2$) ppm. $^{13}$C-NMR (75 MHz, CDCl$_3$) δ=155.8, 139.3, 134.5, 130.2, 123.5, 121.1, 48.3, 41.1, 35.5, 33.2, 16.9, 14.5, 13.6, 12.0 ppm. MS: (m/z)=281.1 (M+H$^+$), 303.1 (M+Na$^+$).

5',7',8'-Trimethyl-2',3'-dihydrospiro[cyclobutane-1,4'-thiochromen]-6'-ol 1',1'-oxide $^1$H-NMR (300 MHz, CDCl$_3$+MeOD) δ=2.60 (s, 6H, ArCH$_3$), 2.18 (s, 3H, ArCH$_3$), 3.56-1.90 (m, 8H, CH$_2$) ppm. $^{13}$C NMR (75 MHz, CDCl$_3$+MeOD,) δ=157.6, 139.4, 138.1, 125.9, 123.8, 123.3, 40.6, 40.0, 33.7, 32.2, 29.3, 15.7, 15.0, 13.5, 12.1 ppm. MS: (m/z)=265.1 (M+H$^+$), 287.1 (M+Na$^+$).

Example 3

2',2',5',7',8'-Pentamethyl-2',3'-dihydrospiro[cyclobutane-1,4'-thiochromen]-6'-ol

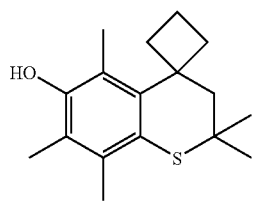

To a stirred mixture of 4-mercapto-2,3,6-trimethyl-phenol (1.35 g) in 6 mL of dioxane, and 2.5 mL of BF$_3$-ether, a solution of 1-(2-methyl-propenyl)-cyclobutanol (1.02 g, 8.1 mmol) prepared as described in Example 1, in 10 mL of dioxane was added dropwise at 110° C. Subsequently the reaction was allowed to stir for 20 min at 110° C. After the reaction was cooled down, the mixture was extracted with ethyl acetate. The organic layer was washed with water and dried over anhydrous Na$_2$SO$_4$, and concentrated in vacuo. The residue was purified by flash chromatography eluted with 10% ethyl acetate in hexane to give 1.0 g of product as a colorless liquid. NMR indicated that it is a mixture of cyclized and un-cyclized products with approximately 1:1 ratio.

The mixture containing cyclized and un-cyclized products was then treated with two equivalents of dimethylamino acetyl chloride in the presence of triethylamine in dichloromethane. After aqueous work-up and wash with saturated NaHCO$_3$, the organic layer was dried over anhydrous Na$_2$SO$_4$, and concentrated in vacuo. The residue was purified by flash chromatography eluted with 50% ethyl acetate in hexane to give 85 mg of 5',7',8'-trimethyl-2',3'-dihydrospiro[cyclobutane-1,4'-thiochromen]-6'-yl (dimethylamino)acetate as a white paste.

$^1$H-NMR (300 MHz, CDCl$_3$) δ=3.50 (s, 2H, COCH$_2$), 2.48 (s, 6H, NCH$_3$), 2.26 (s, 3H, ArCH$_3$), 2.25 (s, 3H, ArCH$_3$), 2.17 (s, 2H, CH$_2$), 2.04 (s, 3H, ArCH$_3$), 2.50-1.80 (m, 6H, CH$_2$), 1.49 (s, 6H, CH$_3$) ppm. $^{13}$C-NMR (75 MHz, CDCl$_3$) δ=169.0, 145.7, 138.9, 130.9, 126.5, 126.3, 60.0, 54.7, 45.7, 45.4, 38.5, 37.4, 30.0, 29.0, 16.9, 16.6, 12.3 ppm. MS: (m/z)=362.2 (M+H$^+$), 384.2 (M+Na$^+$).

To a solution of 0.5 N NaOH in MeOH, water and THF was added 20 mg of dimethyl amino acetate as prepared above. The reaction mixture was allowed to stir for 2 hours. After aqueous work-up and wash with saturated NaHCO$_3$, the organic layer was dried over anhydrous Na$_2$SO$_4$, and concentrated in vacuo. The residue was purified by flash chromatography eluted with 10% ethyl acetate in hexane to give 10.4 mg of 2',2',5',7',8'-pentamethyl-2',3'-dihydrospiro[cyclobutane-1,4'-thiochromen]-6'-ol as a yellow paste.

$^1$H-NMR (300 MHz, CDCl$_3$,) δ=4.55 (s, 1H, ArOH), 2.41 (s, 3H, ArCH$_3$), 2.28 (s, 3H, ArCH$_3$), 2.19 (s, 3H, ArCH$_3$), 2.13 (s, 2H, CH$_2$), 2.50-1.80 (m, 6H, CH$_2$), 1.51 (s, 6H, CH$_3$) ppm. $^{13}$C-NMR (75 MHz, CDCl$_3$) δ=149.8, 138.7, 130.7, 124.0, 120.7, 120.4, 60.9, 45.6, 38.3, 37.3, 29.8, 16.9, 16.7, 16.3, 12.7 ppm. MS: (m/z)=277.2 (M+H$^+$).

Example 4

5,7,8-Trimethyl-3,4-dihydrospiro[chromene-2,1'-cyclobutan]-6-ol

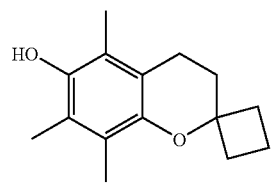

To a solution of trimethyl-1,4-hydroquinone (466 mg) and BF$_3$-ether (0.8 mL) in dioxane (5 mL) was added 1-vinyl-cyclobutanol (300 mg) prepared as in Example 1, in dioxane (4 mL) over 50 min at 110° C. (oil bath) under nitrogen. The reaction was refluxed for one more hour. The solution was diluted with ethyl acetate and washed with water and brine. The crude product obtained after drying over anhydrous sodium sulfate, evaporation and chromatography (silica gel, hexane-ethyl acetate 1% to 4%) was crystallized from hexane to give 195 mg of 5,7,8-trimethyl-3,4-dihydrospiro[chromene-2,1'-cyclobutan]-6-ol.

$^1$H-NMR (300 MHz, CDCl$_3$) δ=4.23 (s, 1H), 2.75-1.60 (m, 17H) ppm. $^{13}$C-NMR (75 MHz, CDCl$_3$) δ=145.5, 145.0, 122.7, 121.1, 118.6, 118.1, 76.3, 34.0, 29.5, 20.7, 12.6, 12.3, 11.9, 11.4 ppm. MS: (m/z)=233 (100, M+H$^+$).

Similarly substituting trimethyl-1,4-hydroquinone with the appropriate quinones the following compounds were synthesized:

8-isopropyl-5methyl-3,4-dihydrospiro[chromene-2,1'-cyclobutan]-6-ol $^1$H-NMR (300 MHz, CDCl$_3$) δ=6.56 (s, 1H), 4.54 (s, 1H), 3.30 (tt, J=6.9 Hz, 1H), 2.69 (br s, 2H), 2.30-1.65 (m, 11H), 1.21 (d, J=6.9 Hz, 6H) ppm. $^{13}$C-NMR (75 MHz, CDCl$_3$) δ=146.5, 144.8, 134.9, 121.3, 119.3, 111.0, 76.3, 33.9, 29.4, 26.6, 22.7, 20.9, 12.7, 11.1 ppm. MS: m/z=205 (53), 247 (100, M+H$^+$).

5,8-dimethylspiro[chroman-2,1'-cyclobutan]-6-ol $^1$H-NMR (CDCl$_3$) 6.43 (1H, s), 4.40 (1H, s), 2.66-2.70 (2H, t), 2.22-2.29 (2H, m), 2.14 (3H, s), 2.11 (3H, s), 2.06-2.10 (2H, m), 1.80-1.97 (3H, m), 1.63-1-70 (1H, m), MS: (m/z)=219, (M+H$^+$)

Example 5

5,8-Dimethyl-7-(3-methylbutyl)-3,4dihydrospiro[chromene-2,1'-cyclobutan]-6-ol

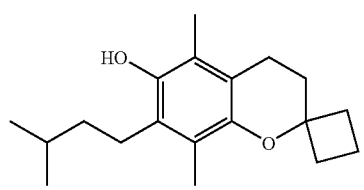

Step 1: 2,5-Dimethyl-3-(3-methyl-butyl)-hydroquinone 2,5-Dimethylbenzoquinone (5 g) in ethyl acetate was shaken with an aqueous solution of sodium hydrosulfite. The organic layer was separated, washed, dried and evaporated to yield 2,5-dimethylhydroquinone. To a solution of 2,5-dimethylhydroquinone (5 g), prepared as described above, and 3-methyl-2-buten-1-ol (3.1 g) in dioxane (20 mL) was added BF$_3$-ether (4.5 mL) at room temperature under nitrogen. The solution was stirred at room temperature for one hour, extracted with ethyl acetate, washed with water and dried. The mixture containing starting material and alkylated product was hydrogenated in methanol (100 mL) with 5 drops of concentrated HCl in the presence of Pd/C (10%, 200 mg) at 60 psi for 18 hours. Workup and chromatography (silica gel hexane-ethyl acetate 5% to 12%) gave 2 g of the desired product, 2,5-dimethyl-3-(3-methyl-butyl)-hydroquinone.

Step 2: 5,8-Dimethyl-7-(3-methylbutyl)-3,4-dihydrospiro[chromene-2,1'-cyclobutan]-6-ol To a solution of 2,5-dimethyl-3-(3-methylbutyl)hydroquinone (208 mg) and BF$_3$-ether (0.25 mL) in dioxane (3 mL) was added 1-vinyl-cyclobutanol (98 mg) in dioxane (3 mL) over 50 min at 110° C. degree under nitrogen. The reaction was refluxed for one additional hour. The solution was diluted with ethyl acetate and washed with water and brine, and dried. After evaporation the residue waschromatographed (silica gel, hexane-ethyl acetate 0% to 3%) gave 5,8-dimethyl-7-(3-methylbutyl)-3,4-dihydrospiro[chromene-2,1'-cyclobutan]-6-ol (130 mg).

$^1$H-NMR (300 MHz, CDCl$_3$) δ=4.31 (s, 1H), 2.75-2.60 (m, 2H), 2.35-1.80 (m, 2H), 1.75-1.70 (m, 2H), 1.50-1.40 (m, 2H), 1.07 (s, 3H), 1.04 (s, 3H) ppm. $^{13}$C-NMR (75 MHz, CDCl$_3$) δ=145.7, 144.7, 126.5, 122.2, 118.7, 118.2, 76.3, 38.7, 34.1, 29.6, 28.7, 25.0, 22.6, 20.8, 12.7, 11.4 ppm. MS: (m/z)=289 (100, M+H$^+$).

Example 6

8-Chloro-5,7-dimethyl-3,4-dihydrospiro[chromene-2,1'-cyclobutan]-6-ol

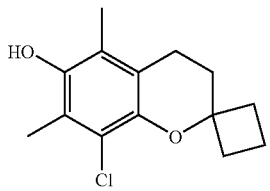

Step 1: 5,7-Dimethyl-3,4-dihydrospiro[chromene-2,1'-cyclobutan]-6-ol

To a solution of 2,6-dimethylhydroquinone (2.36 g) and BF$_3$-ether (4.47 mL) in dioxane (10 mL) was added 1-vinyl-cyclobutanol (1.58 g) in dioxane (5 mL) over 50 min at 110° C. under nitrogen. The reaction was refluxed for one additional hour. The solution was diluted with ethyl acetate and washed with water and brine, dried and evaporated. The residue was chromatographed (silica gel, hexane-ethyl acetate 1% to 5%) gave 1.36 g of 5,7-dimethyl-3,4-dihydrospiro[chromene-2,1'-cyclobutan]-6-ol.

$^1$H-NMR (300 MHz, CDCl$_3$) δ=6.52 (s, 1H), 4.26 (s, 1H), 2.65 (t, J=6.6 Hz, 2H), 2.30-1.80 (m, 13H), 1.75-1.65 (m, 1H) ppm. $^{13}$C-NMR (75 MHz, CDCl$_3$) δ=147.1, 145.5, 122.2, 121.9, 119.0, 116.2, 76.4, 33.8, 29.5, 20.4, 16.1, 12.5, 11.5 ppm. MS: (m/z)=219 (100, M+H$^+$).

Step 2: 8-Chloro-5,7-dimethyl-3,4-dihydrospiro[chromene-2,1'-cyclobutan]-6-ol

To a solution of 5,7-dimethyl-3,4-dihydrospiro[chromene-2,1'-cyclobutan]-6-ol (350 mg) in ethyl ether (6 mL) was added sulfonyl chloride (0.154 mL, 260 mg) dropwise at room temperature under nitrogen. After 2 hours, ethyl acetate was added, washed with an aqueous sodium bicarbonate solution, water and brine, and dried. Evaporation and chromatography (silica gel hexane-ethyl acetate 0% to 4%, hexane-dichloromethane 5% to 20%) yielded the desired compound. Crystallization with hexane gave colorless crystals of 8-chloro-5,7-dimethyl-3,4-dihydrospiro[chromene-2,1'-cyclobutan]-6-ol (60 mg). $^1$H-NMR (300 MHz, CDCl$_3$) δ=4.29 (s, 1H), 2.67 (t, J=6.6 Hz, 2H), 2.35-1.80 (m, 13H), 1.75-1.60 (m, 1H) ppm. $^{13}$C-NMR (75 MHz, CDCl$_3$) δ=145.2, 143.6, 120.9, 120.1, 119.9, 119.7, 77.3, 33.8, 29.2, 20.8, 13.2, 12.5, 11.5 ppm. MS: (m/z)=253 (100, M+H$^+$), 275 (23, M+Na$^+$).

Similarly the following compounds were prepared:

8-Chloro-5-methyl-3,4-dihydrospiro[chromene-2,1'-cyclobutan]-6-ol $^1$HNMR (300 MHz, CDCl$_3$) δ=6.71 (s, 1H), 5.17 (d, 1H, J=7.75 Hz), 4.77 (s, 1H), 2.67 (t, J=6.62 Hz, 2H), 2.33 (q, 2H, J=11 Hz), 2.08- 1.88 (m, 9H), 1.69. (m, 1H) ppm. $^{13}$CNMR (75 MHz, CDCl$_3$) δ=146.5, 143.6, 123.3, 118.7, 114.7, 77.3, 33.8, 29.0, 20.9, 12.5, 11.2 ppm. MS: m/z=239 (100, M+H$^+$), 260 (35, M+Na).

5-chloro-2,3-dimethyl-1,4-hydroquinone gave 7-chloro-5,8-dimethyl-3, 4-dihydrospiro[chromene-2,1'-cyclobutan]-6-ol $^1$H-NMR (300 MHz, CDCl$_3$) δ=5.30 (s, 1H), 2.70-2.60 (m, 2H), 2.28 (s, 3H), 2.27-2.18 (m, 2H), 2.17 (s, 3H), 2.15-1.80 (m, 5H), 1.75-1.60 (m, 1H) ppm. $^{13}$C-NMR (75 MHz, CDCl$_3$) δ=145.5, 142.6, 121.3, 120.0, 120.0, 118.7, 76.8, 33.9, 29.3, 20.5, 12.9, 12.6, 11.7 ppm. MS: (m/z)=253 (100, M+H$^+$), 255 (35);

3-chloro-2,5-dimethyl-1,4-hydroquinone gave 5-chloro-7,8-dimethyl-3, 4-dihydrospiro[chromene-2,1' cyclobutan]-6-ol $^1$H-NMR (300 MHz, CCl$_3$D) δ=5.31 (s, 1H), 2.80-2.70 (m, 2H), 2.35-2.15 (m, 8H), 2.15-1.80 (m, 5H), 1.80-1.65 (m, 1H) ppm. $^{13}$C-NMR (75 MHz, CCl$_3$D) δ=145.5, 142.9, 124.6, 122.4, 116.6, 116.3, 76.9, 33.9, 29.1, 21.1, 12.7, 12.6, 11.8 ppm. MS: (m/z)=253 (100, M+H$^+$).

Example 7

5,7,8-Trimethyl-3,4-dihydrospiro[chromene-2,1'-cyclopropan]-6-ol

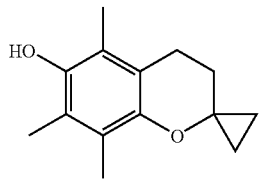

Step 1: 6-Hydroxy-5,7,8-trimethyl-chroman-2-one

To a mixture of trimethyl-hydroquinone (3.04 g) and acrylic acid (1.44 g) was added methyl-sulfonic acid (30 mL). The mixture was heated slowly up to 100° C. under nitrogen. The reaction mixture was stirred at 100° C. for 1 hour. The solution was poured into ice, and extracted with ethyl acetate. The organic layer was washed with saturated sodium bicarbonate water solution, water and brine. Evaporation and chromatography (silica gel, hexane-ethyl acetate 10% to 25%) gave 1.77 g of 6-hydroxy-5,7,8-trimethyl-chroman-2-one.

Step 2: 5,7,8- Trimethyl-6-triisopropylsilanyloxy-chroman-2-one

A solution of 6-hydroxy-5,7,8-trimethyl-chroman-2-one (1.22 g), triisopropylsilyl chloride (1.71 g) and imidazole (806 mg, 11.84 mmol) in anhydrous DMF (2 mL) was stirred at room temperature for two days. The solution was diluted with ethyl acetate, washed with water and brine. Evaporation and chromatography (silica gel, hexane-ethyl acetate) gave 1.25 g of 5,7,8-trimethyl-6-triisopropylsilanyloxy-chroman-2-one.

Step 3: 5,7,8-Trimethyl-3,4-dihydrospiro[chromene-2,1'-cyclopropan]-6-ol

To a solution of 5,7,8-trimethyl-6-triisopropylsilanyloxy-chroman-2-one (1.25 g) in anhydrous tetrahydrofuran (8 mL) was added Tebbe reagent (7.27 mL) at 0° C. (ice-water bath) dropwise under nitrogen. After being stirred at 0° C. for 20 min, the solution was poured into a 1 M sodium hydroxide water solution (1.5 g sodium hydroxide in 38 g of water), and extracted with hexane. The organic layer was passed through a short Celite® and silica gel double layers bed. Evaporation gave 880 mg of crude product, which was used in the next step without further purification.

To a mixture of triisopropyl-(5,7,8-trimethyl-2-methylene-chroman-6-yloxy)-silane (880 mg) and diiodomethane (3.32 g) in hexane (10 mL) was added diethyl zinc (10 mL, 1 M solution in hexane) dropwise at 0° C. (ice-water bath) under nitrogen. The resulted mixture was refluxed for one hour. After being cooled down, the mixture was diluted with hexane, washed with ammonium chloride water and brine. Evaporation and chromatography (silica gel, hexane-ethyl acetate 0.5%) gave 240 mg of product.

To a solution of protected hydroxychroman (240 mg) as prepared above, in anhydrous tetrahydrofuran (4 mL) was added tetrabutylammonium fluoride (2 mL, 1.0 M solution in tetrahydrofuran) at 0° C. The solution was stirred at 0° C. for 30 min. The reaction was quenched by adding water. The solution was diluted with ethyl acetate, washed with water and brine. Evaporation and chromatography (silica gel, hexane-ethyl acetate 0.5% to 1.5%) gave 75 mg of 5,7,8-trimethyl-3,4-dihydrospiro[chromene-2,1'-cyclopropan]-6-ol as a white solid.

$^1$H-NMR (300 MHz, CDCl$_3$) δ=4.34 (s, 1H), 2.85-2.75 (m, 2H), 2.20 (s, 3H), 2.18 (s, 3H), 2.08 (s, 3H), 2.05-1.95 (m, 2H), 1.05-0.95 (m, 2H), 0.65-0.55 (m, 2H) ppm. $^{13}$C-NMR (75 MHz, CDCl$_3$) δ=147.6, 145.3, 122.4, 120.9, 119.2, 119.1, 58.8, 28.2, 23.5, 12.2, 12.0, 11.7, 11.5 ppm. MS: (m/z)=218 (100, M+H$^+$)

Example 8

6'-(Methoxymethoxy)-5',7',8'-trimethyl-4'H-spiro[cyclopropane-1,3'-thiochromen]-4'-one

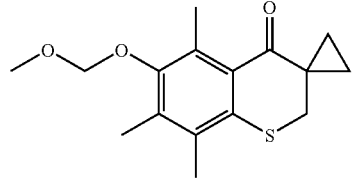

Step 1: 4-Mercapto-2,3,6-trimethyl-phenol

A solution of 2,3,6-trimethylphenol (40 g) and sodium thiocyanate (76.44 g) in MeOH (200 mL) was cooled to 0° C. and treated by slow addition of a solution of NaBr (30.28 g) and Br$_2$ (15.6 mL) in MeOH (300 mL). The resulting reaction mixture was stirred for 5 h, diluted with sat. aq. NaHCO$_3$ followed by H$_2$O resulting in formation of a precipitate of 2,3,6-trimethyl-4-thiocyanato-phenol. The solid was collected by filtration and dried by lyophilization (54.7 g).

$^1$H-NMR (300 MHz, CDCl$_3$) δ=7.32 (s, 1H), 5.14 (s, 1H), 2.48 (s, 3H), 2.24 (s, 3H), 2.25 (s, 3H) ppm. $^{13}$C-NMR (75 MHz, CDCl$_3$) δ=154.5, 138.7, 133.8, 124.5, 122.4, 113.0, 112.1, 17.9, 15.8, 12.8 ppm. MS: (m/z)=167.1 (M−CN$^+$).

A solution of 2,3,6-trimethyl-4-thiocyanato-phenol (45.7 g, 237 mmol) in anhydrous THF (300 mL) was added to a suspension of LiAlH$_4$ (9.09 g) in anhydrous THF (600 mL) stirred at 0° C. The reaction mixture was allowed to warm to room temperature and stirred for 15 h. It was subsequently quenched with THF, followed by H$_2$O and 0.5 M aq. HCl. Extraction with EtOAc (3×) was followed by washing the collected organic fractions with brine, drying over Na$_2$SO$_4$ and solvent evaporation. Column chromatography (SiO$_2$: hexane:EtOAc, 9:1 v/v) yielded 4-mercapto-2,3,6-trimethyl-phenol as a white solid (32 g).

$^1$H-NMR (CDCl$_3$, 300 MHz) δ=7.05 (s, 1H), 4.65 (s, 1H), 3.17 (s, 1H), 2.34 (s, 3H), 2.22 (s, 6H) ppm. MS: (m/z)=169.1 (M+H$^+$)

Step 2: 2,3,5Trimethyl-phenylsulfanyl3-(4-hydroxy)-propionic acid

4-Mercapto-2,3,6-trimethyl-phenol (3.03 g) was added to a solution of trimethylorthoformate (4.0 mL) in MeOH (150 mL), which had been degassed by bubbling N$_2$ over 50 min. The resulting reaction mixture was treated with methyl acrylate (14.1 mL) and conc. H$_2$SO$_4$ (0.55 mL) and stirred under reflux for 2 days. Upon cooling the reaction mixture was treated with NaHCO$_3$ (1.50 g) followed by solvent evaporation and preloading the residue onto SiO$_2$. Column chromatography (SiO$_2$: hexane:EtOAc, 95:5 eluting residual mercaptophenol followed by 9:1 v/v) yielded 2,3,5-trimethyl-phenylsulfanyl-3-(4-hydroxy)-propionic acid methyl ester as a white solid (4.31 g). $^1$H-NMR (300 MHz, CDCl$_3$) δ☐ 7.18 (s, 1H), 4.69 (s, 1H), 3.69 (s, 3H), 2.98 (t, J=7 Hz, 2H), 2.56 (t, J=7 Hz, 2H), 2.44 (s, 3H), 2.24 (s, 3H), 2.22 (s, 3H) ppm. MS: (m/z)=255 (M+H$^+$).

A solution of the ester (4.31 g) in MeOH (85 mL) was treated with a 1M aq. NaOH solution (170 mL) and stirred for 1 h. Upon acidifying the reaction mixture with 3N HCl (85 mL), a white precipitate was observed. Solvents were partially evaporated to remove MeOH and the solid, 2,3,5-trimethyl-phenylsulfanyl3-(4-hydroxy)-propionic acid, was collected by filtration (4.04 g). MS: (m/z) 241.1 (M+H$^+$), 263.0 (M+Na$^+$).

Step 3: 6-Hydroxy-5,7,8-trimethyl-2,3-dihydro-4H-thiochromen-4-one 2,3,5-Trimethyl-phenylsulfanyl3-(4-hydroxy)-propionic acid (4.04 g) was dissolved in conc. H$_2$SO$_4$ (84 mL) forming a dark red solution, which was stirred for 30 min and then poured over ice. Upon extraction with EtOAc, the organic phase was washed sequentially with water, sat. NaHCO$_3$, water again and brine. The organic layer was then dried with Na$_2$SO$_4$ and solvents evaporated yielding 6-hydroxy-5,7,8-trimethyl-2,3-dihydro-4H-thiochromen-4-one as a yellow solid (2.24 g).

$^1$H-NMR (300 MHz, CDCl$_3$) δ=4.87 (br s, 1H), 3.09-3.16 (m, 2H), 2.94-3.02 (m, 2H), 2.46 (s, 3H), 2.30 (s, 3H), 2.27 (s, 3H) ppm. MS: (m/z)=223.1 (M+H$^+$).

Step 4: 6'-(Methoxymethoxy)-5',7',8'-trimethyl-4'H-spiro[cyclopropane-1,3'-thiochromen]-4'-one 6-Hydroxy-5,7,8-trimethyl-2,3-dihydro-4H-thiochromen-4-one (2.24 g) was dissolved in anhydrous THF (100 mL) and treated with chloromethyl methyl ether (0.918 mL) and NaH (60% in mineral oil, 483 mg). The resulting reaction mixture was stirred for 2 h turning bright yellow as NaH was added and then gradually becoming pale yellow. The reaction mixture was quenched with a small amount of H$_2$O followed by solvent evaporation and preloading the residue onto SiO$_2$. Column chromatography (SiO$_2$: hexane:EtOAc, 95:5 v/v) yielded 6-methoxymethoxy-5,7,8-trimethyl-2,3-dihydro-4H-thiochromen4-one as a white solid (2.37 g).

$^1$H-NMR (300 MHz, CDCl$_3$) δ=4.86 (s, 2H), 3.62 (s, 3H), 3.11-3.16 (m, 2H), 2.93-2.98 (m, 2H), 2.49 (s, 3H), 2.29 (s, 3H), 2.27 (s, 3H) ppm. $^{13}$C-NMR (75 MHz, CDCl$_3$) δ=197.3, 152.6, 137.8, 135.5, 132.5, 132.4, 130.3, 99.6, 57.8, 41.6, 26.1, 16.8, 15.7, 14.5 ppm. MS: (m/z)=267.1 (M+H$^+$).

6-Methoxymethoxy-5,7,8-trimethyl-2,3-dihydro-4H-thiochromen-4-one (23 mg) was dissolved in anhydrous DMF (5 mL) and treated with 1,2-dichloroethane (6.8 µL) and NaH (60% in mineral oil, 8.2 mg), and stirred for 19 h at ambient temperature. The reaction mixture was poured into H$_2$O and extracted with EtOAc. The organic layer was collected and dried over Na$_2$SO$_4$ followed by solvent evaporation. Column chromatography (SiO$_2$: hexane:EtOAc, from 9:1 to 1:1 v/v) yielded a fraction containing impure desired product 6-methoxymethoxy-5,7,8-trimethyl-2,3-dihydro-4H-thiochromen-4-one (<1 mg).

$^1$H-NMR (300 MHz, CDCl$_3$) δ=4.93 (s, 2H), 3.64 (s, 3H), 2.98 (s, 2H), 2.20 (s, 3H), 2.07 (s, 6H), 1.55-1.58 (m, 2H), 1.04-1.06 (m, 2H) ppm. MS: (m/z)=293.1 (M+H$^+$).

Example 9

7,8-Dimethylspiro[chroman-3,1'-cyclopropan]-6-ol

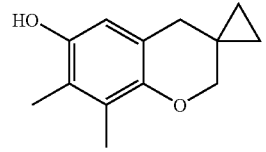

Step 1: 1-Methanesulfonyloxymethyl-cyclopropanecarboxylic acid ethyl ester

A mixture of diethyl cyclopropane-1,1-dicarboyxlate (4.1 g) and lithium tri-t-butoxy aluminohydride (11 g) in anhydrous THF (50 mL) was stirred at 80° C. for 2 h. The mixture was cooled down and water was slowly added to this suspension, followed by ethyl acetate. The organic layer was separated, washed with water and dried over MgSO$_4$. Evaporation and purification with silica gel column eluting with 40-50% EtOAc in hexane gave 1.7 g 1-hydroxymethyl-cyclopropanecarboxylic acid ethyl ester a clear liquid.

A solution of a portion of the alcohol obtained above (674 mg), methanesulfonyl chloride (590 mg), and triethyl amine (567 mg) in DCM (30 mL) was stirred at room temperature for 5 h. The DCM was washed with a diluted NaHCO$_3$ solution, NaH$_2$PO$_4$ solution, and water and dried over MgSO$_4$. Evaporation gave 1-methanesulfonyloxymethyl-cyclopropanecarboxylic acid ethyl ester as a yellow oil. This was used without further purification in the next step.

Step 2: 6-Hydroxy-7,8-dimethyl-4H-spiro[chroman-3,1'-cyclopropan]-4-one

A mixture of 2,3-dimethyl-1,4-dihydroquinone (5 g) and benzyl bromide (6.2 g) and K$_2$CO$_3$ (10 g) in DMF (50 mL) was stirred at 120° C. for 5 h. The mixture was poured into water and extracted with EtOAc. The EtOAc was washed with water, dried and evaporated. The residue was purified by silica gel column eluting with 10% EtOAc in hexane to give 3.2 g of 4-benzyloxy-2,3-dimethyl-phenol as a pale solid.

A suspension of 4-benzyloxy-2,3-dimethyl-phenol (960 mg), 1-methanesulfonyloxymethyl-cyclopropanecarboxylic acid ethyl ester, prepared as in Step 1 (890 mg) and cesium carbonate (1.5 g) in DMF (20 mL) was stirred at 130 ° C for 6 h, and the mixture was partitioned between EtOAc and water. The organic layer was washed with water, dried over MgSO$_4$ and evaporated. The residue was purified by silica gel column eluting with 10% EtOAc in hexane to give 0.78 g of 1-(4-benzyloxy-2,3-dimethyl-phenoxymethyl)-cyclopropanecarboxylic acid ethyl ester as a clear oil.

To a solution of the ester prepared as above (0.78 g) in MeOH (20 mL), was added NaOH solution (10% wt, 3 mL) and water (2 mL). After stirring the solution at 50° C. for 4 h it was poured into water, and diluted HCl solution was added to adjust pH to 3. The mixture was partitioned between EtOAc and water, and the organic layer was washed with water, dried over MgSO₄ and evaporated. The residue was purified by silica gel column eluting with 40% EtOAc in hexane to give 0.6 g of 1-(4-benzyloxy-2,3-dimethyl-phenoxymethyl)-cyclopropanecarboxylic acid as a pale solid.

To 638 mg of the acid were added, under stirring, 2 mL of conc. sulfuric acid (2 mL). The stirring was continued for 1 h until all solid was dissolved. The mixture was partitioned between water and EtOAc, and the organic layer was washed, dried and evaporated. The residue was purified by silica gel column eluting with 20% EtOAc in hexane to give a light yellow solid 90 mg of 6-hydroxy-7,8-dimethyl-4H-spiro[chromene-3,1'-cyclopropan]-4-one:

¹H-NMR (300 MHz, CDCl₃+CD₃COCD₃) δ=7.147. (10ps, 2H), 4.19 (s, 2H), 2.18, 2.16 (2s, 6H), 1.36 (m, 2H), 0.88 (m, 2H) ppm. ¹³C-NMR (75 MHz, CDCl₃+CD₃COCD₃) δ=193.96, 154.23, 148.91, 133.62, 126.73, 119.30, 107.51, 73.01, 26.54, 14.68, 12.89, 11.77 ppm. MS: (m/z)=219 (M+H⁺).

Step 3: 7,8-Dimethyl-4H-spiro[chromene-3,1'-cyclopropane]-4,6-diol

A mixture of 6-hydroxy-7,8-dimethyl-4H-spiro[chromene-3,1'-cyclopropan]-4-one (150 mg) and sodium borohydride (50 mg) in MeOH (15 mL) was stirred at room temperature for 2 h. After evaporation, the residue was applied to silica gel column eluting with 30-60% EtOAc in hexane to give 7,8-dimethyl-4H-spiro[chromene-3,1'-cyclopropane]-4,6-diol as an off-white solid (95 mg).

¹H-NMR (300 MHz, CDCl₃) δ=6.59 (s, 1H), 4.46 (d, J=11.1 Hz, 1H), 4.40 (s, 1H), 3.88 (d, J=3.7 Hz, 1H), 3.46 (d, J=3.7 Hz, 1H), 2.18, 2.16 (2s, 6H), 1.80 (m, 1H), 0.84 (m, 1H), 0.64 (m, 3H) ppm. ¹³C-NMR (75 MHz, CDCl₃+CD₃COCD₃) δ=153.13, 151.09, 130.42, 129.95, 126.59, 117.61, 75.68, 74.15, 27.27, 17.14, 17.08, 15.11, 11.70 ppm. MS: (m/z)=203 ((M–OH⁺), 100).

Step 4: 7,8-Dimethyl-4H-spiro[chromene-3,1'-cyclopropan]-6-ol

To a stirred ice-cold solution of trifluoroacetic acid (2 mL) and acetic acid (2 mL) was added sodium borohydride (30 mg). After stirring 10 min, a solution of 7,8-dimethyl-4H-spiro[chromene-3,1'-cyclopropane]-4,6-diol added (30 mg) in 20 mL of dichloromethane was added in one portion. Immediately thereafter, additional 20 mg of sodium borohydride was added to the solution, which was stirred for another 10 min. The mixture was partitioned with dichloromethane and water, and the organic layer was washed, dried and evaporated. The residue was purified by silica gel column eluting with 15% EtOAc in hexane to give 7,8-dimethyl-4H-spiro[chromene-3,1'-cyclopropan]-6-ol as a white solid (20 mg).

¹H-NMR (300 MHz, CDCl₃), δ=7.27 (s, 1H, ArH), 4.35 (s, 1H, OH), 3.84 (s, 2H), 2.62 (s, 2H), 2.16 (s, 6H), 0.60 (m, 4H), ppm. ¹³C-NMR (75 MHz, CDCl₃) δ=147.06, 146.73, 125.72, 121.73, 119.47, 112.39, 73.30, 34.38, 16.15, 12.15, 11.88, 10.57 ppm. MS: (m/z)=205 (M+H⁺).

Example 10

6-Hydroxy-7,8-dimethylspiro[chroman-3,1'-cyclopropan]-4-one O-methyl oxime

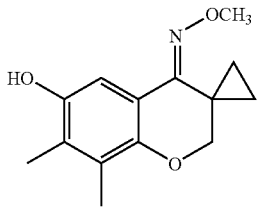

A solution of 6-hydroxy-7,8-dimethyl-4H-spiro[chromene-3, 1'-cyclopropan]-4-one (10 mg), prepared as described above, methoxyamine hydrochloride (110 mg) in pyridine (3 mL) was stirred in a microwave reaction tube (200° C., 30 min). After cooling down, the mixture was partitioned between water and ethylacetate, and the organic layer was washed with dil. HCl, dried, and evaporated. The residue was purified by silica gel column eluting with 15% EtOAc in hexane to give a 3.6 mg of 6-hydroxy-7,8-dimethylspiro[chroman-3,1'-cyclopropan]-4-one O-methyl oxime.

¹H-NMR (300 MHz, CDCl₃), δ=8.02, 7.18 (2s, 1H), 4.47, 4.44 (2s, 1H), 3.97, 3.91 (2s, 3H), 3.82, 3.71 (2s, 2H), 2.18 (m, 6H), 1.98 (m,1H), 1.21 (m, 1H), 0.75 (m, 2H) ppm. ¹³C-NMR (75 MHz, CDCl₃) δ=150.07, 149.76, 149.58, 147.71, 147.04, 145.50, 128.00, 126.63, 126.50, 126.23, 119.97, 113.98, 113.62, 106.33, 75.20, 73.34, 62.38, 62.16, 29.73, 21.24, 21.11, 12.53, 12.28, 12.25, 11.95, 11.75 ppm. MS: (m/z)=248 (M+H⁺).

Example 11

5,7,8-Trimethylspiro[chroman-3,1'-cyclobutane]-4,6-diol

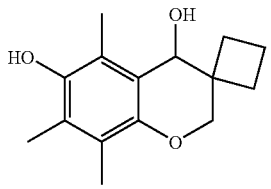

Step 1: 1-Methanesulfonyloxymethyl-cyclobutanecarboxylic acid ethyl ester

Following Step 1 described above in Example 9 but substituting diethyl cyclopropane-1,1-dicarboyxlate with diethyl cyclobutane-1,1-dicarboxylate; 1-methanesulfonyloxymethyl-cyclobutanecarboxylic acid ethyl ester was produced.

Step 2: 6-Hydroxy-5,7,8-trimethyl-4H-spiro[chromene-3,1'-cyclobutan]-4-one

Following Step 2 described above in Example 10 but substituting of 2,3-dimethyl-1,4-dihydroquinone with of 2,3,5-trimethyl-1,4-dihydroquinone, and 1-methanesulfonyloxymethyl-cyclopropaneecarboxylic acid ethyl ester with 1-methanesulfonyloxymethyl-cyclobutanecarboxylic acid ethyl ester yielded 6-hydroxy-5,7,8-trimethylspiro[chroman-3,1'-cyclobutan]-4-one.

$^1$H-NMR (300 MHz, CDCl$_3$) δ=4.56 (s, 1H, OH), 4.35 (s, 2H), 2.59 (s, 3H), 2.45(m, 2H), 2.23, 2.16 (2s, 6H), 2.00 (m, 4H) ppm. $^{13}$C-NMR (75 MHz, CDCl$_3$) δ=197.19, 154.88, 146.34, 131.74, 123.35, 121.36, 115.83, 73.05, 47.33, 25.21, 15.03, 13.30, 13.05, 11.86 ppm. MS: (m/z)=247 (M+H$^+$).

Step 3: 5,7,8-Trimethylspiro[chroman-3,1'-cyclobutane]-4,6-diol

6-Hydroxy-5,7,8-trimethyl-4H-spiro[chromene-3,1'-cyclobutan]-4-one from Step 2 was reduced following the procedure of Step 3 Example 10, to yield 5,7,8-trimethyl-4H-spiro[chromene-3,1'-cyclobutane]-4,6-diol, as a pale solid.

$^1$H-NMR (300 MHz, CDCl$_3$): δ=4.56 (s, 1H), 4.55 (s, 1H), 4.12 (m, 1H), 4.00 (m, 1H), 2.30, 2.05, 2.00 (3s, 9H), 2.30-1.80 (m, 10H) ppm. $^{13}$C-NMR (75 MHz, CDCl$_3$): δ=146.18, 145.51, 124.38, 122.55, 120.17, 118.02, 68.86, 67.01, 40.39, 25.94, 25.2, 15.04, 12.41, 11.96, 10.87 ppm. MS (m/z)=231 (M+H$^+$).

Similarly, the following compounds were produced:

7,8-Dimethyl-4H-spiro[chromene-3,1'-cyclobutane]-4,6-diol $^1$H-NMR (300 MHz, CDCl$_3$) δ=6.55 (s, 1H), 4.30 (s, 1H), 4.04 (t, J=10.5 Hz, 2H), 2.18-2.06 (m, 1H), 2.10 (s, 3H), 2.07 (s, 3), 2.00-1.80 (m, 3H), 1.75-1.63 (m, 2H) ppm; $^{13}$C-NMR δ=147.8, 145.4, 125.0, 124.8, 119.5, 112.7, 70.9, 68.4, 40.3, 26.4, 24.3, 14.9, 11.89, 11.83 ppm; MS: (m/z)=: 217 (M–OH, 100).

5,7-Diethylspiro[chroman-3,1'-cyclobutane]-4,6-diol $^1$H NMR (300 MHz, CDCl$_3$) δ=6.52 (s, 1H), 4.56 (m, 1H), 4.43 (s, 1H), 4.05 (s, 2H), 2.78 (m, 2H), 2.57 (m, 2H), 2.2-1.40 (m, 13H) ppm. $^{13}$C NMR (75 MHz, CDCl$_3$) δ=147.76, 145.21, 131.93, 129.98, 118.01, 114.15, 68.24, 66.94, 40.28, 26.99, 25.36, 23.05, 19.17, 14.87, 13.50 ppm. MS: (m/z): 245 (M–OH$^+$, 100).

5,7,8-Trimethylspiro[chroman-3,1'-cyclobutan]-6-ol 5,7,8-Trimethyl-4H-spiro[chromene-3,1'-cyclobutan]-6-ol can be prepared by reduction of 5,7,8-trimethyl-4H-spiro [chromene-3,1'-cyclobutane]-4,6-diol with NaBH$_4$, as described herein, $^1$H-NMR (300 MHz, CDCl$_3$): δ=4.25 (s, 1H, OH), 3.95 (s, 2H, OCH$_2$), 2.66 (s, 2H), 2.30, 2.05, 2.00 (3s, 9H), 2.30-1.80 (m, 6H) ppm. $^{13}$C NMR (75 MHz, CDCl$_3$): δ=146.54, 145.12, 121.94, 121.02, 119.24, 117.56, 72.42, 37.19, 36.30, 30.08, 15.29, 12.19, 11.99, 11.30 ppm. MS (m/z): 233 ((M+H$^+$).

Example 12

5',7',8'-Trimethyl-3',4'-dihydrospiro[cyclobutane-1,2'-thiochromen]-6'-ol

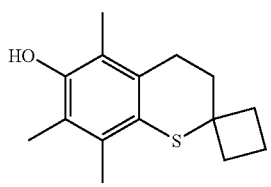

Step 1: Cyclobutylidene-acetic acid ethyl ester.

To a stirred solution of cyclobutanone (5.0 g) in 150 mL of anhydrous THF at 0° C. was slowly added NaH (3.1 g, 60% in mineral oil). After 10 min, triethyl phosphonoacetate (17.6 g) was added to the mixture, and the reaction was allowed to stir at room temperature for 2 hours. After the reaction was quenched by addition of water, the mixture was extracted 3 times with ethyl acetate. The organic layer was separated and dried over anhydrous Na$_2$SO$_4$, and concentrated in vacuo. The residue was purified by flash chromatography eluted with 10% ethyl acetate in hexane to give 7.0 g of cyclobutylidene-acetic acid ethyl ester. $^1$H-NMR (300 MHz, CDCl$_3$) δ=5.54 (m, 1H), 4.11 (q, 2), 3.09 (t, 2H), 2.79 (t, 2H), 2.06 (m, 2H), 1.23 (t, 3H) ppm. $^{13}$C-NMR (75 MHz, CDCl$_3$) δ=167, 166.5, 112.4, 59.5, 33.7, 32.3, 17.6, 14.3 ppm.

Step 2: 6'-Hydroxy-5',7',8'-trimethylspiro[cyclobutane-1,2'-thiochromen]-4'(3'H)-one 4-Mercapto-2,3,6-trimethyl-phenol (1.8 g) was dissolved in anhydrous methanol (30 mL) containing trimethyl orthoformate (2 mL). To this solution was added cyclobutylidene-acetic acid ethyl ester (4.0 g) and then 5 drops of concentrated sulfuric acid. The solution was deoxygenated by bubbling with nitrogen, and was allowed to reflux for 4 days. The mixture was concentrated, washed with NaHCO$_3$ and extracted with ethyl acetate. After concentration in vacuo, the residue was purified by flash chromatography eluted with 10-20% ethyl acetate in hexane to give 2.26 g of [1-(4-Hydroxy-2,3,5-trimethyl-phenylsulfanyl)-cyclobutyl]-acetic acid methyl ester as a white solid.

[1-(4-Hydroxy-2,3,5-trimethyl-phenylsulfanyl)-cyclobutyl]-acetic acid methyl ester (1.16 g) was suspended in 50 mL of 1N NaOH in MeOH and water (1:1, v/v), and the mixture was allowed to stir for 1 hour. The mixture was then acidified with 1 N HCl and extracted 3 times with ethyl acetate. The organic layer was washed with water and dried over anhydrous MgSO$_4$, and concentrated in vacuo. The resulting acid was dissolved in 50 mL of concentrated sulfuric acid to form a homogeneous dark red solution. After 1 hour at room temperature the solution was poured into crushed ice. The resulting green mixture was extracted 3 times with ethyl acetate. The organic layer was washed with water and dried over anhydrous MgSO$_4$, and concentrated in vacuo. The residue was purified by flash chromatography eluted with 10% ethyl acetate in hexane to give 0.9 g of 6'-hydroxy-5',7',8'-trimethylspiro[cyclobutane-1,2'-thiochromen]-4'(3'H)-one as a yellow solid.

$^1$H-NMR (300 MHz, CDCl$_3$) δ=4.83 (s, 1H), 3.08 (s, 2H), 2.46 (s, 3H), 2.28 (s, 3H), 2.26 (s, 3H), 2.28-1.90 (m, 6H) ppm. $^{13}$C-NMR (75 MHz, CDCl$_3$) δ=198.6, 149.9, 132.3, 131.8, 129.1, 128.8, 122.7, 57.9, 46.3, 35.1, 16.6, 15.7, 13.7, 13.3 ppm. MS: (m/z)=263.1 (M+H$^+$), 285.1 (M+Na$^+$).

Step 3: 5,7',8'-Trimethyl-3',4'-dihydrospiro[cyclobutane-1,2'-thiochromen]-6'-ol To a well stirred mixture of 6'-hydroxy-5',7',8'-trimethylspiro[cyclobutane-1,2'-thiochromen]-4'(3'H)-one (100 mg) in 10 mL of toluene were added Zn dust (410 mg), HgCl$_2$ (40 mg), water (0.75 mL) and concentrated HCl (0.75 mL). The heterogeneous mixture was allowed to reflux for 1 hour, and then 0.5 mL of conc. HCl was added and refluxing was continued for a further 1 hour. The mixture was cooled and filtered, and more toluene was added to the filtrate. The organic phase was washed with saturated NaHCO$_3$ and water, dried over anhydrous MgSO$_4$, and concentrated in vacuo. The residue was purified by flash chromatography eluted with 10% ethyl acetate in hexane to give 90 mg of the desired product 5',7',8'-trimethyl-3',4'-dihydrospiro[cyclobutane-1,2'-thiochromen]-6'-ol as a white solid. $^1$H-NMR (300 MHz, CDCl$_3$) δ=4.54 (s, 1H), 2.81 (t, 2H), 2.40-1.90 (m, 17H) ppm.

$^{13}$C-NMR (75 MHz, CDCl$_3$) δ=148.6, 130.4, 129.6, 124.5, 120.5, 119.7, 46.0, 36.5, 34.6, 24.6, 16.0, 15.3, 13.2, 12.4 ppm. MS: (m/z)=249.1 (M+H$^+$).

Example 13

6'-Hydroxy-5',7',8'-trimethylspiro[cyclobutane-1,2'-thiochroman]-4'(3'H)-one O-methyloxime

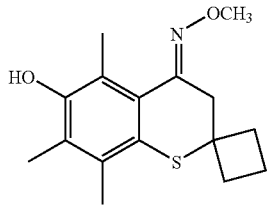

To a solution of 6'-hydroxy-5',7',8'-trimethylspiro[cyclobutane-1,2'-thiochromen]-4'(3'H)-one prepared as described above (300 mg) in 2 mL of pyridine was added methoxyamine hydrochloride (192 mg, 2.3 mmol). The reaction mixture was allowed to stir overnight. The mixture was washed with water and extracted with ethyl acetate. After concentration in vacuo, the residue was purified by flash chromatography eluted with 20% ethyl acetate in hexane to give 150 mg of 6'-hydroxy-5',7',8'-trimethylspiro[cyclobutane-1,2'-thiochromen]-4'(3'H)-one O-methyloxime, as a white solid.

$^1$H-NMR (300 MHz, CDCl$_3$) δ=3.98 (s, 3H), 3.18 (s, 2H), 2.42 (s, 3H), 2.28 (s, 3H), 2.21 (s, 3H), 2.10-1.90 (m, 6H) ppm. $^{13}$C-NMR (75 MHz, CDCl$_3$) δ=155.1, 150.7, 133.3, 128.5, 127.7, 124.3, 120.5, 62.0, 47.3, 41.9, 35.2, 16.8, 15.9, 14.5, 12.9 ppm. MS: (m/z)=292.2 (M+H$^+$).

Example 14

4'-(Methoxyamino)-5',7',8'-trimethyl-3',4'-dihydrospiro[cyclobutane-1,2'-thiochromen]-6'-ol

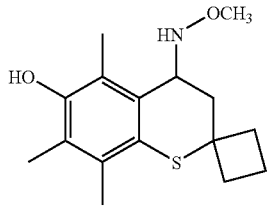

To a solution of 6'-hydroxy-5',7',8'-trimethylspiro[cyclobutane-1 ,2'-thiochromen]-4'(3'H)-one O-methyloxime, prepared as described above (50 mg) in 2 mL of BH$_3$ 1.0 M THF solution was added large excess of NaCNBH$_3$ and 0.5 mL of acetic acid. The reaction mixture was allowed to stir for 5 days. The mixture was washed with water and extracted with ethyl acetate. After concentration in vacuo, the residue was purified by flash chromatography eluted with 20% ethyl acetate in hexane to give 5.4 mg of 4'-(methoxyamino)-5',7', 8'-trimethyl-3',4'-dihydrospiro[cyclobutane-1,2'-thiochromen]-6'-ol as a white paste.

$^1$H-NMR (300 MHz, CDCl$_3$) δ=4.61 (t, 1H), 4.58 (s, 1H), 3.60 (s, 3H), 2.91, 2.55 (m, 2H), 2.33 (s, 3H), 2.26 (s, 3H,), 2.20 (s, 3H,), 2.30-1.80 (m, 6H) ppm. $^{13}$C-NMR (75 MHz, CDCl$_3$) δ=149.2, 131.4, 128.3, 124.9, 122.6, 120.9, 61.4, 55.8, 45.7, 39.1, 38.2, 37.5, 16.4, 16.3, 12.7, 11.4 ppm. MS: (m/z)=247.1 (M−NH$_2$OMe$^+$).

Example 15

7-Chloro-5,8-dimethyl-3,4-dihydrospiro[chromene-2,1'-cyclobutan]-6-yl (dimethylamino)acetate

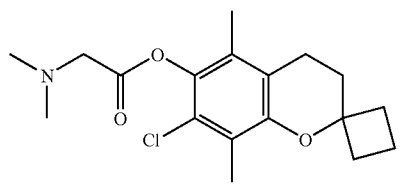

To a solution of 7-chloro-7,8-dimethyl-3,4-dihydrospiro[chromene-2,1'-cyclobutan]-6-ol (300 mg), prepared as described above, and dimethylaminoacetyl chloride hydrochloride (564 mg) in dichloromethane (8 mL) was added N-ethyldiisopropylamine (1.4 mL) dropwise at room temperature under nitrogen. The reaction mixture was stirred at room temperature for 16 hours. The solution was diluted with ethyl acetate and washed with water and brine, dried and evaporated. Chromatography (silica gel, hexane-ethyl acetate 5% to 25%) gave 276 mg of 7-chloro-5,8-dimethyl-3,4-dihydrospiro[chromene-2,1'-cyclobutan]-6-yl (dimethylamino) acetate.

$^1$H-NMR (300 MHz, CDCl$_3$) δ=3.48 (s, 2H), 2.54 (t, J=6.7 Hz, 2H), 2.43 (s, 6H), 2.25-2.15 (m, 5H), 2.00-1.85 (m, 8H), 1.70-1.50 (m, 1H) ppm. $^{13}$C-NMR (75 MHz, CDCl$_3$) δ=168.8, 150.0, 138.0, 126.9, 124.8, 123.0, 119.2, 77.1, 59.8, 45.3, 34.1, 28.8, 20.4, 12.9, 12.5 ppm. MS: (m/z)=338 (M+H$^+$).

Similarly following the procedure described herein, the following compounds were prepared:

5,7,8-Trimethyl-3,4-dihydrospiro[chromene-2,1'-cyclobutan]-6-yl (dimethylamino)acetate $^1$H-NMR (300 MHz, CDCl$_3$) δ=3.51 (s, 2H), 2.65 (t, J=6.7 Hz, 2H), 2.48 (s, 6H), 2.16-2.31 (m, 2H), 2.14 (s, 3H), 1.93-2.10 (m, 4H), 2.04 (s, 3H), 1.99 (s, 3H), 1.80-1.92 (m, 1H), 1.61-1.77 (m, 1H) ppm. $^{13}$C-NMR (75 MHz, CDCl$_3$) δ=169.4, 149.4, 140.6, 126.6, 124.9, 123.0, 118.2, 76.6, 60.0, 45.4, 34.2, 29.1, 20.5, 13.1, 12.6, 12.3, 11.9 ppm. MS: (m/z)=318.2 (M+H$^+$);

5,7-Dimethyl-4-methoxyamino-3,4-dihydrospiro[chromene-2,1'-cyclobutan]-6-yl (dimethylamino)acetate $^1$H-NMR (300 MHz, CDCl$_3$): δ=6.59 (s, 1H), 5.30 (br., 1H), 4.23 (s, 1H), 3.60 (s, 3H), 3.47 (s, 2H), 2.70-1.70 (m+s, 20H) ppm. $^{13}$C-NMR (75 MHz, CDCl$_3$): δ=169.06, 152.15, 141.36, 131.17, 129.92, 117.05, 115.71, 77.10, 61.83, 59.95, 52.43, 45.35, 35.73, 34.50, 32.02, 16.63, 13.73, 11.98 ppm. MS (m/z): 217 (100, MH−NHOMe$^+$).

7-Chloro-5,8-dimethyl-3,4-dihydrospiro[chromene-2,1'-cyclobutan]-6-yl nicotinate $^1$H-NMR (300 MHz, CDCl$_3$) δ=9.46 (s, 1H), 8.87-8.91 (m, 1H), 8.50-8.55 (m, 1H), 7.48-7.53 (m, 1H), 2.68 (t, J=6.6 Hz, 2H), 2.30 (s, 3H), 2.22-2.35 (m, 2H), 2.09 (s, 3H), 1.81-2.12 (m, 5H), 1.61-1.78 (m, 1H) ppm. $^{13}$C-NMR (75 MHz, CDCl$_3$) δ=163.5, 154.1, 151.6, 150.3, 138.0, 137.8, 127.1, 125.2, 124.9, 123.6, 123.3, 119.4, 77.2, 34.2, 28.8, 20.5, 12.9, 12.6, 12.5 ppm. MS: (m/z) 358.1 (M+H⁺).

Ethyl 4-(methoxyamino)-5,7-dimethyl-3,4-dihydrospiro[chromene-2,1'-cyclobutan]-6-yl carbonate ¹H-NMR (300 MHz, CDCl₃): δ=6.00 (s, 1H), 5.30 (br., 1H), 4.23 (s +q, 3H), 3.61 (s, 3H), 2.70-1.70 (m+s, 12H) ppm. ¹³C-NMR (75 MHz, CDCl₃): δ=153.51, 152.20, 141.94, 131.40,130.17, 117.07, 115.73, 64.83, 61.86, 52.42, 36.73, 34.51, 32.04, 16.24, 14.31, 13.74, 11.54 ppm. MS (m/z): 289 (100, MH–NHOMe⁺).

4-(Methoxyamino)-5,7-dimethyl-3,4-dihydrospiro[chromene-2,1'-cyclobutan]-6-yl- pivalate ¹H-NMR (CDCl₃, 300 MHz): δ=7.26 (s, 1H), 5.30 (br., 1H), 4.23 (s, 1H), 3.60 (s, 3H), 3.47 (s, 2H), 2.70-1.70 (m+s, 14H), 1.40 (s, 9H) ppm. ¹³C-NMR (CDCl₃, 75 MHz): δ=176.48, 151.89, 141.64, 131.28, 129.95, 117.02, 115.69, 61.83, 52.45, 39.27, 35.68, 34.48, 32.18, 31.62, 27.37, 22.69, 16.48, 14.18, 13.74, 11.80 ppm. MS (m/z): 301 (100, MH–NHOMe⁺)

Example 16

5,7,8-Trimethyl-3,4-dihydrospiro[chromene-2,1'-cyclobutan]-6-yl- 2-(4-methylpiperazin-1-yl)acetate

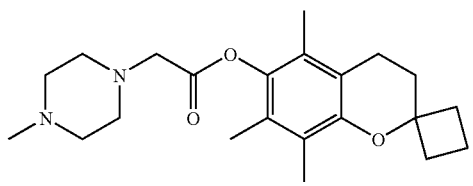

Step 1: 5,7,8-Trimethyl-3,4-dihydrospiro[chromene-2,1'-cyclobutan]-6-yl chloroacetate A solution of 5,7,8-trimethyl-3,4-dihydrospiro[chromene-2,1'-cyclobutan]-6-ol (500 mg) in anhydrous CH₂Cl₂ (3 mL) was mixed with a 15% aq. NaOH solution (2.0 mL). The resulting mixture was cooled to 0° C. and stirred vigorously while being treated with slow addition of a solution of chloroacetyl chloride (0.534 mL) in CH₂Cl₂ (2 mL). The reaction mixture was allowed to warm up to ambient temperature and stirred for an additional 6 h. Upon layer separation, organic phase was collected and dried over Na₂SO₄, followed by solvent evaporation. Column chromatography (SiO₂: hexane:EtOAc, 95:5 v/v) yielded 5,7,8-trimethyl-3,4-dihydrospiro[chromene-2,1'-cyclobutan]-6-yl chloroacetate as a pale yellow solid (204 mg).

¹H-NMR (300 MHz, CDCl₃) δ=4.37 (s, 2H), 2.69 (t, J=6.7 Hz, 2H), 2.21-2.38 (m, 2H), 2.20 (s, 3H), 1.96-2.15 (m, 4H), 2.09 (s, 3H), 2.05 (s, 3H), 1.83-1.96 (m, 1H), 1.65-1.81 (m, 1H) ppm. ¹³C-NMR (75 MHz CDCl₃) δ=166.1, 149.7, 140.5, 126.6, 124.9, 123.3, 118.4, 76.7, 40.7, 34.2, 29.1, 20.5, 13.0, 12.6, 12.1, 11.9 ppm. MS: m/z=309.1 (M+H⁺).

Step 2: 5,7,8-Trimethyl-3,4-dihydrospiro[chromene-2,1'-cyclobutan]-6-yl-2-(4-methylpiperazin-1-yl)acetate A solution of 5,7,8-trimethyl-3,4-dihydrospiro[chromene-2,1'-cyclobutan]-6-yl chloroacetate (32 mg) in CH₂Cl₂ (5 mL) was treated with 1-methylpiperazine (21.5 µL). The resulting mixture was stirred under reflux conditions for 22 h followed by cooling to ambient temperature and solvent evaporation. Column chromatography (SiO₂: hexane:EtOAc, 9:1 v/v to elute impurities followed by EtOAc:MeOH, 8:2 v/v to elute desired product) yielded a white solid, which was a mixture of desired product with SiO₂ (dissolved and eluted by MeOH). This solid was partially dissolved in acetone. The resulting suspension was sonicated and filtered to produce a clear solution, which after solvent evaporation yielded pure desired product as a white solid (27 mg). ¹H-NMR (300 MHz, CD₃OD) δ=3.61 (s, 2H), 2.77 (br s, 4H), 2.68 (t, J=6.6 Hz, 2H), 2.59 (br s, 4H), 2.33 (s, 3H), 1.82-2.30 (m, 7H), 2.13 (s, 3H), 2.01 (s, 3H), 1.97 (s, 3H), 1.65-1.81 (m, 1H) ppm. ¹³C-NMR (75 MHz, CDCl₃) δ=169.0, 149.4, 140.5, 126.6, 124.9, 123.1, 118.2, 76.6, 59.1, 54.8, 53.1, 46.1, 34.2, 29.1, 20.5, 13.1, 12.6, 12.3, 11.9 ppm. MS: (m/z)=373.2 (M+H⁺).

Example 17

7,8-Dimethyl-3,4-dihydrospiro[chromene-2,1'-cyclobutan]-6-yl phenylcarbamate

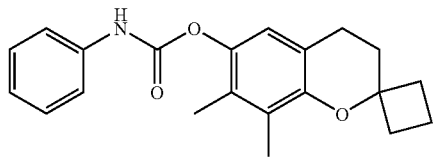

5,7,8-Trimethyl-3,4-dihydrospiro[chromene-2,1'-cyclobutan]-6-yl phenyl(phenylcarbamoyl)-carbamate

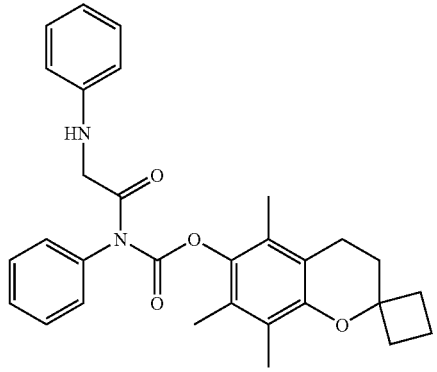

A solution of 5,7,8-trimethyl-3,4-dihydrospiro[chromene-2,1'-cyclobutan]-6-ol (500 mg) and phenyl isocyanate (0.468 mL) in anhydrous CH₂Cl₂ (25 mL) was treated with Et₃N (0.60 mL) and stirred under reflux conditions for 1 h followed by solvent evaporation preloading the residue onto silica. Column chromatography (SiO₂: hexane:EtOAc, 95:5 v/v) yielded 7,8-dimethyl-3,4-dihydrospiro[chromene-2,1'-cyclobutan]-6-yl phenylcarbamate1 as a white solid (359 mg)along with 5,7,8-trimethyl-3,4-dihydrospiro[chromene-2,1'-cyclobutan]-6-yl phenyl(phenylcarbamoyl)carbamate (535 mg).

7,8-Dimethyl-3,4-dihydrospiro[chromene-2,1'-cyclobutan]-6-yl phenylcarbamate:

¹H-NMR (300 MHz, CDCl₃) δ=7.50 (d, J=7.8 Hz, 2H), 7.33-7.39 (m, 2H), 7.12 (t, J=7.4 Hz, 1H), 7.10 (br s, 1H), 2.68 (t, J=6.6 Hz, 2H), 2.20-2.35 (m, 2H), 1.82-2.15 (m, 3H), 2.18 (s, 3H), 2.15 (s, 3H), 2.10 (s, 3H), 2.00 (t, J=6.6 Hz, 2H), 1.60-1.78 (m, 1H) ppm. $^{13}$C-NMR (75 MHz, CDCl$_3$) δ=151.8, 149.4, 140.4, 137.9, 129.2, 127.6, 125.9, 123.7, 123.1, 118.4, 118.2, 76.6, 34.2, 29.1, 20.5, 13.0, 12.6, 12.2, 11.9 ppm. MS (m/z)=352.2 (M+H$^+$).

5,7,8-Trimethyl-3,4-dihydrospiro[chromene-2,1'-cyclobutan]-6-yl phenyl(phenylcarbamoyl)carbamate $^1$H-NMR (300 MHz, CDCl$_3$) δ=10.93 (br s, 1H), 7.43-7.58 (m, 7H), 7.28-7.36 (m, 2H), 7.12 (t, J=7.4 Hz, 1H), 2.65 (t, J=6.6 Hz, 2H), 1.80-2.40 (m, 7H), 2.15 (s, 3H), 2.07 (s, 3H), 2.02 (s, 3H), 1.58-1.77 (m, 1H) ppm. $^{13}$C-NMR (75 MHz, CDCl$_3$) δ=155.0, 151.3, 149.8, 140.3, 137.7, 137.1, 129.4, 129.1, 128.7, 128.6, 126.6, 124.9, 124.1, 123.5, 119.7, 118.5, 76.7, 34.3, 29.0, 20.5, 13.0, 12.6, 12.2, 11.9 ppm. MS: (m/z)= 471.2 (M+H$^+$)

Example 18

5,7,8-Trimethyl-3,4-dihydrospiro[chromene-2,1'-cyclobutan]-6-(2-(dimethylamino)ethylcarbonate

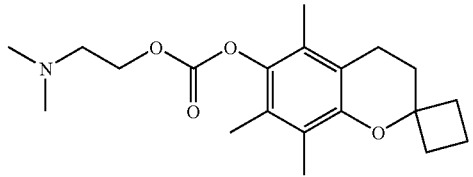

A solution of N,N-dimethylethylenediamine (0.217 mL) in anhydrous CH$_2$Cl$_2$ (25 mL) was treated with 1,1'-carbonyldiimidazole (349 mg) and triethylamine (0.56 mL). The resulting mixture was stirred for 16 h at ambient temperature followed by addition of 5,7,8-trimethyl-3,4-dihydrospiro [chromene-2,1'-cyclobutan]-6-ol (500 mg). The resulting reaction mixture was heated under reflux for 2 h followed by evaporation of solvent and heating neat for another 5 h at 70° C. Column chromatography (SiO$_2$:EtOAc) yielded 5,7,8-trimethyl-3,4-dihydrospiro[chromene-2,1'-cyclobutan]-6-(2-(dimethylamino)ethylcarbonate as a colorless oil (262 mg).

$^1$H-NMR (300 MHz, CDCl$_3$) δ=4.37 (t, J=5.8 Hz, 2H), 2.69 (t, J=5.8 Hz, 2H), 2.65 (t, J=6.6 Hz, 2H), 2.34 (s, 6H), 1.80-2.35 (m, 5H), 2.15 (s, 3H), 2.10 (s, 3H), 2.04 (s, 3H), 1.98 (t, J=6.6 Hz, 2H), 1.60-1.75 (m, 1H) ppm. $^{13}$C-NMR (75 MHz, CDCl$_3$) δ=154.1, 149.6, 141.2, 126.9, 125.1, 123.1, 118.2, 76.6, 66.2, 57.7, 45.8, 34.2, 29.1, 20.5, 12.7, 12.6, 11.9 ppm. MS: (m/z)=348.2 (M+H$^+$).

Example 19

3-(Hydroxymethyl)-5,7,8-trimethylspiro[chromene-2,1'-cyclobutan]-6-ol

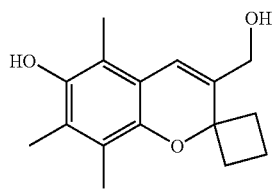

Step 1: 6-Hydroxy-5,7,8-trimethylspiro[chromene-2,1'-cyclobutan]-4(3H)-one

To a solution of trimethylhydroquinone (30 g) in 200 mL of toluene was added acetyl chloride (28 mL). The reaction mixture was allowed to reflux for 2 hours. More acetyl chloride (28 mL) was added, and the reaction mixture was allowed to reflux for additional 2 hours. After the reaction was complete as indicated by TLC (20% ethyl acetate in hexane), the reaction was allowed to cool down and concentrated in vacuo. Recrystallization of the resulting residue from ethyl acetate and hexane gave 42.3 g of 2,3,5-trimethyl-1,4-phenylene diacetate as a white solid.

The above solid 2,3,5-trimethyl-1,4-phenylene diacetate (42.3 g) was then suspended in 100 mL of boron trifluoride-acetic acid complex, and the mixture was allowed to heat at 120° C. for 3 days. The reaction was allowed to cool down and concentrated in vacuo. Recrystallization of the resulting residue from ethyl acetate and hexane gave 35.5 g of 3-acetyl-4-hydroxy-2,5,6-trimethylphenyl acetate as a yellow solid.

To a solution of the above solid 3-acetyl-4-hydroxy-2,5,6-trimethylphenyl acetate (35 g) in 150 mL of toluene was added cyclobutanone (11.4 g) and pyrrolidine (15 mL). The reaction was allowed to reflux for 2 hours and water from the reaction was removed using a Dean-Stark apparatus. After the reaction was complete, the mixture was extracted with ethyl acetate and washed with 1N HCl and water. The organic layer was dried over anhydrous Na$_2$SO$_4$ and concentrated in vacuo to give 34 g of acetyl-protected product as a dark brown residue. This residue was hydrolyzed in 1N NaOH in MeOH/ water for 3 hours. After the reaction was complete as indicated by TLC, the mixture was acidified with 1N HCl and extracted with ethyl acetate and dried over anhydrous Na$_2$SO$_4$. After concentration in vacuo, the resulting dark brown residue (30 g) was loaded onto a short silica gel column, and eluted with 10-40% ethyl acetate in hexane. Recrystallization of the resulting product from ethyl acetate and hexane gave 14.6 g of the desired 6-hydroxy-5,7,8-trimethylspiro[chromene-2,1'-cyclobutan]-4(3H)-one as a yellow solid. The mother liquid was concentrated to give another 4 g of crude 6-hydroxy-5,7,8-trimethylspiro[chromene-2,1'-cyclobutan]-4(3H)-one as a dark brown residue that can further be purified as described above. $^1$H-NMR (300 MHz, CDCl$_3$) δ=4.61 (s, 1H), 2.86 (s, 2H), 2.56 (s, 3H), 2.30-1.70 (m, 12H) ppm. $^{13}$C-NMR (75 MHz, CDCl$_3$) δ=195.3, 152.8, 146.2, 132.3, 124.2, 120.9, 117.3, 79.6, 47.7, 33.2, 13.4, 12.9, 12.4, 12.3 ppm. MS: m/z=247.1 (M+H$^+$)

Step 2: 3-(Chloromethylene)-6-hydroxy-5,7,8-trimethylspiro[chromene-2,1'-cyclobutan]-4(3H)-one To a solution of 6-Hydroxy-5,7,8-trimethylspiro [chromene-2,1'-cyclobutan]-4(3H)-one (2.2 g) in 20 mL of THF at 0° C. was added sodium hydride (370 mg, 60% in mineral oil). After 5 min, MOM-Cl (0.96 mL) was added slowly to the reaction. After the reaction was complete, the mixture was extracted with ethyl acetate and was washed with water. The organic layer was separated and dried over anhydrous Na$_2$SO$_4$, and concentrated in vacuo. The residue was purified by flash chromatography eluted with 20% ethyl acetate in hexane to give 2.0 g of 6-(methoxymethoxy)--5,7, 8-trimethylspiro[chromene-2,1'-cyclobutan]-4(3H)-one as a yellow paste.

To a solution of 6-(methoxymethoxy)--5,7,8-trimethylspiro[chromene-2,1'-cyclobutan]-4(3H)-one (2.0 g) in 20 mL of THF was added under stirring, NaH (1.38 g). After 5 minutes, 8.5 mL of methyl formate (137.4 mmol) were added dropwise to the mixture. The reaction was allowed to stir at room temperature overnight. The organic phase was washed with 1N HCl and water, dried over anhydrous MgSO$_4$, and concentrated in vacuo to give 6-(methoxymethoxy)-5,7,8- trimethyl-4-oxo-3,4-dihydrospiro[chromene-2,1'-cyclobutane]-3-carbaldehyde as a yellow paste. This intermediate was used directly for subsequent reactions without further purification.

To a stirred solution of 6-(methoxymethoxy)-5,7,8-trimethyl-4-oxo-3,4-dihydrospiro[chromene-2,1'-cyclobutane]-3-carbaldehyde (2.0 g) in 20 mL of dichloromethane was added dropwise 5 mL of $SOCl_2$. The reaction was allowed to stir at room temperature for 2 hr. After the reaction was complete, the mixture was concentrated and the residue was purified by flash chromatography eluted with 10-20% ethyl acetate in hexane to give 1.46 g of 3-(chloromethylene)-6-hydroxy-5,7,8-trimethylspiro[chromene-2,1'-cyclobutan]-4(3H)-one, as a yellow solid. It is a mixture of two isomers with a ratio of about 3:1, as indicated by TLC analysis.

Step 3: 6-Hydroxy-5,7,8-trimethyl-2-cyclobutyl-chromene-3-carbaldehyde.

To a stirred solution of above yellow solid (1.46 g) in 20 mL of MeOH was added 2-fold excess of $NaBH_4$ (378 mg). The 4-propylbenzensulfonamide-2- ethyl; 4-methylbenzenesulfonamide-2-ethyl e reaction was allowed to stir at room temperature for 30 min. After the reaction was complete, the mixture was concentrated and the residue was purified by flash chromatography eluted with 20-40% ethyl acetate in hexane to give an off-white solid. After standing for overnight at room temperature, the off-white solid was converted to a yellow solid of 6-hydroxy-5,7,8-trimethyl-2-cyclobutyl-chromene-3-carbaldehyde.

Step 4: 3-(Hydroxymethyl)-5,7,8-trimethylspiro[chromene-2,1'-cyclobutan]-6-ol.

To a stirred solution of 6-hydroxy-5,7,8-trimethyl-2-cyclobutyl-chromene-3-carbaldehyde (250 mg) in 10 mL of THF and 1 mL of AcOH was added $NaCNBH_3$ (305 mg). The reaction mixture was allowed to stir at room temperature for 6 h. The mixture was concentrated and the residue was purified by flash chromatography eluted with 30% ethyl acetate in hexane to give 135 mg of 3-(hydroxymethyl)-5,7,8-trimethylspiro[chromene-2,1'-cyclobutan]-6-ol as a light yellow solid. $^1$H-NMR (300 MHz, MeOD) δ=6.52 (s, 1H, C=CH), 4.35 (s, 1H), 2.36 (m, 4H), 2.20-1.75 (m, 11H) ppm. $^{13}$C-NMR (75 MHz, MeOD) δ=146.5, 144.5, 137.6, 124.9, 122.2, 119.3, 118.4, 117.0, 80.7, 62.0, 32.7, 14.3, 12.2, 11.2, 10.7 ppm. MS:(m/z)=243.2 (M−18$^+$), 283.1 (M+Na$^+$).

3-(Methoxymethyl)-5,7,8-trimethylspiro[chromene-2,1'-cyclobutan]-6-ol was prepared by treating 3-(hydroxymethyl)-5,7,8-trimethylspiro[chromene-2,1'-cyclobutan]-6-ol with methanol in the presence of conc. hydrochloric acid:

$^1$H-NMR (300 MHz, CDCl$_3$) δ=6.51 (s, 1H, =CH), 4.37 (s, 1H), 4.20 (s, 2H, OCH$_2$), 3.44 (s, 3H), 2.22 (s, 3H), 2.20 (s, 3H), 2.19 (s, 3H), 2.40-1.80 (m, 6H) ppm. $^{13}$C-NMR (75 MHz, CDCl$_3$) δ=145.8, 144.5, 134.6, 123.0, 122.8, 119.4, 119.3, 116.3, 80.8, 73.1, 57.9, 33.1, 14.6, 12.5, 11.9, 11.1 ppm. MS: (m/z)=243.2 (M−OMe).

3-(Hydroxymethyl)-5,7,8-trimethyl-3,4-dihydrospiro[chromene-2,1'-cyclobutan]-6-ol was prepared by hydrogenation of 3-(hydroxymethyl)-5,7,8-trimethylspiro[chromene-2,1'-cyclobutan]-6-ol with hydrogen in the presence of Pd/C.

$^1$H-NMR (300 MHz, CD$_3$OD) δ=3.75, 3.36 (m, 2H, OCH$_2$), 3.32 (m, 1H, CH), 2.71 (m, 2H, CH$_2$), 2.13 (s, 3H, ArCH$_3$), 2.09 (s, 6H, ArCH$_3$), 2.35-1.70 (m, 6H) ppm. $^{13}$C-NMR (75 MHz, CD$_3$OD) δ=144.7, 144.5, 123.0, 121.8, 121.2, 116.2, 78.6, 60.6, 40.6, 33.1, 31.2, 22.3, 12.6, 11.4, 10.6, 10.5 ppm. MS: (m/z)=263.2 (M+H$^+$), 285.2 (M+Na$^+$).

Similarly the following compound was prepared:

5,7-Diethyl-3-(hydroxymethyl)spiro[chroman-2,1'-cyclobutan]-6-ol $^1$H NMR (300 MHz, CD$_3$OD) δ=6.36 (s, 1H), 3.69, 3.29 (m, 1H), 2.90-1.50 (m, 13H), 1.1-1.03 (m, 6H) ppm. $^{13}$C NMR (75 MHz, CD$_3$OD) δ=148.5, 147.0, 132.5, 118.2, 116.0, 80.6, 62.5, 42.2, 35.2, 33.2, 24.7, 23.2, 21.0, 15.4, 14.9, 14.5 ppm. MS: m/z=277.2 (M+H$^+$), 299.2 (M+Na$^+$).

The carbamate derivative of the above compound was prepared by ways well known in the art.

(5,7-Diethyl-6-hydroxyspiro[chroman-2,1'-cyclobutane]-3-yl)methyl carbamate $^1$H NMR (300 MHz, CD$_3$OD) δ=6.42 (s, 1H), 4.14, 3.78 (m, 1H), 2.75-1.50 (m, 13H), 1.18 (t, 3H), 1.11 (t, 3H) ppm. $^{13}$C NMR (75 MHz, CD$_3$OD) δ=158.0, 146.5, 145.3, 131.0, 130.6, 115.6, 114.2, 78.4, 63.5, 37.4, 33.0, 31.2, 22.9, 21.3, 19.0, 13.4, 12.7, 12.5 ppm. MS: m/z=320.2 (M+H$^+$, 100%), 342.2 (M+Na$^+$).

Example 20

5',7',8'-Trimethylspiro[cyclobutane-1,2'-thiochromen]-6'-ol

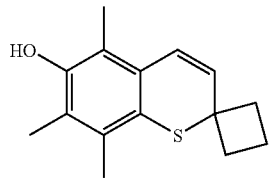

To a solution of 6'-hydroxy-5',7',8'-trimethylspiro[cyclobutane-1,2'-thiochromen]-4'(3')-one, prepared as described in Example 12, Step 2, (0.8 g) in 2 mL of DMF was added t-butyldimethylsilyl chloride (1.38 g) and imidazole (916 mg). The reaction mixture was allowed to stir for overnight. The mixture was washed with water and extracted with ethyl acetate. After concentrated in vacuo, the residue was used directly for next step reaction. To a portion of the residue (200 mg) was dissolved in 20 mL of methanol was added NaBH$_4$ (100 mg). The reaction mixture was allowed to stir for 1 hour. After concentrated in vacuo, the residue was purified by flash chromatography eluted with 20% ethyl acetate in hexane to give 102 mg of t-butyldimethylsilyl protected 5',7',8'-trimethyl-3',4'-dihydrospiro[cyclobutane-1,2'-thiochromene]-4',6'-diol.

A solution of t-butyldimethylsilyl protected alcohol (100 mg) was left in 5 mL of DCM at room temperature for a week. The residue was re-dissolved in THF and treated with 0.5 mL of tetrabutyl ammonium fluoride (1.0 M in THF). After concentrated in vacuo, the residue was purified by flash chromatography eluted with 20% ethyl acetate in hexane to give 42.2 mg of the chromene 5',7',8'-trimethylspiro[cyclobutane-1,2'-thiochromen]-6'-ol as a white solid.

$^1$H-NMR (300 MHz, CDCl$_3$) δ=6.59 (d, 1H), 6.20 (d, 1H), 4.57 (s, 1H), 2.33 (s, 3H), 2.22 (s, 3H), 2.12 (s, 3H), 2.30-1.92 (m, 6H) ppm. $^{13}$C-NMR (75 MHz, CDCl$_3$) δ=149.3, 132.8, 131.8, 128.6, 123.5, 122.3, 118.0, 44.3, 38.2, 18.9, 16.9, 12.7, 11.7 ppm. MS: (m/z)=247.1 (M+H$^+$).

Example 21

4-(Aminomethyl)-5,7,8-trimethyl-3,4-dihydrospiro[chromene-2,1'-cyclobutane]-4,6-diol

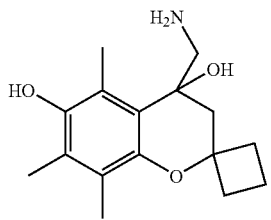

A mixture of 5,7,8-trimethyl-4-oxo-3,4-dihydrospiro[chromene-2,1'-cyclobutan]-6-yl acetate (2 g), $ZnI_2$ (100 mg) and trimethylsilyl cyanide (4 mL) was stirred at 70° C. for 2 h. A homogeneous solution was obtained. The solution was cooled down to room temperature, and THF (30 mL) was added, followed by 1 g of lithium aluminum hydride. After stirring at 60° C. for 3 h, the solution was cooled down and EtOAc was added to destroy excess lithium aluminum hydride. The mixture was poured into water and extracted with EtOAc. The EtOAc was washed with water and dried. After evaporation a white solid was obtained (1 g), which was washed with DCM to give 4-(aminomethyl)-5,7,8-trimethyl-3,4-dihydrospiro[chromene-2,1'-cyclobutane]-4,6-diol.
$^1$H-NMR (300 MHz, CDCl$_3$+CD$_3$OD): δ=2.85 (AB, J=13.44 Hz, 2H), 2.36 (s, 2H), 2.35-1.60 (m, 6H), 2.11 (s, 9H) ppm. $^{13}$C-NMR (75 MHz, CDCl$_3$+CD$_3$OD) δ=146.82, 145.54, 124.91, 123.75, 121.01, 120.48, 76.49, 75.64, 50.07, 44.97, 34.46, 32.36, 13.75, 13.31, 12.50, 12.22 ppm. MS: (m/z)=260 (M$^+$–OH).

Example 22

4-(Aminomethyl)-5,7,8-trimethylspiro[chromene-2,1'-cyclobutan]-6-ol

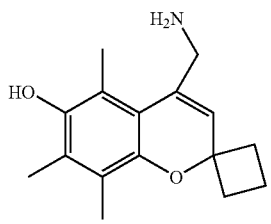

A solution of 4-(aminomethyl)-5,7,8-trimethyl-3,4-dihydrospiro[chromene-2,1'-cyclobutane]-4,6-diol (277 mg) in DCM (10 mL) was slowly added to sodium borohydride (200 mg) in 4 mL of TFA-acetic acid, 1:1 at 0° C. The mixture was stirred at 0° C. for 2 h then poured into water and separated the DCM. The DCM was dried and evaporated. The residue was purified by silica gel column eluting with 7.5% MeOH in DCM to give 4-(aminomethyl)-5,7,8-trimethylspiro[chromene-2,1'-cyclobutan]-6-ol (55 mg). $^1$H-NMR (300 MHz, CDCl$_3$): δ=6.12 (s, 1H), 3.78 (s, 2H), 2.34-1.70 (3s+m, 18H) ppm. $^{13}$C-NMR (75 MHz, CDCl$_3$): δ146.59, 145.56 137.14, 128.02, 124.51, 123.45, 120.62, 117.21, 76.24, 45.56, 36.07, 14.65, 12.85, 12.56, 12.33 ppm. MS: (m/z): 260 (M+H$^+$).

Example 23

4-Ethoxy-5,7,8-trimethylspiro[chroman-3,1'-cyclobutan]-6-ol

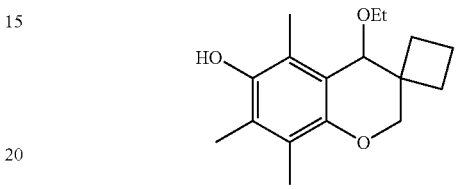

Step 1: 6- t-Butyldimethylsilyl protected 5,7,8-trimethyl-4H-spiro[chromene-3,1'-cyclobutane]-4,6-diol A mixture of 6-hydroxy-5,7,8-trimethyl-4H-spiro[chromene-3,1'-cyclobutan]-4-one (372 mg), tert-butyldimethylsilyl chloride (500 mg) and imidazole (300 mg) in DMF (5 mL) was stirred at room temperature for a few hours. The reaction was monitored by TLC (20% EtOAc in hexane). After completion of the reaction, the mixture was poured into water and extracted with EtOAc. The EtOAc was washed, dried and evaporated. The residue (420 mg) was dissolved in MeOH (20 mL), sodium borohydride (100 mg) was added and it was stirred for 1 h. Evaporation gave 6-t-butyldimethylsilyl protected 5,7,8-trimethyl-4H-spiro[chromene-3,1'-cyclobutane]-4,6-diol, which was purified by silica gel column eluting with 10-20% EtOAc in hexane to give a light yellow pale oil (400 mg).

Step 2: 4-Ethoxy-5,7,8-trimethyl-4H-spiro[chromene-3,1'-cyclobutan]-6-ol

A mixture of t-butyldimethylsilyl protected 5,7,8-trimethyl-4H-spiro[chromene-3,1'-cyclobutane]-4,6-diol (50 mg), ethyl iodide (0.1 mL) and NaH (60% oil suspension, 50 mg) was stirred at room temperature for 2 h. The mixture was poured into water and extracted with EtOAc. The EtOAc was washed with water, dried and concentrated. To the residue dissolved in THF (10 mL) was added a solution of 1M tetrabutylammonium fluoride (TBAF) in THF (0.2 mL). The mixture was stirred for 30 min, poured into water and extracted with EtOAc. The EtOAc was washed with water, dried and concentrated. The residue was purified by silica gel column eluting with 5% EtOAc in hexane giving 4-ethoxy-5,7,8-trimethylspiro[chroman-3,1'-cyclobutan]-6-ol, as a colorless solid (38 mg). $^1$H-NMR (300 MHz, CDCl$_3$): δ=4.40 (s, 1H), 4.28 (s, 1H), 4.20 (m, 2H), 3.75 (m, 2H), 2.23, 2.12, 2.10 (3s, 9H), 2.40-1.40 (m, 6H), 1.20 (m, 3H) ppm. $^{13}$C-NMR (75 MHz, CDCl$_3$): δ=146.18, 144.98, 124.45, 122.06, 120.70, 116.76, 67.08, 66.05, 40.91, 29.45, 27.47, 27.25, 16.24, 15.92, 12.47, 12.05, 11.46 ppm. MS: (m/z):=231 (M$^+$–OEt).

Example 24

4-Methoxy-5,7,8-trimethylspiro[chroman-3,1'-cyclobutan]-6-ol

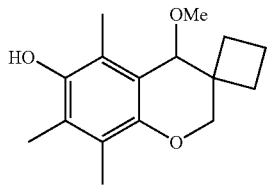

Step 1: 6-Tetra hydropyranyl protected 5,7,8-trimethyl-4H-spiro[chromene-3,1'-cyclobutane]-4,6-diol A mixture of 6-hydroxy-5,7,8-trimethyl-4H-spiro[chromene-3,1'-cyclobutan]-4-one (246 mg), dihydropyran (DHP) (0.15 mL) and pyridinium p-toluene sulfonate (PPTS) (15 mg) in dichloromethane (20 mL) was stirred at room temperature for a few hours. The reaction was monitored by TLC (20% EtOAc in hexane). After completion of the reaction, the solvent was evaporated and the residue was dissolved in MeOH (20 mL). Sodium borohydride (100 mg) was added and it was stirred for 1 h. Evaporation gave 6-tetra hydropyranyl protected 5,7,8-trimethyl-4H-spiro[chromene-3,1'-cyclobutane]-4,6-diol which was purified by silica gel column eluting with 20-30% EtOAc in hexane to give a pale oil (275 mg,).

Step 2: 4-Methoxy-5,7,8-trimethyl-4H-spiro[chromene-3,1'-cyclobutan]-6-ol

A mixture of 6-tetra-hydropyranyl protected 5,7,8-trimethyl-4H-spiro[chromene-3,1'-cyclobutane]-4,6-diol (50 mg), methyl iodide(50 mg) and NaH (60% oil suspension, 15 mg) was stirred at room temperature for 2 h. The mixture was poured into water and extracted with EtOAc. The EtOAc was washed with water, dried and concentrated. The residue was dissolved in methanol, a few drops of 2 N HCl were added. The mixture was stirred for 30 min, poured into water and extracted with EtOAc. The EtOAc was washed with water, dried and concentrated. The residue was purified by silica gel column eluting with 10% EtOAc in hexane giving 4-methoxy-5,7,8-trimethyl-4H-spiro[chromene-3,1'-cyclobutan]-6-ol, as a light brown solid (30 mg). $^1$H-NMR (300 MHz, CDCl$_3$): δ=4.41 (s, OH), 4.124 (s, 1H), 4.18 (s, 2H), 3.52 (s, 3H), 2.23, 2.13, 2.10 (3s, 9H), 2.30-1.6 (m, 6H) ppm. $^{13}$C-NMR (75 MHz, CDCl$_3$): δ=146.20, 144.93, 124.56, 122.13, 77.84, 67.13, 58.13, 40.59, 27.58, 27.13, 15.85, 12.46, 12.02, 11.60 ppm. MS: (m/z)=231 (M−OMe$^+$).

Example 25

5,7,8-Trimethyl-3,4-dihydrospiro[chromene-2,1'-cyclobutane]-3,6-diol

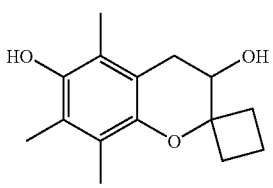

Step 1. 2-(2-Cyclobutylideneethyl)-3,5,6-trimethylbenzo-1,4-quinone

To a solution of trimethyl hydroquinone (3 g) in 100 mL dioxane at room temperature, was added BF$_3$.Et$_2$O (4.26 g). While stirring, a solution of 1-vinylcyclobutanol (1.96 g) in 20 mL dioxane was added dropwise to the mixture. The reaction was stirred for 1 h and quenched by pouring onto ice (50 g). The aqueous layer was saturated with NaCl and extracted with 3:1 hexane/EtOAc. The combined organic phase was washed with brine and NaHCO$_3$ solution, concentrated and diluted with EtOH (30 mL). 10% FeCl$_3$ aqueous solution (40 mL) was added to the solution and the mixture was stirred for 2 h at room temperature. The mixture was diluted with hexane/EtOAc (4:1, 80 mL) and the aqueous layer was saturated with NaCl. After layer separation, the organic layer was washed with brine, dried over Na$_2$SO$_4$ and concentrated. The crude product was chromatographed to afford 2-(2-cyclobutylideneethyl)-3,5,6-trimethylbenzo-1,4-quinone (2.1 g). MS m/z=231 (M−OH).

Step 2. 5,7,8-Trimethylspiro[chromene-2,1'-cyclobutan]-6-ol

The above 2-(2-cyclobutylideneethyl)-3,5,6-trimethyl-benzo-1,4-quinone was dissolved in pyridine and the mixture was heated to reflux for 15 h. The solvent was removed under reduced pressure and the residue was chromatographed to afford 5,7,8-trimethylspiro[chromene-2,1'-cyclobutan]-6-ol (420 mg). $^1$H-NMR (300. MHz, CDCl$_3$) δ=6.59 (d, J=9.9 Hz, 1H), 6.07 (d, J=9.9 Hz, 1H), 4.39 (s, 1H), 2.47 (m, 2H), 2.26-2.17 (m, 11H), 1.90 (m, 1H), 1.75 (m, 1H) ppm. $^{13}$C-NMR (75 MHz, CDCl$_3$) δ=145.6, 144.6, 128.9, 123.0, 122.3, 120.2, 118.5, 116.2, 37.0, 12.5, 12.3, 11.8, 11.0 ppm. MS m/z: 231 (M+H$^+$).

Step 3: 6-tert-Butyldimethylsilyl derivative of 5,7,8-trimethylspiro[chromene-2,1'-cyclobutan]-6-ol To a solution of 5,7,8-trimethylspiro[chromene-2,1'-cyclobutan]-6-ol (420 mg) in 10 mL DCM and 3 mL DMF were added imidazole (367 mg) and tert-butyldimethylsilyl chloride (TBDMSCl) (540 mg). The mixture was stirred at room temperature for 15 h, concentrated, diluted with hexane/EtOAc (3:1, 50 mL), washed with water (3×50 mL), dried over Na$_2$SO$_4$ and concentrated. The crude product was chromatographed to afford the 6-tert-butyldimethylsilyl derivative of 5,7,8-trimethylspiro-[chromene-2,1'-cyclobutan]-6-ol; (560 mg). MS: (m/z)=345 (M+H$^+$).

Step 4: 6-tert-Butyldimethylsilyl derivative of 3-bromo-5,7,8-trimethyl-3,4-dihydrospiro[chromene-2,1'-cyclobutane]-4,6-diol To a solution of the stirred 6-tert-butyldimethylsilyl derivative of 5,7,8-trimethylspiro[chromene-2,1'-cyclobutan]-6-ol (172 mg) in 10 mL dimethoxyethane was added 4 mL of water, dropwise. The solution was cooled to 0° C. with an ice bath and then vigorously stirred while a solution of N-bromosuccinimide (NBS) (43 mg, 0.75 mmol) in 4 mL of DME was added, dropwise. The mixture was stirred at 0° C. for 3 h and allowed to warm to room temperature. The mixture was stirred until all starting material was consumed. The reaction mixture was concentrated under reduced pressure and extracted with EtOAc (3×30 mL). The combined organic layers were washed with water (3×20 mL), dried over Na$_2$SO$_4$ and concentrated. The crude product was chromatographed to afford the 6-tert-butyldimethylsilyl derivative of 3-bromo-5,7,8-trimethyl-3,4-dihydrospiro[chromene-2,1'-cyclobutane]-4,6-diol (200 mg). MS: (m/z)=442 (M+H$^+$), 424 (M−OH$^−$).

Step 5: tert-Butyldimethylsilyl derivative of 5,7,8-trimethyl-3,4-dihydrospiro[chromene-2,1'-cyclobutane]-3,6-diol A solution of the 6-tert-butyldimethylsilyl derivative of 3-bromo-5,7,8-trimethyl-3,4-dihydrospiro[chromene-2,1'-cyclobutane]-4,6-diol (200 mg) in 3 mL of dry THF at 0° C. was added, dropwise, to a suspension of NaH (36 mg, 60%) in dry THF (5 mL). The resulting mixture was stirred at room temperature for 8 h, concentrated and dried under high vacuum. To this crude material was added DCM/hexane (1:1, 30 mL) and the mixture was stirred under nitrogen for 30 min. After setting for 1 h, the solid was filtered off and the solution was concentrated to yield crude epoxide that was used directly for the next reaction.

LiAlH$_4$ (1.8 mL of a 1 M THF solution) and AlCl$_3$ (90 mg) were suspended in dry THF 15 mL and stirred for 20 min to form a milky mixture. To this suspension at 0° C. was added a solution of the chroman epoxide, prepared as above, in 5 mL THF dropwise. After stirring for 2 h at room temperature the reaction was quenched onto ice and extracted with hexane/EtOAc (2:1, 3×30 mL). The combined organic phase was dried over Na$_2$SO$_4$ and concentrated. The product was purified by chromatography to afford the 6-tert-butyidimethylsilyl derivative of 5,7,8-trimethyl-3,4-dihydrospiro[chromene-2,1'-cyclobutane]-3,6-diol (122 mg). MS: (m/z)=385 (M+Na$^+$).

Step 6: 5,7,8-Trimethyl-3,4-dihydrospiro[chromene-2,1'-cyclobutane]-3,6-diol

The solution of tert-butyldimethylsilyl derivative of 5,7,8-trimethyl-3,4-dihydrospiro[chromene-2,1'-cyclobutane]-3,6-diol (20 mg) in 2 mL THF was added to tetrabutylammonium fluoride (TBAF) (0.5 mL of a 1 M THF solution) in 2 mL of THF at 0° C. The resulting mixture was stirred at room temperature for 2 h and diluted with hexane/EtOAc (1:1, 30 mL), washed with brine, dried over Na$_2$SO$_4$ and concentrated. The crude product was purified by chromatography to afford 5,7,8-trimethyl-3,4-dihydrospiro[chromene-2,1'-cyclobutane]-3,6-diol (10 mg).

$^1$H-NMR (300 MHz, CDCl$_3$) δ=4.31 (s, 1H), 4.13 (m, 2H), 2.99-2.70 (m, 2H), 2.45-2.23 (m, 2H), 2.21 (s, 3H), 2.19 (s, 3H), 2.11 (s, 3H), 1.99-1.82 (m, 3H), 1.79-1.67 (m, 1H) ppm; $^{13}$C-NMR δ=145.7, 144.0, 123.1, 121.4, 119.1, 115.7, 78.5, 67.2, 32.2, 30.4, 29.0, 12.2, 11.9, 11.4 ppm; MS: (m/z)=271 (M+Na$^+$).

Example 26

3-Methoxy-5,7,8-trimethyl-3,4-dihydrospiro[chromene-2,1'-cyclobutan]-6-ol

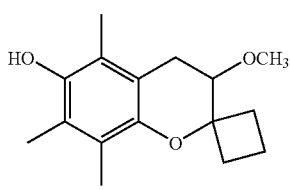

Step 1: 6-tert-Butyldimethylsilyl derivative of 3-methoxy-5,7,8-trimethyl-3,4-dihydrospiro[chromene-2,1'-cyclobutan]-6-ol A solution of tert-butyldimethylsilyl derivative of 5,7,8-trimethyl-3,4-dihydrospiro[chromene-2,1'-cyclobutane]-3,6-diol (30 mg), prepared as described in Example 22, in 1 mL of THF was added to NaH (8 mg) suspended in THF (1.5 mL). The resulting mixture was stirred at room temperature for 10 min and methyl iodide (34 mg) was added. The reaction was stirred at room temperature for 10 h and quenched onto 30 g of ice. It was extracted with hexane/EtOAc (2:1, 3×30 mL) and the combined organic layers were washed with brine, dried over Na$_2$SO$_4$ and concentrated to afford the 6-tert-butyldimethylsilyl derivative of 3-methoxy-5,7,8-trimethyl-3,4-dihydrospiro[chromene-2,1'-cyclobutan]-6-ol which was used directly for the next reaction.

Step 2: 3-Methoxy-5,7,8-trimethyl-3,4-dihydrospiro[chromene-2,1'-cyclobutan]-6-ol A solution of tert-butyldimethylsilyl derivative of 3-methoxy-5,7,8-trimethyl-3,4-dihydrospiro[chromene-2,1'-cyclobutan]-6-ol in 2 mL of THF was added to a cooled (0° C.) solution of TBAF (0.5 mL of a 1 M THF solution) in 2 mL of THF. The mixture was stirred at room temperature for 2 h and diluted with hexane/EtOAc (3:1, 30 mL). It was washed with brine (3×30 mL) and water (3×30 mL), dried over Na$_2$SO$_4$ and concentrated. The crude product was purified by chromatography to afford 3-methoxy-5,7,8-trimethyl-3,4-dihydrospiro[chromene-2,1'-cyclobutan]-6-ol (10 mg). $^1$H-NMR (300 MHz, CDCl$_3$) δ=4.44 (s,1H), 3.65 (t, J=5.1 Hz, 1H), 2.81 (m, 2H), 2.39 (m, 1H) ppm, 2.25-2.14 (m, 3H), 2.21 (s, 3H), 2.18 (s, 3H), 2.14 (s, 3H), 1.97 (m, 1H), 1.78 (m, 1H) ppm; $^{13}$C-NMR δ=145.4, 144.4, 122.9, 121.5, 119.0, 116.1, 78.5, 57.6, 32.2, 30.2, 24.9, 12.9, 12.3, 12.0, 11.4 ppm; MS: (m/z)=262 (M+H$^+$).

Example 27

4-(Methoxyamino)-5,7,8-trimethyl-3,4-dihydrospiro[chromene-2,1'-cyclobutan]-6-ol

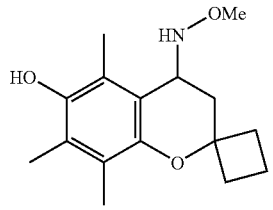

Step 1: 3-Acetyl-4-hydroxy-2,5,6-trimethylphenyl acetate

To a solution of trimethylhydroquinone (10.0 g) and acetic anhydride (10 mL) in dichloromethane (50 mL) was added diisopropylethylamine (10 mL) at room temperature. The solution was stirred at room temperature for 18 hours, diluted with ethyl acetate, washed with water and brine. Evaporation gave the 2,3,5-trimethyl-1,4-phenylene diacetate as solid.

The 2,3,5-trimethyl-1,4-phenylene diacetate was heated up to 110° C. for 24 hours with boron trifluoride-acetic acid complex (Aldrich, 100 mL). After the solution cooled down to room temperature, water and ethyl acetate were added. The organic phase was washed with sodium bicarbonate water solution, water, and brine. The organic phase was then dried, evaporated and chromatographed (silica gel, hexane-ethyl acetate 3% to 10%) to give a pale yellow solid (12.6 g), which was a mixture of 2,3,5-trimethyl-1,4-phenylene diacetate and 3-acetyl-4-hydroxy-2,5,6-trimethylphenyl acetate (11.21 g).

Step 2: 5,7,8-Trimethyl-4-oxo-3,4-dihydrospiro[chromene-2,1'-cyclobutan]-6-yl acetate A solution of the crude 3-acetyl-4-hydroxy-2,5,6-trimethyl-phenyl acetate prepared as in Step 1 (1.0 g), cyclobutanone (415 mg) and piperidine (10 drops) in xylenes (2 mL) was heated at 180° C. for 5 min and then 230° C. for 20 min using a microwave. The solution was diluted with ethyl acetate, washed with water and brine, dried, evaporated, and chromatographed (silica gel, hexane-ethyl acetate 3% to 8%) to give 354 mg of 5,7,8-trimethyl-4-oxo-3,4-dihydrospiro [chromene-2,1'-cyclobutan]-6-yl acetate.

¹H-NMR (300 MHz, D₂O) δ=2.82 (s, 2H), 2.40-2.05 (m, 16H), 1.90-1.70 (m, 1H), 1.70-1.65 (m, 1H) ppm. ¹³C-NMR (75 MHz, CDCl₃) δ=194.2, 169.4, 156.2, 142.1, 136.9, 129.2, 124.5, 117.5, 79.9, 47.3, 33.3, 20.5, 14.1, 14.0, 12.2, 12.1 ppm. MS: (m/z)=289 (M+H⁺), 311 (M+Na).

Step 3: 4-(Methoxyimino)-5,7,8-trimethyl-3,4-dihydrospiro [chromene-2,1'-cyclobutan]-6-yl acetate A mixture of 5,7,8-trimethyl-4-oxo-3,4-dihydrospiro [chromene-2,1'-cyclobutan]-6-yl acetate (110 mg), N-methylhydroxylamine hydrochloride (64 mg), and sodium acetate (63 mg) in methanol (5 mL) was refluxed for 5 h. The mixture was diluted with ethyl acetate, washed with water and brine, dried and evaporated to give 100 mg of 4-(methoxyimino)-5, 7,8-trimethyl-3,4-dihydrospiro[chromene-2,1'-cyclobutan]-6-yl acetate, which was used in the next step without further purification.

Step 4: 4-(Methoxyamino)-5,7,8-trimethyl-3,4-dihydrospiro [chromene-2,1'-cyclobutan]-6-yl acetate To a solution of 4-(methoxyimino)-5,7,8-trimethyl-3,4-dihydrospiro[chromene-2,1'-cyclobutan]-4-yl acetate (150 mg) in THF (2 mL) was added borane-pyridine complex (0.2 mL) at room temperature, and then hydrogen chloride (1 mL, 4.0 M solution in dioxane) during 30 min. After one h, an additional 0.2 mL of the borane-pyridine complex (0.2 mmol) and hydrogen chloride (4.0 M solution in dioxane) were added as before, and the solution was stirred at room temperature for another two hours. Ethyl acetate was added and the solution was washed with saturated sodium bicarbonate water solution, water and brine and then evaporated and chromatographed (silica gel, hexane-ethyl acetate 2% to 8%) to give 83 mg of (4-(methoxyamino)-5,7,8-trimethyl-3,4-dihydrospiro [chromene-2,1'-cyclobutan]-6-yl acetate).

¹H-NMR (300 MHz, CDCl₃) δ=5.30 (s, 1H), 4.29 (s, 1H), 3.63 (s, 3H), 2.75-1.75 (m, 20H) ppm. ¹³C-NMR (75 MHz, CDCl₃) δ=169.7, 150.2, 141.3, 129.5, 126.4, 123.6, 115.1, 77.0, 61.9, 52.7, 36.1, 35.0, 32.1, 20.6, 13.9, 13.2, 12.1, 11.7 ppm. MS: (m/z)=273 (M+H⁺), 342 (33, M+Na).

Step 5: 4-(Methoxyamino)-5,7,8-trimethyl-3,4-dihydrospiro [chromene-2,1'-cyclobutan]-6-ol To a solution of (4-(methoxyamino)-5,7,8-trimethyl-3,4-dihydrospiro[chromene-2,1'-cyclobutan]-4-yl acetate) (80 mg) in methanol (8 mL) was added lithium hydroxide (4%) water solution under nitrogen. The solution was stirred at room temperature for 2 hours. Ethyl acetate was added. The organic layer was washed with ammonium hydrochloride water solution, water and brine. The solution was evaporated and chromatographed (silica gel, hexane-ethyl acetate 2% to 8%) to give 70 mg of 4-(methoxyamino)-5,7,8-trimethyl-3, 4-dihydrospiro[chromene-2,1'-cyclobutan]-6-ol.

¹H-NMR (300 MHz, CDCl₃) δ=6.00-4.20 (br s, 2H), 3.64 (s, 3H), 2.65-1.70 (m, 17H) ppm. ¹³C-NMR (75 MHz, CDCl₃) δ=146.3, 145.5, 123.9, 123.3, 119.6, 115.1, 76.7, 61.9, 52.9, 35.6, 34.7, 33.1, 13.8, 12.5, 12.1, 11.3 ppm. MS: (m/z)=231 (M+H⁺).

Similarly, replacing methylhydroxylamine hydrochloride with ethylhydroxylamine hydrochloride, the following compound was prepared:

4-(Ethoxyamino)-5,7,8-trimethyl-3,4-dihydrospiro [chromene-2,1'-cyclobutan]-6-ol ¹H-NMR (300 MHz, CDCl₃) δ=5.30 (br s, 1H), 4.50 (br s, 1H), 4.29 (t, 1H), 3.90-3.80 (m, 2H), 2.70-2.50 (m, 2H), 2.30-1.75 (m, 15H), 1.26 (t, J=7.0 Hz, 3H) ppm. ¹³C-NMR (75 MHz, CDCl₃) δ=146.3,145.5, 124.0, 123.3, 119.7, 115.4, 76.8, 69.3, 53.1, 35.6, 34.7, 33.2, 14.5, 13.89,12.5, 12.1, 11.4 ppm. MS: (m/z)=231 (M+H⁺), 314 (3, M+Na⁺). Similarly, the following compounds were prepared:

4-(Methoxyamino)-7,8-dimethyl-4H-spiro[chromene-3,1'-cyclobutan]-6-ol

¹H-NMR (CDCl₃, 300 MHz) δ=6.55 (s, 1H), 5.32 (br s, 2H), 4.2 (m, 2H), 3.79 (s, 1H), 3.48 (s, 3H), 2.40 (m, 1H), 2.16 (s, 3H), 2.14 (s, 3), 2.09-1.90 (m, 3H), 1.80-1.67 (m, 2H) ppm; ¹³C-NMR δ=146.9, 146.6, 125.2,124.5, 116.7, 113.6, 68.6, 63.4, 62.1, 39.0, 28.3, 25.9,15.7, 12.14, 12.12 ppm; MS: (m/z)=217 (100, M–NHOMe⁺).

4-(Ethoxyamino)-7,8-dimethyl-4H-spiro[chroman-3,1'-cyclobutan]-6-ol

¹H-NMR (CDCl3, 300 MHz) δ=6.55 (s, 1H), 5.32 (br s, 2H), 4.2 (m, 2H), 3.79 (s, 1H), 3.48 (s, 3H), 2.40 (m, 1H), 2.16 (s, 3H), 2.14 (s, 3), 2.09-1.90 (m, 3H), 1.80-1.67 (m, 2H) ppm; ¹³C-NMR δ=146.9, 146.6, 125.2, 124.5, 116.7, 113.6, 68.6, 63.4, 62.1, 39.0, 28.3, 25.9, 15.7, 12.14, 12.12 ppm; MS: (m/z)=217 (100, M–NHOMe⁺).

Example 28

7,8-Dimethyl-3,4-dihydrospiro[chromene-2,1'-cyclobutan]-6-ol

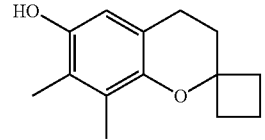

To a solution of vinyl magnesium bromide (60 mL of a 1.0 M solution in THF diluted with 60 mL THF) at 0° C. (ice bath) was added dropwise a solution of cyclobutanone (3.5 g, in 10 mL THF). The reaction was allowed to gradually warm to room temperature (about 1.5 h) and stirring was continued for 30 min. The reaction was quenched by adding 100 mL hexane and the mixture was washed with saturated NaH₂PO₄ (100 mL), brine (100 mL), and dried over Na₂SO₄. The mixture was concentrated under reduced pressure to about 10 mL, diluted with 2:1 hexane/ether (40 mL) and filtered through a short silica pad. The solution was again concentrated and dried under high vacuum for about 1 h to afford the crude alcohol as a clear oil (4.3 g). This crude material was used directly for the next reaction without purification.

To a solution of 3,4-dimethylhydroquinone (1.38 g) in 40 mL of dioxane was added BF₃.Et₂O (25 mmol, 2.5 eq). The mixture was heated to 120° C. and added dropwise (using a syringe pump during a period of 30 min) to a solution of the above made allylic alcohol (980 mg, in 30 mL dioxane). The reaction was stirred at 120° C. for 6 h, cooled to room temperature, and quenched on to ice. The aqueous layer was saturated with NaCl and the layers were separated. The organic layer was diluted with hexane/EtOAc (3:1, 70 mL) and washed with brine (3×80 mL), NaHCO₃ (3×50 mL) and water (100 mL) and dried over Na₂SO₄. After solvent removal, the residue was chromatographed (hexane/EtOAc)

to afford the desired 7,8-dimethyl-3,4-dihydrospiro[chromene-2,1'-cyclobutan]-6-ol (1.25 g).

$^1$H-NMR (300 MHz, CDCl$_3$) δ=6.41 (s, 1H), 5.75 (s, 1H), 2.77 (t, J=6.6 Hz, 2H), 2.42-2.33 (m, 2H), 2.28 (s, 3H), 2.26 (s, 3H), 2.21-2.16 (m, 2H), 2.06-1.99 9m, 2 H) ppm; $^{13}$C-NMR (75 MHz, CDCl$_3$) δ=146.7, 145.5, 125.8, 122.2, 118.9, 112.4, 77.2, 34.3, 29.4, 22.3, 12.6, 12.1, 12.1 ppm; MS: (m/z)=219 (M+H$^+$).

Similarly the following compound was produced:

5,7-Diethylspiro[chroman-2,1'-cyclobutan]-6-ol $^1$H-NMR (300 MHz, CDCl$_3$) δ=6.63 (s, 1H), 5.35 (s, 1H), 4.54 (s, 1H), 4.30 4.25 (m, 1H), 3.65 (s, 3H), 3.15-3.10 (m, 1H), 2.70-2.60 (m, 2H), 2.40-2.10 (m, 6H), 2.10-1.75 (m, 3H), 1.22 (d, J=6.7 Hz, 6H) ppm. $^{13}$C-NMR (75 MHz, CDCl$_3$) δ=147.5, 144.7, 128.8, 128.2, 118.1, 114.6, 76.5, 34.0, 29.5, 23.0, 19.5, 13.8, 13.5, 12.5 ppm. MS (m/z)=179 (34), 219 (17), 247 (100, M+H$^+$−18).

Example 29

7,8-Dimethyl-3,4-dihydrospiro[chromene-2,1'-cyclobutan]-6-yl (dimethylamino)acetate

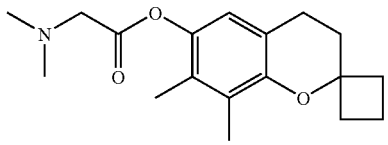

To 7,8-Dimethyl-3,4-dihydrospiro[chromene-2,1'-cyclobutan]-6-ol (145 mg) and triethylamine (0.4 g) in 5 mL of dry dichloro methane at room temperature was added portion wise N,N-dimethyl glycine acyl chloride (185 mg). The mixture was stirred for 1 h and quenched by adding ice. It was extracted with EtOAc (3×20 mL) and the combined organic phase was washed with brine and dried over Na$_2$SO$_4$ and concentrated. The crude product was purified by chromatography (DCM/MeOH) to afford the desired compound 7,8-dimethyl-3,4-dihydrospiro[chromene-2,1'-cyclobutan]-6-yl (dimethylamino)acetate as a light brown oil (175 mg).

$^1$H-NMR (300 MHz, CDCl$_3$) δ=6.57 (s, 1H), 3.46 (s, 2H), 2.75 (t, J=6.5 Hz, 2H), 2,47 (s, 6H), 2.28 (m, 2H), 2.30 (s, 3H), 2.15-2.03 (m, 5H), 1.93 (t, J=6.5 Hz, 2H), 1.70 (m, 1H) ppm; $^{13}$C-NMR δ=169.7, 149.5, 111.5, 127.0, 125.8, 119.2, 118.7, 77.4, 60.2, 45.3, 34.4, 28.9, 22.1, 12.8, 12.5, 12.0 ppm; MS: (m/z)=304 (M+H$^+$)

Example 30

4-(Methoxyamino)-5,7-dimethyl-3,4-dihydrospiro[chromene-2,1'-cyclobutan]-6-ol

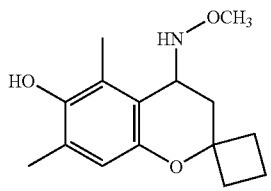

Step 1: 3-Acetyl-4-hydroxy-2,6-dimethylphenyl acetate

A mixture of 2,6-dimehtylhydroquinone (53.6 g) and acetic chloride (83 mL) in toluene (300 mL) was refluxed for 3 hours. The solvent and excessive reagent was removed under vacuum. The residue was heated up with boron trifluoride-acetic acid complex (100 mL) at 120° C. for 20 hours. The mixture was poured into ice, and extracted with ethyl acetate. The organic layer was washed with sodium bicarbonate water solution to pH about 7. Evaporation and purification on silica gel column eluted with hexane and ethyl acetate gave 50 g of 3-acetyl-4-hydroxy-2,6-dimethylphenyl acetate as a thick liquid.

Step 2: 6-Hydroxy-5,7-dimethylspiro[chromene-2,1'-cyclobutan]-4(3H)-one

To a solution 3-acetyl-4-hydroxy-2,6-dimethylphenyl acetate (13 g) and cyclobutanone (4.5 g) in toluene (150 mL) was added pyrrolidine (5.4 mL, 4.6 g). The solution was stirred at room temperature for 15 min and then refluxed for 5 hours equipped with Dean-Stark water trap. The solution was diluted with ethyl acetate, washed with diluted hydrochloride acid water solution, water and brine. Evaporation and chromatography (silica gel, hexane-ethyl acetate 1% to 10%) gave 5.5 g of 5,7-dimethyl-4-oxo-3,4-dihydrospiro[chromene-2,1'-cyclobutan]-6-yl acetate and 3.2 g of 6-hydroxy-5,7-dimethylspiro[chromene-2,1'-cyclobutan]-4(3H)-one.

5,7-Dimethyl-4-oxo-3,4-dihydrospiro[chromene-2,1'-cyclobutan]-6-yl acetate.

$^1$H-NMR (300 MHz, CDCl$_3$) δ=6.68 (s, 1H), 2.81 (s, 2H), 2.39 (s, 3H), 2.35-2.05 (m, 10H), 1.95-1.60 (m, 2H) ppm. $^{13}$CNMR (75 MHz, CDCl$_3$) δ=193.5, 169.1, 158.2, 142.4, 138.7, 132.6, 118.0, 117.8, 80.2, 47.3, 33.1, 20.4, 17.3, 14.1, 12.1 ppm. MS: (m/z)=233 (20), 275 (100, M+H$^+$), 297 (47, M+Na$^+$).

6-Hydroxy-5,7-dimethylspiro[chromene-2,1'-cyclobutan]-4(3H)-one $^1$H-NMR (300 MHz, CDCl$_3$) δ=6.64 (s, 1H), 5.19 (s, 1H), 2.83 (s, 2H), 2.55 (s, 3H), 2.30-2.05 (m, 7H), 1.90-1.60 (m, 2H) ppm. $^{13}$C-NMR (75 MHz, CDCl$_3$) δ=194.9, 154.6, 146.8, 134.1, 124.7, 117.9, 117.5, 79.9, 47.7, 33.0, 17.3, 13.2, 12.2 ppm. MS: (m/z)=233 (100, M+H$^+$), 255 (2, M+Na$^+$).

Step 3: 4-(Methoxyamino)-5,7-dimethyl-3,4-dihydrospiro[chromene-2,1'-cyclobutan]-6-ol A mixture of 6-hydroxy-5,7-dimethylspiro[chromene-2,1'-cyclobutan]-4(3H)-one (990 mg), O-methoxyamine hydrochloride (926 mg), and sodium acetate (911 mg) in methanol (50 mL) was refluxed for 5 hours. Methanol was removed by distillation and the residue was treated with sodium bicarbonate solution and ethyl acetate. The organic phase was washed with water and brine. Dry and evaporation gave 1.0 g of crude intermediate, which was dissolved in anhydrous tetrahydrofuran (10 mL). To the solution was added borane-pyridine complex (3 mL) at 0° C., and then hydrogen chloride (11.6 mL, 4.0 M solution in dioxane) in 50 min. The solution was allowed to warm to room temperature slowly. After 16 hours, ethyl acetate was added. The solution was washed with saturated sodium bicarbonate water solution, water and brine. Evaporation and chromatography (silica gel, hexane-ethyl acetate 2% to 8%) gave 748 mg of 4-(methoxyamino)-5,7-dimethyl-3,4-dihydrospiro[chromene-2,1'-cyclobutan]-6-ol as thick oil.

$^1$H-NMR (300 MHz, CDCl$_3$) δ=6.55 (s, 1H), 4.26 (t, 1H), 3.63 (s, 3H), 2.70-2.50 (m, 2H), 2.30-1.65 (m, 14H) ppm. $^{13}$C-NMR (75 MHz, CDCl$_3$) δ=148.0, 145.9, 125.0, 122.9, 116.8, 115.7, 77.3, 61.9, 52.6, 35.6, 34.3, 32.6, 16.2, 13.8, 11.4 ppm. MS: (m/z)=217 (100, M+H$^+$), 286 (2, M+Na$^+$).

HCl Salt of 4-(methoxyamino)-5,7-dimethyl-3,4-dihydrospiro[chromene-2,1'-cyclobutan]-6-ol To a solution of 0.25 (0.95 mmol) of 4-(methoxyamino)-5,7-dimethyl-3,4-dihydrospiro[chromene-2,1'-cyclobutan]-6-ol in 300 µL of THF, was added via syringe 475 µL (1.9 mmol) of 4M HCl in dioxane and the solution was stirred for 10 min. Diethyl ether was added dropwise until the solution became cloudy and a white ppt began to form. The solution was cooled in an ice bath with stirring for 30 min, and the solid was filtered off and air dried 4-(methoxyamino)-5,7-dimethyl-3,4-dihydrospiro[chromene-2,1'-cyclobutan]-6-ol HCl salt.

$^1$H-NMR (300 MHz, DMSO-CD$_3$COCD$_3$) δ=1.57-1.69 (2H, m), 2.00-2.06 (1H, m), 2.12-2.32 (10H, m), 2.51-2.70 (1H, d), 3.82 (3H, s), 4.84 (1H, br s), 6.49 (1H, s) ppm. $^{13}$C-NMR (DMSO-CD$_3$COCD$_3$) δ=12.51, 13.22, 17.39, 33.28, 34.97, 35.12, 51.73, 61.45, 76.48, 113.55, 116.88, 125.74, 128.40, 147.41, 148.29 ppm. MS: (m/z)=217 (M–CH$_5$NO$^+$)

HBr Salt of 4-(methoxyamino)-5,7-dimethyl-3,4-dihydrospiro[chromene-2,1'-cyclobutan]-6-ol The HBr salt was formed following the procedure for the HCl salt described above and substituting HCl for 33% HBr in acetic acid.

$^1$H-NMR (DMSO-CD$_3$COCD$_3$) δ=1.57-1.69 (2H, m), 2.00-2.06 (1H, m), 2.12-2.32 (10H, m), 2.51-2.70 (1H, d), 3.82 (3H, s), 4.84 (1H, br s), 6.49 (1H, s) ppm. $^{13}$C-NMR (DMSO-CD$_3$COCD$_3$) δ=12.51, 13.22, 17.39, 33.28, 34.97, 35.12, 51.73, 61.45, 76.48, 113.55, 116.88, 125.74, 128.40, 147.41, 148.29 ppm. MS: (m/z)=217, (M–CH$_5$NO$^+$).

(4S)-4-(methoxyamino)-5,7-dimethyl-3,4-dihydrospiro[chromene-2,1'-cyclobutan]-6-ol (4R)-4-(methoxyamino)-5,7-dimethyl-3,4-dihydrospiro[chromene-2,1'-cyclobutan]-6-ol Chiral resolution was achieved with a Chiral Technologies OD-H column Normal phase conditions 5%-2.5% Isopropanol in Hexanes. Flow rate was 0.8-1 mL/min. Optimum resolution at 2.5% isopropanol/Hexane and 0.8 mL/min. Analytical runs were conducted with 20 µg on column. One enantiomer was eluted at 15 min, and the other at 26 min.

Example 31

6-Hydroxy-3,5,7,8-tetramethylspiro[chroman-2,1'-cyclobutan]-4(3H)-one

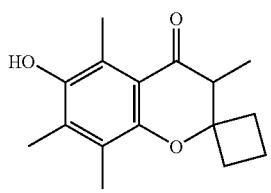

A solution of 6-hydroxy-5,7,8-trimethylspiro[chromene-2,1'-cyclobutan]-4(3H)-one (220 mg), formaldehyde (1 mL, 37% in water), dimethylamine solution (1 mL, 2.0 M in methanol), and concentrated HCl water solution (0.1, mL) was heated by microwave to 150° C. for 10 min. The allyl intermediate was treated with excessive NaBH$_4$ in methanol at room temperature to give 6-hydroxy-3,5,7,8-tetramethylspiro[chromene-2,1'-cyclobutan]-4(3H)-one, which was purified by chromatography (silica gel, hexane-ethyl acetate 3%).

$^1$H-NMR (300 MHz, CDCl$_3$) δ=5.06 (s, 1H), 2.65 (q, J=7.1 Hz, 1H), 2.24 (s, 3H), 2.20-1.70 (m, 12H), 1.18 (d, J=7.1 Hz, 3H) ppm. $^{13}$C-NMR (75 MHz, CDCl$_3$) δ=199.2, 152.1, 146.4, 132.5, 124.0, 121.5, 116.0, 82.6, 49.0, 32.5, 30.2, 13.5, 13.0, 12.6, 12.1, 10.7 ppm. MS: (m/z)=261 (100, M+H$^+$), 283 (6, M+Na$^+$)

Example 32

4-Methoxy-5,7-dimethyl-3,4-dihydrospiro[chromene-2,1'-cyclobutan]-6-ol

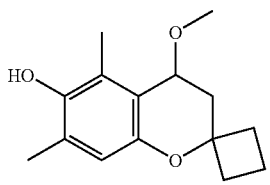

To a solution of 6-hydroxy-5,7-dimethylspiro[chromene-2,1'-cyclobutan]-4(3H)-one,( 345 mg) in methanol (5 mL) was added sodium borohydride (65 mg). The mixture was stirred at room temperature for 30 min. The mixture was concentrated and the methanol removed to give 5,7-dimethyl-3,4-dihydrospiro[chromene-2,1'-cyclobutane]-4,6-diol.

$^1$H-NMR (300 MHz, CDCl$_3$+CD$_3$OD) δ=6.44 (s, 1H), 4.79 (t, 1H), 2.55-2.45 (m, 1H), 2.30-1.60 (m, 14H) ppm. $^{13}$C-NMR (75 MHz, CDCl$_3$+CD$_3$OD) δ=146.5, 146.3, 126.9, 124.5, 120.0, 116.4, 76.1, 62.3, 38.9, 34.8, 32.9, 16.4, 13.1, 11.6 ppm. MS: (m/z)=217 (100, M+H$^+$), 257 (5, M+Na$^+$).

The crude mixture of the diol derivative as produced above, was added concentrated HCl water solution (7 drops). The mixture was stirred at room temperature for 1 hour. The solution was neutralized using sodium bicarbonate water solution to pH about 7. Ethyl acetate was added, washed with water and brine. Evaporation and chromatography (silica gel, 8% of ethyl acetate in hexane) gave 317 mg of 4-methoxy-5,7-dimethyl-3,4-dihydrospiro-[chromene-2,1'-cyclobutan]-6-ol.

$^1$H-NMR (300 MHz, CDCl$_3$) δ=6.54 (s, 1H), 4.33 (t, 1H), 4.28 (s, 1H), 3.47 (s, 3H), 2.60-1.60 (m, 14H) ppm. $^{13}$C-NMR (75 MHz, CDCl$_3$) δ=146.9, 146.0, 125.5, 123.3, 118.8, 116.7, 76.0, 71.6, 55.3, 35.0, 32.9, 32.5, 16.3, 13.2, 11.4 ppm. MS: (m/z)=217 (100, M—OCH$_3$), 271 (5, M+Na$^+$).

Similarly treating the alcohol mixture with an acid and ethanol, isopropanol or cyclopentanol, the following compounds were prepared:

4-Ethoxy-5,7-dimethyl-3,4-dihydrospiro[chromene-2,1'-cyclobutan]-6-ol $^1$H-NMR (300 MHz, CDCl$_3$) δ=6.52 (s, 1H), 4.51 (s, 1H), 4.44 (t, 1H), 3.85-3.75 (m, 1H), 3.60-3.50 (m, 1H), 2.60-2.35 (m, 3H), 2.20-1.60 (m, 11H), 1.27 (t, J=7.0 Hz, 3H) ppm. $^{13}$C-NMR (75 MHz, CDCl$_3$) δ=147.0, 146.0, 126.1, 123.7, 118.6, 116.6, 76.0, 70.2, 63.2, 35.1, 33.2, 33.1, 16.4, 15.7, 13.1, 11.5 ppm. MS: m/z=217 (100, M–OEt), 285 (29, M+Na$^+$).

4-Isopropoxy-5,7-dimethyl-3,4-dihydrospiro[chromene-2,1'-cyclobutan]-6-ol $^1$H-NMR (300 MHz, CDCl$_3$) δ=6.50 (s, 1H), 4.63 (t, 1H), 4.55 (s, 1H), 4.05-3.95 (m, 1H), 2.60-1.60 (m, 14H), 1.35 (d, J=6.2 Hz, 3H), 1.29 (d, J=6.2 Hz, 3H) ppm. $^{13}$C-NMR (75 MHz, CDCl$_3$) δ=147.3, 145.9, 126.3, 123.8, 118.5, 116.6, 75.7, 68.2, 67.0, 35.4, 33.7, 33.5, 23.9, 21.5, 16.5, 13.1, 11.8 ppm. MS: (m/z)=217 (100, M−OiPr), 299 (32, M+Na+).

4-Cyclopentyloxy)-5,7,8-trimethyl-3,4-dihydrospiro[chromene-2,1'-cyclobutane]-6-diol $^1$H-NMR (300 MHz, CDCl$_3$) δ=4.61 (s, 1H), 4.23 (s, 1H), 4.25 (t, 1H), 2.65-1.60 (m, 25H) ppm. $^{13}$C-NMR (75 MHz, CDCl$_3$) δ=145.5, 145.4, 124.8, 123.0, 120.4, 118.0, 79.0, 75.8, 69.0, 35.4, 33.8, 33.7, 33.6, 31.7, 23.3, 23.2, 13.1, 12.6, 12.0, 11.6 ppm. MS: (m/z)=231 (100, M−OC$_5$H$_{11}$), 339 (8, M+Na+).

Similarly starting with 6-hydroxy-5,7,8-trimethylspiro[chromene-2,1'-cyclobutan]-4(3H)-one, and following the procedure in Step 1 above, the following compound was prepared:

5,7,8-Trimethyl-3,4-dihydrospiro[chromene-2,1'-cyclobutane]-4,6-diol $^1$H-NMR (300 MHz, CD$_3$OD) δ=4.30 (t, 1H), 2.50-2.35 (m, 3H), 2.10-1.65 (m, 14H) ppm. MS: (m/z)=231 (100, M−OH), 271 (10, M+Na+).

Example 33

4-(Isopropylthio)-5,7,8-trimethyl-3,4-dihydrospiro[chromene-2,1'-cyclobutan]-6-ol

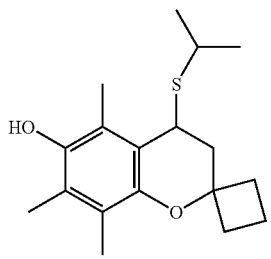

To a solution of 5,7,8-trimethyl-3,4-dihydrospiro[chromene-2,1'-cyclobutane]-4,6-diol (290 mg) in acetonitrle (2 mL) was added 2-propanethiol (0.5 mL) and concentrated HCl water solution (5 drops). The solution was stirred at room temperature for 7 hours. The solution was neutralized using sodium bicarbonate water solution to pH about 7. Ethyl acetate was added, washed with water and brine. Evaporation and chromatography (silica gel, hexane-ethyl acetate 0 to 4%) gave 140 mg of 4-(isopropylthio)-5,7,8-trimethyl-3,4-dihydrospiro[chromene-2,1'-cyclobutan]-6-ol $^1$H-NMR (300 MHz, CDCl$_3$) δ=4.45 (s, 1H), 4.16 (t, 1H), 3.20-3.05 (m, 1H), 2.95-2.75 (m, 1H), 2.60-2.50 (m, 1H), 2.40-1.80 (m, 15H), 1.45 (d, J=6.5 Hz, 3H), 1.31 (d, J=6.5 Hz, 3H) ppm. $^{13}$C-NMR (75 MHz, CDCl$_3$) δ=145.8, 145.5, 123.3, 123.1, 119.4, 117.9, 77.6, 37.2, 36.7, 35.9, 35.5, 35.0, 23.6, 23.5, 14.1, 12.6, 12.1, 11.9 ppm. MS: (m/z)=231 (100, M−SC$_3$H$_7$), 329 (12, M+Na+).

Example 34

7,8-Dimethyl-3,4-dihydrospiro[chromene-2,1'-cyclobutane]-4,6-diol

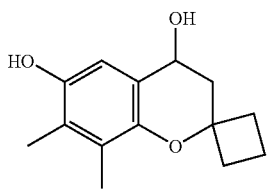

Step 1: 1-(2,5-Dihydroxy-3,4-dimethylphenyl)ethanone 2,3-Dimethyl-1,4-phenylene diacetate (5.5 g) was heated up with boron trifluoride-acetic acid complex (25 mL) at 120° C. for 5 hours. The mixture was poured into ice, and extracted with ethyl acetate. The organic layer was washed with sodium bicarbonate water solution to pH about 7. Evaporation gave 5.5 g of 5-acetyl-4-hydroxy-2,3-dimethylphenyl acetate as yellow solid. Refluxing 5-acetyl-4-hydroxy-2,3-dimethylphenyl acetate (5.5 g) with cyclobutanone (1.9 g, 27 mmol) and pyrrolidine (2.1 mL, 24.8 mmol) in toluene failed to give chromanone but gave 3.4 g of 1-(2,5-dihydroxy-3,4-dimethylphenyl)-ethanone as a solid.

Step 2: 7,8-Dimethyl-cyclobutane(spiro-2)-6-hydroxychroman-4-one 1-(2,5-Dihydroxy-3,4-dimethylphenyl)ethanone from Step 1 was converted to THP mono-protected alfa-acetyl phenol using 1.1 equivalent 3,4-dihydro-2H-pyran under acidic conditions gave 130 mg of 7,8-dimethyl-cyclobutane(spiro-2)-6-hydroxychroman-4-one.

Step 3  7,8-Dimethyl-3,4-dihydrospiro[chromene-2,1'-cyclobutane]-4,6-diol

To a solution of 7,8-dimethyl-cyclobutane(spiro-2)-6-hydroxychroman4-one (50 mg) in methanol (5 mL) was added sodium borohydride (10 mg). The mixture was stirred at room temperature for 30 min. Methanol was removed. Ethyl acetate was added, washed with water and brine. Evaporation and chromatography (silica gel, hexane-ethyl acetate 30%) gave 19 mg of 7,8-dimethyl-3,4-dihydrospiro-[chromene-2,1'-cyclobutane]-4,6-diol.

$^1$H-NMR (300 MHz, CD$_3$COCD$_3$) δ=7.53 (s, 1H), 6.77 (s, 1H), 4.754.65 (m, 1H), 4.104.00 (m, 1H), 2.85-1.65 (m, 14H) ppm. MS: (m/z)=217 (100, M−OH), 257 (9, M+Na+).

Similarly the following compounds were prepared from the appropriate ketones:

5,7-Diethylspiro[chroman-2,1'-cyclobutane]-4,6-diol $^1$H-NMR (300 MHz, CDCl$_3$) δ=6.59 (s, 1H), 4.91 (t, 1H), 4.40 (s, 1H), 2.85-2.50 (m, 5H), 2.45-2.35 (m, 2H), 2.25-1.55 (m, 6H), 1.30-1.15 (m, 6H) ppm. $^{13}$C-NMR (75 MHz, CDCl$_3$) δ=146.8, 145.5, 131.8, 129.2, 119.6, 115.2, 76.2, 62.6, 38.7, 35.2, 33.2, 23.0, 19.6, 14.6, 13.6, 13.4 ppm. MS (m/z)=245 (100, M−OH).

Separation with Chiral Technologies Chiralcel OD-H (dimethylphenyl carbamate derived cellulose). Mobile phase: 3% isopropanal in hexane, flow rate=0.8 mL/min.

(S)-5,7-Diethylspiro[chroman-2,1'-cyclobutane]-4,6-diol (fast-moving isomer)

$^1$H NMR (300 MHz, CD$_3$OD) δ=6.41 (s, 1H), 4.86 (t, 1H,), 2.75-1.50 (m, 12H), 1.12 (t, 6H) ppm. MS: m/z=245.2 (M+H+−18)

(R)-5,7-Diethylspiro[chroman-2,1'-cyclobutane]-4,6-diol (slow-moving isomer)
¹H NMR (300 MHz, CD₃OD) δ=6.41 (s, 1H), 4.86 (t, 1H), 2.75-1.50 (m, 12H), 1.14 (t, 6H) ppm. MS: m/z=245.1 (M+H⁺−18).

7-Isopropyl-5-methylspiro[chroman-2,1'-cyclobutane]-4,6-diol
¹H-NMR (300 MHz, CDCl₃) δ=6.63 (s, 1H), 4.87 (s, 1H), 4.64 (s, 1H), 3.20-3.10 (m, 1H), 2.60-1.65 (m, 12H), 1.25-1.20 (m, 6H) ppm. ¹³C-NMR (75 MHz, CDCl₃) δ=147.0, 145.1, 136.7, 123.1, 119.9, 112.6, 76.2, 62.9, 38.8, 35.0, 33.1, 27.3, 22.6, 13.3.

Separation with Chiral Technologies Chiralcel OD-H (dimethylphenyl carbamate derived cellulose). Mobile phase: 3% isopropanal in hexane, flow rate=0.8 mL/min.

(S)-7-Isopropyl-5-methylspiro[chroman-2,1'-cyclobutane]-4,6-diol, (fast-moving isomer),
¹H NMR (300 MHz, CD₃OD) δ=6.46 (s, 1H), 4.88 (t, 1H), 3.26 (m, 1H), 2.23 (s, 3H), 2.75-1.50 (m, 8H), 1.12 (m, 6H). MS: m/z=245.2 (M+H⁺−18).

(R)-1sopropyl-5-methylspiro[chroman-2,1'-cyclobutane]-4,6-diol, (slow-moving isomer).
¹H NMR (300 MHz, CD₃OD) δ=6.46 (s, 1H), 4.86 (t, 1H), 3.26 (m, 1H), 2.23 (s, 3H), 2.75-1.50 (m, 8H), 1.12 (m, 6H). MS: m/z=245.1 (M+H⁺−18).

Example 35

4-(Methoxyamino)-7,8-dimethyl-3,4-dihydrospiro[chromene-2,1'-cyclobutan]-6-ol

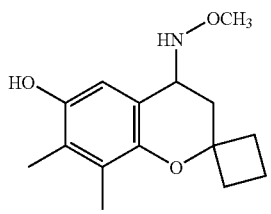

A mixture of 7,8-dimethyl-cyclobutane(spiro-2)-6-hydroxychroman-4-one (80 mg), prepared as described above, O-methoxyamine hydrochloride (80 mg), and sodium acetate (80 mg) in methanol (5 mL) was refluxed for 5 hours. Methanol was removed by distillation and the residue was treated with sodium bicarbonate solution and ethyl acetate. The organic phase was washed with water and brine. Dry and evaporation gave a crude intermediate, which was dissolved in anhydrous tetrahydrofuran (2 mL). To the solution was added borane-pyridine complex (0.4 mL) at 0° C., and then hydrogen chloride (1.2 mL, 4.0 M solution in dioxane) in 20 min. The solution was allowed to warm to room temperature slowly. After 16 hours, ethyl acetate was added. The solution was washed with saturated sodium bicarbonate water solution, water and brine. Evaporation and chromatography (silica gel, hexane-ethyl acetate 10%) gave 46 mg of 4-(methoxyamino)-7,8-dimethyl-3,4-dihydrospiro[chromene-2,1'-cyclobutan]-6-ol.
¹H-NMR (300 MHz, CDCl₃) δ=6.70 (s, 1H), 5.15 (brs, 2H), 4.15 (t, 1H), 3.61 (s, 3H), 2.40-1.70 (m, 14H) ppm. ¹³C-NMR (75 MHz, CDCl₃) δ=147.0, 145.7, 126.3, 124.1, 118.3, 110.7, 77.4, 62.2, 53.5, 34.8, 34.7, 34.3, 13.0, 12.2, 12.1 ppm. MS: (m/z)=217 (100, M−CH₃ONH), 286 (9, M+Na⁺).

Similarly replacing methoxyamine hydrochloride with ethoxyamine hydrochloride, the following compound was prepared:

4-(Ethoxyamino)-5,7-dimethyl-3,4-dihydrospiro[chromene-2,1'-cyclobutan]-6-ol

¹H-NMR (300 MHz, CDCl₃) δ=6.70 (s, 1H), 5.15 (br s, 2H), 4.15 (t, 1H), 3.61 (s, 3H), 2.40-1.70 (m, 14H) ppm. ¹³C-NMR (75 MHz, CDCl₃) δ=147.0, 145.7, 126.3, 124.1, 118.3, 110.7, 77.4, 62.2, 53.5, 34.8, 34.7, 34.3, 13.0, 12.2, 12.1 ppm. MS: (m/z)=217 (100, M−OEt), 286 (9, M+Na⁺).

Example 36

4-[N,N-Methoxy(methyl)amino]-5,7-dimethyl-3,4-dihydrospiro[chromene-2,1'-cyclobutan]-6-ol

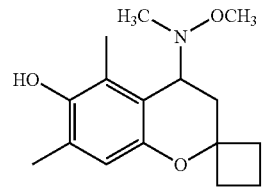

To a solution of 4-(methoxyamino)-5,7-dimethyl-3,4-dihydrospiro[chromene-2,1'-cyclobutan]-6-ol (0.8 g) in 5 mL of MeOH, was added via syringe, 504 µL of (37%) aqueous formaldehyde and stirred for 10 min, followed by an addition of 390 g of sodium cyanoborohydride and the reaction was stirred at room temperature overnight. Next day all solvent was evaporated under vacuum, and the resulting gum was adsorbed onto silica and purified on a silica column, eluting with 1:8 EtOAc/Hexanes to yield 325 mg of 4-[N,N-methoxy(methyl)amino]-5,7-dimethyl-3,4-dihydrospiro[chromene-2,1'-cyclobutan]-6-ol as a colorless oil.

¹H-NMR (300 MHz, CDCl₃) δ=1.60-2.00 (3H, m), 2.10-2.43 (8H, m), 2.48 (3H, s), 3.33 (3H, s), 4.34 (1H, s), 4.37-4.42 (1H, t), 6.52 (1H, s) ppm; ¹³C-NMR (75 MHz, CDCl₃) 12.64, 13.08, 16.23, 29.22, 32.73, 34.80, 38.87, 56.84, 59.77, 77.91, 117.00, 120.15, 123.58, 123.76, 146.34, 148.57 ppm; MS: (m/z)=217, (M−C₂H₇NO⁺)

Similarly following the procedure above and replacing aqueous formaldehyde with acetaldehyde the following compound was prepared:

4-[N,N-Ethyl(methoxy)amino]-5,7-dimethyl-3,4-dihydrospiro[chromene-2,1'-cyclobutan]-6-ol
¹H-NMR (300 MHz, CDCl₃) δ=1.12-1.17 (3H, t), 1.65-1.69 (1H, m), 1.71-1.97 (3H, m), 2.10-2.38 (10H, m), 2.65-2.71 (2H, m), 3.31 (3H, s), 4.42-4.44 (1H, t), 4.56 (1H, s), 6.52 (1H, s) ppm' ¹³C-NMR (75 MHz, CDCl₃) 12.64, 13.21, 13.46, 16.27, 29.65, 32.56, 34.72, 47.66, 55.94, 61.76, 77.96, 116.95, 120.19, 123.96, 146.33, 148.68 ppm; MS: (m/z)=217, (M−C₃H₉NO⁺)

Example 37

4-[N,N-Hydroxy(methyl)amino]-5,7,8-trimethyl-3,4-dihydrospiro[chromene-2,1'-cyclobutan]-6-ol

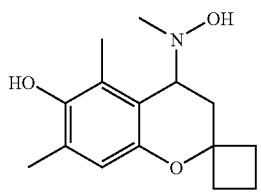

Step 1: 6-Hydroxy-5,7-dimethylspiro[chromene-2,1'-cyclobutan]-4(3H)-one oxime

A mixture of 1 g of 6-hydroxy-5,7-dimethylspiro[chromene-2,1'-cyclobutan]-4(3H)-one and 0.91 g of hydroxylamine hydrochloride was dissolved in 5 mL of MeOH by way of brief heating. After all solids had dissolved, the solution was sealed in a microwave reaction vial and placed in a microwave reactor for 25 min at 125° C. The reaction was cooled to room temperature, added to $H_2O$ and extracted with EtOAc, washed with brine and dried over $Na_2SO_4$. Evaporation of solvent yielded 1.05 g of 6-hydroxy-5,7-dimethylspiro[chromene-2,1'-cyclobutan]-4(3H)-one oxime as a pale yellow solid.

$^1$H-NMR (300 MHz, CDCl$_3$) δ=1.74-1.86 (2H, m), 2.05-2.12 (2H, m), 2.15-2.29 (5H, m), 2.50 (3H, s), 3.12 (2H, s), 4.61 (1H, br s), 6.62 (1H, s), 8.79 (1H, br s) ppm; $^{13}$C-NMR (75MHz, CCl$_3$D) δ=12.16, 14.92, 16.61, 32.69, 33.24, 77.25, 116.10, 117.39, 121.70, 127.23, 146.83, 149.17,152.82 ppm
Similarly, the following compound was prepared:

4-(Hydroxyamino)-5,7,8-trimethyl-3,4-dihydrospiro[chromene-2,1'-cyclobutan]-6-ol $^1$H-NMR (300 MHz, CDCl$_3$) δ=1.71-1.86 (2H, m), 2.05-2.26 (1OH, m), 2.48 (3H, s), 3.12 (2H, s), 4.53 (1H, br s), 8.49 (1H, br s) ppm; $^{13}$C-NMR (75 MHz, CDCl$_3$) δ=12.11, 12.29, 12.83, 14.70, 33.43, 33.54, 77.14, 115.80, 118.18, 124.09, 125.95, 146.47, 147.47, 153.36 ppm.

Step 2: 4-(Hydroxyamino)-5,7-dimethyl-3,4-dihydrospiro[chromene-2,1'-cyclobutan]-6-ol 1.0 g of 6-hydroxy-5,7-dimethylspiro[chromene-2,1'-cyclobutan]-4(3H)-one oxime was dissolved in 20 mL of THF and cooled to 0° C. under nitrogen. 3 mL of (8M) borane-pyridine complex was added via syringe followed by 12 mL of (4 M) HCl-dioxane via a syringe pump over 45 min. After complete addition, the ice bath was removed and the reaction slowly warmed to room temperature then stirred overnight. The next day, the solution was added to sat. NaHCO$_3$, extracted with EtOAc, washed with additional sat. NaHCO$_3$, brine and dried over Na$_2$SO$_4$. The crude material was purified on a silica column eluting with 1:8 EtOAc/Hexanes to yield 699 mg of 4-(hydroxyamino)-5,7-dimethyl-3,4-dihydrospiro[chromene-2,1'-cyclobutan]-6-ol.

$^1$H-NMR (300 MHz, CDCl$_3$) δ=1.76-2.09 (3H, m), 2.10-2.33 (9H, m), 2.35-2.48 (1H, m), 2.72-2.77 (1H, d), 4.26 (1H, s), 6.57 (1H, s) ppm; $^{13}$C-NMR (75 MHz, CDCl$_3$) δ=11.80, 13.70, 16.34, 32.36, 34.42, 35.44, 54.29, 76.82, 115.94, 116.84, 123.26, 125.62, 145.99, 148.01 ppm; MS: (m/z)=217, (M–H$_3$NO$^+$)

Similarly the following compound was prepared:
4-(Hydroxyamino)-5,7,8-trimethyl-3,4-dihydrospiro[chromene-2,1'-cyclobutan]-6-ol;

$^1$H-NMR (300 MHz, CDCl$_3$) δ=1.77-2.01 (4H, m), 2.10-2.32 (11H, m), 2.35-2.48 (1H, m), 2.71-2.75 (1H, d), 4.284.31 (1H, m), 4.89 (1H, br s) ppm; $^{13}$C-NMR (75 MHz, CDCl$_3$) δ=11.58, 12.03, 12.49, 13.75, 32.80, 34.78, 35.56, 54.54, 76.85, 115.44, 119.60, 123.39, 124.05, 145.47, 146.27 ppm; MS: (m/z)=231, (M–NOH)

Step 3: 4-[N,N-Hydroxy(methyl)amino]-5,7-dimethyl-3,4-dihydrospiro[chromene-2,1'-cyclobutan]-6-ol To a solution of 0.5 g (2.0 mmol) of 4-(hydroxyamino)-5,7-dimethyl-3,4-dihydrospiro[chromene-2,1'-cyclobutan]-6-ol in 10 mL of MeOH were added 324 µL (4.0 mmol, 2 eq.) of (37%) aqueous formaldehyde via syringe and stirred for 10 min, followed by an addition of 250 mg (4.0 mmol, 2 eq) of sodium cyanoborohydride. The reaction was stirred at room temperature overnight. Next day the solution was added to saturated NaHCO$_3$, extracted with EtOAc, washed with brine, dried over Na$_2$SO$_4$, and all solvent was evaporated under vacuum. The resulting solid was triturated in EtOAc, filtered and air dried to yield 310 mg of 4-[N,N-hydroxy(methyl)amino]-5,7-dimethyl-3,4-dihydrospiro[chromene-2,1'-cyclobutan]-6-ol as an off-white solid.

$^1$H-NMR (300 MHz, MeOD) δ=1.60-1.89 (2H, m), 1.90-1.99 (2H, m), 2.12-2.35 (9H, m), 2.47-2.54 (4H, m), 4.264.31 (1H, t), 6.41 (1H, s) ppm; $^{13}$C-NMR (75 MHz, MeOD) δ=12.07, 12.26, 15.47, 29.43, 32.93, 34.59, 41.72, 58.77, 77.92, 116.11, 120.42, 125.44, 125.63, 146.76, 148.40 ppm; MS: (m/z)=217, (M–N(OH)CH$_3$)$^+$ Similarly the following compound was prepared:
4-[N,N-Hydroxy(methyl)amino]-5,7,8-trimethyl-3,4-dihydrospiro[chromene-2,1'-cyclobutan]-6-ol $^1$H-NMR (300 MHz, CD$_3$OD) δ=1.77-2.01 (4H, m), 2.10-2.23 (11H, m), 2.34-2.60 (5H, m), 4.28-4.32 (1H, t) ppm, $^{13}$C-NMR (75 MHz, CD$_3$OD) δ=10.71, 11.51, 11.98, 12.21, 30.24, 33.52, 34.80, 41.71, 59.13, 78.11, 120.13, 122.34, 122.60, 124.30, 146.12, 146.73 ppm; MS: (m/z)=231, (M–N(OH)CH$_3$)

Example 38

4'-(Ethoxyamino)-5',7'-dimethyl-3',4'-dihydrospiro[cyclobutane-1,2'-thiochromen]-6'-ol.

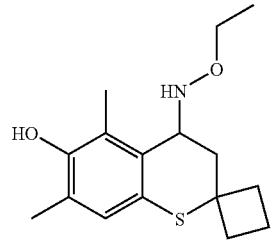

Step 1: Cyclobutylidene-acetic acid ethyl ester

To a stirred solution of triethyl phosphonoacetate (25.7 g) in 150 mL of anhydrous THF at 0° C. was added slowly NaH (4.6 g, 60% in mineral oil). After 10 min., cyclobutanone (7.3 g) was added to the mixture, and the reaction was allowed to stir at room temperature for 2 hours. After the reaction was quenched by adding water, the mixture was extracted 3 times with ethyl acetate. The organic layer was separated and dried over anhydrous Na$_2$SO$_4$, and concentrated in vacuo. The residue was purified by flash chromatography eluted with 10% ethyl acetate in hexane to give 12.0 g of cyclobutylideneacetic acid ethyl ester as a colorless liquid. $^1$H-NMR (300 MHz, CDCl$_3$,) δ=5.54 (m, 1H, =CH), 4.11 (q, 2H, OCH$_2$), 3.09 (t, 2H, CH$_2$), 2.79 (t, 2H, CH$_2$), 2.06 (m, 2H, CH$_2$), 1.23 (t, 3H, CH$_3$) ppm. $^{13}$C-NMR (75 MHz, CDCl$_3$) δ=167.0, 166.5, 112.4, 59.5, 33.7, 32.3, 17.6, 14.3 ppm.

Step 2: 6'-Hydroxy-5',7'-dimethylspiro[cyclobutane-1,2'-thiochromen]-4'(3'H)-one To a solution of 4-mercapto-2,6-dimethylphenol (2.5 g) in anhydrous methanol (40 mL) containing trimethyl orthoformate (3 mL), was added cyclobutylidene-acetic acid ethyl ester (7.6 g) and then 5 drops of concentrated sulfuric acid. The solution was deoxygenated by bubbling with nitrogen, and was allowed to reflux for 4 days. The mixture was concentrated, washed with saturated NaHCO$_3$ and extracted with ethyl acetate. After concentrated in vacuo, the residue was purified by flash chromatography eluted with 10-20% ethyl acetate in hexane to give 3.1 g of methyl {1-[(4-hydroxy-3,5-dimethylphenyl)thio]cyclobutyl}acetate as a white solid.

The above addition product (3.1 g) was suspended in 200 mL of 1N NaOH in MeOH and water (1:1, v/v), and the mixture was allowed to stir for 1 hour. The reaction mixture was then acidified with 1N HCl and extracted 3 times with ethyl acetate. The organic layer was washed with water and dried over anhydrous Na$_2$SO$_4$, and concentrated in vacuo. The resulting acid was dissolved in 100 mL of concentrated sulfuric acid to form a homogeneous dark red solution. After 1 hour at room temperature the solution was poured into crushed ice. The resulting green mixture was extracted 3 times with ethyl acetate. The organic layer was washed with water and dried over anhydrous Na$_2$SO$_4$, and concentrated in vacuo to give 2.7 g of 6'-hydroxy-5',7'-dimethylspiro[cyclobutane-1,2'-thiochromen]-4(3'H)-one as a brown solid, which was used directly for the next step. $^1$H-NMR (300 MHz, CDCl$_3$) δ=6.87 (s, 1H, ArH), 6.00 (s, 1H, ArOH), 3.07 (s, 2H, COCH$_2$), 2.48 (s, 3H, ArCH$_3$), 2.23-1.90 (m, 9H) ppm. $^{13}$C-NMR (75 MHz, CDCl$_3$) δ=198.4, 150.7, 132.7, 130.8, 128.9, 126.9, 126.8, 53.7, 47.2, 34.8, 17.9, 16.9, 13.9. MS: m/z=249.0 (M+H$^+$), 271.0 (M+Na$^+$).

Step 3: 4'-Ethoxyamino)-5',7'-dimethyl-3',4'-dihydrospiro[cyclobutane-1,2'-thiochromen]-6'-ol To a solution of 6'-hydroxy-5',7'-dimethylspiro[cyclobutane-1,2'-thiochromen]-4'(3'H)-one (0.8 g) in 4 mL of pyridine was added ethoxyamine hydrochloride (0.9 g). The reaction mixture was allowed to heat at 80° C. for 1 hr and then stirred at room temperature for overnight. The mixture was extracted with ethyl acetate, and washed with 1N HCl. After concentrated in vacuo, the residue was purified by flash chromatography eluted with 10% ethyl acetate in hexane to give 0.6 g of the product oxime as a yellow paste. To a solution of the oxime (0.6 g) in 10 mL of THF at 0° C. was added BH$_3$/pyridine complex (2.27 mL). Subsequently, 9 mL of HCl in dioxane (4.0 M solution) was added over a period of 1 hour. The reaction mixture was allowed to stir for.overnight. The mixture was extracted with ethyl acetate, washed with saturated NaHCO$_3$. After concentrated in vacuo, the residue was purified by flash chromatography eluted with 5-8% ethyl acetate in hexane to give 403 mg of the product 4'-ethoxyamino)-5',7'-dimethyl-3',4'-dihydrospiro[cyclobutane-1,2'-thiochromen]-6'-ol as a light-yellow paste.

$^1$H-NMR (300 MHz, CDCl$_3$) δ=6.74 (s, 1H, ArH), 5.50 (b, 1H), 4.95 (b, 1H), 4.51 (m, 1H, N-CH), 3.84 (q, 2H, NOCH$_2$), 2.98 (m, 1H), 2.68 (m, 1H), 2.31 (s, 3H, ArCH$_3$), 2.10 (s, 3H, ArCH$_3$), 2.31-1.82 (m, 6H, CH$_2$), 1.21 (t, 3H, CH$_3$) ppm. $^{13}$C-NMR (75 MHz, CDCl$_3$) δ=149.8, 128.8, 126.1, 124.7, 124.3, 124.1, 68.9, 55.9, 45.6, 38.7, 38.1, 37.7, 16.6, 16.1, 14.5, 11.4 ppm. MS: (m/z)=233.0 (M-NHOEt)$^+$.

Similarly the following compounds were prepared:

4'-(Ethoxyamino)-5',7',8'-trimethyl-3',4'-dihydrospiro[cyclobutane-1,2'-thiochromen]-6'-ol $^1$H-NMR (300 MHz, CDCl$_3$) δ=5.60 (b, 1H), 4.70 (b, 1H), 4.56 (m, 1H, N-CH), 3.82 (q, 2H, NOCH$_2$), 2.96 (m, 1H), 2.68 (m, 1H), 2.31 (s, 3H, ArCH$_3$), 2.24 (s, 3H, ArCH$_3$), 2.10 (s, 3H, ArCH$_3$), 2.31-1.82 (m, 6H, CH$_2$), 1.21 (t, 3H, CH$_3$) ppm. $^{13}$C-NMR (75 MHz, CDCl$_3$) δ=149.2, 131.3, 128.6, 124.9, 122.7, 121.1, 68.8, 56.2, 45.7, 39.2, 38.2, 37.6, 16.4, 16.3, 14.4, 12.7, 11.5 ppm. MS: (m/z)=247.1 (M-NH$_2$OEt$^+$)

4-(Ethoxyamino)-7,8-dimethyl-3,4-dihydrospiro[chromene-2,1'-cyclobutan]-6-ol $^1$H-NMR (300 MHz, CDCl$_3$) δ=5.54 (m, 1H, =CH), 4.11 (q, 2H, OCH$_2$), 3.09 (t, 2H, CH$_2$), 2.79 (t, 2H, CH$_2$), 2.06 (m, 2H, CH$_2$), 1.23 (t, 3H, CH$_3$) ppm. $^{13}$C-NMR (75 MHz, CDCl$_3$) δ=167.0, 166.5, 112.4, 59.5, 33.7, 32.3, 17.6, 14.3 ppm By following the procedure as described above, but substituting ethoxyamine hydrochloride with methoxyamine hydrochloride, the following compounds were prepared:

4'-(Methoxyamino)-5',7'-dimethyl-3',4'-dihydrospiro[cyclobutane-1,2'-thiochromen]-6'-ol $^1$H-NMR (300 MHz, CDCl$_3$) δ=6.73 (s, 1H, ArH), 5.60 (b, 1H), 5.00 (b, 1H), 4.54 (m, 1H, N-CH), 3.63 (s, 3H, NOCH$_3$), 2.96 (m, 1H), 2.68 (m, 1H), 2.31 (s, 3H, ArCH$_3$), 2.10 (s, 3H, ArCH$_3$), 2.31-1.82 (m, 6H, CH$_2$) ppm. $^{13}$C-NMR (75 MHz, CDCl$_3$) δ=149.8, 128.5, 126.1, 124.7, 124.4, 124.3, 61.4, 55.5, 45.6, 39.2, 38.7, 38.1, 16.6, 16.1, 11.3 ppm. MS: (m/z)= 233.0 (M-NHOMe$^+$).

Example 39

3,5,7,8-Tetramethylspiro[chromene-2,1'-cyclobutan]-6-ol

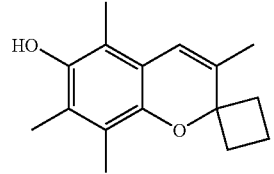

Step 1: 4-Methoxy-3,5,7,8-tetramethyl-3,4-dihydrospiro[chromene-2,1'-cyclobutan]-6-ol To a solution of 6-hydroxy-3,5,7,8-tetramethylspiro[chromene-2,1'-cyclobutan]-4(3H)-one, prepared by reduction of 3-(chloromethylene)-6-hydroxy-5,7,8-trimethylspiro[chromene-2,1'-cyclobutan]-4(3H)-one (see Example 19) (168 mg) in 10 mL of MeOH was added NaBH$_4$ (250 mg). The reaction mixture was allowed to stir at room temperature for 1 hour to give 3,5,7,8-tetramethyl-3,4-dihydrospiro[chromene-2,1'-cyclobutane]-4,6-diol. Subsequently 20 mL of MeOH was added to the reaction mixture, followed by 2 mL of conc. HCl. After 30 min, the reaction mixture was neutralized by adding saturated NaHCO$_3$ and extracted with ethyl acetate. After drying it over anhydrous Na$_2$SO$_4$ and concentrating in vacuo, the residue was purified by flash chromatography eluted with 20% ethyl acetate in hexane to give 113.2 mg of 4-methoxy-3,5,7,8-tetramethyl-3,4-dihydrospiro[chromene-2,1'-cyclobutan]-6-ol as a yellow solid. $^1$H-NMR (300 MHz, CDCl$_3$) δ=4.83 (s, 1H), 3.08 (s, 2H), 2.46 (s, 3H), 2.28 (s, 3H), 2.26 (s, 3H), 2.28-1.90 (m, 6H)

ppm. $^{13}$C-NMR (75 MHz, CDCl$_3$) δ=198.6, 149.9, 132.3, 131.8, 129.1, 128.8, 122.7, 57.9, 46.3, 35.1, 16.6, 15.7, 13.7, 13.3 ppm. MS: (m/z)=245.1 (M−OMe$^+$).

Step 2: 3,5,7,8-Tetramethylspiro[chromene-2,1'-cyclobutan]-6-ol

To a stirred solution of methoxy-3,5,7,8-tetramethyl-3,4-dihydrospiro[chromene-2,1'-cyclobutan]-6-ol (50 mg) in 10 mL of MeOH was added 5 drops of conc. HCl. The reaction mixture was concentrated, and the residue was purified by flash chromatography eluted with 20% ethyl acetate in hexane to give 40.5 mg of the desired product 3,5,7,8-tetramethylspiro[chromene-2,1'-cyclobutan]-6-ol as a white solid. $^1$H-NMR (300 MHz, CDCl$_3$) δ=6.27 (s, 1H, =CH), 4.28 (s, 1H), 2.39 (t, 2H), 2.22 (s, 3H), 2.17 (s, 6H), 2.03 (s, 3H), 2.10-1.70 (m, 4H) ppm. $^{13}$C-NMR (75 MHz, CDCl$_3$) δ=145.7, 143.7, 136.0, 122.3, 121.6, 119.9, 116.6, 115.1, 81.3, 33.3, 19.1, 14.2, 12.7, 11.8, 11.4 ppm. MS: (m/z)=245.1 (M+H$^+$).

Alternative preparation of 3,5,7,8-tetramethyl-3,4-dihydrospiro[chromene-2,1'-cyclobutane]-4,6-diol To a stirred solution of 4-methoxy-3,5,7,8-tetramethyl-3,4-dihydrospiro[chromene-2,1'-cyclobutan]-6-ol. (50 mg) in 10 mL of MeOH was added 5 drops of conc. HCl. The reaction mixture was concentrated, and the residue was purified by flash chromatography eluted with 40% ethyl acetate in hexane to give 7.6 mg of the desired product 3,5,7,8-tetramethyl-3,4-dihydrospiro[chromene-2,1'-cyclobutane]-4,6-diol as a white solid.

$^1$H-NMR (300 MHz, CD$_3$OD) δ=4.40 (d, 1H), 2.50 (m, 1H), 2.32 (s, 3H), 2.15 (s, 3H), 2.13 (s, 3H), 0.80 (d, 3H), 2.2-0.8 (m, 6H) ppm. $^{13}$C-NMR (75 MHz, CD$_3$OD) δ=146.0, 144.5, 126.5, 123.0, 122.5, 117.5, 80.0, 67.5, 42.0, 32.0, 33.0, 14.0, 12.0, 11.5, 11.3 ppm. MS: (m/z)=263.1 (M−OH$^+$).

Example 40

5-[1-(Ethoxyamino)ethyl]-7,8-dimethyl-3,4-dihydrospiro[chromene-2,1'-cyclobutan]-6-ol

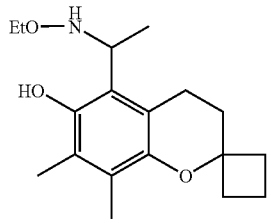

Step 1: 1-(6-Hydroxy-7,8-dimethyl-3,4-dihydrospiro[chromene-2,1'-cyclobutan]-5-yl)ethanone To 7,8-dimethyl-3,4-dihydrospiro[chromene-2,1'-cyclobutan]-6-ol (300 mg) and triethylamine (0.4 g) in 10 mL of dry DCM at room temperature was portionwise added acetyl chloride (162 mg). The mixture was stirred for 1 h and quenched by adding 30 mL of hexane. It was extracted with water (3×30 mL) and the organic phase was dried over Na$_2$SO$_4$ and concentrated. The crude product was purified by chromatography (hexane/EtOAc) to afford the acetyl protected chroman as a yellow solid. MS m/z: 261 (100, M+H$^+$). This compound was dissolved in 5 mL of BF$_3$.AcOH and the mixture was heated to reflux for 5 h. After cooling down, the reaction mixture was quenched onto 20 g of ice. The solid was collected and washed with water and dried under high vacuum to afford 1-(6-hydroxy-7,8-dimethyl-3,4-dihydrospiro[chromene-2,1'-cyclobutan]-5-yl)ethanone as a yellow solid. MS: (m/z)=261 (M+H$^+$, 100). This crude material (400 mg) was directly used for the subsequent reaction without purification.

Step 2: 5-[1-(Ethoxyamino)ethyl]-7,8-dimethyl-3,4-dihydrospiro[chromene-2,1'-cyclobutan]-6-ol A mixture of the ketone (50 mg), ethoxyamine (98 mg), 4 mL of EtOH, and 2 mL of pyridine was heated to reflux for 2 h and cooled to room temperature. Solvent was removed and residue was washed with water and dried under high vacuum to afford a light brown solid. It was purified to afford 1-(6-hydroxy-7,8-dimethyl-3,4-dihydrospiro[chromene-2,1'-cyclobutan]-5-yl)ethanone O-ethyloxime as a yellow solid (20 mg). MS: (m/z)=304 (M+H$^+$). To this oxime in 2 mL EtOH at 0° C. was added BH$_3$.pyridine (50 mg) followed by dropwise addition of HCl in dioxane (0.25 mL of 4 M solution). The reaction was warmed to room temperature and stirred for overnight. It was quenched by adding 20 mL of hexane/EtOAc (1:1) and the mixture was washed with saturated NaHCO$_3$ (2×30 mL) and water (2×30 mL), and the organic phase was dried over Na$_2$SO$_4$ and concentrated. The crude material was chromatographed (hexane/EtOAc) to afford 5-[1-(ethoxyamino)ethyl]-7,8-dimethyl-3,4-dihydrospiro[chromene-2,1'-cyclobutan]-6-ol as a white solid (9.5 mg).

$^1$H-NMR (300 MHz, CDCl3) δ=5.72 (ws, 1H), 4.52 (q, t=6.7 Hz, 1H), 3.83 (t, j=6.8 Hz, 2H), 2.77 (m, 1H), 2.61 (m, 1H), 2.28-2.16 (m, 8H), 2.08-1.94 (m, 4H), 1.71-1.61 (m, 1H), 1.41 (d, J=6.7 Hz, 3H), 1.18 (t, j=6.8 Hz, 3H) ppm; $^{13}$C-NMR δ=147.6, 144.5, 125.2, 123.5, 119.6, 115.9, 70.2, 56.0, 33.9, 29.4, 19.8, 16.8, 14.0, 12.5, 11.9, 11.8 ppm; MS: (m/z)=245 (100, M−EtOH$^+$.)

Example 41

5,7-dimethylspiro[chromene-2,1'-cyclobutan]-6-ol

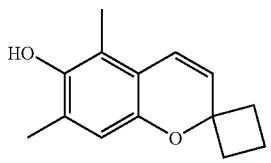

N-(6-hydroxy-5,7-dimethyl-3,4-dihydrospiro[chromene-2,1'-cyclobutan]-4-yl)benzenesulfonamide

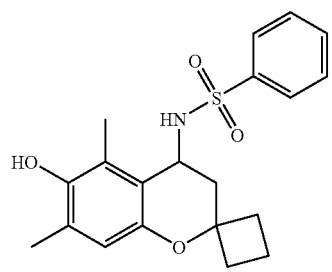

To a solution of 6-hydroxy-5,7-dimethylspiro[chromene-2,1'-cyclobutan]-4(3H)-one (1.0 g) in methanol (15 mL) was added NaBH$_4$ (1.0 g) portionwise over 2 minutes with stirring while cooled with an ice-water bath. The reaction mixture was stirred for 30 minutes at 0° C. and then warmed up to room temperature for an additional 30 minutes. Evaporation of solvents gave a white solid which was taken up with ethyl acetate (40 mL) and subsequently washed with water. The organic solution was dried over Na$_2$SO$_4$ and evaporated to dryness. This gave 5,7-dimethyl-3,4-dihydrospiro[chromene-2,1'-cyclobutane]-4,6-diol as a white solid (0.875 g), which was used for next step reaction without further purification.

To a cold solution of 5,7-dimethyl-3,4-dihydrospiro[chromene-2,1'-cyclobutane]-4,6-diol (200 mg) and phenyl sulfonamide (1.35 g) in THF (15 mL) was added dropwise a sulfuric acid solution in THF (2 drops, 98% sulfuric acid, 5 mL THF). The mixture was allowed to stir 30 minutes at 0° C. and then at room temperature for another 30 minutes. The solution was partitioned between ethyl acetate and water. The aqueous phase was washed with ethyl acetate (2×10 mL). The combined organic solutions were washed with water and dried over Na$_2$SO$_4$. Upon removal of solvents to dryness, the crude products were purified using flash column chromatography (0-20% ethyl acetate in hexanes) to yield 5,7-dimethylspiro[chromene-2,1'-cyclobutan]-6-ol as an off-white solid (106 mg).

$^1$H-NMR (300 MHz, CDCl$_3$) δ=6.55 (s, 1H), 6.57 (d, 1H, J=10 Hz), 6.05 (d, 1H, J=10 Hz), 4.30 (s, 1H), 2.40-2.51 (m, 2H), 1.93-2.16 (m, 8H), 1.65-1.82 (m, 2H) ppm. $^{13}$C-NMR (75 MHz, CDCl$_3$) δ=146.4, 146.1, 128.9, 123.6, 119.7, 119.2, 119.1, 115.5, 77.4, 37.1, 16.4, 12.1, 11.0 ppm. MS: (m/z)=217 (100, M+H$^+$), and N-(6-hydroxy-5,7-dimethyl-3,4-dihydrospiro[chromene-2,1'-cyclobutan]-4-yl)benzenesulfonamide as an off-white solid (18 mg), $^1$H-NMR (300 MHz, CDCl$_3$) δ=7.96 (d, 2H, J =6.84 Hz), 7.59 (m, 3H), 6.53 (s, 1H), 4.63 (br s, 1H), 4.38 (d, 1H, J=5.5 Hz), 4.35 (s, 1H), 2.19 (s, 3H), 1.88 (s, 3H), 2.30-1.31 (m, 8H) ppm. MS: (m/z) 396 (45, M+Na$^+$), 217 (100, M−PhSO$_2$NH$^+$).

Starting from 5,7-diethyl-6-hydroxyspiro[chroman-2,1'-cyclobutan]-4-one, the following compound was prepared:

5,7-Diethylspiro[chromene-2,1'-cyclobutan]-6-ol $^1$H NMR (300 Hz, CDCl$_3$) δ=6.52 (s, 1H), 4.36 (s, 1H), 2.64 (q, 2H), 2.54 (q, 2H), 2.44 (m, 2H), 2.17 (m, 2H), 1.80-1.50 (m, 2H), 1.21 (t, 3H), 1.12 (t, 3H) ppm. $^{13}$C NMR (75 Hz, CDCl$_3$) δ=146.7, 145.0, 130.0, 129.0, 125.7, 119.3, 118.2, 113.8, 77.4, 37.3, 23.2, 18.9, 14.6, 13.7, 12.0 ppm. MS: m/z=245.2 (M+H$^+$).

Example 42

3-[(Methoxyamino)methyl]-5,7-dimethyl-3,4-dihydrospiro[chromene-2,1'-cyclobutan]-6-ol

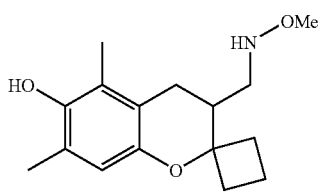

Step 1: 6-Hydroxy-5,7-dimethylspiro[chromene-2,1'-cyclobutane]-3-carbaldehyde O-methyloxime To a solution of 6-hydroxy-5,7-dimethylspiro[chromene-2,1'-cyclobutane]-3-carbaldehyde (421 mg, prepared as described in Example 19) in 8 mL of pyridine was added methoxyamine hydrochloride (628 mg). The reaction mixture was allowed to stir at room temperature overnight. The mixture was extracted with ethyl acetate and washed with 1N HCl. The organic solvent was evaporated in vacuo, the residue was purified by flash chromatography eluted with 10% ethyl acetate in hexane to give 6-hydroxy-5,7-dimethylspiro[chromene-2,1'-cyclobutane]-3-carbaldehyde O-methyloxime as a yellow solid. $^1$H-NMR (300 MHz, CDCl$_3$) δ=7.82 (s, 1H), 6.68 (s, 1H), 6.60 (s, 1H), 4.45 (s, 1H), 3.98 (s, 3H), 2.75 (m, 2H), 2.44 (m, 2H), 2.40 (s, 3H), 2.22 (s, 3H), 1.98 (m, 2H) ppm. $^{13}$C-NMR (75 MHz, CDCl$_3$) δ=148.6, 146.5, 146.4, 131.2, 125.8, 125.1, 119.9, 119.6, 116.0, 80.5, 62.1, 34.2, 16.6, 13.6, 11.4 ppm. MS: (m/z)=274.0 (M+H$^+$).

Step 2: 3-[(Methoxyamino)methyl]-5,7-dimethylspiro[chromene-2,1'-cyclobutan]-6-ol To a solution of 6-hydroxy-5,7-dimethylspiro[chromene-2,1'-cyclobutane]-3-carbaldehyde O-methyloxime (150 mg) in 10 mL of THF at 0° C. was added BH$_3$/pyridine complex (2.27 mL). Subsequently, 9 mL of HCl in dioxane (4.0 M solution) was added over a period of 1 hour. The reaction mixture was allowed to stir overnight. The mixture was extracted with ethyl acetate, washed with saturated NaHCO$_3$, and concentrated in vacuo. The residue was purified by flash chromatography eluted with 30% ethyl acetate in hexane to give 142 mg of 3-[(methoxyamino)methyl]-5,7-dimethylspiro[chromene-2,1'-cyclobutan]-6-ol as a yellow solid. $^1$H-NMR (300 MHz, CDCl$_3$) δ=6.59 (s, 1H, =CH), 6.45 (s, 1H), 5.50 (b, 1H), 4.75 (b, 1H), 3.81 (s, 2H), 3.62 (s, 3H), 2.20 (s, 3H), 2.19 (s, 3H), 2.40-1.75 (m, 6H) ppm. $^{13}$C-NMR (75 MHz, CDCl$_3$) δ=146.3, 146.0, 134.0, 123.9, 120.3, 119.4, 119.1, 114.6, 81.1, 62.0, 54.7, 33.1, 16.5, 14.3, 11.2 ppm. MS: (m/z)=229.1 (M−NH$_2$OMe$^+$).

Step 3: 3-[(Methoxyamino)methyl]-5,7-dimethyl-3,4-dihydrospiro[chromene-2,1'-cyclobutan]-6-ol A solution of 3-[(methoxyamino)methyl]-5,7-dimethylspiro[chromene-2,1'-cyclobutan]-6-ol (300 mg) in 20 mL of ethyl acetate was treated with Pd (100 mg, 10% on activated carbon), flushed with H$_2$, and left stirring in a hydrogen atmosphere overnight. After filtration through a pad of silica, the solvents were evaporated. The residue was purified by flash chromatography eluted with 30% ethyl acetate and hexane to give 54.0 mg of 3-[(methoxyamino)methyl]-5,7-dimethyl-3,4-dihydrospiro[chromene-2,1'-cyclobutan]-6-ol as an off-white solid. $^1$H-NMR (300 MHz, CDCl$_3$) δ=6.51 (s, 1H), 3.57 (s, 3H), 2.20 (s, 3H), 2.13 (s, 3H), 3.20-1.50 (m, 11H) ppm. $^{13}$C-NMR (75 MHz, CDCl$_3$) δ=146.5, 145.9, 122.6, 122.4, 117.7, 116.3, 79.2, 62.0, 50.5, 35.4, 33.5, 31.7, 23.3, 16.2, 12.8, 11.6 ppm. MS: (m/z)=278.2 (M+H$^+$).

Similarly following the procedure as described above, the following compounds were prepared:

6-Hydroxy-5,7-dimethylspiro[chromene-2,1'-cyclobutane]-3-carbaldehyde O-ethyloxime $^1$H-NMR (300 MHz, CDCl$_3$) δ=7.82 (s, 1H), 6.66 (s, 1H), 6.60 (s, 1H), 4.42 (s, 1H), 4.23 (q, 2H), 2.79 (m, 2H), 2.43 (m, 2H), 2.22 (s, 3H), 2.21 (s, 3H), 1.97 (m, 2H), 1.35 (t, 3H) ppm. $^{13}$C-NMR (75 MHz, CDCl$_3$) δ=148.4, 146.5, 146.4, 131.7, 125.6, 125.0, 119.8, 119.6, 116.0, 80.6, 69.8, 34.3, 16.6, 14.8, 13.5, 11.1 ppm. MS: (m/z)=288.2 (M+H$^+$).

3-[(Ethoxyamino)methyl]-5,7-dimethylspiro[chromene-2,1'-cyclobutan]-6-ol $^1$H-NMR (300 MHz, CDCl$_3$) δ=6.59 (s, 1H), 6.46 (s, 1H), 5.50 (b, 1H), 4.50 (b, 1H), 3.80 (s, 2H), 3.82 (q, 2H), 2.21 (s, 3H), 2.20 (s, 3H), 2.40-1.75 (m, 6H), 1.21 (t, 3H) ppm. $^{13}$C-NMR (75 MHz, CDCl$_3$) δ=146.4, 146.0, 134.0, 124.5, 120.2, 120.0, 119.3, 115.9, 81.4, 69.4, 53.7, 33.2, 16.3, 14.3, 11.3 ppm. MS: (m/z)=230.1 (M–NH$_2$OEt$^+$), 312.2 (M+Na$^+$).

3-[(Ethoxyamino)methyl]-5,7-dimethyl-3,4-dihydrospiro[chromene-2,1'-cyclobutan]-6-ol $^1$H-NMR (300 MHz, CDCl$_3$) δ=6.51 (s, 1H), 3.77 (q, 2H), 2.25 (s, 3H), 2.20 (s, 3H), 3.20-1.50 (m, 11H), 1.19 (t, 3H) ppm. $^{13}$C-NMR (75 MHz, CDCl$_3$) δ=146.6, 145.8, 122.4, 122.2, 117.8, 116.3, 79.2, 69.4, 50.8, 35.4, 33.5, 31.7, 23.3, 16.1, 14.3, 12.8, 11.6 ppm. MS: (m/z)=292.2 (M+H$^+$).

Example 43

5,7-Dimethyl-3-(1,3-oxazol-5-yl)spiro[chromene-2,1'-cyclobutan]-6-ol

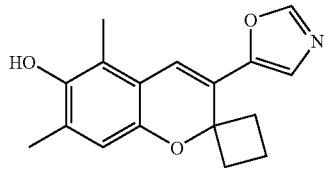

To a solution of 6-hydroxy-5,7-dimethylspiro[chromene-2,1'-cyclobutane]-3-carbaldehyde (315 mg), prepared as described herein, in 4 mL of MeOH was added tosylmethyl isocyanide (TosMIC) reagent (218 mg) and potassium carbonate (310 mg). The reaction mixture was allowed to heat at 80° C. for 20 min. The mixture was quenched with water and extracted with ethyl acetate. After concentrated in vacuo, the residue was purified by flash chromatography eluted with 30% ethyl acetate in hexane to give 118.8 mg of 5,7-dimethyl-3-(1,3-oxazol-5-yl)spiro[chromene-2,1'-cyclobutan]-6-ol as a yellow solid.

$^1$H-NMR (300 MHz, CDCl$_3$ and CD$_3$OD) δ=7.88 (s, 1H), 7.11 (s, 1H), 6.84 (s, 1H), 6.48 (s, 1H), 2.12 (s, 3H), 2.11 (s, 3H), 2.50-1.70 (m, 6H) ppm. $^{13}$C-NMR (75 MHz, CDCl$_3$ and CD$_3$OD) δ=154.5, 154.0,151.0, 149.8, 131.2, 128.9, 126.2, 125.5, 124.7, 123.2, 119.8, 83.6, 37.9, 20.7, 17.5, 15.1 ppm. MS: (m/z)=284.1 (M+H$^+$).

Example 44

5-Ethyl-4-(methoxyamino)-7,8-dimethyl-3,4-dihydrospiro[chromene-2,1'-cyclobutan]-6-ol

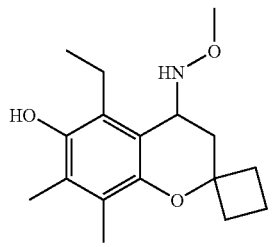

Step 1: 5-Acetyl-4-hydroxy-2,3-dimethylphenyl acetate

To a stirred solution of 2,3-dimethylbenzene-1,4-diol (25.0 g) in 250 mL of toluene was added 40 mL of acetyl chloride. The reaction was allowed to reflux for 2 hours until the reaction was completed as indicated by TLC. After evaporation of the organic solvents, the resulting residue was crystallized from ethyl acetate and hexane to give 46.0 g of 2,3-dimethyl-1,4-phenylene diacetate as a light-green solid. Subsequently, 2,3-dimethyl-1,4-phenylene diacetate (16.0 g) was suspended in 50 mL of boron trifluoride-acetic acid complex, and the reaction mixture was allowed to heat at 120° C. for 6 hr. The reaction mixture was extracted with ethyl acetate, washed with saturated NaHCO$_3$ and water, and dried over anhydrous Na$_2$SO$_4$. Evaporation of the organic solvents and crystallization of the resulting residue from ethyl acetate and hexane gave 15.4 g of 5-acetyl-4-hydroxy-2,3-dimethylphenyl acetate as a light-brown solid.

Step 2: 5-Ethyl-2,3-dimethylbenzene-1,4-diol

To a well stirred solution of 5-acetyl-4-hydroxy-2,3-dimethylphenyl acetate (4.7 g) in 100 mL of toluene were added Zn dust (5.0 g), HgCl$_2$ (480 mg), water (9 mL) and concentrated HCl (9 mL). The heterogeneous mixture was allowed to reflux for 2 days. The mixture was cooled, filtered, and extracted with ethyl acetate. The organic layer was washed with saturated NaHCO$_3$ and water, and dried over anhydrous Na$_2$SO$_4$. Evaporation of the organic solvents gave 3.5 g of 5-ethyl-2,3-dimethylbenzene-1,4-diol as an off-white powder.

Step 3: 3-Acetyl-2-ethyl-4-hydroxy-5,6-dimethylphenyl acetate

To a stirred solution of 5-ethyl-2,3-dimethylbenzene-1,4-diol (3.5 g) in 100 mL of toluene was added 10 mL of acetyl chloride. The reaction was allowed to reflux for 2 hours until the reaction was completed as indicated by TLC. After concentrated in vacuo, crystallization of the resulting residue from ethyl acetate and hexane gave 5.2 g of 5-ethyl-2,3-dimethyl-1,4-phenylene diacetate as a light-green solid. Subsequently 5-ethyl-2,3-dimethylbenzene-1,4-diol (5.1 g) was suspended in 40 mL of boron trifluoride-acetic acid complex and the reaction mixture was allowed to heat at 120° C. for 3 days. The mixture was extracted with ethyl acetate, washed with saturated NaHCO$_3$ and water, and dried over anhydrous Na$_2$SO$_4$. After concentrated in vacuo, crystallization of the resulting residue from ethyl acetate and hexane gave 3.5 g of 3-acetyl-2-ethyl-4-hydroxy-5,6-dimethylphenyl acetate as a yellow solid.

Step 4: 5-Ethyl-6-hydroxy-7,8-dimethylspiro[chromene-2,1'-cyclobutan]-4(3H)-one

To a solution of 3-acetyl-2-ethyl-4-hydroxy-5,6-dimethylphenyl acetate (3.5 g) in 20 mL of toluene was added cyclobutanone (1.16 mL) and pyrrolidine (1.4 mL). The reaction was allowed to reflux for 2 hours and Dean-Stark apparatus was used to remove water from the reaction. After the reaction was complete, the mixture was extracted with ethyl acetate and then was washed with 1N HCl and water. The organic layer was dried over anhydrous Na$_2$SO$_4$ and concentrated in vacuo to give 5-ethyl-7,8-dimethyl-4-oxo-3,4-dihydrospiro[chromene-2,1'-cyclobutan]-6-yl acetate, which was hydrolyzed in 1N NaOH in MeOH/water. After the reaction was complete as indicated by TLC, the mixture was acidified with 1N HCl and extracted with ethyl acetate and dried over anhydrous Na$_2$SO$_4$. Evaporation of the solvents gave 0.8 g of 5-ethyl-6-hydroxy-7,8-dimethylspiro[chromene-2,1'-cyclobutan]-4(3H)-one as a yellow paste.

Step 5: 5-Ethyl-6-hydroxy-7,8-dimethylspiro[chromene-2, 1'-cyclobutan]-4(3H)-one O-methyloxime To a solution of 5-ethyl-6-hydroxy-7,8-dimethylspiro [chromene-2,1'-cyclobutan]-4(3H)-one (0.51 g) in 9 mL of pyridine was added methoxyamine hydrochloride (0.82 g). The reaction mixture was allowed to stir at room temperature overnight. The mixture was extracted with ethyl acetate, washed with 1N HCl, and concentrated in vacuo to give 5-ethyl-6-hydroxy-7,8-dimethylspiro[chromene-2,1'-cyclobutan]-4(3H)-one O-methyloxime. $^1$H-NMR (300 MHz, CDCl$_3$) δ=4.58 (s, 1H, 4.01 (s, 3H), 3.05 (m, 2H), 3.02 (s, 2H), 2.20 (s, 3H), 2.17 (s, 3H), 2.10-1.60 (m, 6H), 1.24 (t, 3H) ppm. $^{13}$C-NMR (75 MHz, CDCl$_3$) δ=151.0, 147.4, 146.3, 125.8, 124.6, 124.3, 115.3, 76.9, 61.9, 33.9, 33.4, 21.2, 13.6, 12.7, 12.3, 12.1 ppm. MS: (m/z)=290.1 (M+H$^+$).

Step 6: 5-Ethyl-4-(methoxyamino)-7,8-dimethyl-3,4-dihydrospiro[chromene-2,1'-cyclobutan]-6-ol 5-Ethyl-6-hydroxy-7,8-dimethylspiro[chromene-2,1'-cyclobutan]-4(3H)-one O-methyloxime was dissolved in 10 mL of THF. To this solution at 0° C. was added BH$_3$/pyrine complex (2.27 mL). Subsequently, a solution of 9 mL of HCl in dioxane (4.0 M) was added over a period of 1 hour. The reaction mixture was allowed to stir overnight. The mixture was extracted with ethyl acetate and washed with saturated NaHCO$_3$. After evaporation of the solvents, the residue was purified by flash chromatography eluted with 5-8% ethyl acetate in hexane to give 136.4 mg of the product 5-ethyl-4-(methoxyamino)-7,8-dimethyl-3,4-dihydrospiro[chromene-2,1'-cyclobutan]-6-ol. $^1$H-NMR (300 MHz, CDCl$_3$) δ=4.40 (b, 1H), 4.30 (m; 1H), 3.66 (s, 3H), 2.19 (s, 3H), 2.17 (s, 3H), 2.70-1.60 (m, 6H), 1.25 (t, 3H) ppm. $^{13}$C-NMR (75 MHz, CDCl$_3$) δ=146.3, 145.2, 126.1, 124.1, 123.4, 114.1, 76.8, 61.8, 52.4, 36.0, 35.0, 32.9, 19.2, 14.9, 13.9, 13.4, 12.4 ppm. MS: (m/z)=245.1 (M−NH$_2$OMe$^+$).

Similarly following the procedure as described above, the following compounds were prepared.

5-Ethyl-6-hydroxy- 7,8-dimethylspiro[chromene-2,1'-cyclobutan]-4(3H)-one O-ethyloxime $^1$H-NMR (300 MHz, CDCl$_3$) δ=5.20 (b, 1H), 4.40 (brs, 1H), 4.30 (m, 1H), 3.84 (q, 2H), 2.18 (s, 3H), 2.17 (s, 3H), 2.70-1.60 (m, 6H), 1.25 (t, 6H) ppm. $^{13}$C-NMR (75 MHz, CDCl$_3$) δ=146.2, 145.2, 126.1, 124.0, 123.4, 114.8, 76.8, 69.1, 52.7, 36.6, 35.9, 32.9, 23.5, 14.9, 14.5, 13.9, 12.4, 12.1 ppm. MS: (m/z)=245.1 (M−NH$_2$OEt$^+$).

4-(Ethoxyamino)-5-ethyl-7,8-dimethyl-3,4-dihydrospiro [chromene-2,1'-cyclobutan]-6-ol $^1$H-NMR (300 MHz, CDCl$_3$) δ=4.58 (s, 1H), 4.25 (q, 2H), 3.06 (m, 2H), 3.03 (s, 2H), 2.18 (s, 3H), 2.14 (s, 3H), 2.10-1.60 (m, 6H), 1.34 (t, 3H), 1.24 (t, 3H) ppm. $^{13}$C-NMR (75 MHz, CDCl$_3$) δ=150.7, 147.3, 146.3, 125.6, 124.6, 124.2, 115.7, 77.0, 69.6, 34.0, 33.5, 21.2, 15.1, 13.7, 12.7, 12.3, 12.1 ppm. MS: (m/z)=304.1 (M+H$^+$).

Example 45

7,8-dimethyl-5-(2-quinolin-2-ylethyl)) 3,4-dihydrospiro-[chromene-2,1'-cyclobutan]-6-ol

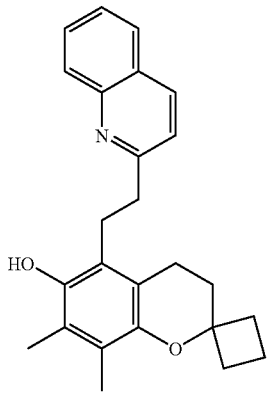

Step 1: 6-Hydroxy-7,8-dimethyl-3,4-dihydrospiro [chromene-2,1'-cyclobutane]-5-carbaldehyde 0.3 g of a solution of 7,8-dimethyl-3,4-dihydrospiro [chromene-2,1'-cyclobutan]-6-ol (prepared as described herein) was dissolved in 20 mL of 4-(dicyanomethylene)-2-methyl-6-(4-dimethylaminostyryl)-4H-pyran (DCM). The solution was flushed with Argon then cooled to 0° C. in an ice bath. 0.151 mL (1.4 mmol) of titanium tetrachloride was added followed by 0.149 mL (1.7 mmol, 1.2 eq) of α,α-dichloromethyl-methyl ether. The solution was stirred at 0° C. for 10 min, warmed to room temperature, and stirred overnight. After addition of EtOAc (50 mL), the solution was washed with water, and then dried over Na$_2$SO$_4$. The crude material was purified on a silica column eluting with 1:8 EtOAc/hexane to yield 180 mg of 6-hydroxy-7,8-dimethyl-3,4-dihydrospiro[chromene-2,1'-cyclobutane]-5-carbaldehyde as a yellow solid. $^1$H-NMR (300 MHz, CDCl$_3$) δ=1.65-1.70 (m, 1H), 1.80-1.97 (m, 2H), 2.06-2.27 (m, 11H), 3.06-3.11 (t, 2H), 10.20 (s, 1H), 12.13 (s, 1H) ppm. MS (m/z)=247 (M+H$^+$).

Step 2: 7,8-Dimethyl-5[(Z)-2-quinolin-2-ylvinyl] 3,4-dihydrospiro-[chromene-2,1'-cyclobutan]-6-ol 2-(Chloromethyl)quinoline (2 g) was converted to the free base by stirring a biphasic mixture of 1.3 g of K$_2$CO$_3$ in dichloromethane/H$_2$O. The organic layer was separated, dried over Na$_2$SO$_4$, and evaporated to a tan solid. This was dissolved in 50 mL of MeOH to which was added 1.15 g (11 mmol, 1.2 eq.) of sodium bromide and refluxed overnight. After evaporation the residue (1 g) was dissolved in 20 mL of toluene and triphenyl phosphine dissolved in another 20 mL of toluene, was added to the reaction, refluxed for 1 hr, and cooled to room temperature to give 500 mg of the triphenylphosphonium derivative.

MS (m/z)=404 (M+H$^+$). To a suspension of 0.35 g of triphenyl(quinolin-2-ylmethyl)phosphonium bromide in 5 mL of THF was added 3 mL of 0.5 M sodium methoxide at 0° C under Argon, followed by a solution of 6-Hydroxy-7,8-dimethyl-3,4-dihydrospiro[chromene-2,1'-cyclobutane]-5-carbaldehyde 0.18 g) in 10 mL of THF. The solution was stirred for 1 hr at 0° C., warmed to room temperature, and stirred for 2 hrs. The tetrahydrofuran was evaporated, and the residue was partitioned between EtOAc and H$_2$O, washed with brine, then dried over Na$_2$SO$_4$. The crude material was purified on a silica column eluting with 1:8 EtOAc/Hexane. 50 mg of 7,8-dimethyl-5-[2-quinolin-2-ylvinyl] 3,4-dihydrospiro-[chromene-2,1'-cyclobutan]-6-ol which was precipitated with hexane. $^1$H-NMR (300 MHz, CDCl$_3$) δ=1.70-1-76 (m, 3H), 1.78-1.97 (m, 5H), 2.09-2.30 (m, 8H), 2.81-2.85 (t, 2H), 5.70 (brs, 1H), 7.18-7.24 (d, 1H), 7.50-7.56 (m, 2H), 7.71-7.82 (m, 3H), 8.08-8.13 (m, 2H) ppm. $^{13}$C-NMR (75 MHz, CDCl$_3$) δ=12.24, 12.34, 12.60, 21.25, 29.31, 34.10, 76.51, 117.47, 119.17, 119.65, 112.33, 126.29, 126.46, 127.45, 127.55, 129.23, 129.88, 130.01, 133.47, 136.49, 145.10, 155.55 ppm. MS (m/z)=372 (M+H$^+$).

Step 4: 7,8-Dimethyl-5(2-quinolin-2-ylethyl))3,4-dihydrospiro-[chromene-2,1'-cyclobutan]-6-ol To a solution of 50 mg of 7,8-dimethyl-5-[2-quinolin-2-ylvinyl]-3,4-dihydrospiro-[chromene-2,1'-cyclobutan]-6- in 15 mL of MeOH, was added a catalytic amount of 10% Pd/C under an atmosphere of Argon. The flask was evacuated under vacuum and flushed with hydrogen gas 3 times via balloon. The mixture was stirred at room temperature overnight. The reaction mixture was filtered through Celite® and washed with 5 mL MeOH. The crude material was purified on a silica column, eluting with 1:10 EtOAc/Hexane to give 17.5 mg of 7,8-dimethyl-5-(2-quinolin-2-ylethyl))3,4-dihydrospiro-[chromene-2,1'-cyclobutan]-6-ol as a light yellow solid. $^1$H-NMR (300 MHz, CDCl$_3$) δ=1.70-1-76 (m, 3H), 1.78-1.97 (m, 5H), 2.09-2.30 (m, 8H), 2.81-2.85 (t, 2H), 3.30-3.34 (t, 2H), 3.48-3.52 (t, 2Ht), 7.24-7.28 (d, 1H), 7.52-7.57 (t, 1H), 7.74-7.79 (m, 2H), 8.04-8.07 (d, 1H), 8.30-8.33 (d, 1H ), 11.39 (1H, s) ppm. $^{13}$C-NMR (75 MHz, CDCl$_3$) δ=12.01, 12.57, 12.74, 20.21, 21.64, 29.57, 34.22, 37.80, 76.11, 117.18, 122.18, 123.79, 123.99, 124.63, 126.33, 126.84, 127.48, 127.53, 130.01, 136.86, 145.08, 146.27, 146.60, 160.59 ppm. MS (m/z)=374 (M+H$^+$).

Similarly the following compounds were produced:

(E)-5,8-Dimethyl-7-(2-(quinolin-2-yl)vinyl)spiro[chroman-2,1'-cyclobutan]-6-ol $^1$H-NMR (CDCl$_3$) δ=8.12-8.10 (d, 1H), 7.82-7.71 (m, 3H), 7.56-7.53 (m, 2H), 7.19-7.13 (d, 1H), 5.69 (s, 1H), 2.75-2.71 (t, 2H), 2.32 (s, 3H), 2.31-2.10 (m, 6H), 2.09-1.95 (m, 3H), 1.94-1.77 (m, 2H), 1.76-1.63 (m, 1H) ppm. $^{13}$C-NMR (CDCl$_3$) δ=155.49, 148.10, 145.26, 144.55, 136.52, 134.05, 130.74, 129.88, 129.23, 127.56, 127.47, 126.33, 122.31, 121.78, 121.52, 119.86, 119.58, 76.45, 34.01, 29.39, 20.94, 12.81, 12.60,11.47 ppm. MS (m/z)=372 (M+H$^+$).

(Z)-5,8-Dimethyl-7-(2-(quinolin-2-yl)vinyl)spiro[chroman-2,1'-cyclobutan]-6-ol $^1$H-NMR (CDCl$_3$) δ=11.07 (s, 1H), 8.16-8.13 (d, 1H), 8.06-8.03 (d, 1H), 7.79-7.68 (m, 2H), 7.55-7.52 (d, 1H, d), 7.43-7.40 (d, 1H), 7.01-6.97 (d, 1H), 6.88-6.84 (d, 1H), 2.78-2.71 (t, 2H), 2.38 (s, 3H), 2.24-2.10 (m, 5H), 2.08-1.96 (m, 3H), 1.95-1.78 (m, 2H), 1.77-1.64 (m, 1H) ppm. $^{13}$C-NMR (CDCl$_3$) δ=155.5, 146.78, 146.29, 145.13, 142.57, 137.29, 132.84, 130.17, 127.89, 127.57, 127.48, 126.85, 126.51, 124.68, 124.29, 122.78, 121.61, 76.32, 34.12, 29.44, 20.99, 12.81, 12.56, 12.17 ppm. MS (m/z)=372 (M+H$^+$).

Example 46

5-(3,7-Dimethylocta-2,6-dienyl)-7,8-dimethylspiro[chroman-2,1'-cyclobutan]-6-ol

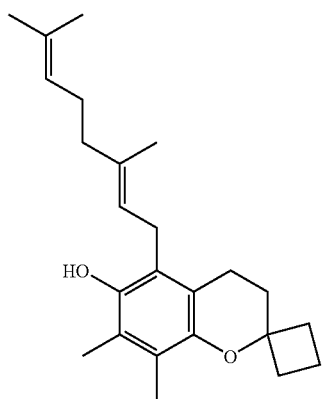

To a solution of 7,8-dimethyl-3,4-dihydrospiro[chromene-2,1'-cyclobutan]-6-ol (0.5 g) in 20 mL of dioxane under argon, was added borontrifluoride-diethyl etherate (0.72 mL) followed by geraniol (0.4 mL) and the reaction was stirred overnight. After addition of water, the solution was extracted with EtOAc, washed with brine, dried over Na$_2$SO$_4$, and evaporated. The residue was purified on a silica column eluting with 1:8 EtOAc/hexane to give 5-(3,7-dimethylocta-2,6-dienyl)-7,8-dimethylspiro[chroman-2,1'-cyclobutan]-6-ol (104 mg ) as an amber oil. $^1$H-NMR (300 MHz, CDCl$_3$) δ=1.65-1.99 (m, 10H), 2.01-2.28 (m, 17H), 2.74-2.79 (t, 2H), 3.35-3.37 (d, H), 4.78 (s, 1H), 5.10-5.12 (t, 1H), 5.17-5.21 (t, 1H) ppm. $^{13}$C-NMR (75 MHz, CDCl$_3$) δ=11.93, 12.15, 12.61, 16.21, 17.80, 20.47, 25.55, 25.80, 26.45, 29.58, 34.05, 39.74, 76.23, 117.15, 121.87, 121.97, 122.48, 123.62, 123.89, 132.02, 138.03, 145.52, 145.89 ppm. MS (m/z)=354 (M+H$^+$).

Similarly the following compound was produced:

7-(3,7-Dimethylocta-2,6-dienyl)-5,8-dimethylspiro[chroman-2,1'-cyclobutan]-6-ol $^1$H-NMR (CDCl$_3$) δ=5.20-5.17 (t, 1H), 5.10-5.07 (t, 1H), 3.42-3.40 (d, 2H), 2.71-2.67 (t, 2H), 2.29-1.98 (m, 18H), 1.86 (s, 3H), 1.72-1.66 (m, 4H), 1.64 (s, 3H) ppm. $^{13}$C-NMR (CDCl$_3$) δ=145.73, 145.53, 137.83, 131.98, 124.47, 123.92, 122.18, 121.93, 119.88, 118.87, 76.33, 39.74, 34.08, 29.44, 26.44, 25.77, 20.69, 17.78, 16.19, 12.60, 11.70, 11.23 ppm. MS (m/z)=354 (M+H$^+$).

Catalytic hydrogenation with Pd/C of 7-(3,7-Dimethylocta-2,6-dienyl)-5,8-dimethylspiro[chroman-2,1'-cyclobutan]-6-ol gave:

7-(3,7-Dimethyloctyl)-5,8-dimethylspiro[chroman-2,1'-cyclobutan]-6-ol $^1$H-NMR (CDCl$_3$) δ=4.25 (1H, s), 2.70-2.66 (m. 4H), 2.25-1.94 (m, 13H), 1.93-1.36 (m, 5H), 1.35-1.20 (m, 6H), 1.03-1.01 (d, 3H), 0.92-0.90 (d, 6H) ppm. $^{13}$C-NMR (CDCl$_3$) δ=145.62, 144.59, 126.37, 122.18, 118.62, 118.14, 76.27, 39.40, 37.15, 36.66, 34.06, 33.48, 29.45, 28.06, 24.82, 24.65, 22.79, 22.71, 20.74, 19.69, 12.59, 11.34 ppm. MS (m/z)=359 (M+H$^+$).

Example 47

Methyl 3-(6-hydroxy-5,7-dimethyl-3,4-dihydrospiro [chromene-2,1'-cyclobutan]-8-yl)4,5-dihydroisoxazole-5carboxylate

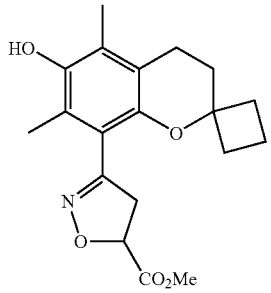

Step 1  6-Hydroxy-5,7-dimethyl-3,4-dihydrospiro [chromene-2,1'-cyclobutane]-8-carbaldehyde To a cooled solution of 5,7-dimethyl-3,4-dihydrospiro [chromene-2,1'-cyclobutan]-6-ol (1 g) in DCM (20 mL) was added TiCl$_4$ (0.53 mL) which turned the solution a red color. To the solution was added dichloromethyl methyl ether (0.42 mL) and stirred at 0° C. for 30 min and then at room temperature for 30 min. The solution was poured into water and the DCM was separated, dried and evaporated. The residue was purified by silica gel column eluting with 20% ethylacetate in hexane to give 700 mg of 6-hydroxy-5,7-dimethyl-3,4-dihydrospiro[chromene-2,1'-cyclobutane]-8-carbaldehyde as a yellow solid.

Step 2: Methyl 3-(6-hydroxy-5,7-dimethyl-3,4-dihydrospiro [chromene-2,1'-cyclobutan]-8-yl)-4,5-dihydroisoxazole-5-carboxylate A mixture of 6-hydroxy-5,7-dimethyl-3,4-dihydrospiro [chromene-2,1'-cyclobutane]-8-carbaldehyde (30 mg), methoxyamine hydrochloride (excess) and sodium acetate (10 mg) in methanol was stirred at 80° C. for 5 h. Workup and purification by silica gel column gave 10 mg of oxime, which was then dissolved in chloroform (15 mL) and stirred. Pyridine was added to the solution (0.02 mL) and then N-chlorosuccinimide (90 mg). The solution was stirred for 15 min. and then an excess of methyl acrylate was added and the mixture was stirred for an additional 5 hours. The solution was poured into water and separated with DCM. The DCM was washed, dried and evaporated and the residue was purified by silica gel column eluting with 30-40% ethyl acetate in hexane to give methyl 3-(6-hydroxy-5,7-dimethyl-3,4-dihydrospiro [chromene-2,1'-cyclobutan]-8-yl)-4,5-dihydroisoxazole-5-carboxylate as an off-white solid (12.5 mg). $^1$H-NMR (300 MHz, CDCl$_3$) δ=5.20 (m, 1H), 4.36 (s, 1H), 3.86 (s, 3H), 3.40 (m, 2H), 2.65 (t, J=6.6 Hz, 2H), 2.20, 2.14 (2s, 6H), 2.20-1.70 (m, 8H) ppm. $^{13}$C-NMR (75 MHz, CDCl$_3$) δ=171.42, 155.64, 145.96, 145.54, 123.99, 121.45, 119.02, 114.83, 77.25, 52.68, 42.83, 33.67, 29.07, 20.34, 13.10, 12.58, 11.71 ppm. MS: (m/z)=345 (100, M+H$^+$).

Similarly following the procedure described above but replacing methyl acrylate with hexyne, the following compound was prepared.

5,7-Dimethyl-8-(5butyl-isoxazol-3-yl)-3,4-dihydrospiro [chromene-2,1'-cyclobutan]-6-ol $^1$H-NMR (300 MHz, CDCl$_3$) δ=6.05 (s, 1H), 4.35 (s, 1H), 2.86 (t, J=7.5 Hz, 2H), 2.68 (t, J=6.6 Hz, 2H), 2.20-1.20 (m, 18H), 0.95 (t, J=7.3 Hz, 3H) ppm. $^{13}$C-NMR (75 MHz, CDCl$_3$) δ=172.30, 159.80, 145.76, 145.41, 123.36, 121.62, 119.05, 116.40, 103.55, 77.24, 33.62, 31.62, 29.63, 29.13, 26.48, 22.69, 20.58, 14.17, 13.77, 13.41, 12.56, 11.70 ppm. MS: (m/z)=342 (100, M+H$^+$).

Similarly following the procedure described above but replacing methyl acrylate with tosylmethyl isocyanide, the following compound was prepared.

5,7-Dimethyl-8-(1,3-oxazol-5yl)-3,4-dihydrospiro [chromene-2,1'-cyclobutan]-6-ol $^1$H-NMR (300 MHz, CDCl$_3$) δ=7.99 (s, 1H), 7.22 (s, 1H), 4.40 (s, 1H), 2.69 (t, J=7.3 Hz, 2H), 2.20-1.50 (m, 14H) ppm. $^{13}$C-NMR (75 MHz, CDCl$_3$) δ=150.26, 147.35, 145.89, 145.36, 126.63, 123.94, 121.84, 119.20, 114.37, 22.25, 33.63, 29.06, 20.63, 13.64, 12.54, 11.82 ppm. MS: (m/z)=286 (100, M+H$^+$).

Example 48

5,7-dimethyl-8-vinyl-3,4-dihydrospiro[chromene-2, 1'-cyclobutan]-6-ol

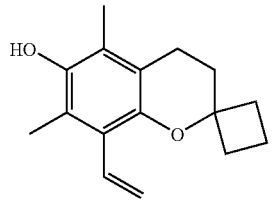

A solution of 5,7-dimethyl-6-(tetrahydro-2H-pyran-2-yloxy)spiro[chroman-2,1'-cyclobutane]-8-carbaldehyde (1.5 g) and triphenylphosphinemethyl bromide (2.5 g) and sodium hydride (400 mg) in DMF (20 mL) was stirred at 40° C. for 5 h. After pouring it into water, it was extracted with ethyl acetate, and the organic layer was dried and evaporated. Then the residue was dissolved in MeOH with dil. HCl and it was stirred at room temperature for 30 min. The mixture was poured into water and extracted with ethyl acetate. The ethyl acetate was washed, dried, and evaporated. The residue was purified by silica gel column eluting with 10% ethyl acetate in hexane, giving 507.7 mg of 5,7-dimethyl-8-vinyl-3,4-dihydrospiro[chromene-2,1'-cyclobutan]-6-ol as a light brown oil.

'H NMR (300 MHz, CDCl$_3$) δ=6.80 (m, 1H), 5.54 (m, 2H), 4.28 (s, 1H), 2.67 (m, 2H), 2.3-1.3 (m+s, 14H) ppm. $^{13}$C NMR (CDCl$_3$, 75 MHz) δ=145.56, 145.32, 131.68, 124.36, 120.91, 120.17, 119.25, 118.48, 77.10, 33.90, 29.24, 20.68, 13.13, 12.65, 11.64 ppm. MS: (m/z): 245 (100, M+H$^+$).

Example 49

5-Ethyl-4-(hydroxy(methyl)amino)-7-methylspiro[chroman-2,1'-cyclobutan]-6-ol

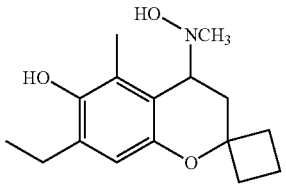

Step 1: 3-Acetyl-6-ethyl-4-hydroxy-2-methylphenyl acetate and 3-acetyl-2-ethyl-4-hydroxy-6-methylphenyl acetate A mixture of 2-ethyl-6-methyl-1,4-phenylene diacetate (6 g) and BF$_3$ acetic acid complex (10 mL) was stirred at 110° C. for 2 days. The mixture was cooled down, poured into water, and extracted with ethyl acetate. The ethyl acetate was washed with water, dried, and evaporated. The residue was purified by silica gel column eluting with 20-30% ethyl acetate in hexane to give two products, 3-acetyl-6-ethyl-4-hydroxy-2-methylphenyl acetate (5 g) and 3-acetyl-2-ethyl4-hydroxy-6-methylphenyl acetate was obtained (800 mg).

Step 2: 7-Ethyl-6-hydroxy-5-methylspiro[chroman-2,1'-cyclobutan]-4-one

A mixture of 3-acetyl-6-ethyl4-hydroxy-2-methylphenyl acetate (5.18 g), cyclobutanone (4.5 g) and pyrrolidine (1.5 mL) in toluene (50 mL) was stirred at refluxing temperature with a Dean Stark. After 8 hours it was poured into water and the toluene was separated, dried, and evaporated. The residue was dissolved in MeOH (50 mL) with LiOH (2 g), stirred at room temperature for 3 hours, poured into water, and extracted with ethyl acetate. The ethyl acetate was washed, dried, and evaporated. The residue was purified by silica gel column eluting with 15% ethyl acetate in hexane, giving 7-ethyl-6-hydroxy-5-methylspiro[chroman-2,1'-cyclobutan]-4-one as a light brown oil (0.82 g).

Step 3: 7-Ethyl-6-hydroxy-5-methylspiro[chroman-2,1'-cyclobutan]-4-one O-methyl oxime A mixture of 7-ethyl-6-hydroxy-5-methylspiro[chroman-2,1'-cyclobutan]-4-one (0.8 g), methoxyamine HCl salt (500 mg) and sodium acetate (300 mg) in MeOH (20 mL) was stirred at 80° C. overnight. The mixture was poured into water and extracted with ethyl acetate. The ethyl acetate was dried and evaporated. The residue was purified by silica gel column eluting with 10% ethyl acetate in hexane, giving 7-ethyl-6-hydroxy-5-methylspiro[chroman-2,1'-cyclobutan]-4-one O-methyl oxime (530 mg).

Step 4: 7-Ethyl-4-(hydroxy(methyl)amino)-5-methylspiro[chroman-2,1'-cyclobutan]-6-ol To a mixture of 7-ethyl-6-hydroxy-5-methylspiro[chroman-2,1'-cyclobutan]-4-one O-methyl oxime (530 mg) and BH$_3$ pyridine complex (8 M, 2 mL) at 0° C., was added a solution of HCl in dioxane (4 M, 8 mL) at 1.5 mL/h. The mixture was cooled with ice-water bath, water was added to quench it, and extracted with ethyl acetate. The organic layer was washed with water, dried, and evaporated. The residue was purified by silica gel column eluting with 10% ethyl acetate in hexane, giving 7-ethyl-4-(hydroxy(methyl) amino)-5-methylspiro[chroman-2,1'-cyclobutan]-6-ol as a clear oil (412 mg) $^1$H-NMR (300 MHz, CDCl$_3$) δ=6.57 (s, 1H), 5.25 (br., 1H), 4.30 (s, 1H), 3.63 (s, 3H), 2.67 (m, 4H), 2.2-1.7 (m, 9H), 1.19 (t, J=7.5 Hz, 3H) ppm. $^{13}$C-NMR (75 MHz, CDCl$_3$) δ=148.20, 145.41, 131.08, 122.82, 115.47, 114.99, 61.94, 52.60, 35.63, 34.36, 32.54, 23.14, 13.76, 13.66, 11.41 ppm. MS (m/z)=231 (100, M−N(OH)CH$_3$).

Similarly following the procedure described above, 3-acetyl-2-ethyl-4-hydroxy-6-methylphenyl acetate prepared as described in step 1, yielded:

5-Ethyl-4-(hydroxy(methyl)amino)-7-methylspiro[chroman-2,1'-cyclobutan]-6-ol.
$^1$H-NMR (300 MHz, CDCl$_3$) δ=6.55 (s, 1H), 5.25 (br., 1H), 4.28 (s, 1H), 3.63 (s, 3H), 2.56 (m, 4H), 2.2-1.7 (m, 9H), 1.29 (t, J=7.5 Hz, 3H) ppm. $^{13}$C-NMR (75 MHz, CDCl$_3$) δ=148.03, 145.59, 129.27, 125.22, 116.90, 115.04, 61.81, 52.18, 35.82, 34.59, 32.40, 19.39, 16.18, 14.74, 13.82 ppm. MS (m/z)=231 (100, M−N(OH)CH$_3$).

Example 50

4-(Ethoxyamino)-5,7-diethylspiro[chroman-2,1'-cyclobutan]-6-ol

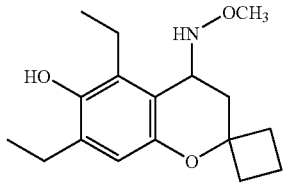

Step 1: 3-Acetyl-2,6-diethyl-4-hydroxyphenyl acetate

To a solution of potassium dichromate (20 g) in water (278 mL) was added a solution (60° C.) of 2,6-diethylaniline (15.5 mL) and conc. sulfuric acid (27.8 mL) in water (580 mL). The solution was stirred for 1 hour and then extracted with ethyl acetate. After removing the solvent, the residue was dissolved in acetone (150 mL) and refluxed with water (150 mL) and conc. sulfuric acid (5 mL) for 3 hours. The acetone was removed and the mixture was extracted with ethyl acetate. Evaporation and a quick flash column (silica gel, ethyl acetate-hexane 0% to 5%) gave a residue that was dissolved in ethyl acetate and shaken with an excess of aqueous sodium hydrosulfite. Evaporation gave 3 g of 2,6-diethylbenzene-1, 4-diol that was combined with acetyl chloride (13 mL, 14.18 g) in toluene (100 mL) and refluxed for 3 hours. The solvent and the excess reagent were removed under vacuum. The residue was heated up to 110° C. with boron trifluoride-acetic acid complex (14 mL) for 48 hours. Work up and chromatography (silica gel, hexane-ethyl acetate 2% to 10%) gave 4 g of 3-acetyl-2,6-diethyl-4-hydroxyphenyl acetate.

Step 2: 5,7-Diethyl-6-hydroxyspiro[chroman-2,1'-cyclobutan]-4-one

To a solution of 3-acetyl-2,6-diethyl-4-hydroxyphenyl acetate (4.0 g) and cyclobutanone (1.23 g) in toluene (150 mL) was added pyrrolidine (568 mg). The solution was left at room temperature for 16 hours, refluxed for two hours, and then a Dean-Stark was used to remove the water. After evaporation, the residue was dissolved in methanol and a lithium hydroxide solution (10%) was added until the solution reached a pH value greater than 9. The solution was stirred at room temperature for 2 hours and then neutralized to pH 7 using diluted hydrochloric acid. Work up and chromatography (silica gel, hexane-ethyl acetate 2% to 8%) gave 1.8 g of 5,7-diethyl-6-hydroxyspiro[chroman-2,1'-cyclobutan]-4-one. $^1$H-NMR (300 MHz, CDCl$_3$) δ=6.67 (s, 1H), 5.14 (s, 1H), 4.01 (s, 3H), 3.11 (q, J=7.4 Hz, 2H), 2.84 (s, 2H), 2.65 (q, J=7.4 Hz, 2H), 2.30-1.65 (m, 6H), 1.30-1.10 (m, 6H) ppm. $^{13}$C-NMR (75 MHz, CDCl$_3$) δ=194.3, 155.0, 146.0, 139.9, 130.6, 117.0, 115.8, 79.8, 47.7, 33.0, 23.8, 19.8, 13.9, 13.2, 12.1 ppm.

Step 3: 5,7-Diethyl-6-hydroxyspiro[chroman-2,1'-cyclobutan]-4-one O-methyl oxime A mixture of 5,7-diethyl-6-hydroxyspiro[chroman-2,1'-cyclobutan]-4-one (400 mg), methoxyamine hydrochloride (385 mg), and sodium acetate (379 mg) in methanol (10 mL) was refluxed for 16 hours. The methanol was removed by distillation and the residue was treated with sodium bicarbonate solution and ethyl acetate. The organic phase was washed with water and brine. Evaporation and chromatography (silica gel, hexane-ethyl acetate, 3.5%) gave 310 mg of (E)-5,7-diethyl-6-hydroxyspiro[chroman-2,1'-cyclobutan]-4-one O-methyl oxime. $^1$H-NMR (300 MHz, CDCl$_3$) δ=6.62 (s, 1H), 4.61 (s, 1H), 4.01 (s, 3H), 3.08 (q, J=7.5 Hz, 2H), 3.01 (s, 2H), 2.61 (q, J=7.5 Hz, 2H), 2.30-1.65 (m, 6H), 1.30-1.20 (m, 6H) ppm. $^{13}$C-NMR (75 MHz, CDCl$_3$) δ=150.5, 149.4, 146.2, 133.1, 128.0, 115.7, 115.4, 77.0, 62.0, 33.3, 33.0, 23.3, 21.2, 13.4, 12.2 ppm. MS (m/z)=290 (100, M+H$^+$).

5,7-Diethyl-6-hydroxyspiro[chroman-2,1'-cyclobutan]-4-one O-ethyl oxime

Similarly following the procedure as described above but replacing methoxyamine hydrochloride with ethoxyamine hydrochloride, the following compound was prepared. $^1$H-NMR (300 MHz, CDCl$_3$) δ=6.61 (s, 1H), 4.58 (br s, 1H), 4.25 (q, J=7.0 Hz, 2H), 3.08 (q, J=7.5 Hz, 2H), 2.58 (q, J=7.5 Hz, 2H), 2.30-1.65 (m, 6H), 1.36 (t, J=7.0 Hz, 3H), 1.30-1.20 (m, 6H) ppm. $^{13}$C-NMR (75 MHz, CDCl$_3$) δ=150.1, 149.3, 146.2, 132.9, 127.9, 115.7, 115.6, 77.1, 69.6, 33.3, 33.1, 23.3, 21.3, 15.1, 13.5, 13.4, 12.2 ppm. MS (m/z)=304 (100, M+H$^+$).

5,7-Diethyl-6-hydroxyspiro[chroman-2,1'-cyclobutan]-4-one oxime

Similarly following the procedure as described above but replacing ethoxyamine hydrochloride with hydroxyamine hydrochloride, the following compound was prepared. $^1$H-NMR (300 MHz, CDCl$_3$) δ=7.37 (s, 1H), 6.61 (s, 1H), 5.16 (d, 1H), 4.50 (br s, 1H), 3.07 (s, 2H), 3.03 (q, J=7.5 Hz, 2H), 2.61 (q, J=7.5 Hz, 2H), 2.25-1.65 (m, 6H), 1.30-1.15 (m, 6H) ppm. $^{13}$C-NMR (75 MHz, CDCl$_3$) δ=152.5, 149.4, 133.2, 127.9, 115.7, 115.2, 33.3, 32.1, 23.3, 21.1, 13.6, 13.4, 12.2 ppm. MS (m/z)=276 (100, M+H$^+$).

Step 4: 5,7-Diethyl-4-(methoxyamino)spiro[chroman-2,1'-cyclobutan]-6-ol

To a solution of 5,7-diethyl-cyclobutane(spiro-2)-6-hydroxychroman-4-one O-methyl oxime (300 mg) in tetrahydrofuran (5 mL) was slowly added borane-pyridine complex (1 mL) at 0° C. followed by hydrogen chloride (4 mL, 4.0 M solution in dioxane). The solution was allowed to warm to room temperature slowly. After 48 hours, ethyl acetate was added. The solution was washed with saturated sodium bicarbonate water solution, water and brine. Evaporation and chromatography (silica gel, hexane-ethyl acetate 1% to 5%) gave 77 mg of 5,7-diethyl4-(methoxyamino)spiro[chroman-2,1'-cyclobutan]-6-ol. $^1$H-NMR (300 MHz, CDCl$_3$) δ=6.58 (s, 1H), 5.29 (s, 1H), 4.41 (s, 1H), 4.30 (s, 1H), 3.64 (s, 3H), 2.85-2.50 (m, 6H), 2.40-1.70 (m, 6H), 1.30-1.20 (m, 6H) ppm. $^{13}$C-NMR (75 MHz, CDCl$_3$) δ=148.2, 145.2, 131.4, 129.4, 115.0, 114.8, 76.7, 61.8, 52.2, 35.9, 34.6, 32.4, 23.0, 19.4, 13.8, 13.5 ppm. MS (m/z)=245 (100, M−NHOCH$_3$).

Similarly following the procedure as described above, the following compound was prepared:

4-(Ethoxyamino)-5,7-diethylspiro[chroman-2,1'-cyclobutan]-6-ol $^1$H-NMR (300 MHz, CDCl$_3$) δ=6.58 (s, 1H), 5.16 (d, 1H), 4.38 (s, 1H), 4.27 (s, 1H), 3.84 (q, J=7.0 Hz, 2H), 2.85-2.50 (m, 6H), 2.40-1.70 (m, 6H), 1.30-1.20 (m, 9H) ppm. $^{13}$C-NMR (75 MHz, CDCl$_3$) δ=148.2, 145.2, 131.3, 129.4, 115.1, 115.0, 76.7, 69.1, 52.5, 35.8, 34.5, 32.4, 23.0, 19.5, 14.8, 14.5, 13.8, 13.5 ppm. MS (m/z)=245 (100, M+H$^+$−18).

Example 51

7-Isopropyl-4-(methoxyamino)-5-methylspiro[chroman-2,1'-cyclobutan]-6-ol

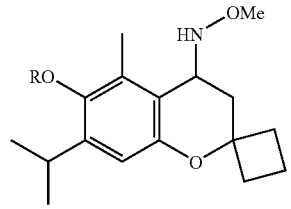

Step 1: 2-Isopropyl-6-methylbenzene-1,4-diol

To a 55° C. solution of potassium dichromate (40 g) in water (400 mL) was added a solution (60° C.) of 2-isopropyl-6-methylaniline (31 mL) and conc. sulfuric acid (65 mL) in water (400 mL). The solution was stirred for 1 hour then extracted with dichloromethane. After removing the solvent, the residue was dissolved in acetone (300 mL) and refluxed with water (150 mL) and conc. sulfuric acid (15 mL) for 3 hours. The acetone was removed and the mixture was extracted with ethyl acetate. Evaporation and a quick flash column (silica gel, hexane-dichloromethane 1:1) gave a quinine residue that was dissolved in ethyl acetate and shaken with excess of sodium hydrosulfite water solution. Evaporation gave 9.5 g of 2-Isopropyl-6-methylbenzene-1,4-diol.

Step 2: 3-Acetyl-4-hydroxy-6-isopropyl-2-methylphenyl acetate

A solution of 2-isopropyl-6-methylbenzene-1,4-diol (9.5 g), acetyl chloride (20 mL), and diisopropylethylamine (20 mL) in dichloromethane (100 mL) was stirred at room temperature for 24 hours. The solvent and excess reagent was removed under vacuum. The residue was dissolved in ethyl acetate and washed with sodium bicarbonate water solution, water and brine. After removing the solvent, the residue was heated up at 110° C. with boron trifluoride-acetic acid complex (30 mL) for 48 hours. Work up and chromatography (silica gel, hexane-ethyl acetate 2% to 10%) gave 8.5 g of 3-acetyl-4-hydroxy-6-isopropyl-2-methylphenyl acetate.

Step 3: 7-Isopropyl-5-methyl-4-oxospiro[chroman-2,1'-cyclobutane]-6-yl acetate

To a solution of 3-acetyl-4-hydroxy-6-isopropyl-2-methylphenyl acetate (8.5 g) and cyclobutanone (2.6 g) in toluene (150 mL) was added pyrrolidine (1.2 g). The solution was left at room temperature for 16 hours, refluxed for two hours, and then a Dean-Stark was used to remove the water. Work up and chromatography (silica gel, hexane-ethyl acetate 2% to 5%) gave 4 g of 7-isopropyl-5-methyl-4-oxospiro[chroman-2,1'-cyclobutane]-6-yl acetate.

Step 4: 7-Isopropyl-4-(methoxyamino)-5-methylspiro[chroman-2,1'-cyclobutan]-6-ol A mixture of 7-isopropyl-5-methyl-4-oxospiro[chroman-2,1'-cyclobutane]-6-yl acetate (1.0 g) and methoxyamine hydrochloride (1.0 g) in methanol (3 mL) was microwave heated at 60° C. for 3 min., 100° C. for 5 min., and 120° C. for 10 min. Two runs (total 2 g, 6.62 mmol) were combined. The solution was diluted with ethyl acetate and washed with water and brine. The crude product obtained (6.62 mmol) was dissolved in tetrahydrofuran (5 mL) and borane-pyridine complex (4 mL) at 0° C. followed by hydrogen chloride (8 mL, 4.0 M solution in dioxane) were added for 50 minutes. The solution was allowed to warm to room temperature slowly. After 48 hours, ethyl acetate was added. The solution was washed with saturated sodium bicarbonate water solution, water and brine. Evaporation and chromatography (silica gel, hexane-ethyl acetate 1% to 8%) gave 573 mg of 7-isopropyl-4-(methoxyamino)-5-methylspiro[chroman-2,1'-cyclobutan]-6-ol.
$^1$H-NMR (300 MHz, CDCl$_3$) δ=6.63 (s, 1H), 4.54 (s, 1H), 5.35 (s, 1H), 4.30-4.25 (m, 1H), 3.65 (s, 3H), 3.15-3.10 (m, 1H), 2.70-2.60 (m, 2H), 2.40-2.10 (m, 6H), 2.10-1.75 (m, 3H), 1.22 (d, J=6.7 Hz, 6H) ppm. $^{13}$C-NMR (75 MHz, CDCl$_3$) δ=148.4, 144.9, 136.1, 123.0, 115.2,112.4, 76.7, 61.9, 52.6, 35.7, 34.4, 32.5, 27.3, 22.7, 22.6, 13.7, 11.5 ppm. MS (m/z)=245 (100, M+H$^+$−18).

Example 52

8-(4,5-Dimethyl-1H-imidazol-2-yl)-5,7-diethylspiro[chroman-2,1'-cyclobutan]-6-ol

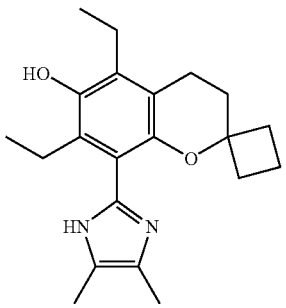

Step 1: 5,7-Diethyl-6-hydroxyspiro[chroman-2,1'-cyclobutane]-8-carbaldehyde To a solution of 5,7-diethylspiro[chroman-2,1'-cyclobutan]-6-ol (900 mg) in dichloromethane (5 mL) was added titanium tetrachloride (670 mg, 0.4 mL) and dichloromethyl methyl ether (505 mg, 0.39 mL). The solution was stirred at room temperature for 5 hours. The reaction was quenched using diluted hydrochloric acid. Work up and chromatography (silica gel, ethyl acetate in hexane 5%) gave 680 mg of 5,7-diethyl-6-hydroxyspiro[chroman-2,1'-cyclobutane]-8-carbaldehyde.

Step 2: 8-(4,5-Dimethyl-1H-imidazol-2-yl)-5,7-diethylspiro[chroman-2,1'-cyclobutan]-6-ol A solution of 5,7-diethyl-6-hydroxyspiro[chroman-2,1'-cyclobutane]-8-carbaldehyde (520 mg), 2,3-butanedione (160 mg, 0.166 mL), and ammonium acetate (1.46 g) in acetic acid (4 mL) was heated up at 180° C. for 6 minutes. The solution was diluted with ethyl acetate and washed with saturated sodium bicarbonate water solution, water and brine. Evaporation and chromatography (silica gel, methanol in dichloromethane 10% plus 10 drops of ammonium hydroxide 30% water solution) gave 350 g of 8-(4,5-dimethyl-1H-imidazol-2-yl)-5,7-diethylspiro[chroman-2,1'-cyclobutan]-6-ol.
$^1$H-NMR (300 MHz, CDCl$_3$+CD$_3$OD) δ=2.70-2.60 (m, 4H), 2.45-2.35 (m, 2H), 2.26 (s, 6H), 2.05-1.90 (m, 6H), 1.75-1.50 (m, 5H), 1.20-0.85 (m, 6H) ppm. $^{13}$C-NMR (75 MHz, CDCl$_3$+CD$_3$OD) δ=178.2, 146.8, 145.0, 139.5, 135.7, 132.2, 124.6, 118.5, 110.3, 77.1, 33.5, 31.6, 28.9, 23.2, 21.1, 19.8, 19.4, 13.1, 12.2, 8.8 ppm. MS (m/z)=273 (21), 341 (100, M+H$^+$).

Similarly the following compounds were produced:

7-(4,5-Dimethyl-1H-imidazol-2-yl)-5,8-dimethylspiro[chroman-2,1'-cyclobutan]-6-ol
$^1$H-NMR (CDCl$_3$) δ=2.75-2.71 (2H, t), 2.24 (s, 3H), 2.15 (3H, s), 2.14-2.08 (m, 8H), 2.07-2.02 (m, 4H), 2.01-1.69 (m, 2H) ppm. $^{13}$C-NMR (CDCl$_3$) δ=148.98, 144.32, 143.75, 122.22, 121.43, 117.45, 111.30, 77.52, 33.91, 29.51, 21.03, 13.69, 12.63, 11.35 ppm. MS (m/z)=313 (M+H$^+$).

7-(5,6-Dimethyl-1H-benzo[d]imidazol-2-yl)-5,8-dimethylspiro[chroman-2,1'-cyclobutan]-6-ol
$^1$H-NMR (CDCl$_3$) δ=7.39 (br s, 2H), 2.78-2.74 (t, 2H), 2.59 (s, 3H), 2.40 s, 6H), 2.33-2.14 (m, 5H), 2.11-1.91 (m, 5H), 1.78-1.75 (m, 1H) ppm. $^{13}$C-NMR (CDCl$_3$) δ=151.28, 150.20, 144.18, 132.17, 124.51, 121.97, 118.95, 111.01, 76.77, 33.91, 29.44, 21.21, 20.46, 13.97, 12.66, 11.45 ppm. MS (m/z)=363 (M+H$^+$).

Example 53

5,7-Diethyl-8-(hydroxymethyl)spiro[chroman-2,1'-cyclobutan]-6-ol

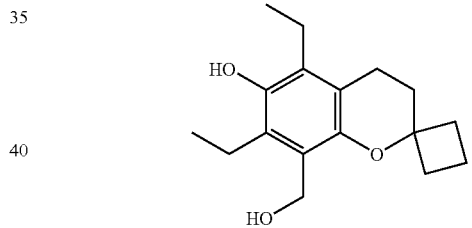

To a solution of 5,7-diethyl-6-hydroxyspiro[chroman-2,1'-cyclobutane]-8-carbaldehyde (160 mg) prepared as described herein, in methanol (10 mL) was added excess of sodium borohydride and stirred at room temperature for 2 hours. Work up and chromatography (silica gel, ethyl acetate in hexane 5% to 15%) gave 130 mg of product. $^1$H-NMR (300 MHz, CDCl$_3$) δ=4.80-4.70 (m, 3H), 2.85-2.55 (m, 7H), 2.30-1.60 (m, 8H), 1.20-1.10 (m, 6H) ppm. $^{13}$C-NMR (75 MHz, CDCl$_3$) δ=146.3, 144.7, 128.2, 127.8, 124.7, 118.1, 76.9, 58.0, 34.2, 29.3, 19.6, 15.3, 13.4, 12.6 ppm. MS (m/z)=259 (100, M−OH)$^+$.

Example 54

7-Tert-butyl-2,2-cyclobutyl-5-methylchroman-6-ol

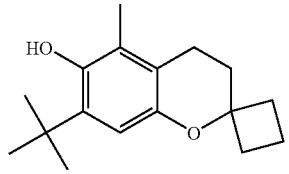

145

Step 1: 7-tert-Butylspiro[chroman-2,1'-cyclobutan]-6-ol & 8-tert-butylspiro[chroman-2,1'-cyclobutan]-6-ol To a solution of 2-Tert-butylbenzene-1,4-diol (6.25 g) in dioxane (200 mL) flushed with argon, was added borontrifluoride diethyletherate (41.2 mL). The reaction was heated in an oil bath at 100° C. and 1-vinylcyclobutanol in dioxane (20 mL) was added over 2.5 hours. The reaction was refluxed (110° C.) overnight then cooled to room temperature and concentrated under vacuum. 1:1 EtOAc/Hexane (200 mL) was added to the solution, washed with brine and dried over $Na_2SO_4$. The solvent was evaporated and the residue was purified on a silica column eluting with 1:10 EtOAc/Hexane to yield 7-tert-butylspiro[chroman-2,1'-cyclobutan]-6-ol and 8-tert-butylspiro[chroman-2,1'-cyclobutan]-6-ol (115 mg).

7-tert-Butylspiro[chroman-2,1'-cyclobutan]-6-ol $^1$H-NMR (CDCl$_3$) δ=6.77 (s, 1H), 6.39 (s, 1H), 4.63 (s, 1H), 2.73-2.68 (t, 2H), 2.33-2.29 (m, 2H), 2.12-2.04 (m, 2H), 1.98-1.94 (m, 3H), 1.70-1.68 (m, 1H), 1.40 (9H, s) ppm. $^{13}$C-NMR (CDCl$_3$) 147.55, 147.04, 135.85, 119.55, 116.46, 115.64, 77.29, 34.46, 34.15, 29.67, 29.29, 21.58, 12.49 ppm.

8-tert-Butylspiro[chroman-2,1'-cyclobutan]-6-ol $^1$H-NMR (300 MHz, CDCl$_3$) δ=6.68-6.67 (d, 1H), 6.44-6.43 (d, 1H), 5.23 (s, 1H), 2.80-2.75 (t, 2H), 2.34-2.31 (m, 2H), 2.14-2.07 (m, 2H), 1.98-1.93 (m, 3H), 1.76-1.74 (m, 1H), 1.42 (s, 9H) ppm. $^{13}$C-NMR (75 MHZ, CDCl$_3$) δ=147.78, 146.35, 139.30, 122.74, 113.06, 112.36, 77.21, 34.83, 33.99, 29.69, 29.35, 22.92, 12.85 ppm. MS (m/z)=191 [M−tBu+H$^+$].

Step 2: 7-tert-Butyl-5-(morpholinomethyl)spiro[chroman-2,1'-cyclobutan]-6-ol

To a suspension of 7-tert-butylspiro[chroman-2,1'-cyclobutan]-6-ol (2.8 g) in dioxane (5 mL) was added an aqueous formaldehyde solution (3.7 mL, 37% in H$_2$O) followed by morpholine (4.0 mL). The reaction was stirred under argon at 90° C. for 2.5 hours, cooled in an ice bath with stirring to precipitate product which was filtered off as a white solid, washed with H$_2$0, and air dried to give 7-tert-butyl-5-(morpholinomethyl)spiro[chroman-2,1'-cyclobutan]-6-ol (2.45 g). $^1$H-NMR (300 MHz, CDCl$_3$) δ=10.74 (s, 1H), 6.73 (s, 1H), 3.77 (br s, 4H), 3.68 (s, 2H), 2.67-2.63 (t, 2H), 2.59 (br s, 4H), 2.29-2.24 (m, 2H), 2.08-1.94 (m, 5H), 1.70-1.65 (m, 1H), 1.40 (s, 9H) ppm. $^{13}$C-NMR (75 MHz, CDCl$_3$) δ=150.32, 145.73, 136.19, 118.32, 117.55, 115.00, 76.22, 66.81, 56.78, 52.69, 34.60, 33.91, 29.53, 20.01, 12.46 ppm. MS (m/z)=346 (M+H$^+$), 259 [M−morpholine+H$^+$].

Step 3: 7-tert-Butyl-2,2-cyclobutyl-5-methylchroman-6-ol

To a suspension of 7-Tert-butyl-5-(morpholinomethyl) spiro[chroman-2,1'-cyclobutan]-6-ol (2.4 g) in 2-butanol (20 mL), was added sodium cyanoborohydride (1.75 g) and the reaction was stirred under argon at 105° C. for 5 hours, then overnight at 110° C. The solution was concentrated under vacuum, water (10 mL) was added, and the precipitate was filtered off, washed with H$_2$O and air dried to yield 7-tert-butyl-2,2-cyclobutyl-5-methylchroman-6-ol (1.1 g) as an off-white solid. $^1$H-NMR (300 MHz, CDCl$_3$) δ=6.70 (s, 1H), 4.44 (s, 1H), 2.70-2.66 (t, 2H), 2.36-2.15 (m, 2H), 2.14-1.80 (m, 8H), 1.79-1.66 (m, 1H), 1.14 (s, 9H) ppm. $^{13}$C-NMR (75 MHz, CDCl$_3$) δ=146.98, 145.90, 135.44, 121.94, 118.51, 113.20, 76.38, 34.46, 33.93, 29.90, 29.45, 20.52, 12.49, 11.49 ppm. MS (m/z)=261 (M+H$^+$), 205 (M−tBu+H$^+$).

146

Example 55

5-Ethyl-7-isopropylspiro[chroman-2,1'-cyclobutane]-4,6-diol

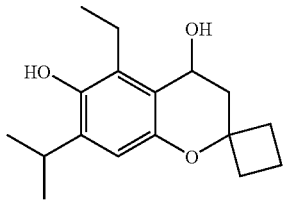

Step 1: 2-Ethyl-6-isopropylphenol

To a solution of isopropyl phenol (10 g) in 200 mL of chlorobenzene was added butyllithium hexane solution (5.9 mL, 2.5 M in hexane) and SnCl$_4$ (0.88 mL) at 0° C. The mixture was stirred at room temperature for 15 min, followed by addition of 2,2,2-trifluoroethanol (0.53 mL) and trimethylsilylethyne (11.5 mL). The mixture was heated at 110° C. for 3 h, THF (120 mL) and KF (4.7 g) were added, and the mixture was stirred for another 5 h. Water (80 mL) was then added and the mixture was stirred for another hour. After separation of the layers, the organic layer was washed with water (2×100 mL) and dried over Na$_2$SO$_4$ and concentrated to about 20 to 25 mL. The crude product including remaining chlorobenzene was chromatographed. The fraction containing 2-isopropyl-6-vinylphenol was collected and concentrated to about 20 mL (but not completely dried). It was diluted with EtOH (50 mL) and concentrated again to about 20 mL. This process was repeated 3 times to reduce the amount of chlorobenzene. A flask containing the EtOH solution (100 mL) of this vinyl phenol was charged with hydrogen in the presence of Pd/C (300 mg) and hydrogenated using a balloon for 5 h. The solid was removed and the filtrate was concentrated to afford 2-ethyl-6-isopropylphenol as a clear oil (8.5 g).

$^1$H-NMR (300 MHz, CDCl$_3$,) δ=7.11 (m, 1H), 7.04 (m, 1H), 6.92 (t, J=7.5 Hz, 1H), 4.82 9s, 1H), 3.22 (7, J=6.8 Hz, 1H), 2.67 (q, J=7.6 Hz, 2H), 1.32-1.27 (m, 9H) ppm.

Step 2: 2-Ethyl-6-isopropyl-1,4-phenylene diacetate

To a solution of K$_2$S$_2$O$_8$ (8.2 g) in 80 mL of water, was added at once a solution of the above 2-ethyl-6-isopropylphenol (2 g, 12.2 mmol in 25 mL 5% NaOH solution). The mixture was stirred for 3 h and extracted with hexane (3×60 mL). The organic extract was stirred with Na$_2$S$_2$SO$_4$ solution (8.5 g, in 100 mL water) for one hour and the layers were separated. The organic layer was dried over Na$_2$S$_2$O$_4$ and concentrated and dried under high vacuum to give 2-ethyl-6-isopropylbenzene-1,4-diol. To a solution of the crude 2-ethyl-6-isopropylbenzene-1,4-diol in dichloromethane (50 mL) was added acetyl chloride (2.9 g, 36 mmol) and then triethylamine (6 g, 60 mmol) slowly at 0° C. The mixture was stirred at room temperature for 2 h and diluted with hexane/EtOAc (4:1). The mixture was filtered and the filtrate was washed with water (3×80 mL) and dried over Na$_2$SO$_4$ and concentrated. The crude product was purified to afford 2-ethyl-6-isopropyl-1,4-phenylene diacetate as a yellow oil (750 mg).

$^1$H-NMR (300 MHz, CDCl$_3$) δ=6.90 (d, J=2.8 Hz, 1H), 6.87 (d, J=2.8 Hz, 1H), 2.94 (7, J=6.8 Hz, 1 H), 2.51 (q, J=7.5 Hz, 2H), 2.37 (s, 3H), 2.30 (s, 3H), 1.24-1.19 (m, 9H) ppm; MS (m/z)=265 (M+H$^+$, 100).

Step 3: 5Ethyl-7-isopropyl-4-oxospiro[chroman-2,1'-cyclobutane]-6-yl acetate

A solution of the above diacetate (750 mg) in 3 mL of $BF_3.AcOH$ was heated at 105° C. for two days and quenched onto ice. The sticky solid was collected and dissolved in EtOAc/hexane (1:1, 30 mL) and washed with water and $Na_2HPO_4$. The organic solution was dried over $Na_2SO_4$ and concentrated. The crude product was purified by chromatography to afford a mixture of two isomers 3-acetyl-2-ethyl-4-hydroxy-6-isopropylphenyl acetate and 3-acetyl-6-ethyl-4-hydroxy-2-isopropylphenyl acetate in a ratio of 2:1 (270 mg MS (m/z)=265 (M+H+, 100).

To a solution of the above material (270 mg) in 5 ml toluene was added cyclobutanone (78.5 mg) and pyrrolidine (36 mg). The mixture was let sit for overnight and heated to reflux for 1 h under azotropic conditions. After cooling to room temperature, 2 M HCl (10 mL) was added and stirred for 2 h at room temperature. The mixture was extracted with EtOAc/hexane (1:1, 30 mL) and the organic phase was dried over $Na_2SO_4$ and concentrated. The crude product was chromatographed to afford the desired 5-ethyl-7-isopropyl-4-oxospiro[chroman-2,1'-cyclobutane]-6-yl acetate as a light yellow solid (53 mg) $^1$H-NMR (300 MHz, $CDCl_3$) δ=6.77 (s, 1H), 3.11 (m, 1H), 2.90-2.68 (m, 4H), 2.37 (s, 3H), 2.36-2.28 (m, 2H), 2.19 (m, 2H), 1.91 (m, 1H), 1.72 (m, 1H), 1.21 (d, J=5.6 hz, 6H), 1.12 (t, J=7.4 Hz, 3H) ppm; MS (m/z)=317 (M+H+, 100).

Step 4: 5-Ethyl-7-isopropylspiro[chroman-2,1'-cyclobutane]-4,6-diol

To a solution of 5-ethyl-7-isopropyl-4-oxospiro[chroman-2,1'-cyclobutane]-6-yl acetate (53 mg) in 5 mL of THF was added $LiAlH_4$ (65 mg) in 3 portions at room temperature. The mixture was stirred for 2 h and quenched by pouring onto ice. The mixture was extracted with EtOAc (3×10 mL) and the organic extract was dried over $Na_2SO_4$ and concentrated. The crude product was purified by chromatography to afford 5-ethyl-7-isopropylspiro[chroman-2,1'-cyclobutane]-4,6-diol as an off-white solid (29 mg, 63%).

$^1$H-NMR (300 MHz, $CDCl_3$) δ=6.66 (s, 1H), 4.92 (s, 1H), 4.53 (s, 1H), 3.15 (7, J=6.8 Hz, 1H), 2.86 (m, 1h), 2.73 (m, 1H), 2.65 (m, 1H), 2.45-2.38 (m, 2H), 2.17 (m, 2H), 2.03 (m, 2H), 1.80 (m, 1H), 1.30-1.22 (m, 9H) ppm; $^{13}$C-NMR (75 MHz, $CDCl_3$) δ=146.9, 144.8, 136.7, 129.2, 119.3, 112.7, 76.1, 62.6, 38.7, 35.2, 33.2, 27.2, 22.6, 19.7, 14.6, 13.3 ppm; MS (m/z)=259 (M–OH−, 100).

Example 56

1'-(4-Chlorophenyl)-5',7',8'-trimethyl-1',4'-dihydro-2'H-spiro[cyclobutane-1,3'-quinolin]-6'-ol

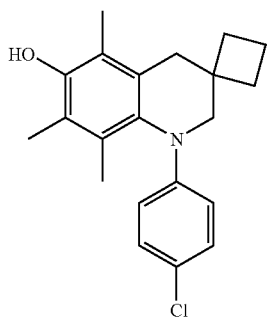

Step 1: Ethyl 1-formylcyclobutanecarboxylate

Diethyl cyclobutane-1,1-dicarboxylate (7.17 mL) was added to a THF (150 mL) suspension of $LiAH(OtBu)_3$ (22.08 g) at room temperature, and the suspension was refluxed for 7 h. The THF was stripped off and the mixture was quenched with water, neutralized with HCl (3 M) and extracted with dichloromethane and ethylacetate. The combined organic phases were washed with brine, dried and evaporated. The crude residue was put on a column and eluted with DCM : EtOAc; 5:1 to give ethyl 1-(hydroxymethyl)-cyclobutanecarboxylate (4.08 g) as a clear oil. $^1$H-NMR (300 MHz, $CDCl_3$), δ=4.3372-4.1188 (q, 2H); 3.9337-3.7479 (d, 2H); 2.5485-2.322 (m, 3H); 2.1117-1.9015 (m, 4H); 1.3963-1.2174 (t, 3H) ppm.

To a dichloromethane (250 mL) solution of ethyl 1-(hydroxymethyl)cyclobutanecarboxylate (12 g) at room temperature, was added a mixture of pyridinium chlorochromate (PCC) (24.5 g) and 20 g $SiO_2$. After 17.5 h, the organic solvent was decanted, and more dichloromethane and ethylacetate were added to wash the $SiO_2$. The combined organic phases were concentrated, the residue and the $SiO_2$ used in the reaction were loaded onto a column and eluted with EtOAc/DCM, 0-17%, to afford ethyl 1-formylcyclobutanecarboxylate (10.2 g) as a clear oil $^1$H-NMR (300 MHz, $CDCl_3$): δ=9.76 (s, 1H); 4.32-4.0751 (d, 2H); 2.7145-2.2827 (t, 4H); 2.1954-1.6632 (m, 2H); 1.4254-1.0664(t, 3H) ppm. $^{13}$C-NMR (75 MHz, $CDCl_3$) δ=196.96, 171.7, 61.54, 57.2, 25.95, 15.64, 14.17 ppm.

Step 2: 4-Methoxy-2,3,5-trimethylaniline 2,3,6-trimethyl phenol 1 (19.1 g) was dissolved in acetic acid (190 mL). This solution was added to an acetic acid solution of $HNO_3$ (150 mL, 1M) at room temperature in 4.5 hours. After another 0.5 hour, the mixture was evaporated, and the residue was taken up by EtOAc (350 mL). This solution was washed with water (150 mL×2), and brine (150 mL), dried and evaporated. Elution on a silica column (Hexane: EtOAc, 5:1-5:2), gave 2,3,6-trimethyl-4-nitrophenol (7.56 g), as a yellow solid. $^1$H-NMR, (300 MHz, $CDCl_3$) δ=7.61 6, (br s, 1H), 2.432 (s, 3H), 2.275 (s, 3H), 2.242 (s, 3H) ppm.

2,3,6-Trimethyl-4-nitrophenol (2.2 g) and $K_2CO_3$ (4.0 g) were added to a flask, to which was slowly added acetone (35 mL), followed by dimethylsulfate (2.09 mL) at room temperature. The suspension was then refluxed for 2.5 hours. After it cooled down, 20 mL water was added and stirred for 15 min. The mixture was taken up by water and ethylacetate and the organic phase was washed with brine, dried and evaporated to give 2-methoxy-1,3,4-trimethyl-5-nitrobenzene as an oil (2.3 g, which still contained 5% dimethylsulfate). $^1$H-NMR, (300 MHz, $CDCl_3$) δ=7.532, (s, 1H), 3.723, (s, 3H), 2.373, (s, 3H), 2.307 (s, 3H), 2.273 (s, 3H) ppm.

2-Methoxy-1,3,4-trimethyl-5-nitrobenzene (2.3 g) from the step above, was dissolved in 250 mL ethylacetate, to which Pd/C (0.6 g) was added. House vacuum was applied to it and then it was flushed with hydrogen. This cycle was repeated three times. The suspension was kept at room temperature with a hydrogen balloon overnight. The suspension was then filtered through a pad of Celite® and evaporated to dryness. Elution on a silicagel column (DCM: EtOAc, 10:1-5:1) gave 4-methoxy-2,3,5-trimethylaniline as a solid with slight pink color (0.9 g). $^1$H-NMR (300 MHz, $CDCl_3$), δ=6.4 (s, 1H), 3.631 (s, 3H), 3.392 (br s, 2H), 2.202 (s, 6H), 2.046 (s, 3H) ppm. $^{13}$C-NMR (75 MHz, $CDCl_3$) δ=149.73, 140.35, 129.85, 128.36, 119.92, 115.17, 60.33, 16.02, 13.24, 12.83 ppm.

Step 3: 6'-Methoxy-5',7',8'-trimethyl-1'H-spiro[cyclobutane-1,3'-quinolin]-4'(2'H)-one To a solution of 4-methoxy-2,3,5-trimethylaniline (400 mg) in dichloromethane (24 mL) was added ethyl 1-formyl-cyclobutanecarboxylate, prepared as described in Step 1 (377.8 µL). Then NaBH(OAc)$_3$ (771.4 mg) and acetic acid (152.2 µL) were added sequentially. After 3.5 h, water was added. The two layers were separated and the aqueous layer was extracted with more dichloromethane. The combined organic phases were washed with brine, dried and evaporated. Elution of the residue on a silica column (EtOAc/DCM, 0-5%) gave ethyl 1-((4-methoxy-2,3,5-trimethylphenylamino)methyl)-cyclobutanecarboxylate (400 mg) as an oil. $^1$H-NMR, (300 MHz, CDCl$_3$) δ=6.37 (s,1H), 4.262-3.974 (q, 2H), 3.63 (s, 3H), 3.745-3.474 (br s, 1H), 3.41 (s, 2H), 2.693-2.339 (m, 2H), 2.27 (s, 3H), 2.21, (s, 3H), 2.14-1.818, (m, 4H), 2.02, (s, 3H), 1.333-1.174 (t, 3H) ppm., $^{13}$C-NMR, (75 MHz, CDCl$_3$) δ=176.51, 142.52, 129.68, 128.09, 119.78, 110.29, 60.85, 60.37, 50.67, 47.2, 28.43, 16.38, 15.9, 14.3, 12.94, 12.85 ppm.

To a solution of ethyl 1-((4-methoxy-2,3,5-trimethylpheny-lamino)methyl)cyclobutane-carboxylate (500 mg) in ethanol (10 mL), was added a KOH solution (2.5 mL). The mixture was left overnight and the ethanol was evaporated. After addition of water, the mixture was acidified with HCl (3 M) to reach a pH of 1-2. The aqueous phase was extracted with ethylacetate and the organic phase was dried with Na$_2$SO$_4$ and evaporated to give 1-((4-methoxy-2,3,5-trimethylphenyl-amino)-methyl)cyclobutane carboxylic acid (440 mg ) as a foam, which was used for next step. 10 mL of the foam was mixed with toluene (10 mL) and phosphoric acid (1 mL). The mixture was heated up in an oil bath, and after 30 min, the mixture was cooled and quenched with water. Dichloromethane was used to extract the aqueous phase several times. The organic phase was then combined, dried and evaporated to give a solid, which was passed through a column (Hexane: EtOAc; 5:2-5:4) to give 6'-methoxy-5',7',8'-trimethyl-1'H-spiro[cyclobutane-1,3'-quinolin]-4'(2'H)-one as a yellow solid. $^1$H-NMR, (300 MHz, CDCl$_3$) δ=4.18 (s, 1H), 3.6 (s, 3H), 3.53(s, 2H), 2.58 (s, 3H), 2.515-2.322 (m, 2H), 2.25 (s, 3H), 2.05 (s, 3H), 2.022-1.769 (m, 4H). ppm. $^{13}$C-NMR, (75 MHz, CDCl$_3$) δ=197.89, 147.22, 136.52, 131.29, 118.77, 114.58, 60.48, 50.64, 47.26, 25.89, 14.9, 14.48, 13.78, 12.91 ppm. MS: m/z 260.2 (M+H$^+$)

Step 4: 1'-(4-chlorophenyl)-6'-methoxy-5',7',8'-trimethyl-1'H-spiro[cyclobutane-1,3'-quinolin]-4'(2'H)-one 6'-Methoxy-5',7',8'-trimethyl-1'H-spiro[cyclobutane-1,3'-quinolin]-4'(2'H)-one (146.7 mg), palladium (II) acetate, 1-chloro-4-iodobenzene (202.5 mg) and NaO-t-Bu (81.6 mg) were added to an oven dried tube. The flask was capped and the air evacuated with a house vacuum line, then refilled with nitrogen. This nitrogen flushing was repeated 3 times. Toluene (1.5 mL) was then added and the suspension was stirred for 15 min at room temperature before ter-butylphosphine (1.7 mL, 0.056 mmol, 33.7 mM in toluene) was added. The mixture was then heated up in oil bath (120° C.) for 2.5 h. It was then quenched with water and extracted with ethylacetate. The organic phase was washed with brine, dried and evaporated to give an oil, which was passed through a silica column (EtOAc/Hexane: 0-10%) to give 1'-(4-chlorophenyl)-6'-methoxy-5',7',8'-trimethyl-1'H-spiro[cyclobutane-1,3'-quinolin]-4'(2'H)-one (137.6 mg) as a solid. $^1$H-NMR (300 MHz, CDCl$_3$) δ=7.257-7.026 (d, 2H), 6.904-6.553 (d, 2H), 4.09 (s, 2H), 3.71 (s, 3H), 2.62 (s, 3H), 2.454-2.276 (m, 2H), 2.24 (s, 3H), 2.125-1.836 (m, 2H), 1.81 (s, 3H), 1.746-1.554 (m, 2H) ppm. $^{13}$CNMR (75 MHz, CDCl$_3$) δ=201.17, 148.99, 144.28, 137.51, 131.65, 129.92, 129.28, 125.56, 125.37, 121.03, 60.28, 60.04, 50.71, 9.71, 15.57, 15.44, 14.63, 13.92 ppm.

Step 5: 1'-(4-Chlorophenyl)-6'-methoxy-5',7',8'-trimethyl-2',4'-dihydro-1'H-spiro[cyclobutane-1,3'-quinolin]-4'-ol To a solution of 1'-(4-chlorophenyl)-6'-methoxy-5',7',8'-trimethyl-1'H-spiro[cyclobutane-1,3'-quinolin]-4'(2'H)-one (80 mg) in THF (6 mL) and methanol (1.5 mL) cooled in ice bath, was added NaBH$_4$ (81.7 mg). After 1.5 h, 5 mL acetone was added to the solution and the mixture was evaporated to yield a thick oil, which was taken up by EtOAc. The organic phase was then washed with brine, dried and evaporated to give 1'-(4-chlorophenyl)-6'-methoxy-5',7',8'-trimethyl-2',4'-dihydro-1'H-spiro[cyclobutane-1,3'-quinolin]-4'-ol (64.3 mg) $^1$H-NMR (300 MHz, CDCl$_3$) δ=7.21-6.977 (d, 2H); 6.67 (br s, 2H); 4.745 (s, 1H); 3.949-3.753 (d, 1H); 3.687 (s, 3H); 3.629-3.54 (d, 1H); 2.426 (s, 3H); 2.312-2.174 (m, 1H); 2.147 (s, 3H); 1.967-1.737 (m, 3H); 1.705 (s, 3H); 1.672-1.489 (m, 2H) ppm.

Step 6: 1'-(4-Chlorophenyl)-6'-methoxy-5',7',8'-trimethyl-2,4'-dihydro-1'H-spiro[cyclobutane-1,3'-quinoline]

To a 2 mL mixture of acetic acid and trifluoroacetic acid (1:1, v/v) cooled in ice bath, was added NaBH$_4$ (71 mg) in portions, followed with 1'-(4-chlorophenyl)-6'-methoxy-5',7',8'-trimethyl-2',4'-dihydro-1'H-spiro[cyclobutane-1,3'-quinolin]-4'-ol (65 mg) in THF (0.5 mL). After 20 min, the mixture was taken up by ethylacetate and water. After separation of the two phases, the aqueous phase was extracted with more ethylacetate, and the combined organic phases were washed with brine, dried and evaporated to yield a thick oil, which was passed through a silica column (EtOAc/Hexane: 0-5% in 30 min) to give 1'-(4-chlorophenyl)-6'-methoxy-5',7',8'-trimethyl-2',4'-dihydro-1'H-spiro[cyclobutane-1,3'-quinoline] (34.6 mg). $^1$H-NMR (300 MHz, CDCl$_3$) δ=7.2-6.933 (d, 2H); 6.783-6.428 (d, 2H); 3.68 (s, 3H); 3.64 (s, 2H); 2.72 (s, 2H); 2.21 (s, 3H); 2.16 (s, 3H); 1.75 (s, 3H); 1.988-1.542 (m, 6H) ppm. $^{13}$C-NMR (75 MHz, CDCl$_3$) δ=152.86, 150.26, 136.97, 129.12, 128.7, 128.11, 128.03, 126.65, 123.67, 119.89, 60.78, 60.39, 40.19, 38.65, 32.78, 15.92, 15.51, 13.02, 12.02 ppm.

Step 7: 1'-(4-Chlorophenyl)-5',7',8'-trimethyl-2,4'-dihydro-1'H-spiro[cyclobutane-1,3'-quinolin]-6'-ol 1'-(4-chlorophenyl)-6'-methoxy-5',7',8'-trimethyl-2',4'-dihydro-1'H-spiro[cyclobutane-1,3'-quinoline] (200 mg) was dissolved in dichloromethane (15 mL) cooled in a bath (−78° C.). To this solution was added BBr$_3$ (4 mL, 1 M in dichloromethane). The temperature was then raised to 10° C. After another 1.5 h, the mixture was quenched with 3 mL saturated NaHCO$_3$, and extracted with ethylacetate. The organic phase was washed with brine, dried and evaporated to an oil, which was passed through a silica column (EtOAc in Hexane: 5-16% in 30 min) to give 1'-(4-chlorophenyl)-5',7',8'-trimethyl-2',4'-dihydro-1'H-spiro[cyclobutane-1,3'-quinolin]-6'-ol (172 mg) as an off-while oil. $^1$H-NMR (300 MHz, CDCl$_3$): δ=7.18-6.94 (d, 2H), 6.74-6.54 (d, 2H), 4.54 (s, 1H), 3.63 (s, 2H), 2.72 (s, 2H), 2.19 (s, 3H), 2.13 (s, 3H), 1.79 (s, 3H), 1.97-1.54 (m, 6H) ppm. $^{13}$C-NMR (75 MHz, CDCl$_3$) δ=150.31, 148.19, 134.19, 129.01, 128.71, 128.23, 123.3, 120.69, 119.34, 119.25, 60.83, 40.61, 38.49, 32.91, 15.82, 15.56, 12.6, 11.57 ppm.

Example 57

6'-Methoxy-7',8'-dimethyl-2',4'-dihydro-1'H-spiro[cyclobutane-1,3'-quinoline]

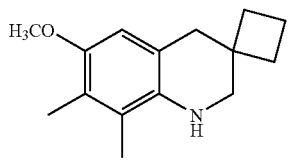

Step 1: 4-Methoxy-2,3-dimethylaniline

A Parr hydrogenation bottle was flushed with nitrogen, to which was added Pd/C (0.5 g, 10%), and a solution of 1-methoxy-2,3-dimethyl-4-nitrobenzene (10 g) in EtOAc (150 mL). The mixture was shaken under 60 psi of hydrogen for 3 days. Celite® was added and the mixture was filtered through a Celite® pad. The cake was washed with extra EtOAc. The combined organic phase was dried and evaporated to give 4-methoxy-2,3-dimethylaniline (7.2 g) as a brown solid, which was used further without further purification. $^1$H-NMR (300 MHz, CDCl$_3$), δ=6.65-6.58 (d, J=8.66 Hz, 1H); 6.58-6.49 (d, 1H); 3.75 (s, 3H); 2.35 (s, 2H); 2.17 (s, 3H); 2.10 (s, 3H) ppm. $^{13}$C-NMR (75 MHz, CDCl$_3$) δ=151.23, 138.29, 126.07, 123.4, 112.95, 109.48, 56.48, 13.51, 12.28 ppm.

Step 2: 6'-Methoxy-7',8'-dimethyl-1'H-spiro[cyclobutane-1,3'-quinolin]-4'(2'H)-one To a solution of 4-methoxy-2,3-dimethylaniline (6 g) in dichloromethane (220 mL) was added ethyl 1-formylcyclobutanecarboxylate, prepared as in Example 56 Step 1, (5.64 g) followed with NaBH(OAc)$_3$ (10.62 g). After three hours at room temperature, the solution was quenched with water, separated and the aqueous phase was extracted with more dichloromethane. The combined organic phases were washed with brine; dried and passed through a silica column (Hexane: EtOAc; 10:2-10:3) to ethyl 1-((4-methoxy-2,3-dimethylphenylamino)methyl)cyclobutanecarboxylate (9.3 g) as an oil. $^1$H-NMR (300 MHz, CDCl$_3$): δ=6.75-6.68 (d, 1H), 6.57-6.42 (d, 1H), 4.4-4.1 (q, 2H), 3.78 (s, 3H), 3.7-3.5 (s, 1H), 3.42 (s, 2H), 2.7-2.5 (m, 2H), 2.21 (s, 3H), 2.06 (s, 3H), 2.1-1.8 (m, 4H), 1.4-1.1 (t, 3H) ppm. $^{13}$C-NMR (75 MHz, CDCl$_3$) δ=176.61, 150.58, 140.81, 126.07, 123.42, 109.27, 108.31, 60.89, 56.54, 51.2, 47.39, 28.51, 16, 14.37, 13.15, 12.41 ppm.

To a solution of ethyl 1-((4-methoxy-2,3-dimethylphenylamino)methyl)-cyclobutanecarboxylate (19 g) in ethanol (120 mL) was added KOH (9 g in 50 mL of water). The solution was then heated up in an 85° C. bath for 2 hours. The solution was then evaporated to dryness, HCl (3 M) was then added while the flask cooled in ice bath to reach a pH of less than 1, and the solution was extracted with ethylacetate. The combined organic phases were then dried and evaporated to give 1-((4-methoxy-2,3-dimethylphenylamino)methyl)cyclobutanecarboxylic acid (21.0 g), which was used in the next step without further purification. $^1$H-NMR (300 MHz, CDCl$_3$) δ=8.78-7.95 (s, 1H), 6.81-6.74 (d, 1H), 6.73-6.66 (d, 1H), 3.77 (s, 3H), 3.44 (s, 2H), 2.68-2.41 (m, 2H), 2.17 (s, 3H); 2.14 (s, 3H), 2.09-1.93 (m, 4H) ppm. $^{13}$C-NMR (75 MHz, CDCl$_3$) δ=181.21, 15.251, 137.65, 126.32, 125.78, 112.31, 108.99, 56.21, 52.84, 46.64, 28.46, 15.93, 13.36, 12.27 ppm.

A solution of 1-((4-methoxy-2,3-dimethylphenylamino)methyl)cyclobutanecarboxylic acid (19 g in toluene (100 mL) was added into phosphoric acid (25 mL). The mixture was heated up in a 116° C. bath and stirred for an hour. The mixture was then cooled down, quenched with ice, and extracted with ethylacetate. The organic phase was then dried and evaporated to dryness. The crude product was passed through a column (Hexane: EtOAc; 10:4) to give 6'-methoxy-7',8'-dimethyl-1'H-spiro[cyclobutane-1,3'-quinolin]-4'(2'H)-one (15 g) as a yellow solid. $^1$H-NMR (300 MHz, CDCl$_3$): δ=7.26 (s, 1H), 4.11 (s, 1H), 3.79 (s, 3H), 3.54 (s, 2H), 2.59-2.29 (m, 2H), 2.38 (3H), 2.34 (3H), 2.06-1.82 (4H) ppm. $^{13}$C-NMR (75 MHz, CDCl$_3$) δ=196.22, 150.49, 144.93, 133.95, 122.36, 115.05, 104.75, 55.77, 51.45, 46.5, 25.95, 15.06, 12.98, 12.77 ppm.

Step 3: 6'-Methoxy-7',8'-dimethyl-2',4'-dihydro-1'H-spiro[cyclobutane-1,3'-quinoline]

To a cold solution of 6'-methoxy-7',8'-dimethyl-1'H-spiro[cyclobutane-1,3'-quinolin]-4'(2'H)-one (2 g) in a mixture of 13 mL of THF and 5 mL of CH$_3$OH cooled in ice bath, was added NaBH$_4$ (2.4 g). After 2 hours, the mixture was quenched with ice, evaporated to dryness to give 6'-methoxy-7',8'-dimethyl-2',4'-dihydro-1'H-spiro[cyclobutane-1,3'-quinolin]-4'-ol as a crude mixture (11 g). NaBH$_4$ (3 g) was added in portions to a mixture of trifluoroacetic acid and acetic acid (25 mL, v/v:1/1) cooled in ice bath, and to this mixture was added the above obtained mixture of 6'-methoxy-7',8'-dimethyl-2',4'-dihydro-1'H-spiro[cyclobutane-1,3'-quinolin]-4'-ol dissolved in 10 mL of THF. After 15 min, the mixture was quenched with ice, extracted with dichloromethane, and washed with brine. The organic phase was then washed with NaOH (2 M) and brine, dried, evaporated to dryness and passed through a silica column (Hexane: EtOAc; 10:1) to give 6'-methoxy-7',8'-dimethyl-2',4'-dihydro-1'H-spiro[cyclobutane-1,3'-quinoline] (1.3 g) as a liquid with slightly yellow color. $^1$H-NMR (300 MHz, CDCl$_3$) δ=6.44071 (s, 1H), 3.74 (s, 3H), 3.59-3.24 (s, 1H), 3.18 (s, 2H), 2.75 (s, 2H), 2.13 (s, 3H), 2.03 (s, 3H), 2.01-1.73 (m, 6H) ppm. $^{13}$C-NMR (75 MHz, CDCl$_3$) δ=149.88, 136.21, 123.51, 131.91, 118.09, 110.83, 56.51, 51.91, 40.82, 36.09, 30.84, 15.25, 13.07, and 12.03 ppm.

Example 58

1'-Ethyl-7',8'-dimethyl-2',4'-dihydro-1'H-spiro[cyclobutane-1,3'-quinolin]-6'-ol

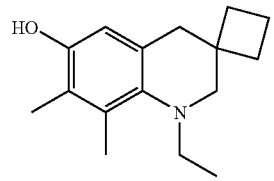

6'-Methoxy-7',8'-dimethyl-2',4'-dihydro-1'H-spiro[cyclobutane-1,3'-quinoline (220 mg), prepared as described in Example 57, was mixed with acetic anhydride (2 mL) and NaOAc (100 mg). The suspension was heated in a 110° C. bath for 4 hours. After it was cooled down it was quenched with water, extracted with EtOAc, washed with brine, dried and evaporated. The crude product was passed through a column (DCM: EtOAc; 5:1) to 1-(6'-methoxy-7',8'-dimethyl-2',4'-dihydro-1'H-spiro[cyclobutane-1,3'-quinoline]-1'-yl) ethanone (260 mg) as oil. The above formed mixture was then dissolved in 5 mL THF and treated with LiAlH$_4$ (100 mg).

After 1 hour under reflux, the reaction mixture was quenched with ice and extracted with EtOAc. The organic phase was washed with brine, dried and evaporated to yield an oil, which was then passed through a silica column (Hexane: EtOAc; 10:0.5-10:1) to give 1'-ethyl-6'-methoxy-7',8'-dimethyl-2',4'-dihydro-1'H-spiro[cyclobutane-1,3'-quinoline] (130 mg) as an oil. $^1$H-NMR (300 MHz, CDCl$_3$) δ=6.40 (s, 1H), 3.76 (s, 3H), 3.05 (s, 2H), 2.97-2.83 (q, 2H), 2.79 (s, 2H), 2.12 (s, 3H), 2.11 (s, 3H), 2.05-1.84 (m, 4H), 1.84-1.68 (m, 2H), 1.26-1.12 (t, 3H) ppm. $^{13}$C-NMR (75 MHz, CDCl$_3$) δ=151.92, 141.03, 130.36, 125.8, 124.18, 108.92, 58.55, 55.76, 51.09, 41.52, 38.39, 32.61, 16.18, 16, 13.52, 12.35 ppm.

To a solution of 1'-ethyl-6'-methoxy-7',8'-dimethyl-2',4'-dihydro-1'H-spiro[cyclobutane-1,3'-quinoline] (100 mg) in 2 mL chloroform cooled in ice bath (10° C.) was added BBr$_3$ (2 mL, 1 M). After 4 hours, ice was added to quench the reaction. After separation of the two layers, dichloromethane was used to extract the aqueous phase. The combined organic phases were then washed with brine, dried and evaporated to give a crude oil which was then passed through a column (EtOAc: Hexane; 2-16%) to give 1'-ethyl-7',8'-dimethyl-2',4'-dihydro-1'H-spiro[cyclobutane-1,3'-quinolin]-6'-ol (35.9 mg). $^1$H-NMR (300 MHz, CDCl$_3$): δ=6.37 (s, 1H), 3.04 (s, 2H), 2.95-2.65 (q, 2H), 2.74 (s, 2H), 2.12 (s, 3H), 2.1 (s, 3H), 2.05-1.85 (m, 4H), 1.84-1.64 (m, 2H), 1.3-1.1 (t, 3H) ppm. $^{13}$C-NMR (75 MHz, CDCl$_3$) δ=152.88, 143.52, 133.97, 130.4, 126.13, 116.74, 62.54, 55.07, 44.81, 42.13, 36.29, 19.77, 19.31, 16.6, and 15.79 ppm. MS: (m/z): 246.2 (M+H$^+$)

6'-Hydroxy-7',8'-dimethyl-2',4'-dihydro-1'H-spiro[cyclobutane-1,3'-quinoline]-1'-carbaldehyde 1-(6'-methoxy-7',8'-dimethyl-2',4'-dihydro-1'H-spiro[cyclobutane-1,3'-quinoline]-1'-yl)ethanone (100 mg) was dissolved in dichloromethane (2 mL), to which solution was added BBr$_3$ (19.3 mL) at 10° C. After 1.5 h, it was quenched with water, extracted with dichloromethane, and the organic layers were washed with brine, dried and evaporated to give an oil. Elution on a column (dichloromethane:methanol=10: 0.2) gave 6'-hydroxy-7',8'-dimethyl-2',4'-dihydro-1'H-spiro[cyclobutane-1,3'-quinoline]-1'-carbaldehyde (70 mg) as a white solid.

Example 59

1'-(4-Chlorophenyl)-7',8'-dimethyl-2',4'-dihydro-1'H-spiro[cyclobutane-1,3'-quinoline]-4',6'-diol

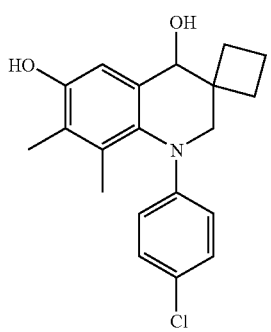

6'-Methoxy-7',8'-dimethyl-1'H-spiro[cyclobutane-1,3'-quinolin]-4'(2'H)-one (300 mg) was mixed with 1-chloro-4-iodobenzene (465 mg), NaOtBu (187.4 mg) and [PdBr(tBu$_3$P)$_2$]$_2$ (20 mg). The reaction tube was then sealed with rubber septum, the air was evacuated, then it was flushed with nitrogen. This process was repeated three times, and then toluene (1.5 mL) was added. The reaction tube was then heated in a 105° C. bath for 2 hours. The mixture was then cooled, quenched with water, and extracted with EtOAc. The organic phase was washed with brine, dried and evaporated to give a crude mixture, that was eluted on a silica column (Hexane: EtOAc; 10:1.5-10:2) to give 1'-(4-chlorophenyl)-6'-methoxy-7',8'-dimethyl-1'H-spiro[cyclobutane-1,3'-quinolin]-4'(2'H)-one (285 mg) as a yellow solid. $^1$H-NMR (300 MHz, CDCl$_3$) δ=7.399 (s, 1H), 7.16-7.09 (m, 2H), 6.81-6.73 (m, 2H), 4.07 (s, 2H), 3.86 (s, 3H), 2.36-2.23 (m, 2H), 2.13 (s, 3H), 1.99-1.78 (m, 1H), 1.76 (s, 3H), 1.69-1.42 (m, 3H) ppm. $^{13}$C-NMR (75 MHz, CDCl$_3$) δ=198.29, 154.39, 149.44, 141.4, 134.46, 132.07, 129.25, 125.87, 124.07, 121.47, 105.15, 60.96, 55.62, 48.86, 28.59, 15.55, 15.52, and 13.09 ppm.

Demethylation as described herein and purification on silica column condition (Hexane: EtOAc; 10:4) yielded 107.6 mg of 1'-(4-chlorophenyl)-6'-hydroxy-7',8'-dimethyl-1'H-spiro[cyclobutane-1,3'-quinolin]-4'(2'H)-one as a yellow powder. $^1$H-NMR (300 MHz, CDCl$_3$+CD$_3$OD): δ=7.32 (s, 1H), 7.25-7.03 (m, 2H), 6.97-6.63 (m, 2H), 4.13 (s, 2H), 2.35-2.19 (m, 2H), 2.17 (s, 3H), 2.03-1.84 (m, 2H), 1.81 (s, 3H), 1.76-1.57 (m, 2H) ppm. $^{13}$C-NMR, (75 MHz, CDCl$_3$) δ=203.68, 155.85, 153.41, 144.49, 137.44, 136.11, 132.97, 129.54, 128.10, 125.15, 113.21, 113.18, 64.48, 52.9, 32.41, 19.12, 18.86, and 16.53 ppm. MS: (m/z): 342 9 (M+H$^+$)

To a cooled solution of 1'-(4-chlorophenyl)-6'-hydroxy-7', 8'-dimethyl-1'H-spiro[cyclobutane-1,3'-quinolin]-4'(2'H)-one (60 mg) in a mixture of THF (2 mL) and methanol (4 mL) was added NaBH$_4$ (60 mg). After 30 minutes, acetone was added and the whole mixture was evaporated to dryness, extracted with EtOAc, washed with saturated NH$_4$Cl, dried and evaporated. The crude product mixture was passed through a silica column (Hexane: EtOAc; 1:1) to give 1'-(4-chlorophenyl)-6'-hydroxy-7',8'-dimethyl-1'H-spiro[cyclobutane-1,3'-quinolin]-4'(2'H)-one (46 mg) as a pink solid. $^1$H-NMR (300 MHz, CDCl$_3$+CD$_3$OD) δ=7.234-6.984 (m, 2H), 6.799 (s, 1H), 6.749-6.546 (m, 2H), 4.41 (s, 1H), 3.751 (s, 2H), 2.10 (s, 3H), 2.18-2.06 (m, 1H), 1.79 (s, 3H), 1.92-1.54 (m, 5H) ppm. $^{13}$C-NMR, (75 MHz, CDCl$_3$+CD$_3$OD) δ=154.56, 154.51, 136.29, 135, 133.75, 132.35, 128.03, 127.66, 123.58, 116.7, 116.66, 76.6, 61.91, 48.14, 32.75, 30.33, 19.63, 18.71, and 15.79 ppm. MS: (m/z): 344.8 (M+H$^+$)

Example 60

6'-Methoxy-5',7'-dimethyl-3',4'-dihydro-1'H-spiro[cyclobutane-1,2'-quinoline]

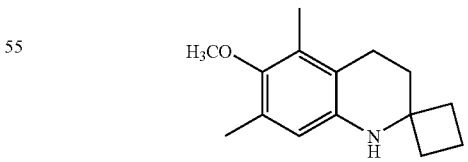

Step 1: Ethyl 2-cyclobutylideneacetate

To a solution of triethyl phosphono acetate (35.2 g) in 100 mL THF, at 0° C., was added slowly via a syringe a solution of NaH (6.2 g) in 60 mL THF. The mixture was stirred at 0° C. for 10 minutes, cyclobutanone (10 g) was added by a syringe, and the resulting mixture was stirred at room temperature for 2 hours, followed by addition of distilled water to quench the reaction. The aqueous solution was extracted by ethyl acetate (3×20 mL), the combined organic layers were dried over Na₂SO₄ and the solvent was removed by evaporation. The crude residue was eluted by column chromatography (10% ethyl acetate/hexane), to give ethyl 2-cyclobutylideneacetate (20 g). ¹HNMR (300 MHz, CDCl₃) δ=5.57 (s, 1H), 4.13 (q, 2H), 3.11 (m, 2H), 2.81 (m, 2H), 2.08(m, 2H), 1.26 (t) ppm. MS: m/z 370 (100, M+H)⁺

Step 2: 2-Methoxy-1,3-dimethyl-5-nitrobenzene 2,6-Dimethyl-4-nitroaniline (15 g) Me₂SO₄ (22 g) and K₂CO₃ (23 g) were dissolved in 150 mL acetone and refluxed for 3 hours. The reaction mixture was filtered and concentrated. The organic residue was dissolved in warm hexane and let to crystallize out in the fridge. After filtration, 2-methoxy-1,3-dimethyl-5-nitrobenzene was collected as white solid (12 g). ¹H-NMR (300 MHz, CDCl₃): δ=7.95 (s, 2H), 3.80 (s, 3H), 2.38 (s, 6H) ppm. MS: m/z 182 (100, M+H)⁺

Step 3: 4-Methoxy-3,5-dimethylaniline

To a solution of 2-methoxy-1,3-dimethyl-5-nitrobenzene (12 g) in ethanol in a Parr hydrogenation bottle, was added Pd/C (0.24 g, 10%). The mixture was shaken at 50 psi of H₂ in the hydrogenator overnight. The reaction mixture was filtered through Celite® and the solvent was removed by evaporation. The crude residue was purified by column chromatography (10% ethyl acetate/hexane), giving 4-methoxy-3,5-dimethylaniline as a light yellow solid (8.2 g). ¹H-NMR (300 MHz, CDCl₃) δ=6.18 (s, 1H), 3.711 (s, 3H), 2.29 (s, 6H) ppm. MS: m/z 152 (100, M+H)⁺

Step 4: Ethyl 2-(1-(4-methoxy-3,5-dimethylphenylamino)cyclobutyl)acetate

To a solution of 4-methoxy-3,5-dimethylaniline (5 g) and ethyl 2-cyclobutylideneacetate (10 g) in 6 mL toluene, under nitrogen was added by syringe 1mL HCl (4M in dioxane). After refluxing the solution for 3 days, the mixture was concentrated, water was added, and the solution was extracted with ethyl acetate (3×20 mL). The combined organic layers were dried over Na₂SO₄ and the solvent was removed by evaporation. The crude compound was purified by column chromatography (10% ethyl acetate/hexane), giving ethyl 2-(1-(4-methoxy-3,5-dimethylphenylamino)-cyclobutyl)acetate (1 g) as a while solid. ¹H-NMR (300 MHz, CDCl₃) δ=6.21 (s, 2H), 4.10(q, 2H), 3.67 (s, 3H), 2.90 (s, 2H), 2.33 (m, 2H), 2.19 (m, 8H), 1.95 (m, 2H), 1.24 (t, J =6.9 Hz, 3H) ppm. MS: m/z 293 (100, M+H)⁺

Step 5: 2-(1-(4-Methoxy-3,5-dimethylphenylamino)cyclobutyl)acetic acid

To a solution of ethyl 2-(1-(4-methoxy-3,5-dimethylphenylamino)cyclobutyl)acetate (1 g) in EtOH was added an aqueous solution of NaOH (2.5 g). The mixture was stirred at room temperature overnight, concentrated and water was added to the residue. After addition of HCl to adjust the pH 2-3, the solution was then washed with ethyl acetate (3×20 mL). The organic layer was dried over Na₂SO₄ and the solvent was removed by evaporation to give 2-(1-(4-methoxy-3,5-dimethylphenylamino)-cyclobutyl)acetic acid (650 mg) as a white solid. MS: m/z 264 (100, M+H)⁺

Step 6: 6'-Methoxy-5,7'-dimethyl-1'H-spiro[cyclobutane-1,2'-quinolin]-4'(3'H)-one To a solution of 2-(1-(4-methoxy-3,5-dimethylphenylamino)cyclobutyl)acetic acid (650 mg) in 10 mL toluene was added a large excess of polyphosphoric acid. The mixture was refluxed for 30 minutes, water was added, and the solution was extracted with ethyl acetate (3×20 mL). The combined organic layers were dried over Na₂SO₄ and the solvent was removed by evaporation, giving 6'-methoxy-5',7'-dimethyl-1'H-spiro[cyclobutane-1,2'-quinolin]-4'(3'H)-one as a yellow solid (1 g). ¹H-NMR (300 MHz, CDCl₃) δ=6.25 (s, 1H), 2.78 (s, 2H), 2.55 (s, 3H), 2.125-2.38 (m, 5H), 1.95-2.06 (m, 2H), 1.73-1.83 (m, 2H) ppm. MS: m/z 246 (100, M+H)⁺

Step 7: 6'-Methoxy-5,7'-dimethyl-3,4'-dihydro-1'H-spiro[cyclobutane-1,2'-quinoline]

To a solution of 6'-methoxy-5',7'-dimethyl-1'H-spiro[cyclobutane-1,2'-quinolin]-4'(3'H)-one (1 g) in a mixture of 35 mL methanol and 15 mL CH₂Cl₂, was added NaBH₄ (2 g) slowly at 0° C. The reaction mixture was stirred at 0° C. for 15 minutes and then at room temperature for three days. The reaction mixture was quenched with water and extracted with ethyl acetate. The organic layer was dried with Na₂SO₄ and evaporated, to yield 6'-methoxy-5',7'-dimethyl-3',4'-dihydro-1'H-spiro[cyclobutane-1,2'-quinolin]-4'-ol was used in the next step without further purification.

To a mixture of NaBH₄ (1 g) added in portions to a solution of cooled trifluoroacetic acid and acetic acid (30 mL, v/v: 1/1), was added 6'-methoxy-5',7'-dimethyl-3',4'-dihydro-1'H-spiro[cyclobutane-1,2'-quinolin]-4'-ol in 10 mL THF. After 30 minutes, the reaction mixture was quenched with water and extracted with ethyl acetate (3×20 mL). The organic layer was dried with Na₂SO₄, evaporated, and purified by column chromatography (1-2% methanol in CH₂Cl₂), to give 6'-methoxy-5',7'-dimethyl-3',4'-dihydro-1'H-spiro[cyclobutane-1,2'-quinoline] as a brown oil (500 mg).

¹H-NMR (300 MHz, CDCl₃): δ=6.22 (s, 1H), 3.68 (s, 3H), 2.66 (t, 2H), 2.22 (s, 3H), 2.18 (s, 3H), 1.91-2.08 (m, 8H), 1.309-1.48 (m, 2H) ppm. MS: m/z 232 (100, M+H)⁺

Example 61

7',8'-dimethyl-2',3'-dihydro-1'H-spiro[cyclobutane-1,4'-quinolin]-6'-ol

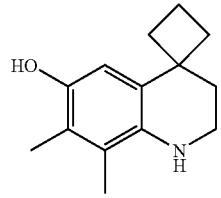

Step 1: Cyclobutylideneacetic acid

To a solution of ethyl 2-cyclobutylideneacetate (5.5 g) in 40 mL EtOH was added an aqueous NaOH solution (10 g NaOH in 40 mL H₂O). The mixture was stirred at room temperature overnight. The volume of the reaction mixture was reduced to one third and the pH was modified to 2-3. The solid present was collected by filtration and dried under high vacuum, giving the pure cyclobutylideneacetic acid as an off-white solid (3.5 g) ¹H-NMR (300 MHz, CDCl₃) δ=5.57 (s, 1H); 4.13 (q, J=7.05 Hz, 2H); 3.11 (m, 2H); 2.81 (m, 2H); 2.08 (m, 2H); 1.26 (t, J=6.97 Hz) ppm. MS: (m/z)=113 (100, M+H)⁺.

Step 2: 2-Cyclobutylidene-N-(4-methoxy-2,3-dimethylphenyl)acetamide

Cyclobutylideneacetic acid (3.8 g), 5,6-dimethyl-4-methoxyaniline (5 g), 1-(3-dimethylaminopropyl)-3-ethylcarbodiimide (EDC) (4.7 g), 1,3-dicyclohexylcarbodiimide (DCC)

(2.4 g), 4-dimethylaminopyridine (DMAP) (805 mg) and triethylamine (TEA) (7.3 g) were dissolved in dichloromethane (80 mL). The mixture was stirred at room temperature overnight, concentrated, and the residue dissolved in ethyl acetate. The organic phase was washed with water (3×20 mL) and 1M HCl (3×20 mL), and a white solid was filtered out. The organic solution was then dried out by evaporation giving 2-cyclobutylidene-N-(4-methoxy-2,3-dimethylphenyl)acetamide as a brown solid (5.3 g). The product was used in the next step without further purification. MS: (m/z)=246 (100, M+H$^+$).

Step 3: 6'-Hydroxy-7',8'-dimethyl-1'H-spiro[cyclobutane-1,4'-quinolin]-2'(3'H)-one A solution of 2-cyclobutylidene-N-(4-methoxy-2,3-dimethylphenyl)acetamide (5 g) in methane sulfonic acid (20 mL) was refluxed at 120° C. overnight. After cooling down, the solution was poured onto ice. The solid present was collected by filtration and washed with water (×3), giving 6'-hydroxy-7',8'-dimethyl-1'H-spiro[cyclobutane-1,4'-quinolin]-2'(3'H)-one (2.5 g) which was used in the next step without further purification. $^1$H-NMR (300 MHz, CDCl$_3$) δ=6.8 (s, 1H); 3.37 (s, 1H); 2.64 (s, 2H); 2.43 (m, 3H); 2.16 (s, 6H); 2.07 (m, 3H) ppm. MS: (m/z)=232 (100, M+H$^+$).

Step 4: 7',8'-Dimethyl-2,3'-dihydro-1'H-spiro[cyclobutane-1,4'-quinolin]-6'-ol

A solution of 6'-hydroxy-7',8'-dimethyl-1'H-spiro[cyclobutane-1,4'-quinolin]-2'(3'H)-one (4.6 g) in THF was added to BH$_3$-THF (45 mL) at 0° C. The mixture was stirred at room temperature for 20 minutes and allowed to reflux overnight. The mixture was cooled down and at 0° C., 3 N HCl was added to quench the excess BH$_3$. The solvent was removed by evaporation. The solid present was collected by filtration and washed with hexane (×3), giving 7',8'-dimethyl-2',3'-dihydro-1'H-spiro[cyclobutane-1,4'-quinolin]-6'-ol (700 mg) as a light yellow solid. $^1$H-NMR (300 MHz, CDCl$_3$) δ=6.54 (s, 2H); 4.21 (t, J=6 Hz, 2H); 2.15 (m, 5H); 2.02 (m, 8H); 2.19 (m, 8H); 1.94 (t, J=6 Hz, 2H) ppm. MS: (m/z)=218 (100, M+H$^+$).

Example 62

7',8'-Dimethyl-1'-(quinolin-2-ylmethyl)-2',3'-dihydro-1'H-spiro[cyclobutane-1,4'-quinolin]-6'-ol

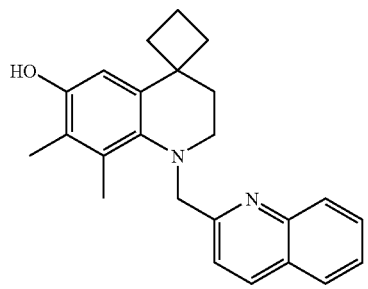

A mixture of 7',8'-dimethyl-2',3'-dihydro-1'H-spiro[cyclobutane-1,4'-quinolin]-6'-ol (300 mg), 2-(chloromethyl)quinoline (600 mg), K$_2$CO$_3$ (637 mg), and sodium iodide (40 mg) in acetone (50 mL) was refluxed overnight under nitrogen. The reaction mixture was then cooled down and concentrated by evaporation. Distilled water was added to the residue and the aqueous solution was extracted with ethyl acetate (3×20 mL). The organic layer was combined, dried over Na$_2$SO$_4$, and evaporated. The crude compound was purified by column chromatography (2% MeOH in CH$_2$Cl$_2$) yielding 7',8'-dimethyl-1'-(quinolin-2-ylmethyl)-2',3'-dihydro-1'H-spiro[cyclobutane-1,4'-quinolin]-6'-ol as an off-white solid. $^1$H-NMR (300 MHz, CDCl$_3$) δ=8.28 (d, J=6 Hz, 1H); 8.15 (d, J=6 Hz, 1H); 8.05 (d, J=9 Hz, 1H); 7.88 (t, J=6 Hz, 1H); 7.76 (t, J=6 Hz, 1H); 7.02 (s, 1H); 4.21 (s, 2H); 2.99 (m, 2H); 2.35 (m, 2H); 2.24 (s, 3H); 2.20 (s, 3H); 1.99 (m, 6H) ppm. $^{13}$C-NMR (75 MHz, CDCl$_3$) δ=161.20; 149.46; 147.54; 139.58; 137.16; 135.93; 131.04; 129.73; 128.54; 127.70; 127.52; 126.18; 122.83; 119.73; 111.48; 92.98; 77.48; 71.26; 68.59; 60.73; 45.03; 43.92; 40.12; 36.74; 29.88; 15.28; 14.79; 12.54 ppm. MS: (m/z)=359 (100, M+H$^+$).

Example 63

5',7'-Dimethyl-1'-(quinolin-2-ylmethyl)-3',4'-dihydro-1'H-spiro[cyclobutane-1,2'-quinolin]-6'-ol

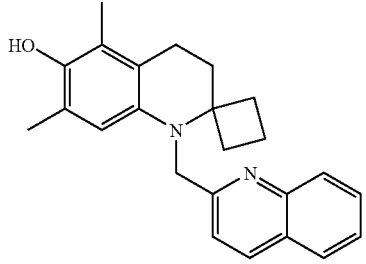

Step 1: 6'-Methoxy-5,7'-dimethyl-1'-(quinolin-2-ylmethyl)-3,4'-dihydro-1'H-spiro[cyclobutane-1,2'-quinoline]

A mixture of 6'-methoxy-5',7'-dimethyl-3',4'-dihydro-1'H-spiro[cyclobutane-1,2'-quinoline] (270 mg), 2-(chloromethyl)quinoline (626 mg), K$_2$CO$_3$ (528 mg) and sodium iodide (30 mg) in acetone (20 mL) was refluxed over night. After evaporation of the solvent, water was added to the residue and the aqueous solution was extracted with ethyl acetate (3×20 mL). The combined organic layers were dried over Na$_2$SO$_4$ and the solvent was removed by evaporation. The residue was purified by column chromatography (10% ethyl acetate/hexane), giving 6'-methoxy-5',7'-dimethyl-1'-(quinolin-2-ylmethyl)-3',4'-dihydro-1'H-spiro[cyclobutane-1,2'-quinoline] as a light yellow solid (250 mg).
MS: (m/z)=375 (100, M+H)$^+$.

Step 2: 5,7'-Dimethyl-1'-(quinolin-2-ylmethyl)-3,4'-dihydro-1'H-spiro[cyclobutane-1,2'-quinolin]-6'-ol 6'-Methoxy-5',7'-dimethyl-1'-(quinolin-2-ylmethyl)-3',4'-dihydro-1'H-spiro[cyclobutane-1,2'-quinoline] (250 mg) was dissolved in CH$_2$Cl$_2$ (10 mL). At 0° C., 2.5 mL of BBr$_3$ (2 mL, 1M solution in CH$_2$Cl$_2$) was added to the flask. The mixture was stirred at 0° C. for 20 minutes and then at room temperature for 30 minutes. After removing the solvent and BBr$_3$, the reaction was quenched by adding into it water. The aqueous solution was then extracted with ethyl acetate (3×20 mL). The organic layer was combined, dried over Na$_2$SO$_4$ and evaporated. The residue was purified by column chromatography (silicagel, 12% ethyl acetate/hexane), giving 5',7'-dimethyl-1'-(quinolin-2-ylmethyl)-3',4'-dihydro-1'H-spiro[cyclobutane-1,2'-quinolin]-6'-ol as a dark yellow solid (26 mg). $^1$H-NMR (300 MHz, CD$_3$OD) δ=8.10 (m, 2H); 7.72-7.92 (m, 2H); 7.74 (m, 2H); 6.00 (s, 1H); 4.83 (s, 2H); 2.76 (s, 6H); 2.32 (m, 2H); 2.07 (s, 5H); 2.00 (s, 3H); 1.94 (m, 2H); 1.72 (m, 2H) ppm. MS: (m/z)=359 (100, M+H$^+$)

Example 64

7',8'-Dimethyl-1'-(4-phenylthiazol-2-yl)-2',4'-dihydro-1'H-spiro[cyclobutane-1,3'-quinolin]-6'-ol

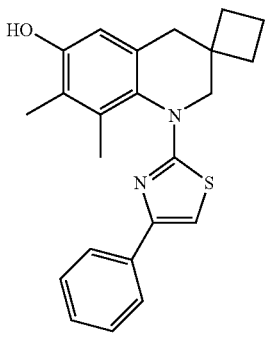

Step 1: 6'-Methoxy-7',8'-dimethyl-2'H-spiro[cyclobutane-1,3'-quinoline]-1'(4'H)-carbothioamide To a solution of 142 mg of 6'-methoxy-7',8'-dimethyl-1',4'-dihydro-2'H-spiro[cyclobutane-1,3'-quinoline] in 2 mL chlorobenzene, was added $H_2SO_4$ (16.56 μL) and NaSCN (55.6 mg) at room temperature. The mixture was then heated in a bath of 110° C. for 2 hours. Water was added and dichloromethane was used for extraction. The combined organic phase was washed with brine, dried and evaporated. The residue was passed through a silicagel column (hexane: ethyl acetate=10:4-10:5) to yield 6'-methoxy-7',8'-dimethyl-2'H-spiro[cyclobutane-1,3'-quinoline]-1'(4'H)-carbothioamide (138.6 mg) as a light yellow solid. $^1$H-NMR (300 MHz, CDCl$_3$) δ=6.623 (s, 1H); 6.07-5.55 (br s; 2H); 5.48-5.23 (d, J=13 Hz, 1H); 3.82 (s, 3H); 3.39-3.16 (d, J=13 Hz, 1H); 2.85-2.51 (m, 2H); 2.46-2.23 (m, 1H); 2.10 (s, 3H); 2.09 (s, 3H); 2.06-1.75 (m, 3H); 1.69-1.53 (m, 2H) ppm.

Step 2: 2-(6'-Methoxy-7',8'-dimethyl-2,4'-dihydro-1'H-spiro[cyclobutane-1,3'-quinoline]-1'-yl)-4-phenylthiazole 110 mg of 6'-methoxy-7',8'-dirmethyl-2'H-spiro[cyclobutane-1,3'-quinoline]-1'(4'H)-carbothioamide was mixed with 113.4 mg of 2-bromo-1-phenylethanone in 3 mL ethanol. After being refluxed for 1 hour, the mixture was evaporated onto SiO$_2$. After purification through a column (Hexane: EtOAc=10:0.5), 2-(6'-methoxy-7',8'-dimethyl-2',4'-dihydro-1'H-spiro[cyclobutane-1,3'-quinoline]-1'-yl)-4-phenylthiazole (53.8 mg) was obtained. $^1$H-NMR (300 MHz, CDCl$_3$) δ=7.97-7.81 (m, 2H); 7.48-7.35 (m, 2H); 7.34-7.21 (m, 1H); 6.71 (s, 1H); 6.62 (s, 1H); 4.39-3.95 (br s, 2H); 3.86 (s, 3H); 2.80 (s, 2H); 2.17 (s, 6H); 2.03-1.59 (m, 6H) ppm.

Step 3: 7',8'-Dimethyl-1'-(4-phenylthiazol-2-yl)-2,4'-dihydro-1'H-spiro[cyclobutane-1,3'-quinolin]-6'-ol After passing through a column (dichloromethane: EtOAc=10:0.5), 7',8'-dimethyl-1'-(4-phenylthiazol-2-yl)-2',4'-dihydro-1'H-spiro[cyclobutane-1,3'-quinolin]-6'-ol (29.6 mg) was obtained as a brown solid. $^1$H-NMR (300 MHz, C$_2$D$_6$O) δ=8.25 (s, 1H); 8.02-7.80 (m, 2H); 7.47-7.33 (m, 2H); 7.32-7.175 (m, 1H); 6.99 (s, 1H); 6.68 (s, 1H); 4.48-3.74 (brs, 2H); 2.69 (s, 2H); 2.14 (s, 3H); 2.11 (s, 3H); 1.98-1.66 (m, 6H) ppm. $^{13}$C-NMR (75 MHz, C$_2$D$_6$O) δ=172.19, 153.07, 150.92, 135.4, 133.16, 132.88, 131.45, 128.42, 127.34, 125.85, 121.95, 113.15, 102.56, 60.99, 41.54, 39.48, 32.65, 15.04, 14.92, and 11.45 ppm.

Similarly following the procedure described above, the following compounds were prepared:

2-(6'-methoxy-7',8'-dimethyl-2,4'-dihydro-1'H-spiro[cyclobutane-1,3'-quinoline]-1'-yl)-4-1H-NMR (300 MHz, CDCl$_3$) δ=6.58 (s, 1H); 6.13-5.92 (d, J=1.1 Hz, 1H); 3.99 (s, 2H); 3.83 (s, 3H); 2.75 (s, 2H); 2.34-2.25 (d, J=1.1 Hz, 3H); 2.13 (s, 3H); 2.09 (s, 3H); 1.97-1.62 (m, 6H) ppm.

2-(6'-methoxy-7',8'-dimethyl-2',4'-dihydro-1'H-spiro[cyclobutane-1,3'-quinoline]-1'-yl)thiazole $^1$H-NMR (300 MHz, CDCl$_3$) δ=7.25-7.174 (d, J=3.7 Hz, 1H); 6.59 (s, 1H); 6.52-6.44 (d, J=3.7 Hz, 1H); 3.99 (s, 2H); 3.85 (s, 3H); 2.77 (s, 2H); 2.13 (s, 3H); 2.08 (s, 3H); 1.98-1.66 (m, 6H) ppm.

1'(1-(2-bromophenyl)-1H-tetrazol-5yl)-6'-methoxy-7',8'-dimethyl-2,4'-dihydro-1'H-spiro[cyclobutane-1,3'-quinoline]

$^1$H-NMR (300 MHz, CD$_3$OD) δ=7.79-7.56 (m, 1H); 7.51-7.17 (m, 3H); 6.45 (s, 1H); 3.76 (s, 3H); 3.52 (s, 2H); 2.84 (s, 2H); 1.97 (s, 3H); 1.91 (s, 3H); 1.95-1.65 (m, 6H) ppm.

1'-(1-(2-bromophenyl)-1H-tetrazol-5yl)-7',8'-dimethyl-2,4'-dihydro-1'H-spiro[cyclobutane-1,3'-quinolin]-6'-ol $^1$H-NMR (300 MHz, C$_2$D$_6$SO) δ=9.061 (s, 1H); 7.969-7.71 (m, 1H); 7.63-7.32 (m, 3H); 6.40 (s, 1H); 3.41 (s, 2H); 2.70 (s, 2H); 1.86 (s, 3H); 1.66 (s, 3H); 1.83-1.50 (m, 6H) ppm.

7',8'-dimethyl-1'-(4-methylthiazol-2-yl)-2',4'-dihydro-1'H-spiro[cyclobutane-1,3'-quinolin]-6'-ol $^1$H-NMR (300 MHz, CD$_3$OD) δ=6.54 (s, 1H); 6.25-6.05 (m, 1H); 3.89 (s, 2H); 2.65 (s, 2H); 2.22 (s, 3H); 2.09 (s, 3H); 2.02 (s, 3H); 1.97-1.63 (m, 6H) ppm. $^{13}$C-NMR (75 MHz, CD$_3$OD) δ=177.86, 156.96, 151.7, 136.5, 136.33, 135.05, 126.04, 116.62, 106.41, 65.48, 45.36, 43.16, 36.11, 19.82, 18.65, 18.15, and 14.77 ppm.

7',8'-dimethyl-1'-(thiazol-2-yl)-2',4'-dihydro-1'H-spiro[cyclobutane-1,3'-quinolin]-6'-ol $^1$H-NMR (300 MHz, CD$_3$OD) δ=7.22-7.12 (d, J=3.73 Hz, 1H); 6.69-6.59 (d, J=3.75 Hz, 1H); 6.55 (s, 1H); 3.91 (s, 2H); 2.66 (s, 2H); 2.09 (s, 3H); 2.02 (s, 3H); 1.98-1.62 (m, 6H) ppm. $^{13}$C-NMR (75 MHz, CD$_3$OD) δ=174.47, 153.08, 137.69, 132.6, 132.46, 131.02, 122.17, 112.69, 108.22, 61.41, 41.33, 39.27, 32.15, 14.7, 14.17, and 10.84 ppm.

1'-(1-(2-bromophenyl)-1H-tetrazol-5yl)-7',8'-dimethyl-2',4'-dihydro-1'H-spiro[cyclobutane-1,3'-quinolin]-6'-ol $^1$H-NMR (300 MHz, C$_2$D$_6$SO) δ=9.061 (s, 1H); 7.97-7.71 (m, 1H); 7.63-7.32 (m, 3H); 6.41 (s, 1H); 3.41 (s, 2H); 2.71 (s, 2H); 1.86 (s, 3H); 1.66 (s, 3H); 1.83-1.50 (m, 6H) ppm.

7',8'-dimethyl-1'-(4-(trifluoromethyl)oxazol-2-yl)-2',4'-dihydro-1'H-spiro[cyclobutane-1,3'-quinolin]-6'-ol $^1$H-NMR (300 MHz, C$_2$D$_6$O) δ=8.15 (s, 1H); 8.08-7.91 (m, 1H); 6.62 (s, 1H); 3.88 (s, 2H); 2.78 (s, 2H); 2.14 (s, 3H); 1.96 (s, 3H); 1.95-1.68 (m, 6H) ppm. $^{13}$C-NMR (75 MHz, C$_2$D$_6$O) δ=161.91, 152.66, 132.64, 132.57, 132.28, 131.39, 130.88, 129.56, 123.01, 121.57, 119.49, 112.63, 58.19, 40.01, 39.44, 31.55, 14.78, 14.52, and 11.37 ppm.

2-(6'-methoxy-7',8'-dimethyl-2',4'-dihydro-1'H-spiro[cyclobutane-1,3'-quinoline]-1'-yl)-4-(trifluoromethyl)oxazole $^1$H-NMR (300 MHz, CDCl$_3$) δ=7.61-7.38 (m, 1H); 6.58 (s, 1H); 3.92 (s, 2H); 3.84 (s, 3H); 2.84 (s, 2H); 2.17 (s, 3H); 1.93 (s, 3H); 2.05-1.69 (m, 6H) ppm

Example 65

5'-(3,7-Dimethylocta-2,6-dienyl)-1'-(4-methoxyphenyl)-7',8'-dimethyl-2',4'-dihydro-1'H-spiro[cyclobutane-1,3'-quinolin]-6'-ol

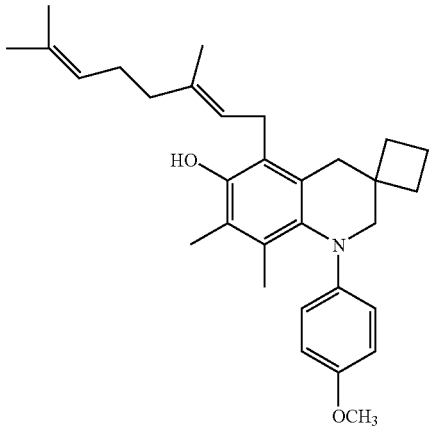

To a solution of 1'-(4-methoxyphenyl)-7',8'-dimethyl-1',4'-dihydro-2'H-spiro[cyclobutane-1,3'-quinolin]-6'-ol (112 mg) in 3.2 mL t-BuOH was added NaOH (224 µL) and geranyl bromide (133 µL). After 20 minutes, saturated NH$_4$Cl was added and the mixture was extracted with dichloromethane. The organic phase was then washed with brine, dried and evaporated. The residue was passed through a column (Hexane:EtOAc=10:1.2-10:2) to give 5'-(3,7-dimethylocta-2,6-dienyl)-1'-(4-methoxyphenyl)-7',8'-dimethyl-2',4'-dihydro-1'H-spiro[cyclobutane-1,3'-quinolin]-6'-ol (14.7 mg) as a semi white solid. $^1$H-NMR (300 MHz, CDCl$_3$) δ=6.79-6.62 (m, 4H); 5.26-5.13 (m, 1H); 5.13-5.01 (m, 1H); 4.93 (s, 1H); 3.76 (s, 3H); 3.61 (s, 2H); 2.79 (s, 2H); 2.17-2.02 (m, 7H); 1.82-1.28 (m, 18H). $^{13}$C-NMR (75 MHz, CDCl$_3$) δ=152.74, 148.42, 146.18, 138.01, 135.33, 131.98, 129.67, 126.73, 123.86, 122.39, 122.12, 121.95, 119.93, 113.99, 76.63, 61.49, 55.51, 40.16, 39.75, 38.33, 32.89, 26.46, 25.75, 25.53, 17.77, 16.27, 15.76, 15.61, 12.39 ppm.

Example 66

1'-(Benzo[d]thiazol-2-yl)-7',8'-dimethyl-2',4'-dihydro-1'H-spiro[cyclobutane-1,3'-quinolin]-6'-ol

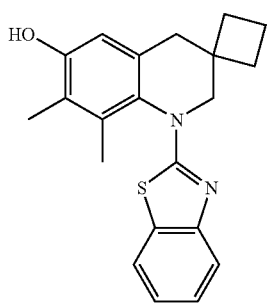

Step 1: N-(2-Bromophenyl)-6'-methoxy-7',8'-dimethyl-2',4'-dihydro-1'H-spiro[cyclobutane-1,3'-quinoline]-1'-carbothioamide To a solution of 6'-methoxy-7',8'-dimethyl-2',4'-dihydro-1'H-spiro[cyclobutane-1,3'-quinoline] (810 mg) in 4 mL dichloromethane was added 1-bromo-2-isothiocyanatobenzene (525 µL) at room temperature. The mixture was allowed to reflux overnight. Water was used to quench the mixture and EtOAc was used for extraction. The combined organic phases were washed with brine, dried and evaporated. The residue was passed through a column (dichloromethane:EtOAc=10:2) to give N-(2-bromophenyl)-6'-methoxy-7',8'-dimethyl-2',4'-dihydro-1'H-spiro[cyclobutane-1,3'-quinoline]-1'-carbothioamide (1.5 g) as a white solid. $^1$H-NMR (300 MHz, CDCl$_3$) δ=8.54-8.22 (d, J=6.95 Hz, 1H); 7.61-7.39 (m, 2H); 7.38-7.22 (m, 1H); 7.15-6.87 (m, 1H); 6.69 (s, 1H); 5.72-5.38 (d, J=13.1 Hz, 1H); 3.86 (s, 3H); 3.39-3.25 (d, J=13.1 Hz, 1H); 2.85-2.67 (m, 2H); 2.46-2.28 (m, 1H); 2.14 (s, 3H); 2.12 (s, 3H); 2.07-1.79 (m, 3H); 1.79-1.62 (m, 2H) ppm.

Step 2: 2-(6'-Methoxy-7',8'-dimethyl-2',4'-dihydro-1'H-spiro[cyclobutane-1,3'-quinoline]-1'-yl)benzo[d]thiazole A mixture was made of N-(2-bromophenyl)-6'-methoxy-7',8'-dimethyl-2',4'-dihydro-1'H-spiro[cyclobutane-1,3'-quinoline]-1'-carbothioamide (200 mg), Cs$_2$CO$_3$ (176 mg), copper iodide (8.5 mg) 1,10-phenanthioline (16.2 mg) and 2 mL 1,2 dimethoxyethane. The mixture was then heated up in a 90° C. oil bath for 1 hour, filtered and evaporated. The residue was passed through a silica gel column (hexane:dichloromethane=10:1), 2-(6'-methoxy-7',8'-dimethyl-2',4'-dihydro-1'H-spiro[cyclobutane-1,3'-quinoline]-1'-yl)benzo[d]thiazole (150 mg) was obtained. $^1$H-NMR (300 MHz, CDCl$_3$) δ=7.86-6.58 (d, J=8.1 Hz, 1H); 6.58-6.44 (m, 1H); 7.41-7.19 (m, 1H); 7.17-6.96 (m, 1H); 6.64 (s, 1H); 3.87 (s, 3H); 2.76 (s, 2H); 2.18 (s, 3H); 2.17 (s, 3H); 1.96-1.52 (m, 6H) ppm.

Step 3: 1'-(Benzo[d]thiazol-2-yl)-7',8'-dimethyl-2',4'-dihydro-1'H-spiro[cyclobutane-1,3'-quinolin]-6'-ol After demethylation as described above, the residue was purified through a silicagel column (Hexane:EtOAc=10:5), to yield 1'-(benzo[d]thiazol-2-yl)-7',8'-dimethyl-2',4'-dihydro-1'H-spiro[cyclobutane-1,3'-quinolin]-6'-ol (64 mg), as a white solid. $^1$H-NMR (300 MHz, C$_2$D$_6$O) δ=8.44 (s, 1H); 7.72-7.39 (m, 2H); 7.37-7.16 (m, 1H); 7.16-6.87 (m, 1H); 6.71 (s, 1H); 5.25-3.20 (m, 2H); 2.65 (s, 2H); 2.16 (s, 3H); 2.12 (s, 3H); 1.98-1.41 (m, 6H) ppm. $^{13}$C-NMR (75 MHz, C$_2$D$_6$O) δ=170.27, 153.53, 152.81, 133.15, 132.58, 132.45, 131.46, 125.62, 122.02, 121.57, 120.77, 119.11, 113.13, 61.01, 41.98, 39.15, 32.73, 15.01, 14.89, and 11.48 ppm.

Example 67

N-(2-(6'-Hydroxy-7',8'-dimethyl-2',4'-dihydro-1'H-spiro[cyclobutane-1,3'-quinoline]-1'-yl)ethyl)-4-methylbenzenesulfonamide

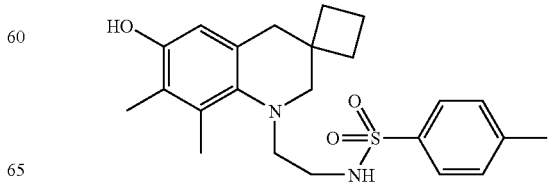

Step 1: 2-(6'-Methoxy-7',8'-dimethyl-2,4'-dihydro-1'H-spiro[cyclobutane-1,3'-quinoline]-1'-yl)ethanamine A solution of 6'-methoxy-7',8'-dimethyl-2',4'-dihydro-1'H-spiro[cyclobutane-1,3'-quinoline] (1.12 g), 1,2-dibromoethane (2 mL) and $Cs_2CO_3$ (3.16 9) in DMF (7 mL) was heated in a bath of 110° C. for 6 hours. The mixture was cooled, water was added, and extracted with dichloromethane. The organic phase was then washed with brine, dried and evaporated. The residue was passed through a column (Hexane/EtOAc, 10:0.6) to give 1'-(2-bromoethyl)-6'-methoxy-7',8'-dimethyl-2',4'-dihydro-1'H-spiro[cyclobutane-1,3'-quinoline] which was then added $NaN_3$ (1.1 g) and dissolved in dichloromethane (7 mL). After heating the solution in a bath of 90° C. for 1 hour, the mixture was cooled, mixed with water and extracted with dichloromethane. The organic phase was washed with brine, dried and evaporated. The residue was passed through a column (Hexane/EtOAc, 10:0.5-10:0.6) to give 1'-(2-azidoethyl)-6'-methoxy-7',8'-dimethyl-2',4'-dihydro-1'H-spiro[cyclobutane-1,3'-quinoline] (340 mg) as an oil. 1'-(2-azidoethyl)-6'-methoxy-7',8'-dimethyl-2',4'-dihydro-1'H-spiro[cyclobutane-1,3'-quinoline] (340 mg) was dissolved in methanol (7 mL) and ethylacetate to which 50 mg Pd/C (10%) was added. The flask was then flushed evacuated and flushed with hydrogen. Under a balloon of hydrogen for 1 hour, the mixture was filtered and evaporated to give 2-(6'-methoxy-7',8'-dimethyl-2',4'-dihydro-1'H-spiro[cyclobutane-1,3'-quinoline]-1'-yl)ethanamine (278 mg) as an oil. $^1$H-NMR (300 MHz, $C_2D_6O$) δ=6.414 (s, 1H); 3.77 (s, 3H); 3.52 (s, 2H); 3.16-2.92 (m, 4H); 2.81 (s, 2H); 2.18 (s, 3H); 2.12 (s, 3H); 2.03-1.86 (m, 4H); 1.84-1.64 (m, 2H) ppm.

Similarly following the procedure described above, the following were prepared:

3-(6'-methoxy-7',8'-dimethyl-2',4'-dihydro-1'H-spiro[cyclobutane-1,3'-quinoline]-1'-yl)propan-1-amine $^1$H-NMR (300 MHz, $CDCl_3$) δ=6.41 (s, 1H); 3.77 (s, 3H); 3.07 (s, 2H); 2.98-2.63 (m, 6H); 2.15 (s, 3H); 2.11 (s, 3H); 2.03-1.68 (m, 8H) ppm.

Step 2: N-(2-(6'-Hydroxy-7',8'-dimethyl-2,4'-dihydro-1'H-spiro[cyclobutane-1,3'-quinoline]-1'-yl)ethyl)-4-methylbenzenesulfonamide 4-methylbenzene-1-sulfonyl chloride was dissolved in dichloromethane and to this solution was added $Et_3N$ and p-toluene sulfonyl chloride at room temperature. After 30 min, the reaction mixture was quenched with saturated sodium bicarbonate, extracted with EtOAc, the organic phase was washed with brine, dried and evaporated. The residue was passed through column (100 mg, 65%, column condition: Hexane/EtOAc, 10:7.5) to give N-(2-(6'-hydroxy-7',8'-dimethyl-2',4'-dihydro-1'H-spiro[cyclobutane-1,3'-quinoline]-1'-yl)ethyl)-4-methylbenzenesulfonamide. $^1$H-NMR (300 MHz, $C_2D_6O$+$CDCl_3$) δ=7.93-7.63 (d, J=8.1 Hz, 2H); 7.53 (s, 1H); 7.46-7.27 (d, J=8.1 Hz, 2H); 6.38 (s, 1H); 5.88 (m, 1H); 3.38-3.05 (m, 2H); 3.05-2.91 (t, J=7.5 Hz, 2H); 2.86 (s, 2H); 2.67 (s, 2H); 2.45 (s, 3H); 2.09 (s, 3H); 2.05 (s, 3H); 1.99-1.53 (m, 6H) ppm. $^{13}$C-NMR (75 MHz, $CDCl_3$+$C_2D_6O$) δ=154.18, 147.94, 143.86, 142.06, 134.75, 134.41, 131.85, 131.59, 126.79, 117.7, 63.95, 60.27, 45.77, 45.45, 43.18, 37.25, 26.11, 20.69, 30.38, and 16.98 ppm.Similarly following the above procedure but substituting p-toluene sulfonyl chloride with 4-propylbenzene-1-sulfonyl chloride the following compound was prepared:

N-(2-(6'-Hydroxy-7',8'-dimethyl-2',4'-dihydro-1'H-spiro[cyclobutane-1,3'-quinoline]-1'-yl)ethyl)-4-propylbenzenesulfonamide $^1$H-NMR (300 MHz, $CDCl_3$) δ=7.92-7.69 (d, J=8.3 Hz, 2H); 7.39-7.29 (d, J=8.3 Hz, 2H); 6.34 (s, 1H); 5.08 (s, 1H); 4.86 (s, 1H); 3.25-3.107 (m, 2H); 2.98-2.86 (t, J=6.6 Hz, 2H); 2.76 (s, 2H); 2.72-2.61 (m, 4H); 2.08 (s, 3H); 2.04 (s, 3H); 1.99-1.55 (m, 8H); 1.06-0.82 (t, J=7.3 Hz, 3H) ppm. $^{13}$C-NMR (75 MHz, $CDCl_3$) δ=148.69, 148.27, 139.43, 136.66, 130.42, 129.22, 127.63, 127.27, 121.85, 113.2, 58.55, 54.49, 40.66, 40.61, 38.32, 37.88, 32.71, 24.31, 16.04, 15.88, 13.79, and 12.31 ppm.

Similarly following the above procedure but substituting 2-(6'-methoxy-7',8'-dimethyl-2',4'-dihydro-1'H-spiro[cyclobutane-1,3'-quinoline]-1'-yl)ethanamine with 3-(6'-methoxy-7',8'-dimethyl-2',4'-dihydro-1'H-spiro[cyclobutane-1,3'-quinoline]-1'-yl)propan-1-amine, the following compounds were prepared:

N-(3-(6'-Hydroxy-7',8'-dimethyl-2',4'-dihydro-1'H-spiro[cyclobutane-1,3'-quinoline]-1'-yl)propyl)-4-propylbenzenesulfonamide $^1$H-NMR (300 MHz, $C_2D_6O$) δ=7.87-7.72 (d, J=8.3 Hz, 2H); 7.57 (s, 1H); 7.47-7.31 (d, J=8.3 Hz, 2H); 6.55-6.39 (t, J=6 Hz, 1H); 6.38 (s, 1H); 3.13-2.90 (m, 4H); 2.90-2.75 (m, 2H); 2.75-2.55 (m, 4H); 2.06 (s, 3H); 2.04 (s, 3H); 1.99-1.54 (m, 10H); 1.05-0.78 (t, J=7.4 Hz, 3H) ppm. $^{13}$C-NMR (75 MHz, $C_2D_6O$) δ=149.45, 147.45, 139.52, 138.47, 129.76, 129.02, 126.95, 126.54, 121.53, 112.71, 59.3, 54.44, 41.36, 40.68, 38.67, 37.4, 32.21, 27.87, 24.18, 15.58, 15.17, 13.14, and 11.66 ppm.

N-(3-(6'-Hydroxy-7',8'-dimethyl-2',4'-dihydro-1'H-spiro[cyclobutane-1,3'-quinoline]-1'-yl)propyl)-4-methylbenzenesulfonamide $^1$H-NMR (300 MHz, $C_2D_6O$) δ=7.98-7.66 (d, J=8.1 Hz, 2H); 7.56 (s, 1H); 7.48-7.15 (d, J=7.9 Hz, 2H); 6.60-6.21 (m, 2H); 3.14-2.9 (m, 4H); 2.9-2.74 (m, 2H); 2.66 (s, 2H); 2.42 (s, 3H); 2.06 (s, 3H); 2.04 (s, 3H); 1.99-1.536 (m, 8H) ppm. $^{13}$C-NMR (75 MHz, $C_2D_6O$) δ=149.44, 142.85, 139.53, 138.26, 129.76, 129.55, 126.94, 126.56, 121.53, 112.71, 59.31, 54.42, 41.32, 40.68, 38.68, 32.21, 27.88, 20.53, 15.57, 15.15, and 11.66 ppm.

N-(3-(6'-Hydroxy-7',8'-dimethyl-2',4'-dihydro-1'H-spiro[cyclobutane-1,3'-quinoline]-1'-yl)propyl)methanesulfonamide $^1$H-NMR (300 MHz, $C_2D_6O$) δ=7.54 (s, 1H); 6.39 (s, 1H); 6.16-5.85 (m, 1H); 3.26-3.12 (m, 2H); 3.08 (s, 2H); 2.93 (s, 3H); 2.95-2.82 (m, 2H); 2.70 (s, 2H); 2.12 (s, 3H); 2.08 (s, 3H); 2.03-1.82 (m, 6H); 1.81-1.60 (m, 2H) ppm. $^{13}$C-NMR (75 MHz, $C_2D_6O$) δ=149.44, 139.66, 129.82, 126.59, 121.57, 112.74, 59.44, 54.54, 41.3, 40.73, 38.74, 32.24, 28.45, 15.6, 15.23, and 11.68 ppm.

Example 68

N-(3-(6'-Hydroxy-7',8'-dimethyl-2',4'-dihydro-1'H-spiro[cyclobutane-1,3'-quinoline]-1'-yl)propyl)benzamide

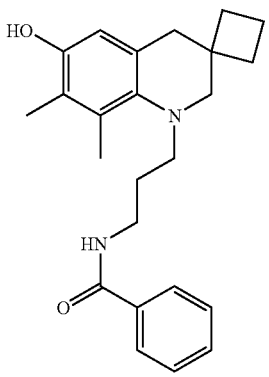

To a solution of 3-(6'-methoxy-7',8'-dimethyl-2',4'-dihydro-1'H-spiro[cyclobutane-1,3'-quinoline]-1'-yl)propan-1-amine (80 mg) prepared as described herein, dissolved in 2 mL dichloromethane, was added benzoic acid (67.6 g), 1,3-dicyclohexylcarbodiimide (68.4 mg), 4-dimethylaminopyridine (18 mg) at room temperature. After 2 hours, more dichloromethane was added and the mixture was filtered. The filtrate was concentrated onto silica gel and purified through a column (Hexane/EtOAc, 10:6-10:7), to give N-(3-(6'-methoxy-7',8'-dimethyl-2',4'-dihydro-1'H-spiro[cyclobutane-1,3'-quinoline]-1'-yl)propyl)benzamide (95 mg). Demethylation as described herein gave N-(3-(6'-hydroxy-7',8'-dimethyl-2',4'-dihydro-1'H-spiro[cyclobutane-1,3'-quinoline]-1'-yl)propyl)benzamide (62.4 mg, Hexane/EtOAc, 10:12 as a light yellow oil.

$^1$H-NMR (300 MHz, $C_2D_6O$) δ=8.10-7.77 (m, 3H); 7.62 (s, 1H); 7.56-7.23 (m, 3H); 6.40 (s, 1H); 3.65-3.32 (m, 2H); 3.08 (s, 2H); 3.03-2.83 (m, 3H); 2.69 (s, 2H); 2.09 (s, 3H); 2.07 (s, 3H); 2.03-1.79 (m, 6H); 1.79-1.59 (m, 2H) ppm. $^{13}$C-NMR (75 MHz, $C_2D_6O$) δ=166.49, 149.45, 139.74, 135.18, 130.97, 129.73, 128.27, 127.05, 126.49, 121.57, 112.75, 59.32, 54.88, 40.78, 38.71, 37.75, 32.26, 28.15, 15.59, 15.16, and 11.66 ppm.

Example 69

Preparation of Additional Compounds

Following the procedures described above the following compounds were prepared from the appropriate 6'-methoxy-spiro-quinolinones and the appropriate halides, followed by demethylation:

1-(4-Chlorophenyl)-6-methoxy-7',8'-dimethyl-2',4'-dihydro-1'H-spiro[cyclobutane-1,3'-quinoline]

$^1$H-NMR (300 MHz, CDCl$_3$): δ=7.14-6.99 (m, 2H); 6.71-6.59 (m, 2H); 6.64 (s, 1H); 3.81 (s, 3H); 3.64 (s, 2H); 2.78 (s, 2H); 2.10 (s, 3H); 1.78 (s, 3H); 1.94-1.58 (m, 6H) ppm. $^{13}$C-NMR, (75MHz, CDCl$_3$) δ=153.8, 150.13, 133.99, 132.01, 129.04, 128.67, 123.98, 123.48, 119.17, 108.96, 61.85, 55.71, 40.86, 40.72, 32.47, 15.9, 15.51, and 12.17 ppm.

1'-(4-Chlorophenyl)-7',8'-dimethyl-2,4'-dihydro-1'H-spiro[cyclobutane-1,3'-quinolin]-6'-ol $^1$H-NMR (300 MHz, CDCl$_3$): δ=7.21-6.97 (m, 2H); 6.78-6.60 (m, 2H); 6.52 (s, 1H); 4.69 (s, 1H); 3.66 (s, 2H); 2.73 (s, 2H); 2.14 (s, 3H); 1.83 (s, 3H); 1.98-1.58 (s, 6H). $^{13}$C-NMR (75MHz, CDCl$_3$) δ=149.98, 149.61, 134.17, 132.15, 129.89, 128.67, 123.42, 121.46, 118.96, 113.28, 61.89, 40.76, 40.29, 32.44, 15.97, 14.47, and 12.2 ppm. MS: (m/z): 328 (M+H$^+$)

6'-Methoxy-1'-(4-methoxyphenyl)-7',8'-dimethyl-2',4'-dihydro-1'H-spiro[cyclobutane-1,3'-quinoline]

$^1$H-NMR (300 MHz, CDCl$_3$): δ=6.76-6.73 (m, 4H); 6.58 (s, 1H); 3.85 (s, 3H); 3.78 (s, 3H); 3.66 (s, 2H); 2.88 (s, 2H); 2.13 (s, 3H); 1.80 (s, 3H); 1.96-1.61 (m, 6H) ppm. $^{13}$C-NMR, (75MHz, CDCl$_3$) δ=153.24, 153.08, 146.23, 135.33, 131.74, 127.71, 123.93, 120.48, 113.99, 108.95, 62.39, 55.72, 55.49, 41.23, 39.62, 32.41, 15.91, 15.64, and 12.18 ppm.

1'-(4-Hydroxyphenyl)-7',8'-dimethyl-2',4'-dihydro-1'H-spiro[cyclobutane-1,3'-quinolin]-6'-ol $^1$H-NMR (300 MHz, CDCl$_3$): δ=6.57 (s, 4H); 6.46 (s, 1H); 3.57 (s, 2H); 2.73 (s, 2H); 2.03 (s, 3H); 1.758 (s, 3H); 1.93-1.53 (m, 6H) ppm. $^{13}$C-NMR, (75 MHz, CDCl$_3$) δ=150.168, 150.097, 145.591, 134.459, 130.956, 127.734, 121.565, 120.214, 114.918, 112.589, 62.191, 40.562, 39.399, 31.964, 14.879, 14.531, and 10.916 ppm.

6'-Methoxy-7',8'-dimethyl-1'-(pyridin-2-yl)-2',4'-dihydro-1'H-spiro[cyclobutane-1,3'-quinoline]

$^1$H-NMR (300 MHz, CDCl$_3$): δ=8.36-8.15 (m, 1H); 7.36-7.21 (m, 1H); 6.67-6.52 (m, 2H); 6.28-6.11 (d, 1H); 4.2-3.9 (s, 2H); 3.82 (s, 3H); 2.74 (s, 2H); 2.15 (s, 3H); 1.87 (s, 3H); 1.86-1.76 (m, 4H); 1.76-1.58 (m, 2H) ppm. $^{13}$C-NMR, (75 MHz, CDCl$_3$) δ=159.75, 154.32, 147.98, 136.84, 132.79, 132.64, 130.7, 123.67, 113.53, 109.9, 108.86, 57.79, 55.68, 41.61, 40.83, 32.63, 15.75, 15.39, and 12.19 ppm.

7',8'-Dimethyl-1'-(pyridin-2-yl)-2',4'-dihydro-1'H-spiro[cyclobutane-1,3'-quinolin]-6'-ol $^1$H-NMR (300 MHz, CDCl$_3$): δ=8.16-7.98 (m, 1H); 7.49-7.26 (m, 1H); 6.69-6.60 (m, 1H); 6.56 (s, 1H); 6.33-6.06 (d, 1H); 4.26-3.58 (s, 2H); 2.62 (s, 2H); 2.09 (s, 3H); 1.81 (s, 3H); 1.99-1.56 (m, 6H). $^{13}$C-NMR, (75 MHz, CDCl$_3$) δ=159.91, 151.98, 146.87, 137.48, 131.94, 131.17, 130.94, 121.57, 113.41, 112.72, 110.32, 58.35, 41.57, 39.71, 32.17, 14.68, 14.26, 10.95 ppm.

1'-(4-Fluorophenyl)-6'-methoxy-7',8'-dimethyl-2',4'-dihydro-1'H-spiro[cyclobutane-1,3'-quinoline]

$^1$H-NMR (300 MHz, CDCl$_3$): δ=6.96-6.80 (m, 2H); 6.79-6.64 (m, 2H); 6.55 (s, 1H); 3.86 (s, 3H); 3.68 (s, 2H); 2.87 (s, 2H); 2.14 (s, 3H); 1.81 (s, 3H); 2.04-1.58 (m, 6H) ppm. $^{13}$C-NMR, (75 MHz, CDCl$_3$) δ=158.18, 155.02, 153.57, 148.34, 148.31, 134.73, 131.8, 128.32, 124.03, 119.87, 119.77, 115.34, 115.05, 108.99, 62.32, 55.71, 41.04, 40.12, 32.45, 15.83, 15.57, 12.14 ppm.

1'-(4-Fluorophenyl)-7',8'-dimethyl-2',4'-dihydro-1'H-spiro[cyclobutane-1,3'-quinolin]-6'-ol $^1$H-NMR (300 MHz, CDCl$_3$): δ=6.99-6.77 (m, 2H); 6.77-6.59 (m, 2H); 6.57-6.35 (m, 1H); 4.56 (s, 1H); 3.64 (s, 2H); 2.76 (s, 2H); 2.12 (s, 3H); 1.78 (s, 3H); 2.00-1.49 (m, 6H) ppm. $^{13}$C-NMR, (75 MHz, CDCl$_3$) δ=157.94, 154.79, 150.28, 148.26, 133.92, 131.63, 128.81, 121.96, 119.45, 119.36, 115.13, 114.84, 112.93, 76.69, 62.22, 40.46, 40.13, 32.34, 15.48, 15.38 and 11.97 ppm.

1'-(4-(tert-Butyldimethylsilyloxy)phenyl)-6'-methoxy-7',8'-dimethyl-2',4'-dihydro-1'H-spiro[cyclobutane-1,3'-quinoline]

$^1$H-NMR (300 MHz, CDCl$_3$): δ=6.66-6.59 (m, 4H); 6.54 (s, 1H); 3.82 (s, 3H); 3.62 (s, 2H); 2.85 (s, 2H); 2.09 (s, 3H); 1.76 (s, 3H); 1.94-1.49 (m, 6H); 0.98 (s, 9H); 0.16 (s, 6H) ppm. $^{13}$C-NMR, (75 MHz, CDCl$_3$) δ=153.18, 148.58, 146.58, 135.37, 131.73, 127.66, 123.91, 120.34, 120.01, 108.93, 62.31, 55.73, 41.21, 39.66, 32.37, 25.76, 18.21, 15.79, 15.58, 12.12 and 4.42 ppm.

4-(6'-Methoxy-7',8'-dimethyl-2',4'-dihydro-1'H-spiro[cyclobutane-1,3'-quinoline]-1'-yl)phenol

$^1$H-NMR (300 MHz, CDCl$_3$): δ=6.82-6.33 (m, 5H); 3.77 (s, 3H); 3.71-3.22 (m, 2H); 2.83 (s, 2H); 2.04 (s, 3H); 1.93-1.48 (m, 9H) ppm. $^{13}$C-NMR, (75 MHz, CDCl$_3$) δ=153.21, 150.86, 145.39, 135.37, 131.01, 127.44, 123.17, 120.68, 115.22, 108.94, 62.18, 54.96, 40.98, 39.31, 32.09, 15.17, 15.14 and 11.39 ppm.

1'-(4-Chlorobenzyl)-5',7'-dimethyl-3',4'-dihydro-1'H-spiro[cyclobutane-1,2'-quinolin]-6'-ol

$^1$H-NMR (300 MHz, CD$_3$OD): δ=7.29 (m, 4H); 5.94 (s, 1H); 4.66 (s, 2H);.3.33 (m, 1H); 2.69 (s, 2H); 2.25 (m, 2H); 2.13 (s, 3H); 2.02 (m, 2H); 2.0 (s, 3H); 1.87 (m, 2H); 1.77 (m, 2H) ppm. $^{13}$C-NMR (75 MHz, CD$_3$OD): δ=143.65; 140.83; 139.29; 131.56; 128.11; 127.57; 123.10; 120.12; 112.90; 58.60; 50.32; 32.95; 32.49; 21.25; 15.93; 12.52; 10.96 ppm. MS m/z 342 (100, M +H)$^+$

4-((6'-Hydroxy-5',7'-dimethyl-3',4'-dihydro-1'H-spiro[cyclobutane-1,2'-quinoline]-1'-yl)methyl)benzoic acid

$^1$H-NMR (300 MHz, CD$_3$OD): δ=8.45 (d, J=1.25 Hz, 2H); 7.39 (d, J=1.25 Hz, 2H); 5.93 (s, 1H); 4.60 (s, 2H); 3.33 (s, 2H); 2.69 (m, 2H); 2.36 (m, 2H); 2.14 (s, 3H); 1.98 (s, 3H); 1.81 (m, 2H); 1.74 (m, 2H) ppm. MS m/z 366 (100, M+H)$^+$

Methyl 4-((6'-hydroxy-5',7'-dimethyl-3',4'-dihydro-1'H-spiro[cyclobutane-1,2'-quinoline]-1'-yl)methyl)benzoate

$^1$H-NMR (300 MHz, CD$_3$OD): δ=7.99 (s, 2H); 7.63(s, 2H); 5.91 (s, 1H); 4.63 (d, J=12 Hz, 2H); 3.90 (s, 3H); 3.33 (m, 2H); 2.71 (m, 2H); 2.34 (m, 2H); 2.14 (s, 3H); 1.98 (m, 2H); 1.75 (m, 2H) ppm. MS m/z 352 (100, M+H)$^+$

Methyl 6'-hydroxy-7',8'-dimethyl-2',4'-dihydro-1'H-spiro[cyclopropane-1,3'-quinoline]-1'-carboxylate

$^1$H-NMR (400 MHz, CDCl$_3$) δ=0.71-0.72 (m, cyclopropyl), 2.11 (s, CH$_3$), 2.35 (s, CH$_3$), 2.69 (s, CH$_2$), 3.57 (s, CH$_2$), 3.87 (s, OCH$_3$), 4.11 (s, CH$_2$), 6.32 (s, Ar-H) ppm. MS: (m/z) 275 (M+H$^+$)

1'-(4-Chlorophenyl)-6'-hydroxy-5',7',8'-trimethyl-1'H-spiro[cyclobutane-1,3'-quinolin]-4'(2'H)-one

$^1$H-NMR (300 MHz, CD$_3$OD): δ=7.15-7.01 (d, J=8.7 Hz, 2H); 6.81-6.65 (d, J=8.7 Hz, 2H); 5.1 (s, 1H); 4.07 (s, 2H); 2.57 (s, 3H); 2.41-2.01 (m, 2H); 2.21 (s, 3H); 2.01-1.91 (m, 4H); 1.82 (s, 3H) ppm.$^{13}$C-NMR (75 MHz, CDCl$_3$) δ=201.83, 149.71, 148.98, 141.54, 130.65, 129.85, 129.31, 125.42, 125.27, 122.22, 120.69, 60.01, 50.97, 30.04, 15.59, 15.17, 13.59 and 13.54 ppm. MS m/z 356.2 (M+H$^+$)

1'-(4-Chlorophenyl)-5',7',8'-trimethyl-2',4'-dihydro-1'H-spiro[cyclobutane-1,3'-quinoline]-4',6'-diol

$^1$H-NMR (300 MHz, CDCl$_3$): δ=7.19-6.98 (d, J=8.1 Hz, 2H); 6.65 (s, 2H); 4.87-4.66 (d, J=5.5 Hz, 1H); 4.55 (s, 1H); 3.97-3.78 (d, J=13 Hz, 1H); 3.66-3.42 (d, J=13 Hz, 1H); 2.38 (s, 3H); 2.30-2.17 (m, 1H); 2.14 (s, 3H); 1.98-1.76 (m, 3H); 1.75 (s, 3H); 1.66-1.49 (m, 1H) ppm. $^{13}$C-NMR (75 MHz, CDCl$_3$) δ=151.04, 148.39, 133.84, 128.85, 127.36, 124.39, 124.13, 120.77, 120.6, 76.74, 70.41, 56.16, 43.71, 29.62, 27.55, 16.32, 15.2, 12.87, and 11.46 ppm.

1'-(4-Methoxyphenyl)-7',8'-dimethyl-2',4'-dihydro-1'H-spiro[cyclobutane-1,3'-quinolin]-6'-ol

$^1$H-NMR (300 MHz, CDCl$_3$): δ=6.78-6.59 (m, 4H); 6.55 (s, 1H); 3.67 (s, 3H); 3.59 (s, 2H); 2.72 (s, 2H); 2.05 (s, 3H); 1.95-1.66 (m, 4H); 1.74 (s, 3H); 1.66-1.47 (m, 2H) ppm. $^{13}$C-NMR (75 MHz, CDCl$_3$) δ=153.14, 150.72, 146.15, 134.22, 131.16, 128.12, 121.49, 119.86, 113.92, 112.97, 62.04, 54.71, 40.54, 39.76, 32.18, 15.13, 15.09, 11.53 ppm.

7',8'-Dimethyl-1'-(4-(methylsulfonyl)phenyl)-2',4'-dihydro-1'H-spiro[cyclobutane-1,3'-quinolin]-6'-ol

$^1$H-NMR (300 MHz, CDCl$_3$): δ=8.11 (s, 1H); 7.75-7.45 (m, 2H); 7.07-6.47 (m, 3H); 3.79 (s, 2H); 2.99 (s, 3H); 2.64 (s, 2H); 2.11 (s, 3H); 1.83 (s, 3H); 1.92-1.52 (m, 6H) ppm. $^{13}$C-NMR (75 MHz, C$_2$D$_6$O): δ=154.036, 152.159, 132.09, 131.58, 131.46, 129.08, 128.62, 121.62, 114.92, 113.17, 60.96, 43.97, 42.06, 39.44, 32.33, 15.08, 14.94, and 11.46 ppm.

Methyl 4-(6'-hydroxy-7',8'-dimethyl-2',4'-dihydro-1'H-spiro[cyclobutane-1,3'-quinoline]-1'-yl)benzoate

$^1$H-NMR (300 MHz, C$_2$D$_6$O): δ=8.04 (s, 1H); 7.96-7.66 (d, J=8.9 Hz, 2H); 7.1-6.33 (m, 3H); 3.78 (s, 3H); 3.75 (s, 2H); 2.63 (s, 2H); 2.11 (s, 3H); 1.83 (s, 3H); 1.92-1.53 (m, 6H) ppm. $^{13}$C-NMR (75 MHz, C$_2$D$_6$O): δ=166.32, 154.2, 151.95, 132.07, 131.98, 131.04, 130.69,121.57, 119.02, 114.98, 113.14, 60.85, 50.81, 41.85, 39.65, 32.32, 15.12, 14.97, 11.51 ppm.

3-(6'-Methoxy-7',8'-dimethyl-2',4'-dihydro-1'H-spiro[cyclobutane-1,3'-quinoline]-1'-yl)benzoic acid

$^1$H-NMR (300 MHz, CDCl$_3$): δ=7.74-7.38 (m, 2H); 7.37-7.09 (m, 1H); 7.03-6.74 (m, 1H); 6.61 (s, 1H); 3.86 (s, 3H); 3.76 (s, 2H); 2.81 (s, 2H); 2.14 (s, 3H); 1.82 (s, 3H); 2.04-1.46 (m, 6H) ppm. $^{13}$C-NMR (75 MHz, C$_2$D$_6$O): δ=172.89, 153.93, 151.39, 133.66, 131.94, 130.01, 129.47, 128.81, 124.04, 122.69, 120.49, 118.95, 109.09, 61.79, 55.74, 41.05, 40.78, 32.5, 15.95, 15.48, and 12.19 ppm.

3-(6'-Hydroxy-7',8'-dimethyl-2',4'-dihydro-1'H-spiro[cyclobutane-1,3-quinoline]-1'-yl)benzoic acid

$^1$H-NMR (300 MHz, CDCl$_3$): δ=7.42 (s, 1H); 7.50-7.31 (m, 2H); 7.29-7.14 (t, J=8.1 Hz, 1H); 7.00-6.81 (d, J=7.7 Hz, 1H); 6.63 (s, 1H); 3.74 (s, 2H); 2.69 (s, 2H); 2.09 (s, 3H); 1.77 (s, 3H); 1.91-1.41 (m, 6H) ppm. $^{13}$C-NMR (75 MHz, C$_2$D$_6$O): δ=167.38, 151.44, 151.41, 132.72, 131.58, 131.21, 129.95, 128.76, 121.55, 121.26, 11962, 117.94, 113.16, 61.44, 41.16, 39.99, 32.23, 15.11, 15.01, and 11.5 ppm.

7',8'-Dimethyl-1'-p-tolyl-2',4'-dihydro-1'H-spiro[cyclobutane-1,3'-quinolin]-6'-ol

$^1$H-NMR (300 MHz, C$_2$D$_6$O): δ=6.98-6.84 (d, J=8.22 Hz, 2H); 6.68-6.54 (m, 3H); 3.64 (s, 3H); 2.69 (s, 2H); 2.18 (s, 3H); 2.08 (s, 3H); 1.76 (s, 3H); 1.91-1.67 (m, 4H); 1.67-1.52 (m, 2H) ppm. $^{13}$C-NMR (75 MHz, C$_2$D$_6$O): δ=150.86, 149.58, 133.72, 131.49, 129.18, 128.92, 127.59, 121.34, 117.94, 113.01, 112.89, 61.61, 40.48, 40.39, 32.24, 19.76, 15.16, 15.09, and 11.56 ppm.

1'-(3-Hydroxyphenyl)-7',8'-dimethyl-2',4'-dihydro-1'H-spiro[cyclobutane-1,3'-quinolin]-6-ol

$^1$H-NMR (300 MHz, C$_2$D$_6$O): δ=7.94 (s, 1H); 7.84 (s, 1H); 6.99-6.85 (t, J=8 Hz, 1H); 6.59 (s, 1H); 6.335-6.18 (m, 2H); 6.18-6.02 (m, 1H); 3.65 (s, 2H); 2.66 (s, 2H); 2.08 (s, 3H); 1.79 (s, 3H); 1.92-1.49 (m, 6H) ppm. $^{13}$C-NMR (75 MHz, C$_2$D$_6$O): δ=157.94, 152.9, 151.1, 133.56, 131.98, 129.64, 129.37, 121.28, 112.91, 109.08, 105.92, 104.42, 61.32, 40.99, 40.19, 32.31, 15.04, and 11.55 ppm 4-(6'-Hydroxy-7',8'-dimethyl-2',4'-dihydro-1'H-spiro[cyclobutane-1,3'-quinoline]-1'-yl)benzoic acid $^1$H-NMR (300 MHz, C$_2$D$_6$O): δ=7.94-7.70 (d, J=8.66 Hz, 2H); 6.94-6.47 (m, 3H); 3.77 (s, 2H); 2.64 (s, 2H); 2.11 (s, 3H); 1.80 (s, 3H); 1.94-1.75 (m, 4H); 1.74-1.56 (m, 2H) ppm. $^{13}$C-NMR (75 MHz, C$_2$D$_6$O): δ=167.132, 154.23, 151.92, 132.08, 132.04, 131.02, 121.53, 119.25, 114.94, 113.09, 60.87, 41.87, 39.65, 32.32, 15.08, 14.95, and 11.47 ppm.

7',8'-Dimethyl-1'-(6-(piperazin-1-yl)pyridin-3-yl)-2',4'-dihydro-1'H-spiro[cyclobutane-1,3'-quinolin]-6'-ol $^1$H-NMR (300 MHz, C$_2$D$_6$O): δ=7.28-7.06 (t, J=8 Hz, 1H); 6.60 (d, J=1 Hz, 1H); 6.18-5.92 (d, J=8 Hz, 1H); 5.56-5.40 (d, J=8 Hz, 1H); 4.97-3.62 (m, 2H); 3.62-3.34,(m, 4H); 3.06-2.77 (m, 4H); 2.59 (s, 2H); 2.11 (s, 3H); 1.90 (s, 3H); 1.88-1.59 (m, 6H) ppm. $^{13}$C-NMR (75 MHz, C$_2$D$_6$O): δ=138.76, 157.91, 151.84, 138.35, 132.93, 132.85, 131.15, 120.93, 112.64, 97.53, 95.61, 56.67, 54.11, 46.1, 45.8, 41.96, 40.29, 33.01, 15.11, 14.77, and 11.44 ppm.

7',8'-Dimethyl-1'-(pyridin-3-yl)-2',4'-dihydro-1'H-spiro[cyclobutane-1,3'-quinolin]-6'-ol $^1$H-NMR (300 MHz, C$_2$D$_6$O): δ=8.053 (s, 1H); 8.02-7.97 (s, 1H); 7.97-7.89 (d1H); 7.14-7.04 (m, 1H); 7.034-6.90 (m, 1H); 6.63 (s, 1H); 3.73 (s, 2H); 2.71 (s, 2H); 2.09 (s, 3H); 1.79 (s, 3H); 1.97-1.59 (m, 6H). $^{13}$C-NMR (75 MHz, C$_2$D$_6$O): δ=152.88, 148.55, 140.55, 140.45, 133.13, 132.55, 131.26, 144.63, 124.49, 122.87, 114.38, 62.31, 42.21, 41.07, 33.45, 16.23, and 12.65 ppm 1'-(6-(Dimethylamino)pyridin-3-yl)-7',8'-dimethyl-2',4'-dihydro-1'H-spiro[cyclobutane-1,3'-quinolin]-6'-ol $^1$H-NMR (300 MHz, C$_2$D$_6$O): δ=7.79 (s, 1H); 7.72-7.60 (m, 1H); 7.08-6.92 (m, 1H); 6.54 (s, 1H); 6.52-6.42 (d, J=8 Hz, 1H); 3.56 (s, 2H); 2.96 (s, 6H); 2.79 (s, 2H); 2.03 (s, 3H); 1.79 (s, 3H); 1.94-1.71 (m, 4H); 1.71-1.55 (m, 2H) ppm. $^{13}$C-NMR (75 MHz, C$_2$D$_6$O): δ=156.59, 152.85, 141.93, 141.84, 136.24, 132.68, 131.65, 129.63, 123.86, 115.26, 107.71, 64.33, 42.71, 41.21, 39.85, 34.33, 17.37, 17.28, and 13.64 ppm.

2-tert-butoxy-6-(6'-methoxy-7',8'-dimethyl-2',4'-dihydro-1'H-spiro[cyclobutane-1,3'-quinoline]-1'-yl)pyridin-3-ol $^1$H-NMR (300 MHz, CDCl$_3$) δ=6.99-6.75 (d, J=8.1 Hz, 1H); 6.55 (s, 1H); 5.85-5.62 (d, J=8.3 Hz, 1H); 4.95 (s, 1H); 3.89 (s, 2H); 3.82 (s, 3H); 2.80 (s, 2H); 2.11 (s, 3H); 1.87 (s, 3H); 1.84-1.75 (m, 6H); 1.61 (s, 9H) ppm 1'-(5-hydroxypyridin-2-yl)-7',8'-dimethyl-2',4'-dihydro-1'H-spiro[cyclobutane-1,3'-quinolin]-6'-ol $^1$H-NMR (300 MHz, DMSO+CDCl$_3$) δ=7.87-7.61 (d, J=3 Hz, 1H); 7.00-6.79 (m, 1H); 6.507 (s, 1H); 6.1355.09 (d, J=8.9 Hz, 1H); 3.82 (s, 2H); 2.63 (s, 2H); 1.99 (s, 3H); 1.68 (s, 3H); 1.88-1.48 (m, 6H) ppm. $^{13}$C-NMR (75 MHz, DMSO) δ=153.9, 151.71, 146.81, 134.76, 132.61, 131.87, 129.38, 125.28, 121.3, 113.28, 110.57, 58.02, 32.51, 15.75, 15.39, and 12.58 ppm.

1'-(4-Hydroxyphenyl)-7',8'-dimethyl-3',4'-dihydro-1'H-spiro[cyclopropane-1,2'-quinolin]-6'-ol $^1$HNMR (400 MHz, CDCl$_3$) δ=6.63 (d, 2H, J=8.8 Hz), 6.59 (d, 2H, J=9.2 Hz), 6.49 (s, 1H), 2.71 (t, 2H, J=7.2 Hz), 1.97 (s, 3H), 1.74 (s, 3H), 1.70-1.64 (m, 2H), 0.85 (s, br, 2H), and 0.55 (s, 2H) ppm. MS: m/z =296 (M+H$^+$).

1',7',8'-Trimethyl-3',4'-dihydro-1'H-spiro[cyclopropane-1,2'-quinolin]-6'-ol

MS: m/z=218 (M+H$^+$).

Methyl 2-(6'-hydroxy-7',8'-dimethyl-2',4'-dihydro-1'H-spiro[cyclopropane-1,3'-quinoline]-1'-yl)acetate $^1$HNMR (400 MHz, CDCl$_3$) δ=6.31 (s, 1H), 4.11 (s, 2H), 3.87 (s, 3H), 3.57 (s, 2H), 2.69 (s, 2H), 2.27 (s, 3H), 2.11 (s, 3H), 0.73 (d, 4H) ppm. MS: m/z 276 (M+H$^+$).

7',8'-Dimethyl-2',4'-dihydro-1'H-spiro[cyclopropane-1,3'-quinolin]-6'-ol $^1$HNMR (400 MHz, CDCl$_3$) δ=6.33 (s, 1H), 3.02 (s, 2H), 2.60 (s, 2H), 2.17 (s, 3H), 2.07 (s, 3H), 0.53 (t, 2H, J=3.6 Hz), 0.49 (t, 2H, J=3.6 Hz) ppm. MS: m/z=204 (M+H$^+$).

1',7',8'-Trimethyl-2',4'-dihydro-1'H-spiro[cyclopropane-1,3'-quinolin]-6'-ol $^1$HNMR (400 MHz, CDCl$_3$) δ=6.35 (s, 1H), 2.94 (s, 2H), 2.75 (s, 3H), 2.69 (s, 2H), 2.25 (s, 3H), 2.15 (s, 3H), 0.56 (t, 2H, J=4.8 Hz), 0.48 (t, 2H, J=4.8 Hz) ppm. MS: m/z=218 (M+H$^+$).

Example 70

5-Lipoxygenase Enzyme Assay

This procedure was used for measuring the enzymatic activity of human recombinant 5-Lipoxygenase using a colorimetric method based on the ferric oxidation of xylenol orange.

Materials 96 well flat bottom microfilter plates (VWR, Catalog # 62402-933 9295)

Lipoxygenase screening assay buffer (Cayman, Catalog # 760710)

Human recombinant 5-Lipoxygenase (Cayman, Catalog # 60402)

Arachidonic Acid (Sigma, Catalog # A3555)

Xylenol orange tetra sodium salt (Aldrich, Catalog # 227854)

Iron (II) sulfate heptahydrate (Sigma, Catalog # F7002)

Sulfuric acid (95-98%) [18 M]

Methanol

Procedure

Human recombinant 5-Lipoxygenase (Cayman Cat # 60402) was used in this assay. The test compound and/or vehicle was added to 0.5 µL 5-Lipoxygenase in 50 mM Tris-HCl buffer, pH 7.4. The reaction was initiated by addition of 70 µM arachidonic acid in Tris-HCl buffer, pH 7.4, and terminated after a 10 minute incubation at room temperature by addition of FOX reagent (25 mM sulfuric acid, 100 µM xylenol orange, 100 µM iron (II) sulfate, methanol:water 9:1). The yellow color of acidified xylenol orange was converted to a blue color by the lipid hydroperoxide-mediated oxidation of $Fe^{2+}$ ions and the interaction of the resulting $Fe^{3+}$ ions with the dye. The complex was allowed to form during a 1 hour incubation at room temperature with shaking. Absorbance of the $Fe^{3+}$ complex was then measured at 620 nM using a spectrophotometer.

Negative controls contained enzyme during the incubation step but substrate was not added until after the FOX reagent. Compounds were screened at 5 concentrations in triplicate starting at 10 µM Certain compounds of the present invention such as:
5,7,8-trimethyl-3,4-dihydrospiro[chromene-2,1'-cyclobutan]-6-ol;
5-chloro-7,8-dimethyl-3,4-dihydrospiro[chromene-2,1'-cyclobutan]-6-ol;
5',7',8'-trimethyl-2',3'-dihydrospiro[cyclobutane, 1,4'-thiochromen]-6'-ol;
7-chloro-5,8-dimethyl-3,4-dihydrospiro[chromene-2,1'-cyclobutan]-6-ol;
5,7,8-trimethyl-3,4-dihydrospiro[chromene-2,1'-cyclopropan]-6-ol;
5,8-dimethyl-7-(3-methylbutyl)-3,4-dihydrospiro[chromene-2,1'-cyclobutan]-6-ol;
2',2',5',7',8'-pentamethyl-2',3'-dihydrospiro[cyclobutane-1,4'-thiochromen]-6'-ol;
5,7-dimethyl-3,4-dihydrospiro[chromene-2,1'-cyclobutan]-6-ol;
8-chloro-5,7-dimethyl-3,4-dihydrospiro[chromene-2,1'-cyclobutan]-6-ol;
8-chloro-5-methyl-3,4-dihydrospiro[chromene-2,1'-cyclobutan]-6-ol;
8-isopropyl-5-methyl-3,4-dihydrospiro[chromene-2,1'-cyclobutan]-4-ol;
7-chloro-5,8-dimethyl-3,4-dihydrospiro[chromene-2,1'-cyclobutan]-6-yl (dimethylamino)acetate;
7,8-dimethylspiro[chroman-3,1'-cyclopropan]-6-ol;
6'-hydroxy-5',7',8'-trimethylspiro[cyclobutane-1,2'-thiochromen]-4'(3'H)-one;
5',7',8'-trimethyl-3',4'-dihydrospiro[cyclobutane-1,2'-thiochromen]-6'-ol;
5,7,8-trimethylspiro[chroman-3,1'-cyclobutane]-4,6-diol;
6'-hydroxy-5',7',8'-trimethylspiro[cyclobutane-1,2'-thiochroman]-4'(3'H)-one O-methyloxime;
4'-(methoxyamino)-5',7',8'-trimethyl-3',4'-dihydrospiro[cyclobutane-1,2'-thiochromen]-6'-ol;
7-chloro-5,8-dimethyl-3,4-dihydrospiro[chromene-2,1'-cyclobutan]-6-yl nicotinate;
5,7,8-trimethylspiro[chroman-3,1'-cyclobutan]-6-ol;
4-methoxy-5,7,8-trimethylspiro[chroman-3,1'-cyclobutan]-6-ol;
5',7',8'-trimethyl-3',4'-dihydrospiro[cyclobutane-1,2'-thiochromen]-6'-yl (dimethylamino)acetate;
5,7,8-trimethyl-3,4-dihydrospiro[chromene-2,1'-cyclobutan]-6-yl (dimethylamino)acetate;
6-hydroxy-5,7,8-trimethylthiochroman-4-yl phenylcarbamate;
5',7',8'-trimethylspiro[cyclobutane-1,2'-thiochromen]-6'-ol;
4-ethoxy-5,7,8-trimethylspiro[chroman-3,1'-cyclobutan]-6-ol;
4-(methoxyamino)-5,7,8-trimethyl-3,4-dihydrospiro[chromene-2,1'-cyclobutan]-6-ol;
5,7,8-trimethyl-3,4-dihydrospiro[chromene-2,1'-cyclobutan]-6-yl 1H-imidazole-1-carboxylate;
4-(hexylamino)-5,7,8-trimethylspiro[chroman-3,1'-cyclobutan]-6-ol;
3-(hydroxymethyl)-5,7,8-trimethylspiro[chromene-2,1'-cyclobutan]-6-ol;
4-(aminomethyl)-5,7,8-trimethylspiro[chromene-2,1'-cyclobutan]-6-ol;
3-(methoxymethyl)-5,7,8-trimethylspiro[chromene-2,1'-cyclobutan]-6-ol;
6-hydroxy-5,7,8-trimethyl-3,4-dihydrospiro[chromene-2,1'-cyclobutane]-4-carbonitrile;
methyl {[(6-hydroxy-5,7,8-trimethyl-3,4-dihydrospiro[chromene-2,1'-cyclobutan]-3-yl)methyl]thio}acetate;
4-ethoxy-5,7,8-trimethyl-3,4-dihydrospiro[chromene-2,1'-cyclobutan]-6-ol;
7,8-dimethyl-3,4-dihydrospiro[chromene-2,1'-cyclobutan]-6-ol;
7,8-dimethylspiro[chroman-3,1'-cyclobutan]-6-ol;
4-methoxy-5,7-dimethyl-3,4-dihydrospiro[chromene-2,1'-cyclobutan]-6-ol;
4-ethoxy-5,7-dimethyl-3,4-dihydrospiro[chromene-2,1'-cyclobutan]-6-ol;
4-(methoxyamino)-5,7-dimethyl-3,4-dihydrospiro[chromene-2,1'-cyclobutan]-6-ol;
4-isopropoxy-5,7-dimethyl-3,4-dihydrospiro[chromene-2,1'-cyclobutan]-6-ol;
5,7-dimethylspiro[chroman-3,1'-cyclobutan]-6-ol;
3-(1-methoxyethyl)-5,7,8-trimethylspiro[chromene-2,1'-cyclobutan]-6-ol;
8-(methoxymethyl)-5,7-dimethyl-3,4-dihydrospiro[chromene-2,1'-cyclobutan]-6-ol;
4-(cyclopentyloxy)-5,7,8-trimethyl-3,4-dihydrospiro[chromene-2,1'-cyclobutane]-6-diol;
4-(ethoxyamino)-5,7,8-trimethyl-3,4-dihydrospiro[chromene-2,1'-cyclobutan]-6-ol;
4-(isopropylthio)-5,7,8-trimethyl-3,4-dihydrospiro[chromene-2,1'-cyclobutan]-6-ol;
4'-(ethoxyamino)-5',7',8'-trimethyl-3',4'-dihydrospiro[cyclobutane-1,2'-thiochromen]-6'-ol;
4'-(ethoxyamino)-5',7'-dimethyl-3',4'-dihydrospiro[cyclobutane-1,2'-thiochromen]-6'-ol;
4-(ethoxyamino)-5,7-dimethyl-3,4-dihydrospiro[chromene-2,1'-cyclobutan]-6-ol;
4'-(methoxyamino)-5',7'-dimethyl-3',4'-dihydrospiro[cyclobutane-1,2'-thiochromen]-6'-ol;
4-(hydroxyamino)-5,7,8-trimethyl-3,4-dihydrospiro[chromene-2,1'-cyclobutan]-6-ol;
8-[(methoxyamino)methyl]-5,7-dimethyl-3,4-dihydrospiro[chromene-2,1'-cyclobutan]-6-ol
5,7-dimethyl-8-vinyl-3,4-dihydrospiro[chromene-2,1'-cyclobutan]-6-ol;
4-[hydroxy(methyl)amino]-5,7,8-trimethyl-3,4-dihydrospiro[chromene-2,1'-cyclobutan]-6-ol;
6-hydroxy-5,7-dimethylspiro[chromene-2,1'-cyclobutan]-4(3H)-one oxime;
8-[(ethoxyamino)methyl]-5,7-dimethyl-3,4-dihydrospiro[chromene-2,1'-cyclobutan]-6-ol;
7-tert-butyl-3,4-dihydrospiro[chromene-2,1'-cyclobutan]-6-ol;
4-[methoxy(methyl)amino]-5,7-dimethyl-3,4-dihydrospiro[chromene-2,1'-cyclobutan]-6-ol;
6-hydroxy-5,7-dimethylspiro[chromene-2,1'-cyclobutan]-4(3H)-one O-methyloxime;
(4E)-6-hydroxy-5,7-dimethylspiro[chromene-2,1'-cyclobutan]-4(3H)-one O-ethyloxime;
(4Z)-6-hydroxy-5,7-dimethylspiro[chromene-2,1'-cyclobutan]-4(3H)-one O-ethyloxime;
5-ethyl4-(methoxyamino)-7,8-dimethyl-3,4-dihydrospiro[chromene-2,1'-cyclobutan]-6-ol;
4-(ethoxyamino)-5-ethyl-7,8-dimethyl-3,4-dihydrospiro[chromene-2,1'-cyclobutan]-6-ol;
N-(6-hydroxy-5,7,8-trimethyl-3,4-dihydrospiro[chromene-2,1'-cyclobutan]-4-yl)acetamide;
5-ethyl-6-hydroxy-7,8-dimethylspiro[chromene-2,1'-cyclobutan]-4(3H)-one O-methyloxime;
5-ethyl-6-hydroxy-7,8-dimethylspiro[chromene-2,1'-cyclobutan]-4(3H)-one O-ethyloxime;
6'-hydroxy-5',7',8'-trimethylspiro[cyclobutane-1,2'-thiochromen]-4'(3'H)-one O-methyloxime;

6'-hydroxy-5',7',8'-trimethylspiro[cyclobutane-1,2'-thiochromen]-4'(3'H)-one O-ethyloxime;
6'-hydroxy-5',7'-dimethylspiro[cyclobutane-1,2'-thiochromen]-4'(3'H)-one O-methyloxime;
methyl 3-(6-hydroxy-5,7-dimethyl-3,4-dihydrospiro[chromene-2,1'-cyclobutan]-8-yl)-4,5-dihydroisoxazole-5-carboxylate;
6'-hydroxy-5',7'-dimethylspiro[cyclobutane-1,2'-thiochromen]-4'(3'H)-one O-ethyloxime;
N-(6-hydroxy-5,7,8-trimethyl-3,4-dihydrospiro[chromene-2,1'-cyclobutan]-4-yl)butanamide;
5,7-diethyl-6-hydroxyspiro[chromene-2,1'-cyclobutan]-4(3H)-one O-methyloxime;
5,7-diethyl-6-hydroxyspiro[chromene-2,1'-cyclobutan]-4(3H)-one O-ethyloxime;
5,7-diethyl-6-hydroxyspiro[chromene-2,1'-cyclobutan]-4(3H)-one oxime;
(4S)-4-(methoxyamino)-5,7-dimethyl-3,4-dihydrospiro[chromene-2,1'-cyclobutan]-6-ol;
(4R)-4-(methoxyamino)-5,7-dimethyl-3,4-dihydrospiro[chromene-2,1'-cyclobutan]-6-ol;
5,7-dimethyl-8-(5-butyl-isoxazol-3-yl)-3,4-d ihydrospiro[chromene-2,1'-cyclobutan]-6-ol;
4-(ethoxyamino)-5,7-diethyl-3,4-dihydrospiro[chromene-2,1'-cyclobutan]-6-ol;
4-(methoxyamino)-5,7-diethyl-3,4-dihydrospiro[chromene-2,1'-cyclobutan]-6-ol;
5,7-dimethylspiro[chromene-2,1'-cyclobutan]-6-ol;
6-hydroxy-5,7-dimethylspiro[chromene-2,1'-cyclobutane]-3-carbaldehyde O-ethyloxime;
3-[(ethoxyamino)methyl]-5,7-dimethylspiro[chromene-2,1'-cyclobutan]-6-ol;
7-tert-butyl-5-methyl-3,4-dihydrospiro[chromene-2,1'-cyclobutan]-6-ol;
5,7-dimethyl-8-(1,3-oxazol-5-yl)-3,4-dihydrospiro[chromene-2,1'-cyclobutan]-6-ol;
N-(6-hydroxy-5,7-dimethyl-3,4-dihydrospiro[chromene-2, 1'-cyclobutan]-4-yl)benzenesulfonamide;
5,7-diisopropyl-3,4-dihydrospiro[chromene-2,1'-cyclobutan]-6-ol;
6-hydroxy-5,7-diisopropyl-3,4-dihydrospiro[chromene-2,1'-cyclobutane]-8-carbaldehyde;
5,7-dimethyl-3-(1,3-oxazol-5-yl)spiro[chromene-2,1'-cyclobutan]-6-ol;
5,7-diisopropyl-8-[(methoxyamino)methyl]-3,4-dihydrospiro[chromene-2,1'-cyclobutan]-ol;
5-(3,7-dimethylocta-2,6-dienyl)-7,8-dimethylspiro[chroman-2,1'-cyclobutan]-6-ol;
5,7-diethyl-3,4-dihydrospiro[chromene-2,1'-cyclobutan]-6-ol;
7-isopropyl-4-(methoxyamino)-5-methyl-3,4-dihydrospiro[chromene-2,1'-cyclobutan]-6-ol;
5,7-dimethyl-3-(-(4,5-dimethyl-1H-imidazol-2-yl)spiro[chromene-2,1'-cyclobutan]-6-ol;
7-ethyl4-(methoxyamino)-5-methyl-3,4-dihydrospiro[chromene-2,1'-cyclobutan]-6-ol;
5-ethyl4-(methoxyamino)-7-methyl-3,4-dihydrospiro[chromene-2,1'-cyclobutan]-6-ol;
(Z)-5,7-diethyl-8-(hydroxymethyl)-3,4-dihydrospiro[chromene-2,1'-cyclobutan]-6-ol;
5,7-diethyl-8-(hydroxymethyl)-3,4-dihydrospiro[chromene-2,1'-cyclobutan]-6-ol;
7-isopropyl-5-methyl-3,4-dihydrospiro[chromene-2,1'-cyclobutan]-6-ol;
8-(hydroxymethyl)-7-isopropyl-5-methylspiro[chroman-2,1'-cyclobutan]-6-ol;
5,7-dimethyl-3-(oxazol-5-yl)spiro[chroman-2,1'-cyclobutan]-6-ol;
7-isopropyl-5-methylspiro[chroman-2,1'-cyclobutane]-4,6-diol;
7-isopropyl-5-methylspiro[chromene-2,1'-cyclobutane]-6-ol;
7-isopropyl-4-methoxy-5-methylspiro[chroman-2,1'-cyclobutan]-6-ol;
5,7-diethylspiro[chromene-2,1'-cyclobutan]-6-ol;
5,7-diisopropylspiro[chromene-2,1'-cyclobutan]-6-ol;
methyl 2-((5,7-diethyl-6-hydroxyspiro[chroman-2,1'-cyclobutane]-3-yl)methylthio)acetate;
(S)-5,7-diethylspiro[chroman-2,1'-cyclobutane]-4,6-diol;
(R)-5,7-diethylspiro[chroman-2,1'-cyclobutane]-4,6-diol;
(S)-7-isopropyl-5-methylspiro[chroman-2,1'-cyclobutane]-4,6-diol;
(R)-7-isopropyl-5-methylspiro[chroman-2,1'-cyclobutane]-4,6-diol;
5,7-diethylspiro[chroman-3,1'-cyclobutane]-4,6-diol;
1'-(4-chlorophenyl)-5',7',8'-trimethyl-2',4'-dihydro-1'H-spiro[cyclobutane-1,3'-quinoline]-4',6'-diol;
1'-(4-hydroxyphenyl)-7',8'-dimethyl-2',4'-dihydro-1'H-spiro[cyclobutane-1,3'-quinolin]-6'-ol;
4-(6'-methoxy-7',8'-dimethyl-2',4'-dihydro-1'H-spiro[cyclobutane-1,3'-quinoline]-1'-yl)phenol;
7',8'-dimethyl-1'-p-tolyl-2',4'-dihydro-1'H-spiro[cyclobutane-1,3'-quinolin]-6'-ol;
1'-(3-hydroxyphenyl)-7',8'-dimethyl-2',4'-dihydro-l'H-spiro[cyclobutane-1,3'-quinolin]-6'-ol; 7',8'-dimethyl-1'-(4-(methylsulfonyl)phenyl)-2',4'-dihydro-1'H-spiro[cyclobutane-1,3'-quinolin]-6'-ol;
methyl 4-(6'-hydroxy-7',8'-dimethyl-2',4'-dihydro-1'H-spiro[cyclobutane-1,3'-quinoline]-1'-yl)benzoate;
7',8'-dimethyl-1'-(6-(piperazin-1-yl)pyridin-3-yl)-2',4'-dihydro-1'H-spiro[cyclobutane-1,3'-quinolin]-6'-ol;
1'-(4-chlorobenzyl)-5',7'-dimethyl-3',4'-dihydro-1'H-spiro[cyclobutane-1,2'-quinolin]-6'-ol;
1'-(4-hydroxyphenyl)-7',8'-dimethyl-3',4'-dihydro-1'H-spiro[cyclopropane-1,2'-quinolin]-6'-ol;
methyl 2-(6'-hydroxy-7',8'-dimethyl-2',4'-dihydro-1'H-spiro[cyclopropane-1,3'-quinoline]-1'-yl)acetate;
methyl 4-((6'-hydroxy-5',7'-dimethyl-3',4'-dihydro-1'H-spiro[cyclobutane-1,2'-quinoline]-1'-yl)methyl)benzoate;
1'-(6-(dimethylamino)pyridin-3-yl)-7',8'-dimethyl-2',4'-dihydro-1'H-spiro[cyclobutane-1,3'-quinolin]-6'-ol;
5',7'-dimethyl-1'-(quinolin-2-ylmethyl)-3',4'-dihydro-1'H-spiro[cyclobutane-1,2'-quinolin]-6'-ol;
N-(2-(6'-hydroxy-7',8'-dimethyl-2',4'-dihydro-1'H-spiro[cyclobutane-1,3'-quinoline]-1'-yl)ethyl)-4-propylbenzenesulfonamide;
N-(2-(6'-hydroxy-7',8'-dimethyl-2',4'-dihydro-l'H-spiro[cyclobutane-1,3'-quinoline]-1'-yl)ethyl)-4-methylbenzenesulfonamide;
1'-(5-hydroxypyridin-2-yl)-7',8'-dimethyl-2',4'-dihydro-1'H-spiro[cyclobutane-1,3'-quinolin]-6'-ol;
N-(3-(6'-hydroxy-7',8'-dimethyl-2',4'-dihydro-1'H-spiro[cyclobutane-1,3'-quinoline]-1'-yl)propyl)-4-propylbenzenesulfonamide;
N-(3-(6'-hydroxy-7',8'-dimethyl-2',4'-dihydro-1'H-spiro[cyclobutane-1,3'-quinoline]-1'-yl)propyl)-4-methylbenzenesulfonamide;
N-(3-(6'-hydroxy-7',8'-dimethyl-2',4'-dihydro-1'H-spiro[cyclobutane-1,3'-quinoline]-1'-yl)propyl)benzamide;

were considered to be active when they exhibited inhibition of 5-Lipoxygenase with an $IC_{50}$ in a range of less than about 0.3 µM.

Example 71

12/15-Lipoxygenase Enzyme Assay

This procedure was used for measuring the enzymatic activity of porcine leukocyte 12/15-Lipoxygenase using a calorimetric method based on the ferric oxidation of xylenol orange.

Materials
- 96 well flat bottom microfilter plates (VWR, Catalog # 62402-933 9295)
- Lipoxygenase screening assay buffer (Cayman, Catalog # 760710)
- Porcine leukocyte 12/15-Lipoxygenase (Cayman, Catalog # 60300)
- Arachidonic Acid (Sigma, Catalog # A3555)
- Xylenol orange tetrasodium salt (Aldrich, Catalog # 227854)
- Iron (II) sulfate heptahydrate (Sigma, Catalog # F7002)
- Sulfuric acid (95-98%) [18M]
- Methanol Procedure Porcine Leukocyte 12/15-Lipoxygenase (Cayman Cat # 60300) was used in this assay. Test compound and/or vehicle was added to 1.3 µL 12/15-Lipoxygenase in 50 mM Tris-HCl buffer, pH 7.4. The reaction was initiated by addition of 70 µM arachidonic acid in Tris-HCl buffer, pH 7.4, and terminated after a 10 minute incubation at room temperature by addition of FOX reagent (25 mM sulfuric acid, 100 µM xylenol orange, 100 µM iron (II) sulfate, methanol:water 9:1). The yellow color of acidified xylenol orange was converted to a blue color by the lipid hydroperoxide-mediated oxidation of $Fe^{2+}$ ions and the interaction of the resulting $Fe^{3+}$ ions with the dye. The complex was allowed to form during a 1 hour incubation at room temperature with shaking. Absorbance of the $Fe^{3+}$ complex was then measured at 620 nM using a spectrophotometer.

Negative controls contained enzyme during the incubation step but substrate was not added until after the FOX reagent. Compounds are screened at 5 concentrations in triplicate starting at 10 µM Certain compounds of the present invention such as:
- 5,7,8-trimethyl-3,4-dihydrospiro[chromene-2,1'-cyclobutan]-6-ol;
- 5-chloro-7,8-dimethyl-3,4-dihydrospiro[chromene-2,1'-cyclobutan]-6-ol;
- 5',7',8'-trimethyl-2',3'-dihydrospiro[cyclobutane, 1,4'-thiochromen]-6'-ol
- 7-chloro-5,8-dimethyl-3,4-dihydrospiro[chromene-2,1'-cyclobutan]-6-ol;
- 5,7,8-trimethyl-3,4-dihydrospiro[chromene-2,1'-cyclopropan]-6-ol;
- 5,8-dimethyl-7-(3-methylbutyl)-3,4-dihydrospiro[chromene-2,1'-cyclobutan]-6-ol;
- 2',2',5',7',8'-pentamethyl-2',3'-dihydrospiro[cyclobutane-1,4'-thiochromen]-6'-ol;
- 5,7-dimethyl-3,4-dihydrospiro[chromene-2,1'-cyclobutan]-6-ol;
- 8-chloro-5,7-dimethyl-3,4-dihydrospiro[chromene-2,1'-cyclobutan]-6-ol;
- 8-chloro-5-methyl-3,4-dihydrospiro[chromene-2,1'-cyclobutan]-6-ol;
- 5',7',8'-trimethyl-3',4'-dihydrospiro[cyclobutane-1,2'-thiochromen]-6'-ol
- 6'-hydroxy-5',7',8'-trimethylspiro[cyclobutane-1,2'-thiochroman]-4'(3'H)-one O-methyloxime;
- 4'-(methoxyamino)-5',7',8'-trimethyl-3',4'-dihydrospiro[cyclobutane-1,2'-thiochromen]-6'-ol;
- 5,7,8-trimethylspiro[chroman-3,1'-cyclobutan]-6-ol;
- 6-hydroxy-5,7,8-trimethylthiochroman-4-yl phenylcarbamate;
- 5,7,8-trimethyl-3,4-dihydrospiro[chromene-2,1'-cyclobutan]-6-yl-2-(4-methylpiperazin-1-yl)acetate;
- 6-hydroxy-5,7-dimethylspiro[chromene-2,1'-cyclobutane]-3-carbaldehyde O-methyloxime;
- 5',7',8'-trimethylspiro[cyclobutane-1,2'-thiochromen]-6'-ol;
- methyl {[(6-hydroxy-5,7,8-trimethyl-3,4-dihydrospiro[chromene-2,1'-cyclobutan]-3-yl)methyl]thio}acetate;
- 4-ethoxy-5,7,8-trimethyl-3,4-dihydrospiro[chromene-2,1'-cyclobutan]-6-ol;
- 7,8-dimethyl-3,4-dihydrospiro[chromene-2,1'-cyclobutan]-6-ol;
- 5,7-dimethylspiro[chroman-3,1'-cyclobutan]-6-ol;
- 3-(1-methoxyethyl)-5,7,8-trimethylspiro[chromene-2,1'-cyclobutan]-6-ol;
- 4-(cyclopentyloxy)-5,7,8-trimethyl-3,4-dihydrospiro[chromene-2,1'-cyclobutane]-6-diol;
- 4-(isopropylthio)-5,7,8-trimethyl-3,4-dihydrospiro[chromene-2,1'-cyclobutan]-6-ol;
- 4'-(ethoxyamino)-5',7',8'-trimethyl-3',4'-dihydrospiro[cyclobutane-1,2'-thiochromen]-6'-ol;
- 4'-(ethoxyamino)-5',7'-dimethyl-3',4'-dihydrospiro[cyclobutane-1,2'-thiochromen]-6'-ol;
- 4'-(methoxyamino)-5',7'-dimethyl-3',4'-dihydrospiro[cyclobutane-1,2'-thiochromen]-6'-ol;
- 7-tert-butyl-3,4-dihydrospiro[chromene-2,1'-cyclobutan]-6-ol;
- 5,7-dimethylspiro[chromene-2,1'-cyclobutan]-6-ol;
- 6-hydroxy-5,7-dimethylspiro[chromene-2,1'-cyclobutane]-3-carbaldehyde O-ethyloxime;
- 3-[(ethoxyamino)methyl]-5,7-dimethylspiro[chromene-2,1'-cyclobutan]-6-ol;
- 7-tert-butyl-5-methyl-3,4-dihydrospiro[chromene-2,1'-cyclobutan]-6-ol;
- 5,7-dimethyl-3-(1,3-oxazol-5-yl)spiro[chromene-2,1'-cyclobutan]-6-ol;
- 7-isopropyl-5-methyl-3,4-dihydrospiro[chromene-2,1'-cyclobutan]-6-ol;
- 7-(1-benzofuran-2-yl)-2,2,5,8-tetramethylchroman-6-ol;
- 5,7-dimethyl-3-(oxazol-5-yl)spiro[chroman-2,1'-cyclobutan]-6-ol;
- 7-isopropyl-5-methylspiro[chromene-2,1'-cyclobutan]-6-ol;
- 5,8-dimethyl-7-(2-(quinolin-2-yl)ethyl)spiro[chroman-2,1'-cyclobutan]-6-ol;
- 5,7-diethylspiro[chromene-2,1'-cyclobutan]-6-ol;
- 5,7-diisopropylspiro[chromene-2,1'-cyclobutan]-6-ol
- methyl 2-((5,7-diethyl-6-hydroxyspiro[chroman-2,1'-cyclobutane]-3-yl)methylthio)acetate;
- 1'-ethyl-7',8'-dimethyl-2',4'-dihydro-1'H-spiro[cyclobutane-1,3'-quinolin]-6'-ol;
- 1'-(4-chlorophenyl)-7',8'-dimethyl-2',4'-dihydro-1'H-spiro[cyclobutane-1,3'-quinoline]-4',6'-diol;
- 1'-(4-fluorophenyl)-7',8'-dimethyl-2',4'-dihydro-1'H-spiro[cyclobutane-1,3'-quinolin]-6'-ol;
- 1'-(4-methoxyphenyl)-7',8'-dimethyl-2',4'-dihydro-1'H-spiro[cyclobutane-1,3'-quinolin]-6'-ol;

4-(6'-methoxy-7',8'-dimethyl-2',4'-dihydro-1'H-spiro[cyclobutane-1,3'-quinoline]-1'-yl)phenol;

7',8'-dimethyl-1'-p-tolyl-2',4'-dihydro-1'H-spiro[cyclobutane-1,3'-quinolin]-6'-ol;

1'-(3-hydroxyphenyl)-7',8'-dimethyl-2',4'-dihydro-1'H-spiro[cyclobutane-1,3'-quinolin]-6'-ol;

1'-(5-hydroxypyridin-2-yl)-7',8'-dimethyl-2',4'-dihydro-1'H-spiro[cyclobutane-1,3'-quinolin]-6'-ol;

N-(3-(6'-hydroxy-7',8'-dimethyl-2',4'-dihydro-1'H-spiro[cyclobutane-1,3'-quinoline]-1'-yl)propyl)-4-propyl-benzenesulfonamide;

6-(7'-tert-butyl-6'-methoxy-5'-methyl-2',4'-dihydro-1'H-spiro[cyclobutane-1,3'-quinoline]-1'-yl)pyridin-3-ol;

7'-tert-butyl-1'-(5-hydroxypyridin-2-yl)-5'-methyl-2',4'-dihydro-1'H-spiro[cyclobutane-1,3'-quinolin]-6'-ol exhibited inhibition of 12/15-Lipoxygenase with an $IC_{50}$ in a range of less than 5 μM.

Example 72

Inhibition of $LTB_4$ Production in Blood

Materials
Human whole blood (Na citrate) (Stanford Blood Center)
A23187, (Sigma, Cat# C-7522)
Leukotriene $B_4$ EIA reagents (Cayman Chemical, Cat # 520111)
BWA4C (Sigma, Cat # B7559)

Procedure

Preparation of A23187:
A23187 was prepared as a 10 mM stock solution in DMSO (aliquots can be stored at −20° C.). On the day of the assay the stock solution was diluted as follows: 70 μL 10 mM stock added to 1.6 mL plasma to give a working concentration of 0.42 mM.

Preparation of Test Articles
From a 30 mM stock solution in DMSO, test articles were diluted to a working concentration of 600 μM in PBS (i.e. 10 μL stock solution+490 μL PBS). This is the highest concentration (gives a final testing concentration of 30 μM). From this 600 μM solution test articles were serially diluted 1:3 in PBS to give a dose-response curve. 10 μL of each concentration of test article was then added to 4 wells of a 96-well plate (i.e. testing in quadruplicate). A positive control compound, BWA4C was used in every assay.

Blood Stimulation Procedure
Human whole blood was added to the plates containing compounds (190 μL per well) and mixed well. The blood was incubated with compound at 37° C. for 15 minutes. Following this incubation, 10 μL of 0.42 mM A23187 was added to each well except the negative control wells to give a final calcium ionophore concentration of 20 μM. The plates were then incubated at 37° C. for 60 minutes. After the incubation period, plates were centrifuged for 15 min at 2000 g at 4° C. in sealed microplate buckets. Plasma was then removed for quantitation of $LTB_4$ levels by ELISA.

Measurement of $LTB_4$ Levels by ELISA
$LTB_4$ levels in the plasma were determined using a commercially available ELISA kit from Cayman Chemicals. The ELISA was run according to the manufacturer's instructions. The $LTB_4$ levels in the vehicle control sample were then compared to those in which the test article had been added.

From this a percent inhibition of $LTB_4$ production by each concentration of test article was calculated and the $IC_{50}$ was determined.

Certain compounds of this invention such as:

5,7,8-trimethyl-3,4-dihydrospiro[chromene-2,1'-cyclopropan]-6-ol;

2',2',5',7',8'-pentamethyl-2',3'-dihydrospiro[cyclobutane-1,4'-thiochromen]-6'-ol;

5,7-dimethyl-3,4-dihydrospiro[chromene-2,1'-cyclobutan]-6-ol;

7,8-dimethylspiro[chroman-3,1'-cyclopropan]-6-ol;

5,7,8-trimethylspiro[chroman-3,1'-cyclobutane]-4,6-diol;

4'-(methoxyamino)-5',7',8'-trimethyl-3',4'-dihydrospiro[cyclobutane-1,2'-thiochromen]-6'-ol;

5,7,8-trimethylspiro[chroman-3,1'-cyclobutan]-6-ol;

4-methoxy-5,7,8-trimethylspiro[chroman-3,1'-cyclobutan]-6-ol;

4-ethoxy-5,7,8-trimethylspiro[chroman-3,1'-cyclobutan]-6-ol;

3-(hydroxymethyl)-5,7,8-trimethylspiro[chromene-2,1'-cyclobutan]-ol;

5,7,8-trimethyl-3,4-dihydrospiro[chromene-2,1'-cyclobutane]-3,6-diol;

3-methoxy-5,7,8-trimethyl-3,4-dihydrospiro[chromene-2,1'-cyclobutan]-6-ol;

3-(hydroxymethyl)-5,7,8-trimethyl-3,4-dihydrospiro[chromene-2,1'-cyclobutan]-6-ol;

3-(methoxymethyl)-5,7,8-trimethylspiro[chromene-2,1'-cyclobutan]-6-ol;

4-methoxy-3,5,7,8-tetramethyl-3,4-dihydrospiro[chromene-2,1'-cyclobutan]-6-ol;

3,5,7,8-tetramethylspiro[chromene-2,1'-cyclobutan]-6-ol;

4-methoxy-3,5,7,8-tetramethyl-3,4-dihydrospiro[chromene-2,1'-cyclobutan]-6-ol;

6-hydroxy-5,7,8-trimethyl-3,4-dihydrospiro[chromene-2,1'-cyclobutane]-4-carbonitrile;

7,8-dimethyl-3,4-dihydrospiro[chromene-2,1'-cyclobutan]-6-ol;

7,8-dimethylspiro[chroman-3,1'-cyclobutan]-6-ol;

4-methoxy-5,7-dimethyl-3,4-dihydrospiro[chromene-2,1'-cyclobutan]-6-ol;

4-ethoxy-5,7-dimethyl-3,4-dihydrospiro[chromene-2,1'-cyclobutan]-6-ol;

4-(methoxyamino)-5,7-dimethyl-3,4-dihydrospiro[chromene-2,1'-cyclobutan]-6-ol;

5,7-dimethylspiro[chroman-3,1'-cyclobutan]-6-ol;

3-(1-methoxyethyl)-5,7,8-trimethylspiro[chromene-2,1'-cyclobutan]-6-ol;

5,7-dimethyl-4H-spiro[chromene-3,1'-cyclobutane]-4,6-diol;

5,7-dimethyl-3,4-dihydrospiro[chromene-2,1'-cyclobutane]-4,6-diol;

3-(1-hydroxyethyl)-5,7,8-trimethylspiro[chromene-2,1'-cyclobutan]-6-ol;

8-(hydroxymethyl)-5,7-dimethyl-3,4-dihydrospiro[chromene-2,1'-cyclobutan]-6-ol;

4-(ethoxyamino)-5,7,8-trimethyl-3,4-dihydrospiro[chromene-2,1'-cyclobutan]-6-ol;

4'-(ethoxyamino)-5',7',8'-trimethyl-3',4'-dihydrospiro[cyclobutane-1,2'-thiochromen]-6'-ol;

4'-(ethoxyamino)-5',7'-dimethyl-3',4'-dihydrospiro[cyclobutane-1,2'-thiochromen]-6'-ol;
4'-(methoxyamino)-5',7'-dimethyl-3',4'-dihydrospiro[cyclobutane-1,2'-thiochromen]-6'-ol;
6-hydroxy-5,7,8-trimethylspiro[chromene-2,1'-cyclobutan]-4(3H)-one oxime;
4-(hydroxyamino)-5,7,8-trimethyl-3,4-dihydrospiro[chromene-2,1'-cyclobutan]-6-ol;
8-[(methoxyamino)methyl]-5,7-dimethyl-3,4-dihydrospiro[chromene-2,1'-cyclobutan]-6-ol
4-[hydroxy(methyl)amino]-5,7,8-trimethyl-3,4-dihydrospiro[chromene-2,1'-cyclobutan]-6-ol;
6-hydroxy-5,7-dimethylspiro[chromene-2,1'-cyclobutan]-4(3H)-one oxime;
4-[hydroxy(methyl)amino]-5,7-dimethyl-3,4-dihydrospiro[chromene-2,1'-cyclobutan]-6-ol;
8-[(ethoxyamino)methyl]-5,7-dimethyl-3,4-dihydrospiro[chromene-2,1'-cyclobutan]-6-ol;
7-tert-butyl-3,4-dihydrospiro[chromene-2,1'-cyclobutan]-6-ol;
6'-hydroxy-5',7',8'-trimethylspiro[cyclobutane-1,2'-thiochromen]-4'(3'H)-one O-methyloxime;
6'-hydroxy-5',7',8'-trimethylspiro[cyclobutane-1,2'-thiochromen]-4'(3'H)-one O-ethyloxime;
6'-hydroxy-5',7'-dimethylspiro[cyclobutane-1,2'-thiochromen]-4'(3'H)-one O-methyloxime;
6-hydroxy-5,7-dimethylspiro[chromene-2,1'-cyclobutane]-3-carbaldehyde O-methyloxime;
3-[(methoxyamino)methyl]-5,7-dimethylspiro[chromene-2,1'-cyclobutan]-6-ol;
6'-hydroxy-5',7'-dimethylspiro[cyclobutane-1,2'-thiochromen]-4'(3'H)-one O-ethyloxime;
5,7-diethyl-6-hydroxyspiro[chromene-2,1'-cyclobutan]-4(3H)-one O-methyloxime;
5,7-diethyl-6-hydroxyspiro[chromene-2,1'-cyclobutan]-4(3H)-one oxime;
(4S)-4-(methoxyamino)-5,7-dimethyl-3,4-dihydrospiro[chromene-2,1'-cyclobutan]-6-ol;
(4R)-4-(methoxyamino)-5,7-dimethyl-3,4-dihydrospiro[chromene-2,1'-cyclobutan]-6-ol;
5,7-dimethyl-8-(5-butyl-isoxazol-3-yl)-3,4-dihydrospiro[chromene-2,1'-cyclobutan]-6-ol;
4-(methoxyamino)-5,7-diethyl-3,4-dihydrospiro[chromene-2,1'-cyclobutan]-6-ol;
5,7-dimethylspiro[chromene-2,1'-cyclobutan]-6-ol;
6-hydroxy-5,7-dimethylspiro[chromene-2,1'-cyclobutane]-3-carbaldehyde O-ethyloxime;
3-[(ethoxyamino)methyl]-5,7-dimethylspiro[chromene-2,1'-cyclobutan]-6-ol;
7-tert-butyl-5-methyl-3,4-dihydrospiro[chromene-2,1'-cyclobutan]-6-ol;
5,7-dimethyl-8-(1,3-oxazol-5-yl)-3,4-dihydrospiro[chromene-2,1'-cyclobutan]-6-ol;
5,7-diisopropyl-3,4-dihydrospiro[chromene-2,1'-cyclobutan]-6-ol;
3-[(ethoxyamino)methyl]-5,7-dimethyl-3,4-dihydrospiro-[chromene-2,1'-cyclobutan]-6-ol;
3-[(methoxyamino)methyl]-5,7-dimethyl-3,4-dihydrospiro-[chromene-2,1'-cyclobutan]-6-ol;
5,7-dimethyl-3-(1,3-oxazol-5-yl)spiro[chromene-2,1'-cyclobutan]-6-ol;
5-(3,7-dimethylocta-2,6-dienyl)-7,8-dimethylspiro[chroman-2,1'-cyclobutan]-6-ol;
5,7-diethyl-3,4-dihydrospiro[chromene-2,1'-cyclobutan]-6-ol;
7-isopropyl-4-(methoxyamino)-5-methyl-3,4-dihydrospiro[chromene-2,1'-cyclobutan]-6-ol;
5,7-dimethyl-3-(-(4,5-dimethyl-1H-imidazol-2-yl)spiro[chromene-2,1'-cyclobutan]-6-ol;
7-ethyl-4-(methoxyamino)-5-methyl-3,4-dihydrospiro[chromene-2,1'-cyclobutan]-6-ol;
5-ethyl-4-(methoxyamino)-7-methyl-3,4-dihydrospiro[chromene-2,1'-cyclobutan]-6-ol;
(Z)-5,7-diethyl-8-(hydroxymethyl)-3,4-dihydrospiro[chromene-2,1'-cyclobutan]-6-ol;
5,7-diethyl-8-(hydroxymethyl)-3,4-dihydrospiro[chromene-2,1'-cyclobutan]-6-ol;
7-isopropyl-5-methyl-3,4-dihydrospiro[chromene-2,1'-cyclobutan]-6-ol;
8-(hydroxymethyl)-7-isopropyl-5-methylspiro[chroman-2,1'-cyclobutan]-6-ol;
5,7-dimethyl-3-(oxazol-5-yl)spiro[chroman-2,1'-cyclobutan]-6-ol;
7-isopropyl-5-methylspiro[chroman-2,1'-cyclobutane]-4,6-diol;
7-isopropyl-5-methylspiro[chromene-2,1'-cyclobutan]-6-ol;
7-isopropyl-4-methoxy-5-methylspiro[chroman-2,1'-cyclobutan]-6-ol;
5,7-diethylspiro[chromene-2,1'-cyclobutan]-6-ol;
5,7-diisopropylspiro[chromene-2,1'-cyclobutan]-6-ol
5,7-diethyl-3-(hydroxymethyl)spiro[chroman-2,1'-cyclobutan]-6-ol;
methyl 2-((5,7-diethyl-6-hydroxyspiro[chroman-2,1'-cyclobutane]-3-yl)methylthio)acetate;
(5,7-diethyl-6-hydroxyspiro[chroman-2,1'-cyclobutane]-3-yl)methyl carbamate;
7-isopropyl-5-methylspiro[chroman-3,1'-cyclobutane]-4,6-diol;
5-ethyl-7-isopropylspiro[chroman-2,1'-cyclobutane]-4,6-diol.
(S)-5,7-diethylspiro[chroman-2,1'-cyclobutane]-4,6-diol;
(R)-5,7-diethylspiro[chroman-2,1'-cyclobutane]-4,6-diol;
(S)-7-isopropyl-5-methylspiro[chroman-2,1'-cyclobutane]-4,6-diol;
(R)-7-isopropyl-5-methylspiro[chroman-2,1'-cyclobutane]-4,6-diol;
1'-(4-hydroxyphenyl)-7',8'-dimethyl-3',4'-dihydro-1'H-spiro[cyclopropane-1,2'-quinolin]-6'-ol;
1'-(6-(dimethylamino)pyridin-3-yl)-7',8'-dimethyl-2',4'-dihydro-1'H-spiro[cyclobutane-1,3'-quinolin]-6'-ol;
5',7'-dimethyl-1'-(quinolin-2-ylmethyl)-3',4'-dihydro-1'H-spiro[cyclobutane-1,2'-quinolin]-6'-ol;
N-(2-(6'-hydroxy-7',8'-dimethyl-2',4'-dihydro-1'H-spiro[cyclobutane-1,3'-quinoline]-1'-yl)ethyl)-4-methylbenzenesulfonamide;
1'-(5-hydroxypyridin-2-yl)-7',8'-dimethyl-2',4'-dihydro-1'H-spiro[cyclobutane-1,3'-quinolin]-6'-ol;
N-(3-(6'-hydroxy-7',8'-dimethyl-2',4'-dihydro-1'H-spiro[cyclobutane-1,3'-quinoline]-1'-yl)propyl)-4-propylbenzenesulfonamide;
N-(3-(6'-hydroxy-7',8'-dimethyl-2',4'-dihydro-1'H-spiro[cyclobutane-1,3'-quinoline]-1'-yl)propyl)-4-methylbenzenesulfonamide;
N-(3-(6'-hydroxy-7',8'-dimethyl-2',4'-dihydro-1'H-spiro[cyclobutane-1,3'-quinoline]-1'-yl)propyl)benzamide;

when tested as described provided protection against $LTB_4$ at an $EC_{50}$ in a range of less than 10 μM.

Example 73

LTB$_4$-Cell Assay

This procedure was used for measuring the release of the leukotriene LTB4 from a neutrophil cell line using a competitive ELISA technique.

Materials and Equipments

Materials for Cell Preparation and Experiment
  MPRO cell line (ATCC, Catalog # CRL-11422)
  Calcium ionophore (A23187) (Sigma, Catalog # C7522)
  Nordihydroguaiaretic acid (NDGA) (BioMol ,Catalog # EI101-0001)
  Retinoic Acid (all-trans) (ATRA) (Sigma, Catalog # 95152)
  Sterile, tissue-culture treated 96-well plates (Corning, Catalog # 3614)

Materials for LTB$_4$ ELISA
  Precoated (Mouse Anti-Rabbit IgG) EIA 96 Well Strip Plates (Cayman, Catalog # 400004)
  Leukotriene B4 AChE Tracer (Cayman Catalog # 420110)
  Leukotriene B4 EIA Antiserum (Cayman Catalog # 420112)
  Ellman's Reagent (Cayman Catalog # 400050)
  EIA Buffer Concentrate (10×) (Cayman Catalog # 400060)
  Wash Buffer Concentrate (400×) (Cayman Catalog # 400062)
  Plastic plate covers (Cayman Catalog # 400012)

Procedure

A mouse promyelocytic cell line (MPRO) was used in this assay. These cells are committed immature neutrophils that can be differentiated into mature neutrophils by treatment with 10 μM all-trans retinoic acid for 72 hours.

Following 72 hours of differentiation, cells were stimulated with 1 μM of a calcium ionophore (A23187) in the presence or absence of test compound or vehicle for 1 hour at 37° C. After this time, supernatant was removed from the cells and the LTB$_4$ levels were determined following manufacturer's instructions, using a Leukotriene B4 EIA kit from Cayman (Cat # 5201 11). The negative controls were media samples from differentiated but un-stimulated cells. The compounds were screened at 5 concentrations in quadruplicate starting at 10 μM.

Following the procedure described above certain compounds of the present invention, such as:

5,7,8-trimethyl-3,4-dihydrospiro[chromene-2,1'-cyclobutan]-6-ol;
5-chloro-7,8-dimethyl-3,4-dihydrospiro[chromene-2,1'-cyclobutan]-6-ol;
5',7',8'-trimethyl-2',3'-dihydrospiro[cyclobutane, 1,4'-thiochromen]-6'-ol;
7-chloro-5,8-dimethyl-3,4-dihydrospiro[chromene-2,1'-cyclobutan]-6-ol;
5,7,8-trimethyl-3,4-dihydrospiro[chromene-2,1'-cyclopropan]-6-ol;
5-chloro-8-methyl-3,4-dihydrospiro[chromene-2,1'-cyclobutan]-6-ol;
5,8-dimethyl-7-(3-methylbutyl)-3,4-dihydrospiro[chromene-2,1'-cyclobutan]-6-ol;
2',2',5',7',8'-pentamethyl-2',3'-dihydrospiro[cyclobutane-1,4'-thiochromen]-6'-ol;
5,7-dimethyl-3,4-dihydrospiro[chromene-2,1'-cyclobutan]-6-ol;
8-chloro-5,7-dimethyl-3,4-dihydrospiro[chromene-2,1'-cyclobutan]-6-ol;
8-chloro-5-methyl-3,4-dihydrospiro[chromene-2,1'-cyclobutan]-6-ol;
7-chloro-5,8-dimethyl-3,4-dihydrospiro[chromene-2,1'-cyclobutan]-6-yl (dimethylamino)acetate;
5-isopropyl-8-methyl-3,4-dihydrospiro[chromene-2,1'-cyclobutan]-6-ol;
7,8-dimethylspiro[chroman-3,1'-cyclopropan]-6-ol;
6'-hydroxy-5',7',8'-trimethylspiro[cyclobutane-1,2'-thiochromen]-4'(3')-one;
5',7',8'-trimethyl-3',4'-dihydrospiro[cyclobutane-1,2'-thiochromen]-6'-ol;
4'(methoxyamino)-5',7',8'-trimethyl-3',4'-dihydrospiro[cyclobutane-1,2'-thiochromen]-6'-ol;
4-methoxy-5,7,8-trimethylspiro[chroman-3,1'-cyclobutan]-6-ol;
6-hydroxy-5,7,8-trimethylthiochroman-4-yl phenylcarbamate;
5',7',8'-trimethylspiro[cyclobutane-1,2'-thiochromen]-6'-ol;
4-ethoxy-5,7,8-trimethylspiro[chroman-3,1'-cyclobutan]-6-ol;
4-(hexylamino)-5,7,8-trimethylspiro[chroman-3,1'-cyclobutan]-6-ol;
3-(hydroxymethyl)-5,7,8-trimethylspiro[chromene-2,1'-cyclobutan]-6-ol;
5,7,8-trimethyl-3,4-dihydrospiro[chromene-2,1'-cyclobutane]-3,6-diol;
3-methoxy-5,7,8-trimethyl-3,4-dihydrospiro[chromene-2,1'-cyclobutan]-6-ol;
3-(hydroxymethyl)-5,7,8-trimethyl-3,4-dihydrospiro[chromene-2,1'-cyclobutan]-6-ol;
2-{[(5,7,8-trimethyl-3,4-dihydrospiro[chromene-2,1'-cyclobutan]-6-yl)oxy]methyl}quinoline;
3-(methoxymethyl)-5,7,8-trimethylspiro[chromene-2,1'-cyclobutan]-6-ol;
4-methoxy-3,5,7,8-tetramethyl-3,4-dihydrospiro[chromene-2,1'-cyclobutan]-6-ol;
3,5,7,8-tetramethylspiro[chromene-2,1'-cyclobutan]-6-ol;
6-hydroxy-5,7,8-trimethylspiro[chromene-2,1'-cyclobutane]-4-carbonitrile;
6-hydroxy-5,7,8-trimethyl-3,4-dihydrospiro[chromene-2,1'-cyclobutane]-4-carbonitrile;
methyl {[(6-hydroxy-5,7,8-trimethyl-3,4-dihydrospiro[chromene-2,1'-cyclobutan]-3-yl)methyl]thio}acetate;
4-ethoxy-5,7,8-trimethyl-3,4-dihydrospiro[chromene-2,1'-cyclobutan]-6-ol;
7,8-dimethyl-3,4-dihydrospiro[chromene-2,1'-cyclobutan]-6-ol;
7,8-dimethylspiro[chroman-3,1'-cyclobutan]-6-ol;
4-methoxy-5,7-dimethyl-3,4-dihydrospiro[chromene-2,1'-cyclobutan]-6-ol;
4-ethoxy-5,7-dimethyl-3,4-dihydrospiro[chromene-2,1'-cyclobutan]-6-ol;
4-(methoxyamino)-5,7-dimethyl-3,4-dihydrospiro[chromene-2,1'-cyclobutan]-6-ol;
5,7-dimethylspiro[chroman-3,1'-cyclobutan]-6-ol;
3-(1-methoxyethyl)-5,7,8-trimethylspiro[chromene-2,1'-cyclobutan]-6-ol;
5,7,8-trimethyl-3,4-dihydrospiro[chromene-2,1'-cyclobutane]-4,6-diol;
3-(1-hydroxyethyl)-5,7,8-trimethylspiro[chromene-2,1'-cyclobutan]-6-ol;
4-(cyclopentyloxy)-5,7,8-trimethyl-3,4-dihydrospiro[chromene-2,1'-cyclobutane]-6-diol;
4-(ethoxyamino)-5,7,8-trimethyl-3,4-dihydrospiro[chromene-2,1'-cyclobutan]-6-ol;

4-(isopropylthio)-5,7,8-trimethyl-3,4-dihydrospiro [chromene-2,1'-cyclobutan]-6-ol;

7,8-dimethyl-3,4-dihydrospiro[chromene-2,1'-cyclobutan]-6-yl (dimethylamino)acetate;

4'-(ethoxyamino)-5',7',8'-trimethyl-3',4'-dihydrospiro[cyclobutane-1,2'-thiochromen]-6'-ol;

4'-(ethoxyamino)-5',7'-dimethyl-3',4'-dihydrospiro[cyclobutane-1,2'-thiochromen]-6'-ol;

4-(ethoxyamino)-5,7-dimethyl-3,4-dihydrospiro [chromene-2,1'-cyclobutan]-6-ol;

4'-(methoxyamino)-5',7'-dimethyl-3',4'-dihydrospiro[cyclobutane-1,2'-thiochromen]-6'-ol;

4-[methoxy(methyl)amino]-5,7,8-trimethyl-3,4-dihydrospiro[chromene-2,1'-cyclobutan]-6-ol;

6-hydroxy-5,7,8-trimethylspiro[chromene-2,1'-cyclobutan]-4(3H)-one oxime;

4-(hydroxyamino)-5,7,8-trimethyl-3,4-dihydrospiro [chromene-2,1'-cyclobutan]-6-ol;

8-[(methoxyamino)methyl]-5,7-dimethyl-3,4-dihydrospiro[chromene-2,1'-cyclobutan]-6-ol 5,7-dimethyl-8-vinyl-3,4-dihydrospiro[chromene-2,1'-cyclobutan]-6-ol;

6-hydroxy-5,7-dimethylspiro[chromene-2,1'-cyclobutan]-4(3H)-one oxime;

8-[(ethoxyamino)methyl]-5,7-dimethyl-3,4-dihydrospiro [chromene-2,1'-cyclobutan]-6-ol;

7-tert-butyl-3,4-dihydrospiro[chromene-2,1'-cyclobutan]-6-ol;

5-ethyl-6-hydroxy-7,8-dimethylspiro[chromene-2,1'-cyclobutan]-4(3H)-one O-methyloxime;

5-ethyl-6-hydroxy-7,8-dimethylspiro[chromene-2,1'-cyclobutan]-4(3H)-one O-ethyloxime;

6'-hydroxy-5',7',8'-trimethylspiro[cyclobutane-1,2'-thiochromen]-4'(3'H)-one O-methyloxime;

6'-hydroxy-5',7',8'-trimethylspiro[cyclobutane-1,2'-thiochromen]-4'(3'H)-one O-ethyloxime;

6'-hydroxy-5',7'-dimethylspiro[cyclobutane-1,2'-thiochromen]-4'(3'H)-one O-methyloxime;

6-hydroxy-5,7-dimethylspiro[chromene-2,1'-cyclobutane]-3-carbaldehyde O-methyloxime;

3-[(methoxyamino)methyl]-5,7-dimethylspiro [chromene-2,1'-cyclobutan]-6-ol;

3-[(methoxyamino)methyl]-5,7-dimethylspiro [chromene-2,1'-cyclobutan]-6-yl pivalate;

methyl 3-(6-hydroxy-5,7-dimethyl-3,4-dihydrospiro [chromene-2,1'-cyclobutan]-8-yl)4,5-dihydroisoxazole-5-carboxylate;

6'-hydroxy-5',7'-dimethylspiro[cyclobutane-1,2'-thiochromen]-4'(3'H)-one O-ethyloxime;

5,7-diethyl-6-hydroxyspiro[chromene-2,1'-cyclobutan]-4(3H)-one O-methyloxime;

5,7-diethyl-6-hydroxyspiro[chromene-2,1'-cyclobutan]-4(3H)-one O-ethyloxime;

5,7flethyl-6-hydroxyspiro[chromene-2,1'-cyclobutan]-4(3H)-one oxime;

(4S)-4-(methoxyamino)-5,7-dimethyl-3,4-dihydrospiro [chromene-2,1'-cyclobutan]-6-ol;

(4R)-4-(methoxyamino)-5,7-dimethyl-3,4-dihydrospiro [chromene-2,1'-cyclobutan]-6-ol;

5,7-dimethyl-8-(5-butyl-isoxazol-3-yl)-3,4-d ihydrospiro [chromene-2,1'-cyclobutan]-6-ol;

4-(methoxyamino)-5,7-diethyl-3,4-dihydrospiro [chromene-2,1'-cyclobutan]-6-ol;

5,7-dimethylspiro[chromene-2,1'-cyclobutan]-6-ol;

6-hydroxy-5,7-dimethylspiro[chromene-2,1'-cyclobutane]-3-carbaldehyde O-ethyloxime;

3-[(ethoxyamino)methyl]-5,7-dimethylspiro[chromene-2,1'-cyclobutan]-6-ol;

7-tert-butyl-5-methyl-3,4-dihydrospiro[chromene-2,1'-cyclobutan]-6-ol;

5,7-dimethyl-8-(1,3-oxazol-5-yl)-3,4-dihydrospiro [chromene-2,1'-cyclobutan]-6-ol;

N-(6-hydroxy-5,7-dimethyl-3,4-dihydrospiro[chromene-2,1'-cyclobutan]-4-yl)benzenesulfonamide;

5,7-diisopropyl-3,4-dihydrospiro[chromene-2,1'-cyclobutan]-6-ol;

3-[(ethoxyamino)methyl]-5,7-dimethyl-3,4-dihydrospiro-[chromene-2,1'-cyclobutan]-6-ol;

5,7-diethyl-3-(hydroxymethyl)spiro[chroman-2,1'-cyclobutan]-6-ol;

methyl 2-((5,7-diethyl-6-hydroxyspiro[chroman-2,1'-cyclobutane]-3-yl)methylthio)acetate;

(5,7-diethyl-6-hydroxyspiro[ch roman-2,1'-cyclobutane]-3-yl)methyl carbamate;

7-tert-butyl-5-methylspiro[chroman-2,1'-cyclobutane]-4,6-diol;

2-(3-(6'-hydroxy-7',8'-dimethyl-2',4'-dihydro-1'H-spiro [cyclopropane-1,3'-quinoline]-1'-yl)propyl)isoindoline-1,3-dione;

were considered to be active if they exhibited inhibition of LTB4 with an $EC_{50}$ in a range of less than 5 µM.

Example 74

Inflammation Assay— Cell-ELAM Assay

Endothelial-Leukocyte Adhesion Molecule (ELAM), also known as E-selectin, is expressed on the surface of endothelial cells. In this assay, lipopolysaccharide (LPS) and IL-1β are used to stimulate the expression of ELAM; test agents are tested for their abilities to reduce this expression, in accordance with studies showing that reduction of leukocyte adhesion to endothelial cell surface is associated with decreased cellular damage (e.g., Takada, M., et. al. *Transplantation*, Vol. 64 (1997), pp. 1520-25; Steinberg, J. B., et al. *J. Heart Lung Trans.*, Vol. 13 (1994), pp. 306-313).

Endothelial cells may be selected from any of a number of sources and cultured according to methods known in the art; including, for example, coronary artery endothelial cells, human brain microvascular endothelial cells (Hess, D. C., et al. *Neurosci. Lett.*, Vol. 213, issue 1 (1996), pp. 37-40), or lung endothelial cells. Cells are conveniently cultured in 96-well plates. Cells are stimulated by adding a solution to each well containing 10 µg/mL LPS and 100 µg/mL IL-1β for 6 hours in the presence of test agent (specific concentrations and time may be adjusted depending on the cell type). Treatment buffer is removed and replaced with pre-warmed Fixing Solution® (100 µL/well) for 25 minutes at room temperature. Cells are then washed 3×, then incubated with Blocking Buffer (PBS+2% FBS) for 25 minutes at room temperature. Blocking Buffer containing Monoclonal E-Selectin Antibody (1:750, Sigma Catalog #S-9555) is added to each well. Plates are sealed and stored at 4° C. overnight. Plates are washed 4× with 160 µL Blocking Buffer per well. Second Antibody-HRP diluted 1:5000 in Blocking Buffer is then added (100 µL/well), and plates are incubated at room temperature (protected from light) for two hours. Plates are then washed 4× with Blocking Buffer before addition of 100 µL of ABTS Substrate solution at room temperature (Zymed, Catalog #00-2024). Wells are allowed to develop for 35 minutes, before measurement at 402 nm in a Fluoroskan® Reader with shake program for 10 seconds. Positive results are recorded as a decrease in ELAM concentration in tested wells, as compared to control wells.

Certain compounds of this invention when tested as described above, may show activity in this assay.

Example 75

Rat Paw Edema Assay

Animal Preparation:

Male Sprague-Dawley rats weighing between 175 to 200 g are used in this study. Animals are allowed free access to water and commercial rodent diet under standard laboratory conditions. Room temperature is maintained at 20-23° C. and room illumination is on a 12/12-hour light/dark cycle. Animals are acclimatized to the laboratory environment 5 to 7 days prior to the study.

Experimental Procedure:

Each animal was treated by administration of vehicle, reference or test substance one hour prior to carrageenan injection, as follows:

I.V. Infusion via Femoral Vein:

Anesthesia is maintained by inhalation of 3.0% isoflurane (Aerrane, Front Dodge, Iowa) in oxygen throughout the entire procedure. The exterior site of the right femoral vein is shaved and sterilized prior to surgery. A 3 cm incision is made in the right groin region and the femoral vein is isolated. The femoral vein is temporarily ligated with a micro-vascular clip, and a small incision is made on the femoral vein to introduce and advance a polyethylene (PE-50) catheter (Becton, Dickinson and Co., Sparks, Md.). The catheter is secured in place with suture (silk 5/0, Carlisle Laboratories, Farmers Branch, Tex.). The other end of the catheter is attached to a syringe filled with the saline for the bolus injection. Using a hemostat, a pocket is made subcutaneously on the back of the animal so the PE catheter can be brought up to the exteriorization point between the shoulder blade for either a bolus injection or a continuous injection by an osmotic pump.

I.P. Injection:

An awake rat is held in a standard hand held position. A 23 ¾G needle is injected into the lower right quarter of the abdomen pass the peritoneum, slightly off the midline. To avoid organ injection, the plunger of the syringe is slightly pulled back. If no fluid is withdrawn, the content of the syringe is delivered into the abdominal cavity.

Gavage Feeding:

A standard rat gavage tube (Popper & Sons Inc, NY) is attached to a 3 cc hypodermic syringe. The animal is held in a vertical position. The feeding tube is placed into the mouth and then gently advanced until it reached the stomach (the approximate insertion length of the tube should be measured prior to feeding). The content of the syringe is slowly delivered, and then the tube is withdrawn.

One hour post treatment each animal is anesthetized with 3.0% isoflurane (Aerane, Front Dodge, Iowa) in oxygen and administered 100 µL of 1% Carrageenan Lambda type IV (Sigma Chemical Company, St. Louis, Mo.) suspension in saline, into the intraplantar surface of the right hind paw. Paw edema is measured four hours after carrageenan injection, either by measuring the increase in paw volume using a plethysmometer or the increase in paw weight using a fine scale. Immediately prior to edema measurement, the animals are euthanized via $CO_2$ asphyxiation and 500 µL blood is withdrawn by cardiac puncture for later analysis. Paw volume is determined by the extent to which water is displaced by the paw from a pre-calibrated chamber. The volume of the left hind paw (control) is subtracted from the volume of the right hind paw (carrageenan-treated) to determine the volume of carrageenan-induced edema. To measure the weight difference between paws, both hind paws are removed and weighed separately.

To minimize the variation in the model following steps are taken:

Carrageenan is made fresh every day prior to the study (2-3 hours before injection).

The plethysmometer is calibrated each day prior to the study.

If carrageenan injection causes significant bleeding or a hematoma on the treated foot, the animal is excluded from the study.

Each paw is marked at the tibia-tarsal joint across the ankle prior to measurements, to ensure each paw was submerged at the same level.

If reading on the volume needs to be repeated, the paw has to be dried off completely.

Statistical Analysis

The difference of the weight or the volume between right and left paw is calculated for each animal for the analysis. Group data are presented as means +/−SEM and p<0.05 are considered significant. Inter-group comparisons are carried out by unpaired student t test (between two groups) or one-way ANOVA followed by post hoc Bonferroni's multiple comparisons.

Results

Certain compounds of the present invention showed reduction (22%-39%) in edema when tested by this method.

Example 76

Mouse Ear Inflammatory Response to Topical Arachidonic Acid

Animals:

Balb C Mice 23-28 gms, from Simonsen Labs, Gilroy, Calif.

Materials:

Arachidonic Acid, 99% pure from Porcine Liver (Sigma Aldrich) reconstituted in acetone 2 mg/20 µL (200 mg/mL).

Inhalation anesthesia: Isoflurane 3% (Baxter).

Blood Sample tubes: Microtainer tubes w/ heparin (Becton Dickinson).

TNFα Elisa assay (R&D Science).

Experimental Procedure

Test compounds, positive control (arachidonic acid only) and standard (Dexamethasone at 0.1 mg/kg) prepared in solutions of acetone, ethanol or aqueous ethanol, were applied to both sides of the right ear with an Eppendorf repipettor pipette, in a volume of 10 µL each side (20 µL total). 30 Minutes later, 10 µL of arachidonic acid was applied to both sides of the right ear (20 µL total). One hour after the application of arachidonic acid, the mice were deeply anesthetized with isoflurane and a blood sample is taken via the orbital sinuses and placed in Microtainer tubes. The animals were then euthanized by $CO_2$ inhalation and the right ears removed at the base. A uniform plug of ear tissue was obtained using an 8 mm dermal punch. The earplugs were quickly weighed to the nearest 0.1 mg and then flash frozen for TNFα determination.

Statistical Analysis:

Group data was presented as means +/−SEM and p<0.05 is considered significant. Inter-group comparisons were carried out by unpaired student t tests (between two groups) or ANOVA (three or more groups) followed by post hoc Dunnet's test.

Example 77

High Glutamate-Induced Oxidative Stress Assay (HGOS)

This procedure was used to induce high glutamate-induced oxidative stress (HGOS) in a dopaminergic neuronal cell line. Using this assay the potency and efficacy of test articles against HGOS neuronal cell injury and cell death was established in a high throughput manner.

Materials
Dopaminergic neuronal cell lines
DMEM-No Glucose (Life Technologies Cat # 11966-025)
L-glutamine (Life Technologies Cat # 25030-081)
L-glutamic acid, monosodium salt (Sigma Cat # G5889)
D-glucose (Sigma Cat # G-6151)
10×HBSS buffer(pH 7.4) (950 mL Pyrogen-free water, 2.44 g/L $MgCl_2.6H_20$, 3.73 g/L KCl, 59.58 g/L Hepes, 58.44 g/L NaCl, 1.36 g/L $KH_2PO_4$, 1.91 g/L $CaCl2.2H_2O$ and pH to 4.5 with HCl)
Cell Tracker Green fluorescent dye (Molecular Probes, Cat # 2925). Prepare a 5 μM solution in pre-warmed HBSS just prior to use.
Sterile 96-well plates pre-coated with poly-D-lysine (Corning Catalog # 3665)
96-well deep well mother plate, DyNA Block 1000 (VWR Catalog # 40002-008)

Neuronal Cells

The cells were seeded into 96-well plates at a density of 2000 per well and left to grow for 72 hours in a 33° C. incubator with 5% $CO_2$ in air atmosphere. The passage number of the cells for each assay experiment were no later than p11 in order to minimize experimental variation.

Compound Preparation in Deep-well Mother Plates

VWRBrand DyNA Block 1000, deep well mother plates (VWR Cat. # 40002-008) were used for the preparation of the test compounds.

All compounds were dissolved in DMEM-No Glu containing 1 mM glucose, 30 mM glutamate and 1× Pen/Strep. DMEM-No Glu with 1 mM glucose and 1×P/S was used as the negative control, DMEM-No Glucose with 1 mM glucose, 100 M glutamate was used as a positive control and 100 pM Glutathione was added to the positive control as a standard. All of the procedures for this involving the making and dilution of compounds were performed using aseptic conditions and with minimal light.

Cell Preparation

The plates were removed from the incubator and examined under the microscope for morphological appearance and density. Using an aseptic technique and an 8-channel aspirator the media was carefully removed from the cells and replaced with 200 μL of 1×HBSS. This was done as quickly as possible to prevent the cells drying out. The plates were then placed in the humidified 37° C. incubators of the Biomek 2000 Side Loader. Four plates were washed at a time so as to minimize the time that the cells were sitting in 1×HBSS prior to addition of the compound test solution.

Experimental Setup

The Beckman Biomek workstations were used to load the compounds and controls from the mother plates onto the cell plates that were pre-washed with HBSS under sterile conditions. The plates were incubated in the upper HTS incubator at 37° C. in 5% $CO_2$ for exactly 16 h. The following day, using the Beckman Biomek workstations, the plates were removed from the incubator. Using Cell Tracker Addition, the compounds were removed from the plates, washed once with 200 μM of pre-warmed 1×HBSS and then 100 μL of 5 μM Cell Tracker Green was added to each well. The plates were incubated at 37° C. for 30 min to allow the dye to enter the cell and be cleaved by the esterases. After washing the cells twice with pre-warmed 1×HBSS, the plates were read with the 485 excitation; 538 emission filter pair on a Fluoroskan.

Certain compounds of the present invention such as:
5-chloro-7,8-dimethyl-3,4-dihydrospiro[chromene-2,1'-cyclobutan]-6-ol;
5',7',8'-trimethyl-2',3'-dihydrospiro[cyclobutane, 1,4'-thiochromen]-6'-ol;
5,7,8-trimethyl-3,4-dihydrospiro[chromene-2,1'-cyclopropan]-6-ol;

exhibited protection against HGOS cell injury and cell death with an $EC_{50}$ in a range of less than 1 μM.

Example 78

In vivo Zymosan Peritonitis Assay

Eight male Wistar rats (200-300 g) were dosed intravenously with a formulation containing a compound of this invention (30 mpk in 10% PG/5% Solutol/PBS). One minute post dosage, the inflammatory challenge was induced by intraperitoneal injection of Zymosan-A from *Saccharomyces cerevisiae*, (Sigma-Aldrich Co, St Louis, Mo.) at a dose of 25 mg/kg. The Zymosan-A solution was prepared by dissolving 5 mg per mL of sterile saline at room temperature and vortexed prior to injection to ensure uniform suspension. At 15 minutes post administration of Zymosan-A, the animals were asphyxiated by $CO_2$ inhalation and the peritoneal cavity was ravaged with 10 mL of 5μL/mL of ice cold heparinized saline. The peritoneal lavage fluid from each rat was then assessed for quantitation of $LTB_4$ and CysLT (cysteinyl leukotriene) levels by conventional ELISA procedures.

Certain compounds of this invention showed a significant reduction of $LTB_4$ and CysLT concentrations; and some compounds showed a reduction greater than 60%, and some particular compounds showed a reduction greater than 90% in those assays.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:

1. A compound represented by Formula I:

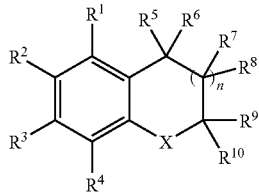

Formula I wherein,

X is O or $S(O)_{0-2}$;

$R^1$, $R^3$, and $R^4$ are independently selected from the group consisting of hydrogen, alkyl, halogen amino, and alkenyl, with the proviso that said alkenyl is not substituted with aryl or heteroaryl;

$R^2$ is hydroxy;

$R^5$ and $R^6$ are independently selected from the group consisting of hydrogen, hydroxy, alkoxy, aminosulfonyl, sulfanyl, cyano, —$NROR^a$, or together with the carbon atom to which they are attached, form C=O, or C=$NOR^a$;

$R^7$ and $R^8$ are independently selected from hydrogen, alkyl, alkoxy, and oxazol-2-yl;

$R^9$ and $R^{10}$ together with the carbon atom to which they are attached, form a ($C_3$-$C_4$)cycloalkyl ring;

R is hydrogen or alkyl;

$R^a$ is hydrogen or alkyl;

and n is 1;

with the following proviso no more than one of $R^1$, $R^3$ and $R^4$ is hydrogen;

or single stereoisomers, mixtures of stereoisomers, or pharmaceutically acceptable salts thereof.

2. A compound of Formula IA:

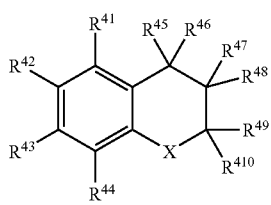

Formula IA wherein

X is O or $S(O)_{0-2}$;

$R^{41}$, $R^{43}$, and $R^{44}$ are independently selected from the group consisting of hydrogen, halo, alkenyl, and alkyl optionally substituted with amino, or alkoxy;

$R^{42}$ is hydroxy;

$R^{45}$ and $R^{46}$ are independently selected from the group consisting of hydrogen, hydroxy, alkoxy, aminosulfonyl, sulfanyl, cyano, —$NROR^a$, or together with the carbon atom to which they are attached, form C=O, or C=$NOR^a$;

$R^{47}$ and $R^{48}$ are independently selected from hydrogen, alkyl, alkoxy, and oxazol-2-yl;

$R^{49}$ and $R^{410}$ together with the carbon atom to which they are attached, form a ($C_3$-$C_4$)cycloalkyl ring;

$R^a$ is hydrogen or alkyl;

provided no more than one of $R^{41}$, $R^{43}$ and $R^{44}$ is hydrogen;

or single stereoisomers, mixtures of stereoisomers, or pharmaceutically acceptable salts thereof.

3. The compound of claim 2, wherein the compound is of Formula IB:

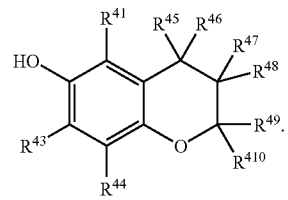

Formula IB

4. The compound of claim 2, wherein $R^{41}$, $R^{43}$ and $R^{44}$ are independently selected from the group consisting of hydrogen, halogen, and alkyl.

5. The compound of claim 2, wherein $R^{45}$ is —$NROR^a$ and $R^{46}$ is hydrogen.

6. The compound of claim 2, wherein $R^{45}$ is hydroxy and $R^{46}$ is hydrogen.

7. The compound of claim 5, wherein —$CR^{49}R^{410}$ is cyclobutyl.

8. The compound of claim 6, wherein —$CR^{49}R^{410}$ is cyclobutyl.

9. The compound of claim 5, wherein $R^{42}$ is hydroxy and $R^{41}$, $R^{43}$, and $R^{44}$ are independently selected from hydrogen, halogen, and C1-C10 alkyl.

10. The compound of claim 6, $R^{42}$ is hydroxy and $R^{41}$, $R^{43}$, and $R^{44}$ are independently of selected from hydrogen, halogen and C1-C10 alkyl.

11. The compound of claim 2, wherein $R^{45}$ and $R^{46}$ are hydrogen.

12. A compound selected from:
5,7,8-trimethyl-3,4-dihydrospiro[chromene-2,1'-cyclobutan]-6-ol;
5-chloro-7,8-dimethyl-3,4-dihydrospiro[chromene-2,1'-cyclobutan]-6-ol;
7-chloro-5,8-dimethyl-3,4-dihydrospiro[chromene-2,1'-cyclobutan]-6-ol;
5,7,8-trimethyl-3,4-dihydrospiro[chromene-2,1'-cyclopropan]-6-ol;
5-chloro-8-methyl-3,4-dihydrospiro[chromene-2,1'-cyclobutan]-6-ol;
5,8-dimethyl-7-(3-methylbutyl)-3,4-dihydrospiro[chromene-2,1'-cyclobutan]-6-ol;
5,7-dimethyl-3,4-dihydrospiro[chromene-2,1'-cyclobutan]-6-ol;
8-chloro-5,7-dimethyl-3,4-dihydrospiro[chromene-2,1'-cyclobutan]-6-ol;
8-chloro-5-methyl-3,4-dihydrospiro[chromene-2,1'-cyclobutan]-6-ol;
8-isopropyl-5-methyl-3,4-dihydrospiro[chromene-2,1'-cyclobutan]-6-ol;
6-hydroxy-7,8-dimethylspiro[chroman-2,1'-cyclopropan]-4(3H)one;
7,8-dimethyl-3,4-dihydrospiro[chromene-2,1'-cyclopropane]-4,6-diol;
7-chloro-5,8-dimethyl-3,4-dihydrospiro[chromene-2,1'-cyclobutan]-6-yl (dimethylamino)acetate;

5-isopropyl-8-methyl-3,4-dihydrospiro[chromene-2,1'-cyclobutan]-6-ol;
6'-hydroxy-5',7',8'-trimethylspiro[cyclobutane-1,2'-thiochromen]-4'(3'H)-one;
5',7',8'-trimethyl-3',4'-dihydrospiro[cyclobutane-1,2'-thiochromen]-6'-ol
6'-hydroxy-5',7',8'-trimethylspiro[cyclobutane-1,2'-thiochroman]-4'(3'H)-one O-methyloxime;
4'(methoxyamino)-5',7',8'-trimethyl-3',4'-dihydrospiro[cyclobutane-1,2'-thiochromen]-6'-ol;
7-chloro-5,8-dimethyl-3,4-dihydrospiro[chromene-2,1'-cyclobutan]-6-yl nicotinate;
5',7',8'-trimethyl-3',4'-dihydrospiro[cyclobutane-1,2'-thiochromen]-6'-yl (dimethylamino)acetate;
5,7,8-trimethyl-3,4-dihydrospiro[chromene-2,1'-cyclobutan]-6-yl (dimethylamino)acetate;
5,7,8-trimethyl-3,4-dihydrospiro[chromene-2,1'-cyclobutan]-6-yl-2-(4-methylpiperazin-1-yl)acetate;
7,8-dimethyl-3,4-dihydrospiro[chromene-2,1'-cyclobutan]-6-yl phenylcarbamate;
5,7,8-trimethyl-3,4-dihydrospiro[chromene-2,1'-cyclobutan]-6-yl phenyl(phenylcarbamoyl)carbamate;
2-(7-chloro-5,8-dimethylspiro[chroman-2,1'-cyclobutane]-6-yloxy)-N,N-dimethylethanamine;
4-(methoxyamino)-5,7,8-trimethyl-3,4-dihydrospiro[chromene-2,1'-cyclobutan]-6-yl acetate;
4-(methoxyamino)-5,7,8-trimethyl-3,4-dihydrospiro[chromene-2,1'-cyclobutan]-6-ol;
2-(dimethylamino)ethyl 5,7,8-trimethylspiro[chroman-2,1'-cyclobutane]-6-yl carbonate;
5,7,8-trimethyl-3,4-dihydrospiro[chromene-2,1'-cyclobutan]-6-yl 1H-imidazole-1-carboxylate;
2-(7-chloro-5,8-dimethylspiro[chroman-2,1'-cyclobutane]-6-yloxy)-N,N-dimethylpropan-1-amine;
4-amino-5,7,8-trimethyl-3,4-dihydrospiro[chromene-2,1'-cyclobutan]-6-yl acetate;
1-(dimethylamino)-3-[(5,7,8-trimethyl-3,4-dihydro-2H-spiro-[chromen-2,1'-cyclobutan]-6-yl)oxy]propan-2-ol;
1-(pyrrolindiny)-3-[(5,7,8-trimethyl-3,4-dihydro-2H-spiro-[chromen-2,1'-cyclobutan]-6-yl)oxy]propan-2-ol;
5,7,8-trimethyl-4-pyrrolidin-1-yl-3,4-dihydrospiro[chromene-2,1'-cyclobutan]-6-ol;
4-(aminomethyl)-5,7,8-trimethyl-3,4-dihydrospiro[chromene-2,1'-cyclobutane]-4,6-diol;
5,7,8-trimethyl-4-morpholin-4-yl-3,4-dihydrospiro[chromene-2,1'-cyclobutan]-6-ol;
4-(1H-imidazol-1-yl)-5,7,8-trimethyl-3,4-dihydrospiro[chromene-2,1'-cyclobutan]-6-ol;
5,7,8-trimethyl-3,4-dihydrospiro[chromene-2,1'-cyclobutane]-3,6-diol;
3-methoxy-5,7,8-trimethyl-3,4-dihydrospiro[chromene-2,1'-cyclobutan]-6-ol;
4-(aminomethyl)-5,7,8-trimethyl-3,4-dihydrospiro[chromene-2,1'-cyclobutan]-6-ol;
N-[(6-hydroxy-5,7,8-trimethyl-3,4-dihydrospiro[chromene-2,1'-cyclobutan]-4-yl)methyl]acetamide;
4-[(ethylamino)methyl]-5,7,8-trimethyl-3,4-dihydrospiro[chromene-2,1'-cyclobutan]-6-ol;
3-(hydroxymethyl)-5,7,8-trimethyl-3,4-dihydrospiro[chromene-2,1'-cyclobutan]-6-ol;
2-{[(5,7,8-trimethyl-3,4-dihydrospiro[chromene-2,1'-cyclobutan]-6-yl)oxy]methyl}pyridine;
2-{[(5,7,8-trimethyl-3,4-dihydrospiro[chromene-2,1'-cyclobutan]-6-yl)oxy]methyl}quinoline;
6-hydroxy-3,5,7,8-tetramethylspiro[chroman-2,1'-cyclobutan]-4(3H)-one;
3-(morpholinomethyl)-5,7,8-trimethyl-4-oxo-3,4-dihydrospiro[chromene-2,1'-cyclobutan]-6-yl acetate;
3-(morpholinomethyl)-5,7,8-trimethyl-3,4-dihydrospiro[chromene-2,1'-cyclobutane]-4,6-diol;
4-[(diethylamino)methyl]-5,7,8-trimethyl-3,4-dihydrospiro[chromene-2,1'-cyclobutan]-6-ol;
4-methoxy-3,5,7,8-tetramethyl-3,4-dihydrospiro[chromene-2,1'-cyclobutan]-6-ol;
3,5,7,8-tetramethyl-3,4-dihydrospiro[chromene-2,1'-cyclobutane]-4,6-diol;
4-methoxy-3,5,7,8-tetramethyl-3,4-dihydrospiro[chromene-2,1'-cyclobutan]-6-ol;
6-hydroxy-5,7,8-trimethyl-3,4-dihydrospiro[chromene-2,1'-cyclobutane]-4-carbonitrile;
methyl{[(6-hydroxy-5,7,8-trimethyl-3,4-dihydrospiro[chromene-2,1'-cyclobutan]-3-yl)methyl]thio}acetate;
4-ethoxy-5,7,8-trimethyl-3,4-dihydrospiro[chromene-2,1'-cyclobutan]-6-ol;
7,8-dimethyl-3,4-dihydrospiro[chromene-2,1'-cyclobutan]-6-ol;
4-methoxy-5,7-dimethyl-3,4-dihydrospiro[chromene-2,1'-cyclobutan]-6-ol;
4-ethoxy-5,7-dimethyl-3,4-dihydrospiro[chromene-2,1'-cyclobutan]-6-ol;
4-(methoxyamino)-5,7-dimethyl-3,4-dihydrospiro[chromene-2,1'-cyclobutan]-6-ol;
4-isopropoxy-5,7-dimethyl-3,4-dihydrospiro[chromene-2,1'-cyclobutan]-6-ol;
5,7,8-trimethyl-3,4-dihydrospiro[chromene-2,1'-cyclobutane]-4,6-diol;
5,7-dimethyl-3,4-dihydrospiro[chromene-2,1'-cyclobutane]-4,6-diol;
8-(hydroxymethyl)-5,7-dimethyl-3,4-dihydrospiro[chromene-2,1'-cyclobutan]-6-ol;
8-(methoxymethyl)-5,7-dimethyl-3,4-dihydrospiro[chromene-2,1'-cyclobutan]-6-ol;
4-(cyclopentyloxy)-5,7,8-trimethyl-3,4-dihydrospiro[chromene-2,1'-cyclobutane]-6-diol;
4-(ethoxyamino)-5,7,8-trimethyl-3,4-dihydrospiro[chromene-2,1'-cyclobutan]-6-ol;
4-(isopropylthio)-5,7,8-trimethyl-3,4-dihydrospiro[chromene-2,1'-cyclobutan]-6-ol;
7,8-dimethyl-3,4-dihydrospiro[chromene-2,1'-cyclobutane]-4,6-diol;
7,8-dimethyl-3,4-dihydrospiro[chromene-2,1'-cyclobutan]-6-yl(dimethylamino)acetate;
4-(methoxyamino)-7,8-dimethyl-3,4-dihydrospiro[chromene-2,1'-cyclobutan]-6-ol;
4'-(ethoxyamino)-5',7',8'-trimethyl-3',4'-dihydrospiro[cyclobutane-1,2'-thiochromen]-6'-ol;
4'-(ethoxyamino)-5',7'-dimethyl-3',4'-dihydrospiro[cyclobutan-1,2'-thiochromen]-6'-ol;
4-(ethoxyamino)-5,7-dimethyl-3,4-dihydrospiro[chromene-2,1'-cyclobutan]-6-ol;
5-[1-(ethoxyamino)ethyl]-7,8-dimethyl-3,4-dihydrospiro[chromene-2,1'-cyclobutan]-6-ol;
4-(methoxyamino)-5,7-dimethyl-3,4-dihydrospiro[chromene-2,1'-cyclobutan]-6-yl acetate;
4'-(methoxyamino)-5',7'-dimethyl-3',4'-dihydrospiro[cyclobutane-1,2'-thiochromen]-6'-ol;
4-(ethoxyamino)-7,8-dimethyl-3,4-dihydrospiro[chromene-2,1'-cyclobutan]-6-ol;
4-[methoxy(methyl)amino]-5,7,8-trimethyl-3,4-dihydrospiro[chromene-2,1'-cyclobutan]-6-ol;

6-hydroxy-5,7,8-trimethylspiro[chromene-2,1'-cyclobutan]-4(3H)-one oxime;
4-(hydroxyamino)-5,7,8-trimethyl-3,4-dihydrospiro[chromene-2,1'-cyclobutan]-6-ol;
8-[(methoxyamino)methyl]-5,7-dimethyl-3,4-dihydrospiro[chromene-2,1'-cyclobutan]-6-ol
5,7-dimethyl-8-vinyl-3,4-dihydrospiro[chromene-2,1'-cyclobutan]-6-ol;
4-[hydroxy(methyl)amino]-5,7,8-trimethyl-3,4-dihydrospiro[chromene-2,1'-cyclobutan]-6-ol;
6-hydroxy-5,7-dimethylspiro[chromene-2,1'-cyclobutan]-4(3H)-one oxime;
4-(hydroxyamino)-5,7-dimethyl-3,4-dihydrospiro[chromene-2,1'-cyclobutan]-6-ol;
4-[hydroxy(methyl)amino]-5,7-dimethyl-3,4-dihydrospiro[chromene-2,1'-cyclobutan]-6-ol;
8-[(ethoxyamino)methyl]-5,7-dimethyl-3,4-dihydrospiro[chromene-2,1'-cyclobutan]-6-ol;
4-[methoxy(methyl)amino]-5,7-dimethyl-3,4-dihydrospiro[chromene-2,1'-cyclobutan]-6-ol;
4-[ethyl(methoxy)amino]-5,7-dimethyl-3,4-dihydrospiro[chromene-2,1'-cyclobutan]-6-ol;
5,7-dimethyl-4-methoxyamino-3,4-dihydrospiro[chromene-2,1'-cyclobutan]-6-yl (dimethylamino)-acetate;
ethyl 4-(methoxyamino)-5,7-dimethyl-3,4-dihydrospiro[chromene-2,1'-cyclobutan]-6-yl carbonate;
6-hydroxy-5,7-dimethylspiro[chromene-2,1'-cyclobutan]-4(3H)-one O-methyloxime;
(4E)-6-hydroxy-5,7-dimethylspiro[chromene-2,1'-cyclobutan]-4(3H)-one O-ethyloxime;
(4Z)-6-hydroxy-5,7-dimethylspiro[chromene-2,1'-cyclobutan]-4(3H)-one O-ethyloxime;
5-ethyl-4-(methoxyamino)-7,8-dimethyl-3,4-dihydrospiro[chromene-2,1'-cyclobutan]-6-ol;
4-(ethoxyamino)-5-ethyl-7,8-dimethyl-3,4-dihydrospiro[chromene-2,1'-cyclobutan]-6-ol;
5-ethyl-6-hydroxy-7,8-dimethylspiro[chromene-2,1'-cyclobutan]-4(3H)-one O-methyloxime;
5-ethyl-6-hydroxy-7,8-dimethylspiro[chromene-2,1'-cyclobutan]-4(3H)-one O-ethyloxime;
6'-hydroxy-5',7',8'-trimethylspiro[cyclobutane-1,2'-thiochromen]-4'(3H)-one O-methyloxime;
6'-hydroxy-5',7',8'-trimethylspiro[cyclobutane-1,2'-thiochromen]-4'(3'H)-one O-ethyloxime;
6'-hydroxy-5',7'-dimethylspiro[cyclobutane-1,2'-thiochromen]-4'(3'H)-one O-methyloxime;
3-[(methoxyamino)methyl]-5,7-dimethylspiro[chromene-2,1'-cyclobutan]-6-yl pivalate;
methyl 3-(6-hydroxy-5,7-dimethyl-3,4-dihydrospiro[chromene-2,1'-cyclobutan]-8-yl)-4,5-dihydroisoxazole-5-carboxylate;
6'-hydroxy-5',7'-dimethylspiro[cyclobutane-1,2'-thiochromen]-4'(3'H)-one O-ethyloxime;
5,7-diethyl-6-hydroxyspiro[chromene-2,1'-cyclobutan]-4(3H)-one O-methyloxime;
5,7-diethyl-6-hydroxyspiro[chromene-2,1'-cyclobutan]-4(3H)-one O-ethyloxime;
5,7-diethyl-6-hydroxyspiro[chromene-2,1'-cyclobutan]-4(3H)-one oxime;
(4S)-4-(methoxyamino)-5,7-dimethyl-3,4-dihydrospiro[chromene-2,1'-cyclobutan]-6-ol;
(4R)-4-(methoxyamino)-5,7-dimethyl-3,4-dihydrospiro[chromene-2,1'-cyclobutan]-6-ol;
5,7-dimethyl-8-(5-butyl-isoxazol-3-yl)-3,4-dihydrospiro[chromene-2,1'-cyclobutan]-6-ol;
4-(ethoxyamino)-5,7-diethyl-3,4-dihydrospiro[chromene-2,1'-cyclobutan]-6-ol;
4-(methoxyamino)-5,7-diethyl-3,4-dihydrospiro[chromene-2,1'-cyclobutan]-6-ol;
N-(6-hydroxy-5,7-dimethyl-3,4-dihydrospiro[chromene-2,1'-cyclobutan]-4-yl)methanesulfonamide;
7-tert-butyl-5-methyl-3,4-dihydrospiro[chromene-2,1'-cyclobutan]-6-ol;
5,7-dimethyl-8-(1,3-oxazol-5-yl)-3,4-dihydrospiro[chromene-2,1'-cyclobutan]-6-ol;
N-(6-hydroxy-5,7-dimethyl-3,4-dihydrospiro[chromene-2,1'-cyclobutan]-4-yl)benzenesulfonamide;
5,7-diisopropyl-3,4-dihydrospiro[chromene-2,1'-cyclobutan]-6-ol;
6-hydroxy-5,7-diisopropyl-3,4-dihydrospiro[chromene-2,1'-yclobutane]-8-carbaldehyde;
4-(methoxyamino)-5,7-dimethyl-3,4-dihydrospiro[chromene-2,1'-cyclobutan]-6-yl isobutyrate;
3-[(ethoxyamino)methyl]-5,7-dimethyl-3,4-dihydrospiro-[chromene-2,1'-cyclobutan]-6-ol;
3-[(methoxyamino)methyl]-5,7-dimethyl-3,4-dihydrospiro-[chromene-2,1'-cyclobutan]-6-ol;
7,8-dimethyl-5-(2-quinolin-2-ylethyl)) 3,4-dihydrospiro-[chromene-2,1'-cyclobutan]-6-ol;
5,7-diisopropyl-8-[(methoxyamino)methyl]3,4-dihydrospiro[chromene-2,1'-cyclobutan]-6-ol;
5-(3,7-dimethylocta-2,6-dienyl)-7,8-dimethylspiro[chroman-2,1'-cyclobutan]-6-ol;
5,7-diethyl-3,4-dihydrospiro[chromene-2,1'-cyclobutan]-6-ol;
7-isopropyl-4-(methoxyamino)-5-methyl-3,4-dihydrospiro[chromene-2,1'-cyclobutan]-6-ol;
7-(3,7-dimethylocta-2,6-dienyl)-5,8-dimethylspiro[chroman-2,1'-cyclobutan]-6-ol;
8-(4,5-dimethyl-1H-imidazol-2-yl)-5,7-diethyl-3,4-dihydrospiro[chromene-2,1'-cyclobutan]-6-ol;
7-(4,5-dimethyl-1H-imidazol-2-yl)-5,8-dimethyl-3,4-dihydrospiro[chromene-2,1'-cyclobutan]-6-ol;
7-ethyl-4-(methoxyamino)-5-methyl-3,4-dihydrospiro[chromene-2,1'-cyclobutan]-6-ol;
5-ethyl-4-(methoxyamino)-7-methyl-3,4-dihydrospiro[chromene-2,1'-cyclobutan]-6-ol;
(Z)-5,7-diethyl-8-(hydroxymethyl)-3,4-dihydrospiro[chromene-2,1'-cyclobutan]-6-ol;
5,7-diethyl-8-(hydroxymethyl)-3,4-dihydrospiro[chromene-2,1'-cyclobutan]-6-ol;
7-isopropyl-5-methyl-3,4-dihydrospiro[chromene-2,1'-cyclobutan]-6-ol;
7-(3,7-dimethyloctyl)-5,8-dimethylspiro[chroman-2,1'-cyclobutan]-6-ol;
8-(hydroxymethyl)-7-isopropyl-5-methylspiro[chroman-2,1'-cyclobutan]-6-ol;
5,7-dimethyl-3-(oxazol-5-yl)spiro[chroman-2,1'-cyclobutan]-6-ol;
7-isopropyl-5-methylspiro[chroman-2,1'-cyclobutane]-4,6-diol;
7-isopropyl-4-methoxy-5-methylspiro[chroman-2,1'-cyclobutan]-6-ol;
7-(5,6-dimethyl-1H-benzo[d]imidazol-2-yl)-5,8-dimethylspiro[chroman-2,1'-cyclobutan]-6-ol;
7-tert-butyl-5-(morpholinomethyl)spiro[chroman-2,1'-cyclobutan]-6-ol;
8-(hydroxymethyl)-5,7-diisopropylspiro[chroman-2,1'-cyclobutan]-6-ol;
8-((hydroxyamino)methyl)-5,7-diisopropylspiro[chroman-2,1'-cyclobutan]-6-ol;

5,8-dimethyl-7-(2-(quinolin-2-yl)ethyl)spiro[chroman-2,1'-cyclobutan]-6-ol;
N-((6-hydroxy-5,7-diisopropylspiro[chroman-2,1'-cyclobutane]-8-yl)methyl)-N-methylacetamide;
5,7-diisopropyl-8-(methoxymethyl)spiro[chroman-2,1'-cyclobutan]-6-ol;
5,7-diethyl-3-(hydroxymethyl)spiro[chroman-2,1'-cyclobutan]-6-ol;
8-(acetamidomethyl)-5,7-diisopropylspiro[chroman-2,1'-cyclobutan]-6-ol;
methyl 2-((5,7-diethyl-6-hydroxyspiro[chroman-2,1'-cyclobutane]-3-yl)methylthio)acetate;
(5,7-diethyl-6-hydroxyspiro[chroman-2,1'-cyclobutane]-3-yl)methyl carbamates;
7-tert-butyl-5-methylspiro[chroman-2,1'-cyclobutane]-4,6-diol;
7-tert-butyl-4-hydroxy-5-methylspiro[chroman-2,1'-cyclobutane]-6-yl acetate;
5,7-diisopropylspiro[chroman-2,1'-cyclobutane]-6-yl 2-amino-2-oxoacetate;
2-hydroxy-2-(6-hydroxy-5,7-diisopropylspiro[chroman-2,1'-cyclobutane]-8-yl)acetonitrile;
5-ethyl-7-isopropylspiro[chroman-2,1'-cyclobutane]-4,6-diol;
(S)-5,7-diethylspiro[chroman-2,1'-cyclobutane]-4,6-diol;
(R)-5,7-diethylspiro[chroman-2,1'-cyclobutane]-4,6-diol;
(S)-7-isopropyl-5-methylspiro[chroman-2,1'-cyclobutane]-4,6-diol;
(R)-7-isopropyl-5-methylspiro[chroman-2,1'-cyclobutane]-4,6-diol;
and single stereoisomers, mixtures of stereoisomers, or pharmaceutically acceptable salts thereof.

13. A compound selected from:
N-(6-hydroxy-5,7,8-trimethyl-3,4-dihydrospiro[chromene-2,1'-cyclobutan]-4-yl)acetamide;
N-(6-hydroxy-5,7-dimethyl-3,4-dihydrospiro[chromene-2,1'-cyclobutan]-4-yl)acetamide;
N-(6-hydroxy-5,7,8-trimethyl-3,4-dihydrospiro[chromene-2,1'-cyclobutan]-4-yl)butanamide;
and single stereoisomers, mixtures of stereoisomers, or pharmaceutically acceptable salts thereof.

14. A compound selected from:
4'(methoxyamino)-5',7',8'-trimethyl-3',4'-dihydrospiro[cyclobutane-1,2'-thiochromen]-6'-ol;
4-(methoxyamino)-5,7-dimethyl-3,4-dihydrospiro[chromene-2,1'-cyclobutan]-6-ol;
4-(ethoxyamino)-5,7,8-trimethyl-3,4-dihydrospiro[chromene-2,1'-cyclobutan]-6-ol;
4'-(ethoxyamino)-5',7',8'-trimethyl-3',4'-dihydrospiro[cyclobutane-1,2'-thiochromen]-6'-ol;
4'-(ethoxyamino)-5',7'-dimethyl-3',4'-dihydrospiro[cyclobutane-1,2'-thiochromen]-6'-ol;
4-(ethoxyamino)-5,7-dimethyl-3,4-dihydrospiro[chromene-2,1'-cyclobutan]-6-ol;
4'-(methoxyamino)-5',7'-dimethyl-3',4'-dihydrospiro[cyclobutane-1,2'-thiochromen]-6'-ol;
4-[ethyl(methoxy)amino]-5,7-dimethyl-3,4-dihydrospiro[chromene-2,1'-cyclobutan]-6-ol;
5-ethyl-4-(methoxyamino)-7,8-dimethyl-3,4-dihydrospiro[chromene-2,1'-cyclobutan]-6-ol;
4-(ethoxyamino)-5-ethyl-7,8-dimethyl-3,4-dihydrospiro[chromene-2,1'-cyclobutan]-6-ol;
(4S)-4-(methoxyamino)-5,7-dimethyl-3,4-dihydrospiro[chromene-2,1'-cyclobutan]-6-ol;
(4R)-4-(methoxyamino)-5,7-dimethyl-3,4-dihydrospiro[chromene-2,1'-cyclobutan]-6-ol;
4-(methoxyamino)-5,7-diethyl-3,4-dihydrospiro[chromene-2,1'-cyclobutan]-6-ol;
3-[(methoxyamino)methyl]-5,7-dimethyl-3,4-dihydrospiro-[chromene-2,1'-cyclobutan]-6-ol;
7-isopropyl-4-(methoxyamino)-5-methyl-3,4-dihydrospiro[chromene-2,1'-cyclobutan]-6-ol;
7-ethyl-4-(methoxyamino)-5-methyl-3,4-dihydrospiro[chromene-2,1'-cyclobutan]-6-ol;
5-ethyl-4-(methoxyamino)-7-methyl-3,4-dihydrospiro[chromene-2,1'-cyclobutan]-6-ol;
and single stereolsomers, mixtures of stereolsomers, or pharmaceutically acceptable salts thereof.

15. A compound selected from: 5,7,8-trimethyl-3,4-dihydrospiro[chromene-2,1'-cyclobutane]-4,6-diol;
5,7-dimethyl-3,4-dihydrospiro[chromene-2,1'-cyclobutane]-4,6-diol;
5,7-diethyl-8-(hydroxymethyl)-3,4-dihydrospiro[chromene-2,1'-cyclobutan]-6-ol;
7-isopropyl-5-methylspiro[chroman-2,1'-cyclobutane]-4,6-diol;
7-tert-butyl-5-methylspiro[chroman-2,1'-cyclobutane]-4,6-diol;
5-ethyl-7-isopropylspiro[chroman-2,1'-cyclobutane]-4,6-diol;
(S)-5,7-diethylspiro[chroman-2,1'-cyclobutane]-4,6-diol;
(R)-5,7-diethylspiro[chroman-2,1'-cyclobutane]-4,6-diol;
(S)-7-isopropyl-5-methylspiro[chroman-2,1'-cyclobutane]-4,6-diol;
(R)-7-isopropyl-5-methylspiro[chroman-2,1'-cyclobutane]-4,6-diol;
and single stereoisomers, mixtures of stereoisomers, or pharmaceutically acceptable salts thereof.

16. A compound selected from:
7-isopropyl-5-methyl-3,4-dihydrospiro[chromene-2,1'-cyclobutan]-6-ol;
5,7-diethyl-3,4-dihydrospiro[chromene-2,1'-cyclobutan]-6-ol;
7-tert-butyl-5-methyl-3,4-dihydrospiro[chromene-2,1'-cyclobutan]-6-ol;
5,7-dimethyl-8-vinyl-3,4-dihydrospiro[chromene-2,1'-cyclobutan]-6-ol;
7,8-dimethyl-3,4-dihydrospiro[chromene-2,1'-cyclobutan]-6-ol;
8-chloro-5,7-dimethyl-3,4-dihydrospiro[chromene-2,1'-cyclobutan]-6-ol;
5,7-dimethyl-3,4-dihydrospiro[chromene-2,1-cyclobutan]-6-ol;
5,7,8-trimethyl-3,4-dihydrospiro[chromene-2,1'-cyclopropan]-6-ol;
and single stereoisomers, mixtures of stereoisomers, or pharmaceutically acceptable salts thereof.

17. A pharmaceutical composition comprising a compound of claim 1 admixed with a pharmaceutically acceptable excipient.

18. A pharmaceutical composition comprising a compound of claim 12 admixed with a pharmaceutically acceptable excipient.

19. A method of treating a subject suffering from rheumatoid arthritis or atherosclerosis comprising administering to said subject a therapeutically effective amount of a compound of claim 1.

20. A compound represented by Formula II:

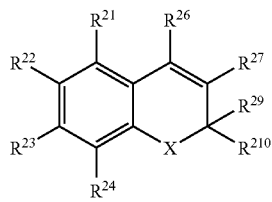

Formula II wherein,
X is O or $S(O)_{0-2}$;
$R^{21}$, $R^{23}$, and $R^{24}$ are independently selected from hydrogen or alkyl;
$R^{22}$ is hydroxy;
$R^{26}$ and $R^{27}$ are independently selected from: hydrogen, alkyl, alkoxy, cyano, —CN=N—$OR^{20}$, $NR^{20}OR^{2a}$ and -alkyl$NR^{20}OR^{2a}$;
$R^{29}$ and $R^{210}$ together with the carbon atom to which they are attached form a $(C_3-C_4)$cycloalkyl ring;
$R^{20}$ is hydrogen or alkyl;
$R^{2a}$ is hydrogen or alkyl;
with the proviso that when $R^{26}$ or $R^{27}$ is —$NHOR^{2a}$, then no more than one of $R^{21}$, $R^{22}$, $R^{23}$ and $R^{24}$ is hydrogen;
or single stereoisomers, mixtures of stereoisomers, or pharmaceutically acceptable salts thereof.

21. A compound of Formula IIA:

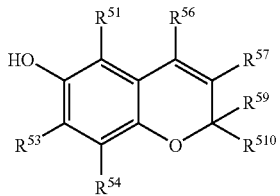

Formula IIA wherein,
$R^{51}$, $R^{53}$, and $R^{54}$ are independently hydrogen or alkyl;
$R^{56}$ and $R^{57}$ are independently selected from: hydrogen, alkyl, and cyano;
$R^{59}$ and $R^{510}$ together with the carbon atom to which they are attached form a $(C_3-C_4)$cycloalkyl ring;
or single stereoisomers, mixtures of stereoisomers, or pharmaceutically acceptable salts thereof.

22. The compound of claim 20, wherein $R^{27}$ is —$NR^{20}OR^{2a}$.

23. The compound of claim 20, selected from the group consisting of:
5',7',8'-trimethylspiro[cyclobutane-1,2'-thiochromen]-6'-ol;
3-(hydroxymethyl)-5,7,8-trimethylspiro[chromene-2,1'-cyclobutan]-6-ol;
4-(aminomethyl)-5,7,8-trimethylspiro[chromene-2,1'-cyclobutan]-6-ol;
N-[(6-hydroxy-5,7,8-trimethylspiro[chromene-2,1'-cyclobutan]-4-yl)methyl]acetamide;
3-(methoxymethyl)-5,7,8-trimethylspiro[chromene-2,1'-cyclobutan]-6-ol;
3,5,7,8-tetramethylspiro[chromene-2,1'-cyclobutan]-6-ol;
6-hydroxy-5,7,8-trimethylspiro[chromene-2,1'-cyclobutane]-4-carbonitrile;
6-hydroxy-5,7-dimethylspiro[chromene-2,1'-cyclobutane]-3-carbaldehyde O-methyloxime;
3-[(methoxyamino)methyl]-5,7-dimethylspiro[chromene-2,1'-cyclobutan]-6-ol;
3-(1-methoxyethyl)-5,7,8-trimethylspiro[chromene-2,1'-cyclobutan]-6-ol;
3-(1-hydroxyethyl)-5,7,8-trimethylspiro[chromene-2,1'-cyclobutan]-6-ol;
5,7-dimethylspiro[chromene-2,1'-cyclobutan]-6-ol;
6-hydroxy-5,7-dimethylspiro[chromene-2,1'-cyclobutane]-3-carbaldehyde O-ethyloxime;
3-[(ethoxyamino)methyl]-5,7-dimethylspiro[chromene-2,1'-cyclobutan]-6-ol;
5,7-dimethyl-3-(1,3-oxazol-5-yl)spiro[chromene-2,1'-cyclobutan]-6-ol;
5,7-dimethyl-3-(-(4,5-dimethyl-1H-imidazol-2-yl)spiro[chromene-2,1'-cyclobutan]-6-ol;
7-isopropyl-5-methylspiro[chromene-2,1'-cyclobutan]-6-ol;
5,7-diethylspiro[chromene-2,1'-cyclobutan]-6-ol;
5,7-diisopropylspiro[chromene-2,1'-cyclobutan]-6-ol
and single stereoisomers, mixtures of stereoisomers, or pharmaceutically acceptable salts thereof.

24. A pharmaceutical composition comprising a compound of claim 20 admixed with a pharmaceutically acceptable excipient.

25. pharmaceutical composition comprising a compound of claim 23 admixed with a pharmaceutically acceptable excipient.

26. A method of treating a subject suffering from a disorder selected from the group consisting of rheumatoid arthritis or atherosclerosis comprising administering to said subject a therapeutically effective amount of a compound of claim 20.

27. A compound represented by Formula III:

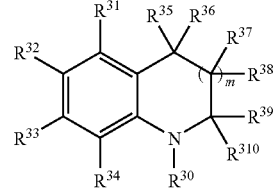

Formula III wherein,
$R^{30}$ is selected from the group consisting of alkyl, aralkyl, heterocyclyl and aryl;
$R^{31}$, $R^{33}$, and $R^{34}$ are independently hydrogen or alkyl;
$R^{32}$ is hydroxy or alkoxy;
$R^{35}$, $R^{36}$, $R^{37}$, and $R^{38}$ are hydrogen or together with the carbon atom to which they are attached form C=O;
$R^{39}$ and $R^{310}$ together with the carbon atom to which they are attached form a $(C_3-C_4)$cycloalkyl ring;
m is 1;
with the proviso no more than one of $R^{31}$, $R^{33}$ and $R^{34}$ is hydrogen;
or single stereoisomers, mixtures of stereoisomers, or pharmaceutically acceptable salts thereof.

28. A compound of Formula IIIA:

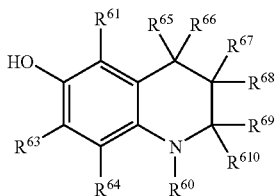

Formula IIIA $R^{60}$ is selected from the group consisting of alkyl, aralkyl, acyl, heterocyclyl and aryl;
$R^{61}$, $R^{63}$, and $R^{64}$ are independently selected from the group consisting of hydrogen or alkyl;
$R^{65}$ $R^{66}$, $R^{67}$, and $R^{68}$ are hydrogen;
$R^{69}$ and $R^{610}$ together with the carbon atom to which they are attached form a $(C_3-C_4)$cycloalkyl ring;
with the following provisos: no more than one of $R^{61}$, $R^{63}$ and $R^{64}$ is hydrogen;
or single stereoisomers, mixtures of stereoisomers, or pharmaceutically acceptable salts thereof.

29. The compound of claim 27, wherein —$CR^{35}R^{36}$ is C=O.

30. The compound of claim 27, wherein —$CR^{37}R^{38}$ is C=O.

31. The compound of claim 27, wherein $R^{35}$ and $R^{36}$ are both hydrogen.

32. The compound of claim 27 wherein $R^{30}$ is alkyl substituted with an amido, a sulfonylamino or an aminosulfonyl group.

33. The compound of claim 32, wherein $R^{30}$ is —$(CH_2)_{2-6}$—NHS(O)$_2$-aryl, —$(CH_2)_{2-6}$—S(O)$_2$NH-aryl, —$(CH_2)_{2-6}$—NHC(O)-aryl, or —$(CH_2)_{2-6}$—C(O)NH-aryl.

34. The compound of claim 27, selected from:
1'-(4-chlorobenzyl)-5',7'-dimethyl-3',4'-dihydro-1'H-spiro[cyclobutane-1,2'-quinolin]-6'-ol;
1'-(4-hydroxyphenyl)-7',8'-dimethyl-3',4'-dihydro-1'H-spiro[cyclopropane-1,2'-quinolin]-6'-ol;
1',7',8'-trimethyl-3',4'-dihydro-1'H-spiro[cyclopropane-1,2'-quinolin]-6'-ol;
4-((6'-hydroxy-5',7'-dimethyl-3',4'-dihydro-1'H-spiro[cyclobutane-1,2'-quinoline]-1'-yl)methyl)benzoic acid;
methyl 4-((6'-hydroxy-5',7'-dimethyl-3',4'-dihydro-1'H-spiro[cyclobutane-1,2'-quinoline]-1'-yl)methyl)benzoate;
5',7'-dimethyl-1'-(quinolin-2-ylmethyl)-3',4'-dihydro-1'H-spiro[cyclobutane-1,2'-quinolin]-6'-ol;
and single stereoisomers, mixtures of stereoisomers, or pharmaceutically acceptable salts thereof.

35. A pharmaceutical composition comprising a compound of claim 27 admixed with a pharmaceutically acceptable excipient.

36. A pharmaceutical composition comprising a compound of claim 34 admixed with a pharmaceutically acceptable excipient.

37. A method of treating a mammal suffering from rheumatoid arthritis or atherosclerosis comprising contacting a cell with an effective amount of a compound of claim 27.

* * * * *